United States Patent
Drysdale et al.

(10) Patent No.: US 7,247,734 B2
(45) Date of Patent: Jul. 24, 2007

(54) 3,4-DIARYLPYRAZOLES AND THEIR USE IN THE THERAPY OF CANCER

(75) Inventors: Martin James Drysdale, Cambridge (GB); Brian William Dymock, Cambridge (GB); Xavier Barril-Alonso, Cambridge (GB); Paul Workman, London (GB); Laurence Harris Pearl, London (GB); Chrisostomos Prodromou, London (GB); Edward McDonald, London (GB)

(73) Assignees: Vernalis (Cambridge) Limited (GB); Cancer Research Technology Ltd. (GB); Institute of Cancer Research of Royal Cancer Hospital (GB)

( * ) Notice: Subject to any disclaimer, the term of this patent is extended or adjusted under 35 U.S.C. 154(b) by 0 days.

(21) Appl. No.: 10/499,030

(22) PCT Filed: Dec. 19, 2002

(86) PCT No.: PCT/GB02/05778
§ 371 (c)(1),
(2), (4) Date: Apr. 25, 2005

(87) PCT Pub. No.: WO03/055860
PCT Pub. Date: Jul. 10, 2003

(65) Prior Publication Data
US 2005/0222230 A1    Oct. 6, 2005

(30) Foreign Application Priority Data
Dec. 21, 2001 (GB) .................................. 0130733.9
Nov. 4, 2002 (GB) .................................. 0225688.1

(51) Int. Cl.
C07D 231/10 (2006.01)
(52) U.S. Cl. .............................. 548/364.1; 548/373.1; 548/377.1
(58) Field of Classification Search ............. 548/374.1, 548/375.1, 376.1, 203, 179, 373.1, 377.1, 548/364.1; 514/406; 544/333; 549/365, 549/448, 464
See application file for complete search history.

(56) References Cited

FOREIGN PATENT DOCUMENTS

| WO | WO 95 31451 A | 11/1995 |
|----|---------------|---------|
| WO | WO 96 03385 A | 2/1996 |
| WO | WO 98 52937 A | 11/1998 |
| WO | WO 00 07996 A | 2/2000 |
| WO | WO 00 19994 A | 4/2000 |
| WO | WO 02 062804 A | 8/2002 |
| WO | WO 02 066462 A | 8/2002 |
| WO | WO 02 092593 A | 11/2002 |

OTHER PUBLICATIONS

Ohsumi et al.: "Syntheses and antitumor activity of cisrestricted combretastatins: 5-membered heterocyclic analogs"; Bioorganic & Medicinal Chemistry Letters; vol. 8, No. 22; pp. 3153-3158; XP002235812.
Penning et al.: "3,4-Diarylpyrazoles: potent and selective inhibitors of cyclooxygenase-2"; Bioorganic & Medicinal Chemistry Letters; vol. 7, No. 16; 1997; pp. 2121-2124; XP002235813.
Bannier et al.: "Determination of a new anti-inflammatory agent, 1-isobutyl-3,4-diphenyl-pyrazole-5-acetic acid, by high-performance liquid chromatography"; Journal of Chromatograph; vol. 227, No. 1, 1982, pp. 213-218; XP009008354.
Meanwell et al.: "Structure-activity relationships associated with 3,4,5-triphenyl-1H-pyrazole-1-nonanoic acid, a nonprostanoid prostacyclin mimetic"; Journal of Medicinal Chemistry; vol. 35, No. 2; 1992; pp. 389-397; XP002235815.
DATABASE WPI; Section Ch, Week 200312; Derwent Publications Ltd.; AN 2003-129155; XP002235817.
DATABASE CA 'Online!; Chemical Abstracts Service; Khilya et al.: "Synthetic and modified isoflavonoids. XV. Reaction of synthetic isoflavone analogs with hydrazine hydrate derivatives"; retrieved from STN; Database accession No. 124:8437 CA; XP002235816; & Khimiy a Prirodnykh Soedinenii (1994), (5), 629-33, 1994.

*Primary Examiner*—Kamal A. Saeed
*Assistant Examiner*—Yong Chu
(74) *Attorney, Agent, or Firm*—Banner & Witcoff, Ltd.

(57) ABSTRACT

The present invention pertains to the use of certain 3,4-diarylpyazoles of formula (I), both in vitro and in vivo, to inhibit heat shock protein 90 (HSP90), and in the treatment of conditions mediated by HSP90, including, for example, cancer; wherein: $Ar^3$ is independently: a $C_{5-20}$aryl group, and is optionally substituted; $Ar^4$ is independently: a $C_{5-20}$aryl group, and is optionally substituted; $R^5$ is independently: hydrogen; halo; hydroxyl; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamide; $C_{1-7}$alkyl; $C_{3-20}$heterocycyl; or $C_{5-20}$aryl; R<SP>N</SP> is independently: —H; $C_{1-7}$alkyl; $C_{3-20}$heterocycyl; or, $C_{5-20}$aryl; and pharmaceutically acceptable salts, solvates, amides, esters, ethers, chemically protected forms, and prodrugs thereof. The present invention also pertains to such compounds, pharmaceutical compositions comprising such compounds, such compounds for medical use, such compounds use in the treatment of conditions mediated by HSP90, including, for example, cancer, and use of such compounds in the preparation of medicaments for such treatments.

20 Claims, 1 Drawing Sheet

3,4-DIARYLPYRAZOLES AND THEIR USE IN THE THERAPY OF CANCER

This application is a U.S. National Stage application of co-pending PCT application PCT/GB02/05778 filed 19 Dec. 2002, which claims the priority of United Kingdom Patent Application No. 0130733.9 filed 21 Dec. 2001 and United Kingdom Patent Application No. 0225688.1 filed 4 Nov. 2001. These applications are incorporated herein by reference in there entireties.

TECHNICAL FIELD

The present invention pertains generally to therapeutic compounds, and their use in therapy. More particularly, the present invention pertains to the use of certain 3,4-diarylpyrazoles, described herein, both in vitro and in vivo, to inhibit heat shock protein 90 (HSP90), and in the treatment of conditions mediated by HSP90, including, for example, cancer. The present invention also pertains to such compounds, pharmaceutical compositions comprising such compounds, such compounds for medical use, such compounds for use in the treatment of conditions mediated by HSP90, including, for example, cancer, and use of the such compounds in the preparation of medicaments for such treatments.

BACKGROUND

Molecular chaperones maintain the appropriate folding and conformation of proteins and are crucial in regulating the balance between protein synthesis and degradation. They have been shown not only to play a vital role in the cellular stress response but also to be important in regulating many important cellular functions, such as cell proliferation and apoptosis (Jolly and Morimoto, 2000; Smith et al., 1998; Smith, 2001).

Heat Shock Proteins (HSPs)

Exposure of cells to a number of environmental stresses, including heat shock, alcohols, heavy metals and oxidative stress, results in the cellular accumulation of a number of chaperones, commonly known as heat shock proteins (HSPs). This effect is mediated by the transcription factor heat shock factor 1 (HSF1) and is termed the 'heat shock response' (Morimoto, 1998). Induction of HSPs protects the cell against the initial stress insult, enhances recovery and leads to maintenance of a stress tolerant state. It has also become clear, however, that certain HSPs may also play a major molecular chaperone role under normal, stress-free conditions by regulating the correct folding, degradation, localization and function of a growing list of important cellular proteins.

A number of multigene familes of HSPs exist, with individual gene products varying in cellular expression, function and localization. They are classified according to molecular weight, e.g., HSP70, HSP90, and HSP27. Exceptions to this nomenclature rule are a small subset of chaperones that were identified as glucose regulated proteins, e.g., GRP94 and GRP75.

Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases and Huntington's disease), misfolded proteins can cause protein aggregation resulting in neurodegenerative disorders. Also, misfolded proteins may result in loss of wild type protein function, leading to deregulated molecular and physiological functions in the cell.

HSPs have also been implicated in cancer. For example, there is evidence of differential expression of HSPs which may relate to the stage of tumour progression (Martin et al., 2000; Conroy et al., 1996; Kawanishi et al., 1999; Jameel et al., 1992; Hoang et al., 2000; Lebeau et al., 1991). As a result of the involvement of HSP90 in various critical oncogenic pathways and the discovery that certain natural products with anticancer activity are targeting this molecular chaperone, the fascinating new concept has been developed that inhibiting HSP function may be useful in the treatment of cancer. The first molecular chaperone inhibitor is currently undergoing clinical trials.

HSP90

HSP90 constitutes about 1–2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, recent results suggest that HSP90 may also play a role in buffering against the effects of mutation, presumably by correcting the inappropriate folding of mutant proteins (Rutherford and Lindquist, 1998). However, HSP90 also has an important regulatory role. Under normal physiological conditions, together with its endoplasmic reticulum homologue GRP94, HSP90 plays a housekeeping role in the cell, maintaining the conformational stability and maturation of several key client proteins. These can be subdivided into three groups: (a) steroid hormone receptors, (b) Ser/Thr or tyrosine kinases (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New HSP90 client proteins are continuously being identified.

The highly conserved HSP90 family in humans consists of four genes, namely the cytosolic HSP90α and HSP90β isoforms (Hickey et al., 1989), GRP94 in the endoplasmic reticulum (Argon et al., 1999) and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

HSP90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of HSP90.

The monomer of HSP90 consists of conserved 25 kDa N terminal and 55 kDa C terminal domains joined together by a charged linker region (not present in TRAP1) (Prodromou and Pearl, 2000a). Both the N and C termini of HSP90 are reported to bind to substrate polypeptides including client proteins and co-chaperones. The N terminus contains an unusual ATP binding site that has structural homology with type II topoisomerase gyrase B, an N-terminal fragment of the MutL DNA mismatch repair protein and a C-terminal fragment of the histidine kinase Che A (Prodromou and Pearl, 2000a).

Following earlier controversy on this issue, it is now clear that HSP90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the 'clamp mechanism' (Prodromou and Pearl, 2000b).

The function of HSP90 is regulated by association with a number of co-chaperones that combine in various ways to form a series of multimeric protein complexes. Interactions with these various partners in different heterocomplexes may be restricted by temporal, spatial and biochemical factors. A number of these cochaperones contain a tetracopeptide repeat and binding of these proteins to HSP90 has been localised to the C terminal MEEVD motif (Prodromou and Pearl, 2000a).

A number of reviews describe in detail the molecular chaperone role of HSP90 and its importance in the conformational stability and function of the currently identified client proteins (Scheibel et al, 1998; Smith et al., 2001).

Known HSP90 Inhibitors

The first class of HSP90 inhibitors to be discovered was the benzoquinone ansamycin class, which includes the compounds herbimycin A and geldanamycin.

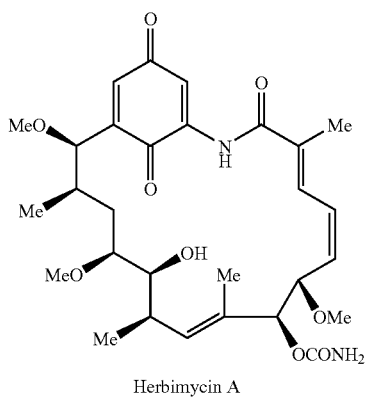

Herbimycin A

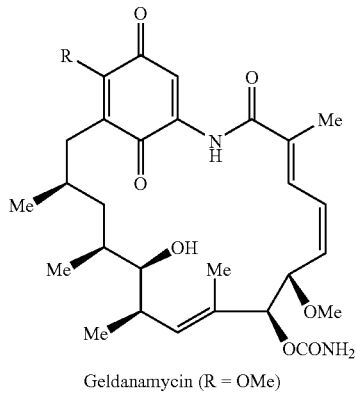

Geldanamycin (R = OMe)

These agents are natural products, initially isolated from actinomycete broths (DeBoer, 1970). However, it was not until the 1980s that their potential application as antitumour agents was discovered. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Initially, the benzoquinone ansamycins were thought to act as tyrosine kinase inhibitors. However, it has since transpired that depletion of oncogenic protein kinases via the ubiquitin proteasome pathway, rather than inhibition of their catalytic activity, is predominantly responsible for their antitumour activity. Subsequent immunoprecipitation and affinity matrix studies have shown that the major mechanism of action of geldanamycin involves binding to HSP90 (Whitesell et al., 1994; Schulte and Neckers, 1998). Moreover, X-ray crystallographic studies have shown that geldanamycin competes at the ATP binding site and inhibits the intrinsic ATPase activity of HSP90 (Prodromou et al., 1997; Panaretou et al., 1998). This in turn prevents the formation of mature multimeric HSP90 complexes capable of chaperoning client proteins. As a result, the client proteins are targeted for degradation via the ubiquitin proteasome pathway. Recent results suggest that this involves the recruitment of other regulatory proteins—such as the ubiquitin ligase, carboxy terminus of HSC70 interacting protein (CHIP)—to the HSP90 complex (Connell et al., 2001). The particular functions of these HSP90 client proteins and how they may be affected by HSP90 inhibition is discussed in two earlier reviews on HSP90 inhibitors (Neckers et al., 1999; Ochel et al., 2001).

Geldanamycin showed activity in human tumour xenograft models but progression of this compound to clinical trial was halted due to unacceptable levels of hepatotoxicity which was seen at doses required for therapeutic activity (Supko et al, 1995). However, following screening of a range of geldanamycin analogues at the US National Cancer Institute (NCI) it was discovered that 17-allylamino, 17-demethoxygeldanamycin (17AAG) retains the property of HSP90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17AAG is currently being evaluated in Phase I clinical trials using a number of different scheduling regimens under the auspices of the NCI and the UK Cancer Research Campaign (CRC).

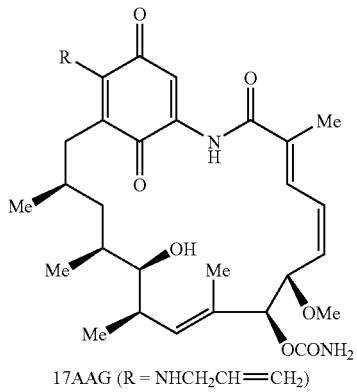

17AAG (R = NHCH$_2$CH=CH$_2$)

A range of geldanamycin analogues has already been described (Schnur et al, 1995a and b), of which 17AAG appeared to be the most promising in terms of therapeutic index. The clinical development of 17AAG and the search for additional analogues that may have improved pharmaceutical properties (e.g., solubility, oral bioavailability) and different pharmacological behaviour (Sybert and Spiegel, 2001) continues. Structure-activity relationships (SAR) with 17AAG analogues have shed more light on the chemical features required for HSP90 inhibitory activity and also for the NQO1 potentiation effect (Schnur et al, 1995a and b, Maloney et al, 1999).

Radicicol is a macrocyclic antibiotic isolated from *Monosporium bonorden*. It was shown to reverse the malignant phenotype of v-Src and v-Ha-Ras transformed fibroblasts (Kwon et al, 1992; Zhao et al, 1995).

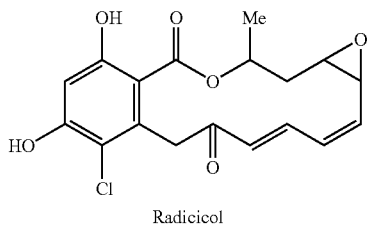

Radicicol

Like the benzoquinone ansamycins, radicicol was at first thought to act as a tyrosine kinase inhibitor. However, it was shown subsequently to degrade a number of signalling proteins as a consequence of HSP90 inhibition (Schulte et al., 1998). X-ray crystallographic data confirmed that radicicol also binds to the N terminal domain of HSP90 and inhibits the intrinsic ATPase activity (Roe et al., 1998). Interestingly, radicicol is more potent at inhibiting HSP90 ATPase activity compared to geldanamycin and 17AAG (Panaretou et al., 1998), even though they have similar growth inhibitory effects on tumour cells. This may be a consequence of differences in the cellular uptake or metabolism of these compounds. Radicicol binds to all HSP90 family members, although it has a weaker binding affinity to both GRP94 and TRAP1 than the cytosolic HSP90 isoforms (Schulte et al., 1999).

However, like 17AAG, the structure of radicicol has a number of adverse pharmacological properties that could lead to unfavourable metabolism. These include an epoxide residue, keto group, two phenolic hydroxyl groups and Michael acceptor. Radicicol lacks antitumour activity in vivo due to the unstable chemical nature of the compound. Oxime derivatives of radicicol (KF25706 and KF58333) have been synthesised which retain the HSP90 inhibitory activity of radicicol, and KF25706 has been shown to exhibit in vivo antitumour activity in human tumour xenograft models (Soga et al., 1999).

Coumarin antibiotics are known to bind to bacterial DNA gyrase at an ATP binding site homologous to that of the HSP90. The coumarin, novobiocin, was shown to bind to the carboxy terminus of HSP90, i.e., at a different site to that occupied by the benzoquinone ansamycins and radicicol which bind at the N-terminus (Marcu et al., 2000b). However, this still resulted in inhibition of HSP90 function and degradation of a number of HSP90-chaperoned signalling proteins (Marcu et al., 2000a). Geldanamcyin cannot bind HSP90 subsequent to novobiocin; this suggests that some interaction between the N and C terminal domains must exist and is consistent with the view that both sites are important for HSP90 chaperone properties.

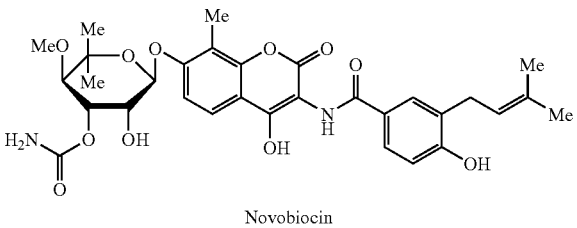

Novobiocin

A purine-based HSP90 inhibitor, PU3, has been synthesized based on rationale drug design with the aid of the X-ray crystal structure (Chiosis et al., 2001). This agent was shown to result in the degradation of signalling molecules, including ERBB2, and to cause cell cycle arrest and differentiation in breast cancer cells (Chiosis et al., 2001). Although less potent than 17AAG, it is more soluble and so may be formulated in more conventional vehicles and could potentially have more favourable oral bioavailability.

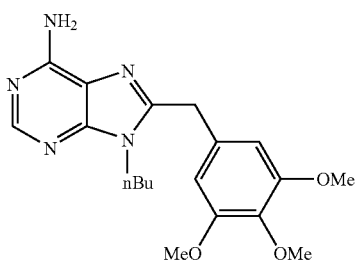

HSP90 as a Therapeutic Target

Due to its involvement in regulating a number of signalling pathways that are crucially important in driving the phenotype of a tumour, and the discovery that certain bioactive natural products exert their effects via HSP90 activity, the molecular chaperone HSP90 is currently being assessed as a new target for anticancer drug development (Neckers et al., 1999).

The predominant mechanism of action of geldanamycin, 17AAG, and radicicol involves binding to HSP90 at the ATP binding site located in the N-terminal domain of the protein, leading to inhibition of the intrinsic ATPase activity of HSP90 (see, e.g., Prodromou et al., 1997; Stebbins et al., 1997; Panaretou et al., 1998).

Inhibition of HSP90 ATPase activity prevents recruitment of co-chaperones and encourages the formation of a type of HSP90 heterocomplex from which these client proteins are targeted for degradation via the ubiquitin proteasome pathway (see, e.g., Neckers et al., 1999; Kelland et al., 1999).

Treatment with HSP90 inhibitors leads to selective degradation of important proteins involved in cell proliferation, cell cycle regulation and apoptosis, processes which are fundamentally important in cancer.

Inhibition of HSP90 function has been shown to cause selective degradation of important signalling proteins involved in cell proliferation, cell cycle regulation and apoptosis, processes which are fundamentally important and which are commonly deregulated in cancer (see, e.g., Hostein et al., 2001). An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of HSP90 inhibition are believed to be responsible for the antitumour activity of HSP90 inhibitors in cell culture and animal models (see, e.g., Schulte et al., 1998; Kelland et al., 1999).

Khilya et al., 1994, describe the synthesis of a number of 3,4-diaryl pyrazoles (see the following table), by reaction of isoflavones with benzodioxolane (n=1), benzodioxane (n=2), or benzodioxepane (n=3) upon boiling in alcohol with hydrazine hydrate. However, nowhere in the document is there provided any teaching of possible uses of these compounds.

TABLE 1

Compounds in Khilya et al., 1994

| Compound | R | $R^1$ | $R^2$ | n | $R^3$ |
|---|---|---|---|---|---|
| 2a | H | Et | H | 1 | H |
| 2b | H | Pr | H | 1 | H |
| 2c | Me | Et | H | 1 | H |
| 2d | H | H | H | 2 | H |
| 2e | H | Et | H | 2 | H |
| 2g | H | Pr | H | 2(*) | H |
| 2h | Me | H | H | 2 | H |
| 2i | Me | Et | H | 2 | H |
| 2j | Me | Pr | H | 2 | H |
| 2k | H | Et | Me | 1 | H |
| 2l | H | Pr | Me | 1 | H |
| 2m | H | H | Me | 2 | H |
| 2n | H | Et | Me | 2 | H |
| 2o | H | Pr | Me | 2 | H |
| 2p | H | Pr | Me | 3 | H |
| 3 | H | Pr | Me | 3 | Me |

(*) based on the empirical formula in Table 1 therein, and the fact that this compound would otherwise be identical to 2b.

Penning et al., 1997, describe various 3,4-diarylpyrazoles (see the following table) which apparently are potent and selective inhibitors of cyclooxygenase-2 (COX-2), some of which apparently have anti-inflammatory activity.

TABLE 2

Compounds in Penning et al., 1997

| Compound | $R^1$ | $R^2$ | $R^3$ |
|---|---|---|---|
| 4 | —H | —H | —Me |
| 5 | —$CF_3$ | —H | —Me |
| 6a | —H | —$CH_2CH_2$=$CH_2$ | —Me |
| 6b | —H | —$CH_2CH_2Ph$ | —Me |
| 7a | —$CF_3$ | —$CH_2CH_2$=$CH_2$ | —Me |
| 7b | —$CF_3$ | —$CH_2CH_2Ph$ | —Me |
| 7c | —$CF_3$ | —Et | —Me |
| 7d | —$CF_3$ | —$CH_2CO_2Et$ | —Me |
| 7e | —$CF_3$ | —$CH_2CONHPh$ | —Me |
| 10 | —$CF_3$ | —Et | —$NH_2$ |

Although HSP90 inhibitors are known, there remains a great need for potent HSP90 inhibitors which offer one or more of the following advantages:

(a) improved activity.
(b) improved selectivity (e.g., against tumour cells versus normal cells).
(c) complement the activity of other treatments (e.g., chemotherapeutic agents);
(d) reduced intensity of undesired side-effects;
(e) fewer undesired side-effects;
(f) simpler methods of administration;
(g) reduction in required dosage amounts;
(h) reduction in required frequency of administration;
(i) increased ease of synthesis, purification, handling, storage, etc.;
(j) reduced cost of synthesis, purification, handling, storage, etc.

Thus, one aim of the present invention is the provision of compounds which are potent HSP90 inhibitors, anticancer agents, etc. which offer one or more of the above properties and advantages.

The inventors have discovered that certain 3,4-diarylpyrazoles, described herein, offer one or more of the above properties and advantages, and additionally are surprisingly and unexpectedly more active than many of the corresponding known analogues.

The present invention pertains to certain 3,4-diarylpyrazoles, described herein, and the discovery of their surprising and unexpected activity as HSP90 inhibitors.

SUMMARY OF THE INVENTION

The present invention pertains generally to certain active 3,4-diarylpyrazoles, as described herein, which inhibit HSP90, and their uses.

One aspect of the present invention pertains to a method of inhibiting HSP90, in vitro or in vivo, comprising contacting a cell with an effective amount of a compound, as described herein.

Another aspect of the present invention pertains to a method of inhibiting the ATPase activity of HSP90, in vitro or in vivo, comprising contacting a cell with an effective amount of a compound as described herein.

Another aspect of the present invention pertains to methods of (a) inhibiting cell proliferation; (b) inhibiting cell cycle progression; (c) promoting apoptosis; or (d) a combination of one or more of these, in vitro or in vivo, comprising contacting a cell with an effective amount of an active compound, as described herein.

Another aspect of the present invention pertains to methods of treating a condition mediated by HSP90 in a subject comprising administering to said subject a therapeutically-effective amount of an active compound, as described herein.

Another aspect of the present invention pertains to methods of treating cancer in a subject comprising administering to said subject a therapeutically-effective amount of an active compound, as described herein.

Another aspect of the present invention pertains to an active compound, as described herein, for use in a method of treatment of the human or animal body.

Another aspect of the present invention pertains to an active compound, as described herein, for use in a method of treatment of a condition mediated by HSP90 of the human or animal body.

Another aspect of the present invention pertains to an active compound, as described herein, for use in a method of treatment of cancer of the human or animal body.

Another aspect of the present invention pertains to use of an active compound, as described herein, for the manufacture of a medicament for use in the treatment of a condition mediated by HSP90.

Another aspect of the present invention pertains to use of an active compound, as described herein, for the manufacture of a medicament for use in the treatment of cancer.

Another aspect of the present invention pertains to a kit comprising (a) an active compound, preferably provided as a pharmaceutical composition and in a suitable container and/or with suitable packaging; and (b) instructions for use, for example, written instructions on how to administer the active compound.

Another aspect of the present invention pertains to certain active compounds, as described here.

Another aspect of the present invention pertains to a composition comprising a compound as described herein and a pharmaceutically acceptable carrier.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION

Compounds

Figure 1:
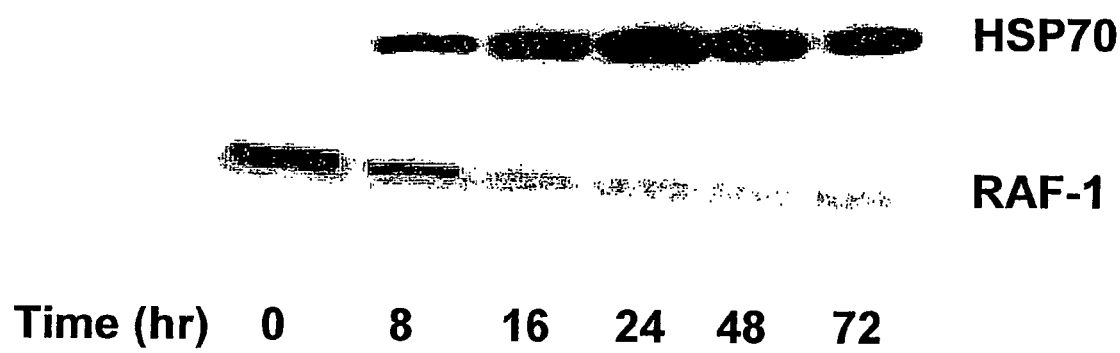
FIG. 1 is an immunoblot showing expression of HSP70 (induced) and RAF-1 (depleted) at various times following exposure of A2780 human ovarian cancer cells to 17AAG (60 nM equivalent to 5×IC50).

The compounds of the present invention may be conveniently described as 3,4-diarylpyrazoles, of the following formula:

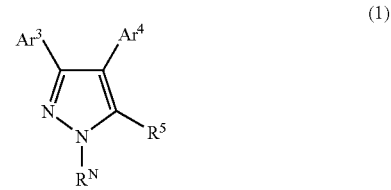

(1)

wherein:
Ar$^3$ is independently: a $C_{5-20}$aryl group, and is optionally substituted;
Ar$^4$ is independently: a $C_{5-20}$aryl group, and is optionally substituted;
R$^5$ is independently: hydrogen; halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; $C_{1-7}$alkyl; $C_{3-20}$heterocycyl; or $C_{5-20}$aryl;
R$^N$ is independently: —H; $C_{1-7}$alkyl; $C_{3-20}$heterocyclyl; or, $C_{5-20}$aryl;
and pharmaceutically acceptable salts, solvates, amides, esters, ethers, chemically protected forms, and prodrugs thereof.

As will be appreciated by the skilled artisan, the above structure is one of many possible resonance structures which may be drawn to depict the same compound. As used herein, and unless otherwise specified, a reference to one structure is to be considered a reference to all possible corresponding resonance structures.

The Aryl Substituents, Ar$^3$

The aryl substituent, Ar$^3$, is a $C_{5-20}$aryl group, and is optionally substituted.

In one embodiment, Ar$^3$ is a $C_{5-20}$heteroaryl group, and is optionally substituted. In one embodiment, Ar$^3$ is a monocyclic $C_{5-20}$heteroaryl group, and is optionally substituted. In one embodiment, Ar$^3$ is a monocyclic $C_{5-6}$heteroaryl group, and is optionally substituted.

In one embodiment, Ar$^3$ is a $C_{5-20}$carboaryl group, and is optionally substituted. In one embodiment, Ar$^3$ is a monocyclic $C_{5-20}$carboaryl group, and is optionally substituted. In one embodiment, Ar$^3$ is a monocyclic $C_{5-6}$carboaryl group, and is optionally substituted. In one embodiment, Ar$^3$ is a phenyl group, and is optionally substituted.

In one embodiment, Ar$^3$ is a $C_{5-20}$aryl group derived from one of the following: benzene, pyridine, pyrimidine, furan, indole, indazole, benztriazole, pyrrole, imidazole, thiazole, isothiazole, oxazole, isoxazole, naphthalene, quinoline, benzimidazole, benzoxazole, benzothiazole, fluorene, acridine, and carbazole.

In one embodiment, $Ar^3$ is a $C_{5-20}$aryl group derived from one of the following: benzene, pyridine, furan, indole, pyrrole, imidazole, thiazole, isothiazole, naphthalene, quinoline, benzimidazole, benzothiofuran, benzothiazole, fluorene, acridine, and carbazole.

In one preferred embodiment, $Ar^3$ is an optionally substituted phenyl group, and the compound has the following formula, wherein n is an integer from 0 to 5, and each $R^P$ is independently a phenyl substituent.

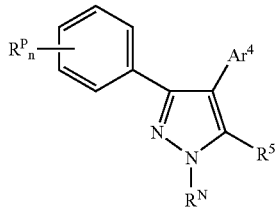

(2)

In one embodiment, n is an integer from 0 to 5.
In one embodiment, n is an integer from 1 to 5.
In one embodiment, n is an integer from 0 to 4.
In one embodiment, n is an integer from 1 to 4.
In one embodiment, n is an integer from 0 to 3.
In one embodiment, n is an integer from 1 to 3.
In one embodiment, n is an integer from 0 to 2.
In one embodiment, n is 1 or 2.
In one embodiment, n is 0 or 1.
In one embodiment, n is 5.
In one embodiment, n is 4.
In one embodiment, n is 3.
In one embodiment, n is 2.
In one embodiment, n is 1.
In one embodiment, n is 0.

In one preferred embodiment, $Ar^3$ is a substituted phenyl group, and the compound has the following formula, m is an integer from 0 to 4, and each $R^P$ is independently a phenyl substituent.

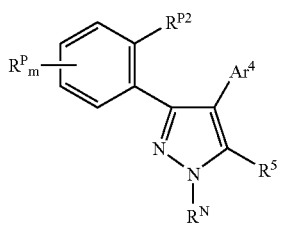

(3)

In one embodiment, m is an integer from 0 to 4.
In one embodiment, m is an integer from 1 to 4.
In one embodiment, m is an integer from 0 to 3.
In one embodiment, m is an integer from 1 to 3.
In one embodiment, m is an integer from 0 to 2.
In one embodiment, m is 1 or 2.
In one embodiment, m is 0 or 2.
In one embodiment, m is 4.
In one embodiment, m is 3.
In one embodiment, m is 2.
In one embodiment, m is 2.
In one embodiment, m is 0.

In one embodiment, the compound has the following formula:

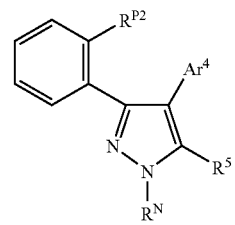

(4)

In one preferred embodiment, $Ar^3$ is a substituted phenyl group, and the compound has the following formula, p is an integer from 0 to 3, and each $R^P$ is independently a phenyl substituent.

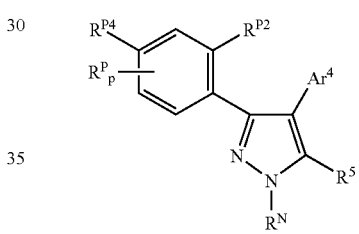

(5)

In one embodiment, p is an integer from 0 to 3.
In one embodiment, p is an integer from 1 to 3.
In one embodiment, p is an integer from 0 to 2.
In one embodiment, p is 1 or 2.
In one embodiment, p is 0 or 1.
In one embodiment, p is 3.
In one embodiment, p is 2.
In one embodiment, p is 1.
In one embodiment, p is 0.

In one embodiment, the compound has the following formula:

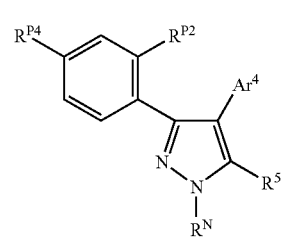

(6)

In one preferred embodiment, $Ar^3$ is a substituted phenyl group, and the compound has the following formula, m is an integer from 0 to 4 (as defined above), and each $R^P$ is independently a phenyl substituent.

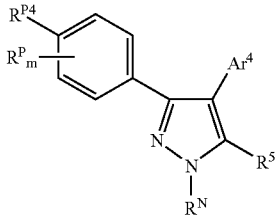
(7)

In one embodiment, the compound has the following formula:

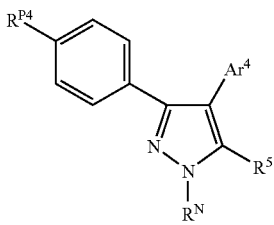
(8)

In one preferred embodiment, $Ar^3$ is a substituted phenyl group, and the compound has the following formula, q is an integer from 0 to 2, and each $R^P$ is independently a phenyl substituent.

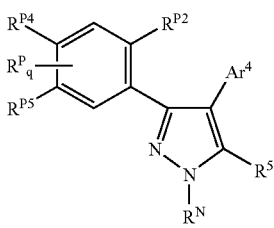
(9)

In one embodiment, q is an integer from 0 to 2.
In one embodiment, q is 1 or 2.
In one embodiment, q is 0 or 1.
In one embodiment, q is 2.
In one embodiment, q is 1.
In one embodiment, q is 0.
In one embodiment, the compound has the following formula:

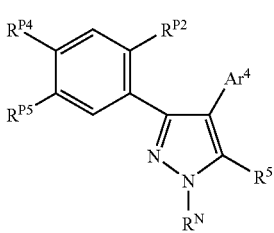
(10)

In one preferred embodiment, $Ar^3$ is a substituted phenyl group, and the compound has the following formula, p is an integer from 0 to 3 (as defined above), and each $R^P$ is independently a phenyl substituent.

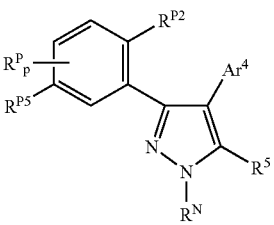
(11)

In one embodiment, the compound has the following formula:

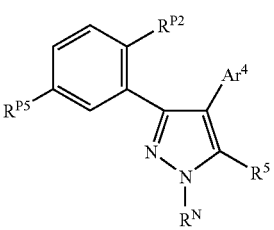
(12)

In one preferred embodiment, $Ar^3$ is a substituted phenyl group, and the compound has the following formula, p is an integer from 0 to 3 (as defined above), and each $R^P$ is independently a phenyl substituent.

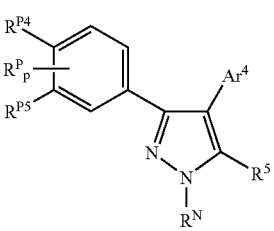
(13)

In one embodiment, the compound has the following formula:

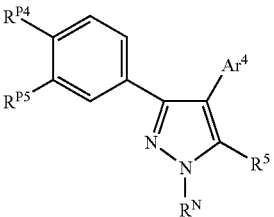
(14)

In one preferred embodiment, $Ar^3$ is a substituted phenyl group, and the compound has the following formula, m is an integer from 0 to 4 (as defined above), and each $R^P$ is independently a phenyl substituent.

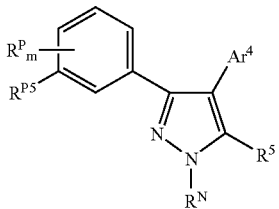

(15)

In one embodiment, the compound has the following formula:

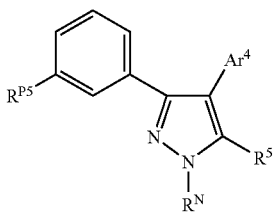

(16)

Phenyl Substituents, $R^P$

Each phenyl substituent, $R^P$ is as defined below.

In certain embodiments, discussed in the following sections, certain phenyl substituents (e.g., $R^{P2}$, $R^{P4}$, $R^{P5}$) are more narrowly defined.

Examples of phenyl substituents, $R^P$, include, but are not limited to, those described under the heading "Substituents" below.

Note that, for $Ar^3$, preferably $R^{P4}$ and $R^{P5}$ together with the ring atoms to which they are attached, do not form a cyclic structure, for example a ring which is fused to the parent phenyl ring.

In one embodiment, each $R^P$ is independently:
halo;
hydroxy;
ether (e.g., $C_{1-7}$alkoxy (including, e.g., unsubstituted $C_{1-7}$alkoxy and substituted $C_{1-7}$alkoxy, such as $C_{1-7}$haloalkoxy, $C_{1-7}$hydroxyalkoxy, $C_{1-7}$carboxyalkoxy, $C_{1-7}$acyloxyalkoxy, $C_{1-7}$oxycarbonylalkoxy, $C_{1-7}$oxycarbonyloxyalkoxy, $C_{1-7}$aminoalkoxy, $C_{1-7}$amidoalkoxy, $C_{1-7}$acylamidoalkoxy, $C_{1-7}$hydrazinocarbonylalkoxy, $C_{1-7}$aminocarbonyloxyalkoxy, $C_{1-7}$cyanoalkoxy, $C_{5-20}$aryl-$C_{1-7}$alkoxy, etc.));
formyl;
acyl (e.g., $C_{1-7}$alkylacyl, $C_{5-20}$arylacyl);
carboxy;
ester;
acyloxy;
oxycarbonyloxy;
amido;
acylamido;
aminocarbonyloxy;
tetrazolyl;
amino (including, e.g., $C_{1-7}$aminoalkylamino);
nitro;
cyano;
azido;
sulfhydryl;
thioether (e.g., $C_{1-7}$alkylthio);
sulfonamido; or $C_{1-7}$alkyl (including, e.g., unsubstituted $C_{1-7}$alkyl and substituted $C_{1-7}$alkyl, such as $C_{1-7}$haloalkyl, $C_{1-7}$hydroxyalkyl, $C_{1-7}$carboxyalkyl, $C_{1-7}$acyloxyalkyl, $C_{1-7}$oxycarbonylalkyl, $C_{1-7}$oxycarbonyloxyalkyl, $C_{1-7}$aminoalkyl, $C_{1-7}$amidoalkyl, $C_{1-7}$acylamidoalkyl, $C_{1-7}$aminocarbonyloxyalkyl, $C_{1-7}$cyanoalkyl, $C_{5-20}$aryl-$C_{1-7}$alkyl, etc.);
$C_{3-20}$heterocyclyl; and,
$C_{5-20}$aryl.

In one embodiment, the substituted $C_{1-7}$alkyl group is a group, Q, of the formula —$(CH_2)_w$J.

In one embodiment, w is an integer from 1 to 7.
In one embodiment, w is an integer from 1 to 6.
In one embodiment, w is an integer from 1 to 5.
In one embodiment, w is an integer from 1 to 4.
In one embodiment, w is an integer from 1 to 3.
In one embodiment, w is 1 or 2.
In one embodiment, w is an integer from 2 to 7.
In one embodiment, w is an integer from 2 to 6.
In one embodiment, w is an integer from 2 to 5.
In one embodiment, w is an integer from 2 to 4.
In one embodiment, w is an integer from 2 or 3.
In one embodiment, w is 7.
In one embodiment, w is 6.
In one embodiment, w is 5.
In one embodiment, w is 4.
In one embodiment, w is 3.
In one embodiment, w is 2.
In one embodiment, w is 1.

In one embodiment, J is independently: halo, hydroxy, carboxy, acyloxy, oxycarbonyl, oxycarbonyloxy, amino, amido, acylamido, aminocarbonyloxy; cyano, sulfonamido, or $C_{5-20}$aryl.

In one embodiment, J is independently: hydroxy, amino, amido, acylamido, aminocarbonyloxy, or sulfonamido.

In one embodiment, J is independently: amino, amido, acylamido, aminocarbonyloxy, or sulfonamido.

In one embodiment, each $R^P$ is independently:
—F, —Cl, —Br, —I;
—OH;
—OMe, —OEt, —O(nPr), —O(iPr), —O(nBu), —O(tBu), —OCH$_2$Ph;
—OCF$_3$, —OCHF$_2$, —OCH$_2$F, —OCCl$_3$, —OCBr$_3$, —OCH$_2$CH$_2$F, —OCH$_2$CHF$_2$, —OCH$_2$CF$_3$;
—C(=O)H;
—C(=O)Me, —C(=O)Et, —C(=O)(nPr), —C(=O)(iPr), —C(=O)(nBu), —C(=O)(tBu), —C(=O)Ph;
—C(=O)OH;
—C(=O)OMe, —C(=O)OEt, —C(=O)O(nPr), —C(=O)O(iPr), —C(=O)O(nBu), —C(=O)O(tBu);
—OC(=O)Me, —OC(=O)Et, —OC(=O)(nPr), —OC(=O)(iPr), —OC(=O)(nBu), —OC(=O)(tBu);
—OC(=O)OMe, —OC(=O)OEt, —OC(=O)O(nPr), —OC(=O)O(iPr), —OC(=O)O(nBu), —OC(=O)O(tBu);
—C(=O)NH$_2$, —C(=O)NHMe, —C(=O)NHEt, —C(=O)NH(nPr), —C(=O)NH(iPr), —C(=O)NH(nBu), —C(=O)NH(tBu), —C(=O)NMe$_2$, —C(=O)NEt$_2$, —C(=O)N(nPr)$_2$, —C(=O)N(iPr)$_2$, —C(=O)N(nBu)$_2$, —C(=O)N(tBu)$_2$;
—NHC(=O)Me, —NHC(=O)Et, —NHC(=O)(nPr), —NHC(=O)(iPr), —NHC(=O)(nBu), —NHC(=O)(tBu), —NHC(=O)Ph, succinimidyl, maleimidyl; tetrazolyl;
—NH$_2$, —NHMe, —NHEt, —NH(nPr), —NH(iPr), —NH(nBu), —NH(tBu), —NMe$_2$, —NEt$_2$, —N(nPr)$_2$, —N(iPr)$_2$, —N(nBu)$_2$, —N(tBu)$_2$;

—NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), —NH(CH$_2$)$_6$NH(Et);

—NO$_2$;

—CN;

—N$_3$;

—SH;

—SMe, —SEt, —S(nPr), —S(iPr), —S(nBu), —S(tBu), —SCH$_2$Ph;

—S(=O)$_2$NH$_2$, —S(=O)$_2$NHMe, —S(=O)$_2$NMe$_2$, —S(=O)$_2$NHEt, —S(=O)$_2$NEt$_2$, —S(=O)$_2$NH(nPr), —S(=O)$_2$N (nPr)$_2$, —S(=O)$_2$NH(iPr), —S(=O)$_2$N (iPr)$_2$, —S(=O)$_2$NH(nBu), —S(=O)$_2$N(nBu)$_2$, —S(=O)$_2$NH(tBu), —S(=O)$_2$N(tBu)$_2$, —S(=O)$_2$NHPh;

-Me, -Et, -nPr, -iPr, -nBu, -tBu;

—CF$_3$, —CHF$_2$, —CH$_2$F, —CCl$_3$, —CBr$_3$, —CH$_2$CH$_2$F, —CH$_2$CHF$_2$, —CH$_2$CF$_3$;

—(CH$_2$)$_w$J (as defined above) including, e.g.,

—CH$_2$OH, —CH$_2$CH$_2$OH, —CH(OH)CH$_2$OH;

—CH$_2$COOH, —CH$_2$CH$_2$COOH, —CH$_2$CH$_2$CH$_2$COOH; —CH$_2$C(=O)Me, —CH$_2$CH$_2$C(=O)Me, —CH=CHOC(=O)Me;

—CH$_2$C(=O)OMe, —CH$_2$CH$_2$C(=O)OMe, —CH=CHC(=O)OMe;

—CH$_2$C(=O)OMe, —CH$_2$CH$_2$C(=O)OMe, —CH=CHOC(=O)OMe;

—CH$_2$NH$_2$, —CH$_2$CH$_2$NH$_2$, —CH=CHNH$_2$, —CH$_2$CH$_2$NMe$_2$;

—CH$_2$NHC(=O)Me, —CH$_2$CH$_2$NHC(=O)Me, —CH=CHNHC(=O)Me;

—CH$_2$C(=O)NH$_2$, —CH$_2$CH$_2$C(=O)NH$_2$, —CH=CHC(=O)NH$_2$;

—CH$_2$C(=O)NH$_2$, —CH$_2$CH$_2$C(=O)NH$_2$, —CH=CHOC(=O)NH$_2$;

—CH$_2$CN, —CH$_2$CH$_2$CN, —CH=CHCN.

In one embodiment, each $R^P$ is independently:

—F, —Cl, —Br, —I, -Me, -Et, -iPr, -tBu, —CN, —CF$_3$, —OH, —OMe, —OEt, —O(iPr), —OCF$_3$, —OPh, —SMe, —SCF$_3$, —NH$_2$, —NMe$_2$, —NEt$_2$, —CONH$_2$, —NHC(=O)Me, —C(=O)Me, —NO$_2$, —SO$_2$NH$_2$, -Ph, or —(CH$_2$)$_w$J (as defined above).

In one embodiment, at least one $R^P$, $R^{P2}$, $R^{P4}$, $R^{P5}$ is —(CH$_2$)$_w$J (as defined above).

In one embodiment, at least $R^{P4}$ is —(CH$_2$)$_w$J (as defined above).

In one embodiment, at least $R^{P5}$ is —(CH$_2$)$_w$J (as defined above).

In one embodiment, only one of the groups $R^P$, $R^{P2}$, $R^{P4}$, $R^{P5}$ is —(CH$_2$)$_w$J (as defined above).

Phenyl Substituent, $R^{P2}$

In one embodiment, $R^{P2}$ is independently as defined above for $R^P$.

In one embodiment, $R^{P2}$ is independently: hydrogen; halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; C$_{1-7}$alkyl; C$_{3-20}$heterocyclyl; or C$_{5-20}$aryl.

In one embodiment, $R^{P2}$ is independently:
hydroxy;
halo; or,
C$_{1-4}$alkyl (including, e.g., substituted C$_{1-4}$alkyl).

In one embodiment, $R^{P2}$ is independently:
—OH, —F, —Cl, —Br, —I, -Me, -Et, -nPr, -iPr, -nBu, -iBu, -sBu, -tBu, or —CF$_3$.

In one embodiment, $R^{P2}$ is independently:
hydroxy;
halo; or,
C$_{1-2}$alkyl (including, e.g., substituted C$_{1-2}$alkyl).

In one embodiment, $R^{P2}$ is independently:
—OH, —F, —Cl, —Br, —I, -Me, -Et, or —CF$_3$.

In one embodiment, $R^{P2}$ is —OH, as in, for example, compounds of the following formulae.

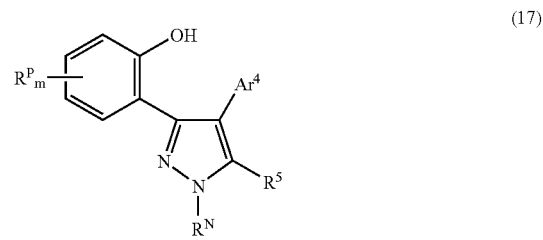

(17)

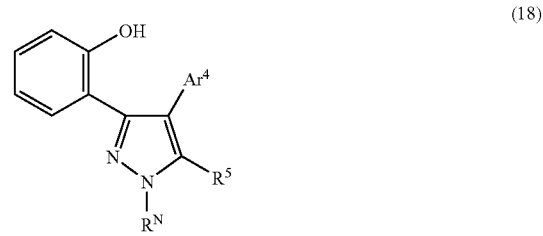

(18)

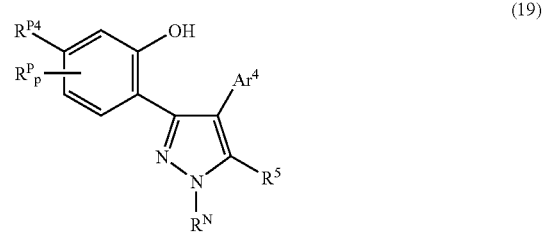

(19)

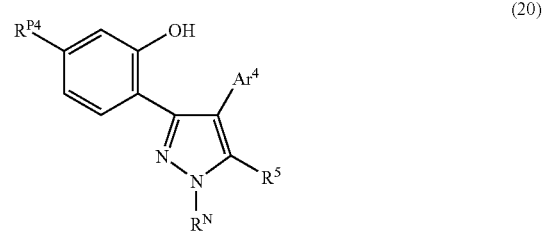

(20)

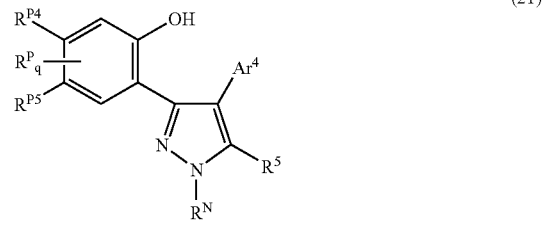

(21)

(22) 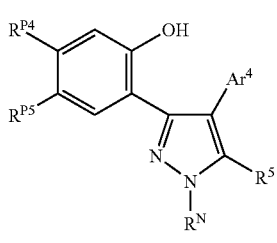

(23) 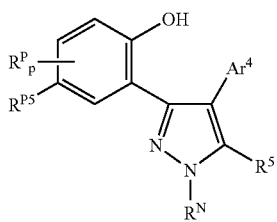

(24) 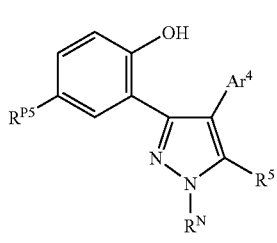

Phenyl Substituent, $R^{P4}$

In one embodiment, $R^{P4}$ is independently as defined above for $R^P$.

In one embodiment, $R^{P4}$ is independently: hydrogen; halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; $C_{1-7}$alkyl; $C_{3-20}$heterocycyl; or $C_{5-20}$aryl.

In one embodiment, $R^{P4}$ is independently:
hydroxy;
halo; or,
$C_{1-4}$alkyl (including, e.g., substituted $C_{1-4}$alkyl).

In one embodiment, $R^{P4}$ is independently:
—OH, —F, —Cl, —Br, —I, -Me, -Et, -nPr, -iPr, -nBu, -iBu, -sBu, -tBu, —CF$_3$, or —(CH$_2$)$_w$J (as defined above).

In one embodiment, $R^{P4}$ is independently:
hydroxy;
halo; or,
$C_{1-2}$alkyl (including, e.g., substituted $C_{1-2}$alkyl).

In one embodiment, $R^{P4}$ is independently:
—OH, —F, —Cl, —Br, —I, -Me, -Et, —CF$_3$, or —(CH$_2$)$_w$J (as defined above).

In one embodiment, $R^{P4}$ is independently —OH, as in, for example, compounds of the following formulae:

(25) 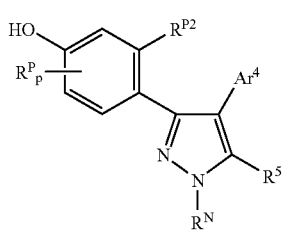

(26) 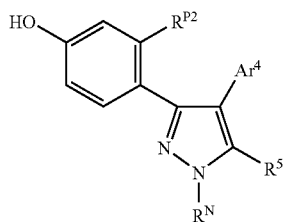

(27)

(28)

(29) 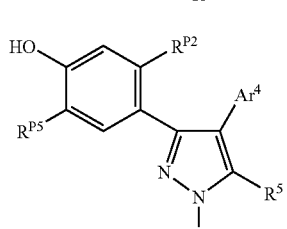

(30) 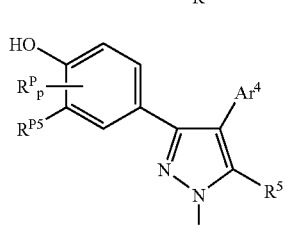

(31) 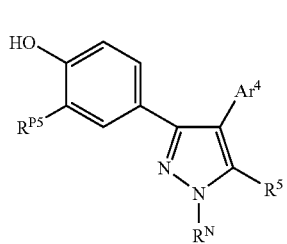

(32)

-continued (33)

(34)

(35)

(36)

Phenyl Substituent, $R^{P5}$

In one embodiment, $R^{P5}$ is independently as defined above for $R^P$.

In one embodiment, $R^{P5}$ is independently: halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; $C_{1-7}$alkyl; $C_{3-20}$heterocycyl; or $C_{5-20}$aryl.

In one embodiment, $R^{P5}$ is independently:
hydroxy;
halo;
$C_{1-4}$alkyl (including, e.g., substituted $C_{1-4}$alkyl); or,
$C_{5-20}$aryl.

In one embodiment, $R^{P5}$ is independently:
—OH, —F, —Cl, —Br, —I, -Me, -Et, -nPr, -iPr, -nBu, -iBu, -sBu, -tBu, —CF$_3$, —(CH$_2$)$_w$J (as defined above), or -Ph.

In one embodiment, $R^{P5}$ is independently:
halo;
$C_{1-4}$alkyl (including, e.g., substituted $C_{1-4}$alkyl); or,
$C_{5-20}$aryl.

In one embodiment, $R^{P5}$ is independently:
—F, —Cl, —Br, —I, -Me, -Et, -nPr, -iPr, -nBu, -iBu, -sBu, -tBu, —CF$_3$, —(CH$_2$)$_w$J (as defined above), or -Ph.

In one embodiment, $R^{P5}$ is independently:
hydroxy;
halo; or,
$C_{1-4}$alkyl (including, e.g., substituted $C_{1-4}$alkyl).

In one embodiment, $R^{P5}$ is independently:
—OH, —F, —Cl, —Br, —I, -Me, -Et, -nPr, -iPr, -nBu, -iBu, -sBu, -tBu, —CF$_3$, or —(CH$_2$)$_w$J (as defined above).

In one embodiment, $R^{P5}$ is independently:
halo; or,
$C_{1-4}$alkyl (including, e.g., substituted $C_{1-4}$alkyl).

In one embodiment, $R^{P5}$ is independently:
—F, —Cl, —Br, —I, -Me, -Et, -nPr, -iPr, -nBu, -iBu, -sBu, -tBu, —CF$_3$, or —(CH$_2$)$_w$J (as defined above).

In one embodiment, $R^{P5}$ is independently: —(CH$_2$)$_w$J (as defined above).

In one embodiment, $R^{P5}$ is independently: -Me or -iPr.

The Aryl Substituents, $Ar^4$

The aryl substituent, $Ar^4$, is independently a $C_{5-20}$aryl group, and is optionally substituted.

In one embodiment, $Ar^4$ is independently a $C_{5-20}$heteroaryl group, and is optionally substituted. In one embodiment, $Ar^4$ is independently a monocyclic $C_{5-20}$heteroaryl group, and is optionally substituted. In one embodiment, $Ar^4$ is independently a monocyclic C heteroaryl group, and is optionally substituted.

In one embodiment, $Ar^4$ is independently a $C_{5-20}$carboaryl group, and is optionally substituted. In one embodiment, $Ar^4$ is independently a monocyclic $C_{5-20}$carboaryl group, and is optionally substituted. In one embodiment, $Ar^4$ is independently a monocyclic $C_{5-6}$carboaryl group, and is optionally substituted.

In one embodiment, $Ar^4$ is independently a $C_{5-20}$aryl group derived from one of the following, and is optionally substituted: benzene, pyridine, furan, indole, pyrrole, imidazole, thiazole, isothiazole, naphthalene, quinoline, benzimidazole, benzothiofuran, benzothiazole, benzodioxolane, benzodioxane, benzodioxetane, fluorene, acridine, and carbazole.

In one embodiment, $Ar^4$ is independently a $C_{5-20}$aryl group derived from one of the following, and is optionally substituted: benzene, thiazole, benzothiazole, benzodioxolane, benzodioxane, and benzodioxetane.

In one embodiment, $Ar^4$ is independently: phenyl, thiazol-5-yl, benzothiazol-2-yl, benzodioxolan-5-yl, benzodioxan-6-yl, or benzodioxetan-7-yl; and is optionally substituted.

phenyl     thiazol-5-yl     benzothiazol-2-yl benzodioxolan-5-yl     benzodioxan-6-yl benzodioxetan-7-yl In one embodiment, $Ar^4$ is independently a $C_{5-20}$aryl group derived from one of the following, and is optionally substituted: benzene, thiazole, and benzothiazole.

In one embodiment, $Ar^4$ is independently: phenyl, thiazol-5-yl, or benzothiazol-2-yl; and is optionally substituted.

In one embodiment, $Ar^4$ is independently phenyl, and is optionally substituted.

In one embodiment, $Ar^4$ is independently a $C_{5-20}$aryl group derived from one of the following, and is optionally substituted: benzodioxolane, benzodioxane, and benzodioxetane.

In one embodiment, $Ar^4$ is independently: benzodioxolan-5-yl, benzodioxan-6-yl, or benzodioxetan-7-yl; and is optionally substituted.

In one embodiment, $Ar^4$ is independently phenyl, and is optionally substituted, but is not substituted so as to form a polycyclic group (that is, groups such as benzodioxolan-5-yl, benzodioxan-6-yl, or benzodioxetan-7-yl are excluded).

In one embodiment, $Ar^4$ is independently phenyl, and is optionally substituted, but is not substituted so as to form a polycyclic group; and, $R^{P4}$ is not $C_{1-7}$alkoxy.

In one embodiment, $Ar^4$ is independently phenyl, and is optionally substituted, but is not substituted so as to form a polycyclic group; and, $R^{P4}$ is not —OMe.

In one embodiment, $Ar^4$ is independently unsubstituted phenyl.

As mentioned above, the aryl substituent, $Ar^4$, is optionally substituted. Examples of substituents include, but are not limited to, those described under the heading "Substituents" below. Additional examples include those descibed above for $R^P$.

The Ring Substituent, $R^5$

The ring substituent, $R^5$, is independently —H, or a substituent as defined above for $R^P$.

In one embodiment, $R^5$ is independently:
—H;
hydroxy;
halo; or,
$C_{1-4}$alkyl (including, e.g., substituted $C_{1-4}$alkyl).

In one embodiment, $R^5$ is independently:
—H, —OH, —F, —Cl, —Br, —I, -Me, -Et, -nPr, -iPr, -nBu, -iBu, -sBu, -tBu, —$CF_3$, or —$(CH_2)_w$J (as defined above).

In one embodiment, $R^5$ is independently:
—H;
halo; or,
$C_{1-4}$alkyl (including, e.g., substituted $C_{1-4}$alkyl).

In one embodiment, $R^5$ is independently:
—H, —F, —Cl, —Br, —I, -Me, -Et, -nPr, -iPr, -nBu, -iBu, -sBu, -tBu, —$CF_3$, or —$(CH_2)_w$J (as defined above).

In one embodiment, $R^5$ is independently:
—H;
hydroxy; or,
$C_{1-4}$alkyl (including, e.g., substituted $C_{1-4}$alkyl).

In one embodiment, $R^5$ is independently:
—H, —OH, -Me, -Et, -nPr, -iPr, -nBu, -iBu, -sBu, -tBu, —$CF_3$, or —$(CH_2)_w$J (as defined above).

In one embodiment, $R^5$ is independently:
—H; or,
$C_{1-4}$alkyl (including, e.g., substituted $C_{1-4}$alkyl).

In one embodiment, $R^5$ is independently:
—H, -Me, -Et, -nPr, -iPr, -nBu, -iBu, -sBu, -tBu, —$CF_3$, or —$(CH_2)_w$J (as defined above).

In one embodiment, $R^5$ is independently as defined above, except that it may not be —H.

In one embodiment, $R^5$ is independently amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)$N(CH_3)_2$, —C(=O)$NHCH_2CH_3$, —C(=O)$N(CH_2CH_3)_2$, —C(=O)NHCH$(CH_3)_2$ and —C(=O)$NHCH_2Ph$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

In one embodiment, $R^5$ is independently —H.

The Nitrogen Substituent, $R^N$

The nitrogen substituent, $R^N$, is independently:
—H;
$C_{1-7}$alkyl (including, e.g., substituted $C_{1-7}$alkyl);
$C_{3-20}$heterocyclyl; or,
$C_{5-20}$aryl.

In one embodiment, $R^N$ is independently:
—H;
$C_{1-4}$alkyl (including, e.g., substituted $C_{1-4}$alkyl);
$C_{5-6}$aryl.

In one embodiment, $R^N$ is independently: —H, -Me, -Et, -nPr, -iPr, -nBu, -iBu, -sBu, -tBu, —$CF_3$, —$(CH_2)_w$J (as defined above), or -Ph.

In one embodiment, $R^N$ is independently —H or $C_{1-4}$alkyl (including, e.g., substituted $C_{1-4}$alkyl).

In one embodiment, $R^N$ is independently: —H, -Me, -Et, -nPr, -iPr, -nBu, -iBu, -sBu, -tBu, —$CF_3$, or —$(CH_2)_w$J (as defined above).

In one embodiment, $R^N$ is independently: —H, -Me, -Et, -nPr, -iPr, -nBu, or -tBu.

In one embodiment, $R^N$ is independently: —H, -Me, -Et.

In one embodiment, $R^N$ is independently —H or -Me.

In one embodiment, $R^N$ is independently as defined above, except that it may not be —H.

In one embodiment, $R^N$ is independently —H.

In one embodiment, the compound is of a formula selected from formulae (17) to (24) above. In a preferred aspect of this embodiment, $R^N$ is independently —H. In a further preferred aspect of this embodiment, $R^{P4}$ is independently: hydroxy or $C_{1-7}$ alkoxy, more preferably hydroxy. In a further preferred aspect of this embodiment, $R^{P5}$ is as defined in any one of the embodiments in the section entitled "Phenyl Substituent $R^{P5}$" above; preferably, $R^{P5}$ is independently: , —Cl, —Br, -Me, -Et, -nPr, -iPr, -nBu, -iBu, -sBu, -tBu, —$CF_3$, —$(CH_2)_w$Ph, or -Ph, wherein w is an integer from 1 to 7. In a further preferred aspect of this embodiment, $R^5$ is as defined in any one of the embodiments in the section entitled "The Ring Substituent, $R^5$" above; preferably, $R^5$ is independently: —H, carboxy, -Me, -Et, -nPr, -iPr, -nBu, -iBu, -sBu, -tBu, —$CF_3$, or —$(CH_2)_w$J, wherein w is an integer from 1 to 7, and J is independently: halo, hydroxy, carboxy, acyloxy, oxycarbonyl, oxycarbonyloxy, amino, amido, acylamido, aminocarbonyloxy, cyano, sulfonamido, or $C_{5-20}$aryl. In a further preferred aspect of this embodiment, $R^5$ is independently amido (carbamoyl, carbamyl, aminocarbonyl, carboxamide): —C(=O)$NR^1R^2$, wherein $R^1$ and $R^2$ are independently amino substituents, as defined for amino groups. In a further preferred aspect of this embodiment, $Ar^4$ is as defined in any one of the embodiments in the section entitled "The Aryl Substituents, $Ar^4$" above; preferably, $Ar^4$ is independently a $C_{5-20}$aryl group derived from one of the following, and is optionally substituted: benzene, pyridine, imidazole, thiazole, methyl-thiazole, pyrazole, furan, benzimidazole, N-methyl-benzimidazole, benzothiazole, benzodioxolane, benzodioxane, and benzodioxetane; more preferably, $Ar^4$ is independently a 4-$C_{1-7}$alkoxy-phenyl group, more preferably a 4-methoxy-phenyl group.

In a further aspect of this embodiment, the invention provides a method of inhibiting the ATPase activity of HSP90, in vitro or in vivo, comprising contacting a cell with an effective amount of compound as described in this embodiment. In a further aspect of this embodiment, the invention provides a method of treating a condition mediated by HSP90 in a subject comprising administering to said subject a therapeutically-effective amount of a compound as described in this embodiment. In a further aspect of this embodiment, the invention provides a compound as described in this embodiment for the manufacture of a medicament for use in the treatment of a condition mediated by HSP90. In a further aspect of this embodiment, the invention provides a method of treating a non-estrogen dependent cancer in a subject comprising administering to said subject a therapeutically-effective amount of a compound as described in this embodiment. In a further aspect of this embodiment, the invention provides use of a compound as described in this embodiment for the manufacture of a medicament for use in the treatment of a non-estrogen dependent cancer. In a further aspect of this embodiment, the invention provides a method of treating cancer in a subject comprising administering to said subject a therapeutically-effective amount of a compound as described in this embodiment. In a further aspect of this embodiment, the invention provides use of a compound as described in this embodiment for the manufacture of a medicament for use in the treatment of cancer. In a further aspect of this embodiment, the invention provides a compound as described in this embodiment for use in a method of treatment of the human or animal body. In a further aspect of this embodiment, the invention provides a compound as described in this embodiment for use in a method of treatment of a condition mediated by HSP90 of the human or animal body. In a further aspect of this embodiment, the invention provides a compound as described in this embodiment for use in a method of treatment of cancer of the human or animal body. In a further aspect of this embodiment, the invention provides a composition comprising a compound according to this embodiment and a pharmaceutically acceptable carrier or diluent. In a further aspect of this embodiment, the invention provides a compound as described in this embodiment, provided that $Ar^4$ is not benzodioxolane, benzodioxane or benzodioxepane.

In a further aspect of the present invention, the invention provides a method of treating a condition mediated by HSP90 in a subject comprising administering to said subject a therapeutically-effective amount of a compound as described in any embodiment of the present invention.

In a further aspect of the present invention, the invention provides use of a compound as described in embodiment of the present invention for the manufacture of a medicament for use in the treatment of a condition mediated by HSP90.

In a further aspect of the present invention, the invention provides method of treating a non-estrogen dependent cancer in a subject comprising administering to said subject a therapeutically-effective amount of a compound as described in any embodiment of the present invention, provided that
  a. $Ar^3$ is not a substituted or unsubstituted pyrrol-3-yl, pyrazol-3-yl, [1,2,4]triazol-3-yl, [1,2,3]triazol-4-yl or tetrazol-5-yl group;
  b. $Ar^4$ is not pyridyl or quinolyl;
  c. when $Ar^3$ is 3,4,5-trimethoxyphenyl, then $Ar^4$ is not 3-amino-4-methoxyphenyl;
  d. $Ar^4$ is not a substituted or unsubstituted 3-hydroxy-pyrazol-4-yl group.

In a further aspect of the present invention, the invention provides use of a compound as described in any embodiment of the present invention for the manufacture of a medicament for use in the treatment of a non-estrogen dependent cancer, provided that
  a. $Ar^3$ is not a substituted or unsubstituted pyrrol-3-yl, pyrazol-3-yl, [1,2,4]triazol-3-yl, [1,2,3]triazol-4-yl or tetrazol-5-yl group;
  b. $Ar^4$ is not pyridyl or quinolyl;
  c. when $Ar^3$ is 3,4,5-trimethoxyphenyl, then $Ar^4$ is not 3-amino-4-methoxyphenyl;
  d. $Ar^4$ is not a substituted or unsubstituted 3-hydroxy-pyrazol-4-yl group.

In a further aspect of the present invention, the invention provides a method of treating cancer in a subject comprising administering to said subject a therapeutically-effective amount of a compound as described in any embodiment of the present invention provided that
  a. $Ar^3$ is not a substituted or unsubstituted pyrrol-3-yl, pyrazol-3-yl, [1,2,4]triazol-3-yl, [1,2,3]triazol-4-yl or tetrazol-5-yl group;
  b. no more than one of $Ar^3$, $Ar^4$, $R^5$ and $R^N$ are phenyl, 4-hydroxyphenyl or 4-alkoxyphenyl groups; preferably no more than one of $Ar^3$, $Ar^4$, $R^5$ and $R^N$ are phenyl, 4-hydroxyphenyl or 4-(substituted or unsubstituted alkoxy-, alkenoxy- or alkynyloxy-)phenyl groups;
  c. $Ar^4$ is not pyridyl or quinolyl;
  d. when $Ar^3$ is 3,4,5-trimethoxyphenyl, then $Ar^4$ is not 3-amino-4-methoxyphenyl;
  e. $Ar^4$ is not a substituted or unsubstituted 3-hydroxy-pyrazol-4-yl group.

In a further aspect of the present invention, the invention provides use of a compound as described in any embodiment of the present invention for the manufacture of a medicament for use in the treatment of cancer provided that
  a. $Ar^3$ is not a substituted or unsubstituted pyrrol-3-yl, pyrazol-3-yl, [1,2,4]triazol-3-yl, [1,2,3]triazol-4-yl or tetrazol-5-yl group;
  b. no more than one of $Ar^3$, $Ar^4$, $R^5$ and $R^N$ are phenyl, 4-hydroxyphenyl or 4-alkoxyphenyl groups; preferably no more than one of $Ar^3$, $Ar^4$, $R^5$ and $R^N$ are phenyl, 4-hydroxyphenyl or 4-(substituted or unsubstituted alkoxy-, alkenoxy- or alkynyloxy-)phenyl groups;
  c. $Ar^4$ is not pyridyl or quinolyl;
  d. when $Ar^3$ is 3,4,5-trimethoxyphenyl, then $Ar^4$ is not 3-amino-4-methoxyphenyl;
  e. $Ar^4$ is not a substituted or unsubstituted 3-hydroxy-pyrazol-4-yl group.

In a further aspect of the present invention, the invention provides a compound as described in any embodiment of the present invention for use in a method of treatment of the human or animal body provided that
  a. $Ar^3$ is not a substituted or unsubstituted pyrrol-3-yl, pyrazol-3-yl, [1,2,4]triazol-3-yl, [1,2,3]triazol-4-yl or tetrazol-5-yl group;
  b. no more than one of $Ar^3$, $Ar^4$, $R^5$ and $R^N$ are phenyl, 4-hydroxyphenyl or 4-alkoxyphenyl groups; preferably no more than one of $Ar^3$, $Ar^4$, $R^5$ and $R^N$ are phenyl, 4-hydroxyphenyl or 4-(substituted or unsubstituted alkoxy-, alkenoxy- or alkynyloxy-)phenyl groups;
  c. $Ar^4$ is not pyridyl or quinolyl;
  d. when $Ar^3$ is 3,4,5-trimethoxyphenyl, then $Ar^4$ is not 3-amino-4-methoxyphenyl;
  e. $Ar^4$ is not a substituted or unsubstituted 3-hydroxy-pyrazol-4-yl group.

In a further aspect of the present invention, the invention provides a compound as described in any embodiment of the present invention for use in a method of treatment of a condition mediated by HSP90 of the human or animal body provided that
a. Ar$^3$ is not a substituted or unsubstituted pyrrol-3-yl, pyrazol-3-yl, [1,2,4]triazol-3-yl, [1,2,3]triazol-4-yl or tetrazol-5-yl group;
b. no more than one of Ar$^3$, Ar$^4$, R$^5$ and R$^N$ are phenyl, 4-hydroxyphenyl or 4-alkoxyphenyl groups; preferably no more than one of Ar$^3$, Ar$^4$, R$^5$ and R$^N$ are phenyl, 4-hydroxyphenyl or 4-(substituted or unsubstituted alkoxy-, alkenoxy- or alkynyloxy-)phenyl groups;
c. Ar$^4$ is not pyridyl or quinolyl;
d. when Ar$^3$ is 3,4,5-trimethoxyphenyl, then Ar$^4$ is not 3-amino-4-methoxyphenyl;
e. Ar$^4$ is not a substituted or unsubstituted 3-hydroxy-pyrazol-4-yl group.

In a further aspect of the present invention, the invention provides a compound as described in any for use in a method of treatment of cancer of the human or animal body provided that
a. Ar$^3$ is not a substituted or unsubstituted pyrrol-3-yl, pyrazol-3-yl, [1,2,4]triazol-3-yl, [1,2,3]triazol-4-yl or tetrazol-5-yl group;
b. no more than one of Ar$^3$, Ar$^4$, R$^5$ and R$^N$ are phenyl, 4-hydroxyphenyl or 4-alkoxyphenyl groups; preferably no more than one of Ar$^3$, Ar$^4$, R$^5$ and R$^N$ are phenyl, 4-hydroxyphenyl or 4-(substituted or unsubstituted alkoxy-, alkenoxy- or alkynyloxy-)phenyl groups;
c. Ar$^4$ is not pyridyl or quinolyl;
d. when Ar$^3$ is 3,4,5-trimethoxyphenyl, then Ar$^4$ is not 3-amino-4-methoxyphenyl;
e. Ar$^4$ is not a substituted or unsubstituted 3-hydroxy-pyrazol-4-yl group.

In a further aspect of the present invention, the invention provides a composition comprising a compound according to any embodiment of the present invention and a pharmaceutically acceptable carrier or diluent provided that
a. Ar$^3$ is not a substituted or unsubstituted pyrrol-3-yl, pyrazol-3-yl, [1,2,4]triazol-3-yl, [1,2,3]triazol-4-yl or tetrazol-5-yl group;
b. no more than one of Ar$^3$, Ar$^4$, R$^5$ and R$^N$ are phenyl, 4-hydroxyphenyl or 4-alkoxyphenyl groups; preferably no more than one of Ar$^3$, Ar$^4$, R$^5$ and R$^N$ are phenyl, 4-hydroxyphenyl or 4-(substituted or unsubstituted alkoxy-, alkenoxy- or alkynyloxy-)phenyl groups;
c. Ar$^4$ is not pyridyl or quinolyl;
d. when Ar$^3$ is 3,4,5-trimethoxyphenyl, then Ar$^4$ is not 3-amino-4-methoxyphenyl;
e. Ar$^4$ is not a substituted or unsubstituted 3-hydroxy-pyrazol-4-yl group.

In a further aspect of the present invention, the invention provides a compound as described in any embodiment of the present invention, provided that
a. Ar$^3$ is not a substituted or unsubstituted pyrrol-3-yl, pyrazol-3-yl, [1,2,4]triazol-3-yl, [1,2,3]triazol-4-yl or tetrazol-5-yl group;
b. no more than one of Ar$^3$, Ar$^4$, R$^5$ and R$^N$ are phenyl, 4-hydroxyphenyl or 4-alkoxyphenyl groups; preferably no more than one of Ar$^3$, Ar$^4$, R$^5$ and R$^N$ are phenyl, 4-hydroxyphenyl or 4-(substituted or unsubstituted alkoxy-, alkenoxy- or alkynyloxy-)phenyl groups;
c. Ar$^4$ is not pyridyl or quinolyl;
d. when Ar$^3$ is 3,4,5-trimethoxyphenyl, then Ar$^4$ is not 3-amino-4-methoxyphenyl;
e. Ar$^4$ is not a substituted or unsubstituted 3-hydroxy-pyrazol-4-yl group;
f. Ar$^4$ is not benzodioxolane, benzodioxane or benzodioxepane.

Some Specific Embodiments

Some specific embodiments of the present invention are shown below.

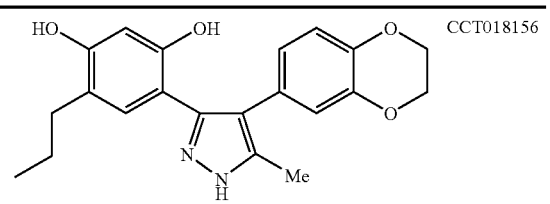

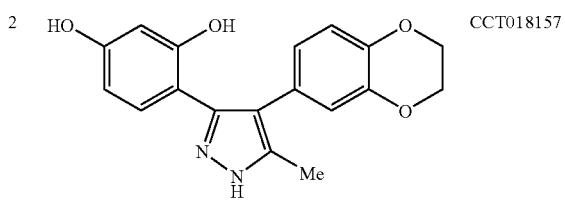

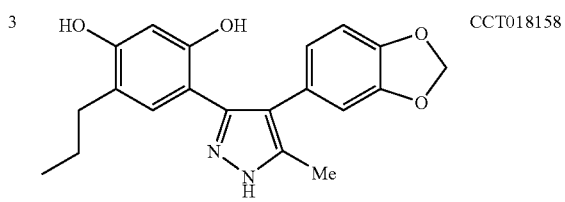

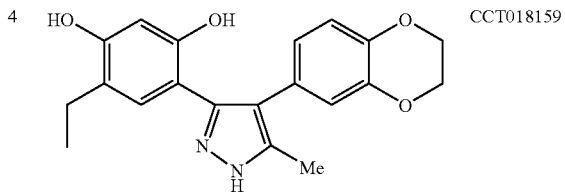

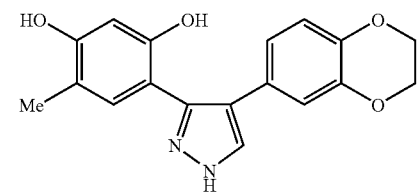

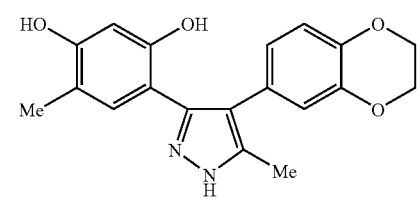

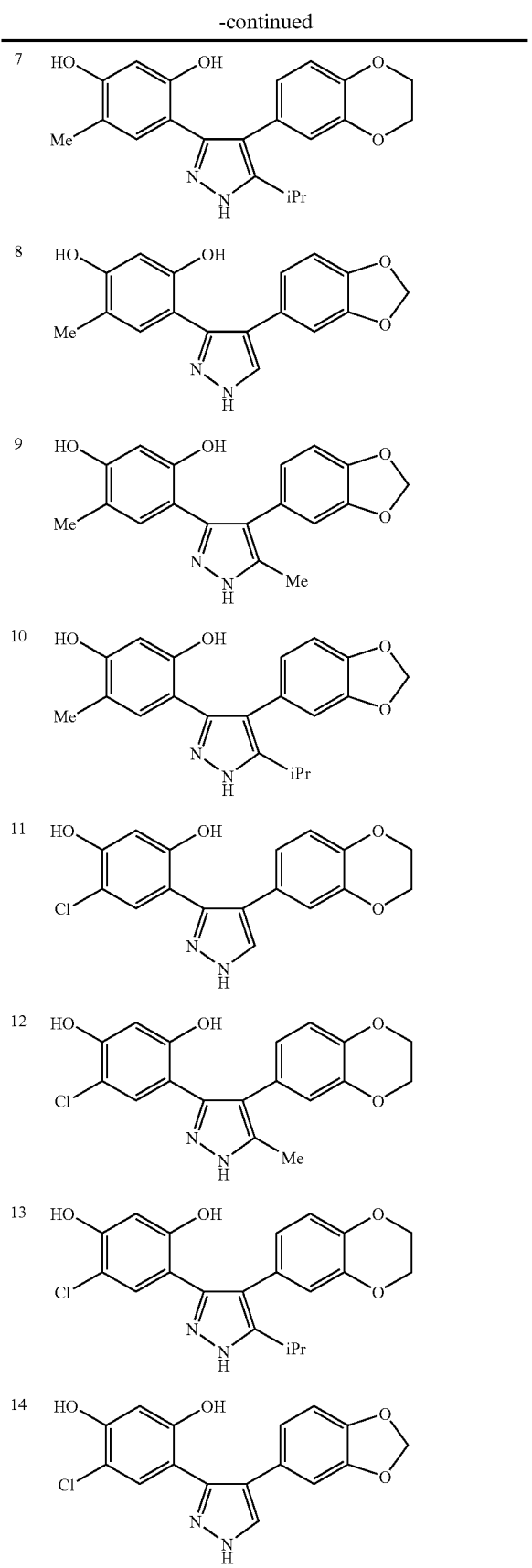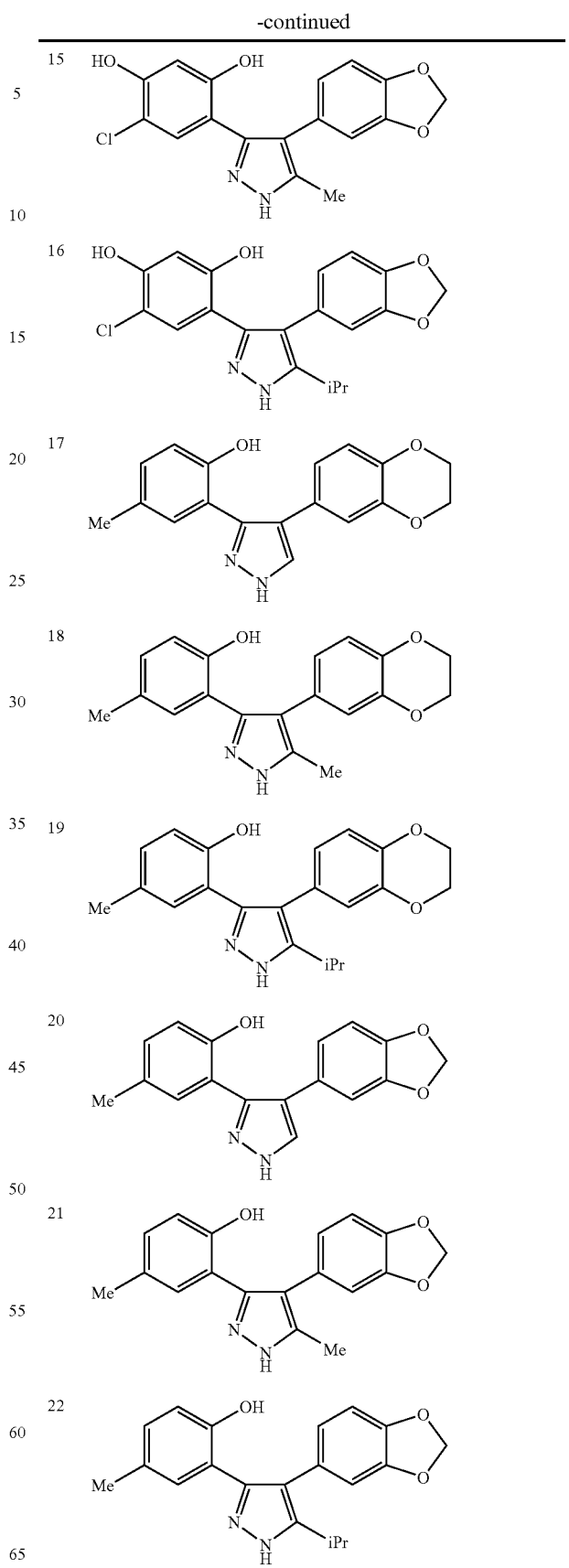

-continued
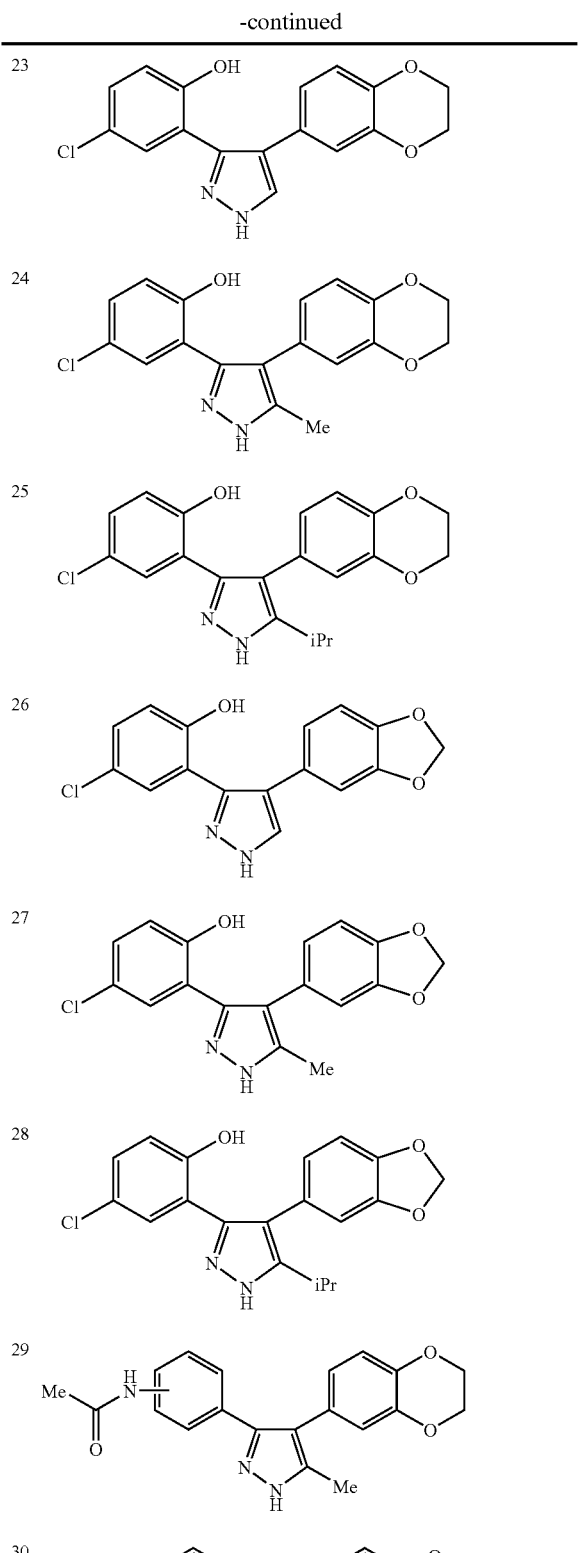
-continued
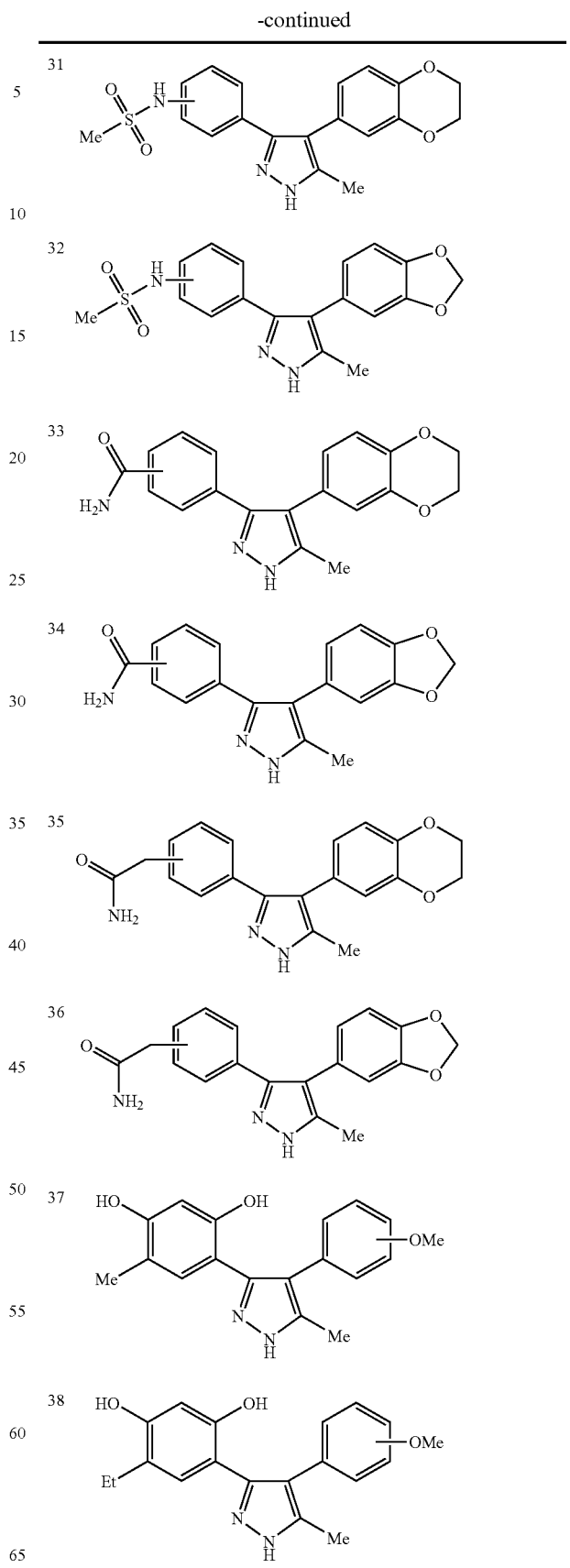

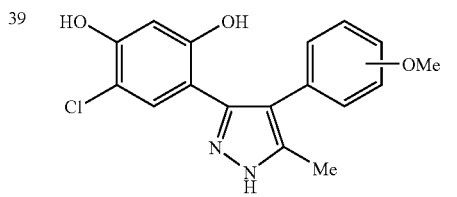
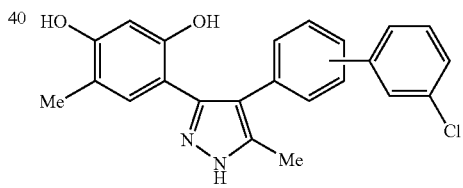
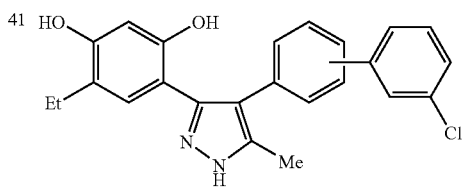
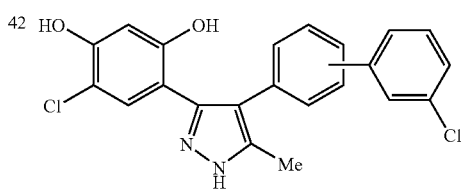
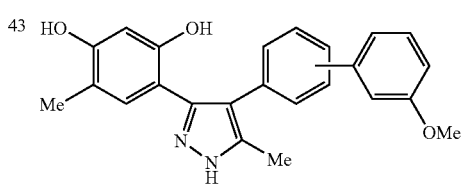
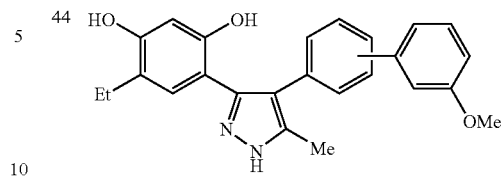
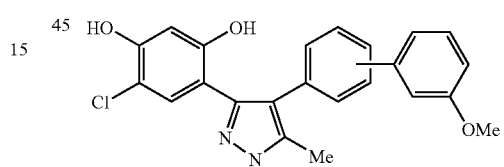
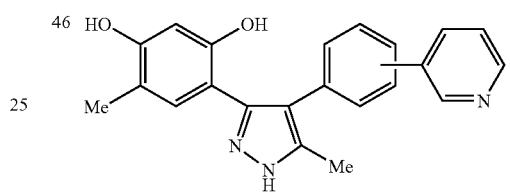
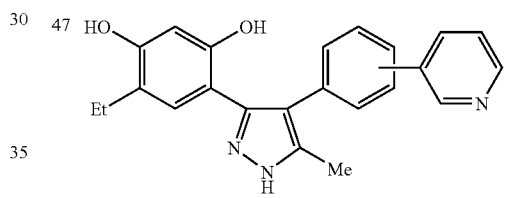
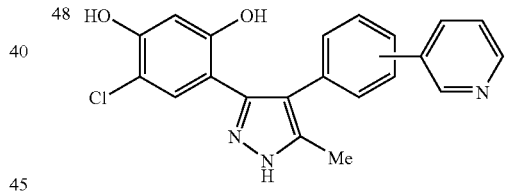
Some further specific embodiments of the present invention are shown below IC50: A=<10 μM; B=10–100 μM; C=>10 μM
| Example | Structure | MWt | Hsp90 IC50 | Comment |
|---|---|---|---|---|
| 49 | 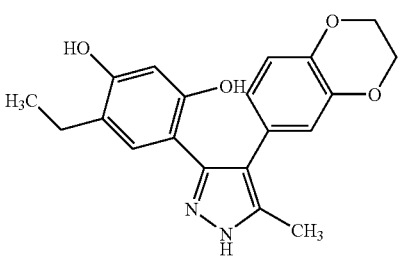 | 352 | A | |

| Example | Structure | MWt | Hsp90 IC50 | Comment |
|---|---|---|---|---|
| 50 | 5-ethyl-2,4-dihydroxyphenyl / 3,4-dimethoxyphenyl pyrazole | 340 | A | |
| 51 | 2,4-dihydroxyphenyl / 3,4-dimethoxyphenyl pyrazole | 312 | B | |
| 52 | 5-chloro-2,4-dihydroxyphenyl / 3,4-dimethoxyphenyl pyrazole | 347 | A | |
| 53 | 5-chloro-2,4-dihydroxyphenyl / phenyl pyrazole | 287 | A | |
| 54 | 5-ethyl-2,4-dihydroxyphenyl / phenyl pyrazole | 280 | A | |
| 55 | 2,4-dihydroxyphenyl / phenyl pyrazole | 252 | B | |

| Example | Structure | MWt | Hsp90 IC50 | Comment |
|---|---|---|---|---|
| 56 | 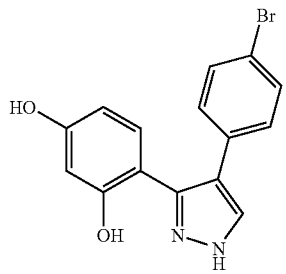 | 331 | C | |
| 57 | 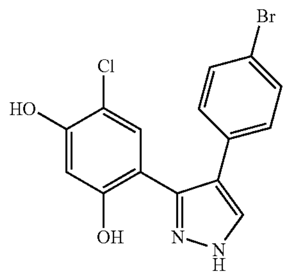 | 365 | A | |
| 58 | 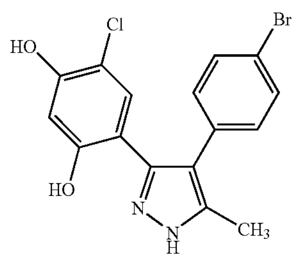 | 380 | A | |
| 59 | 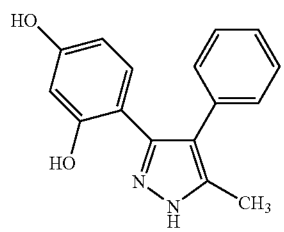 | 266 | C | |
| 60 | 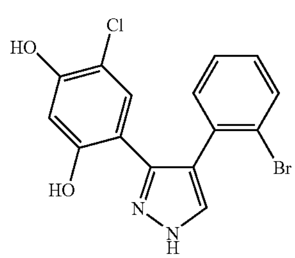 | 365 | A | |
| 61 | 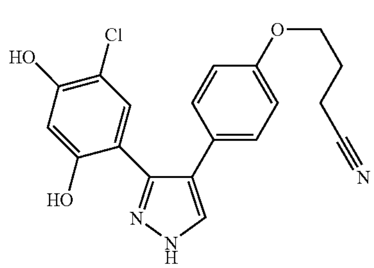 | 370 | A | |

-continued
| Example | Structure | MWt | Hsp90 IC50 | Comment |
|---|---|---|---|---|
| 62 | 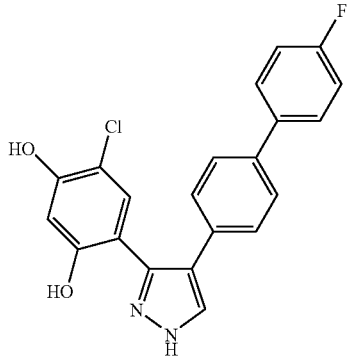 | 381 | A | |
| 63 | 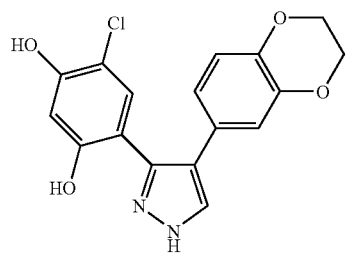 | 345 | A | |
| 64 | 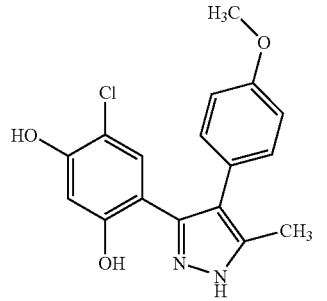 | 330 | A | |
| 65 | 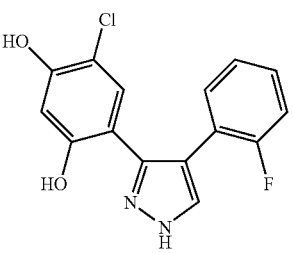 | 305 | A | |
| 66 | 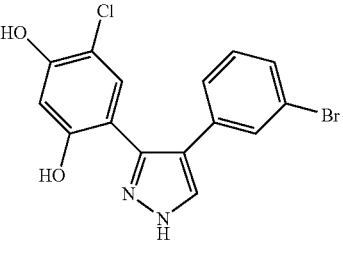 | 366 | A | |

-continued

| Example | Structure | MWt | Hsp90 IC50 | Comment |
|---|---|---|---|---|
| 67 | 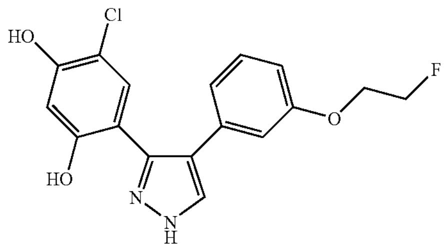 | 349 | A | |
| 68 | 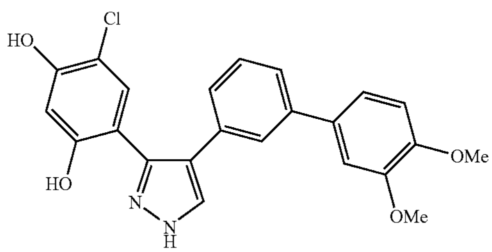 | 423 | B | |
| 69 | 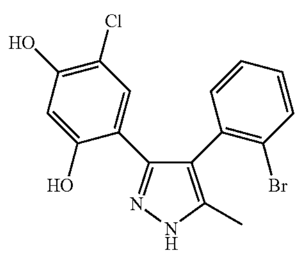 | 380 | B | |
| 70 | 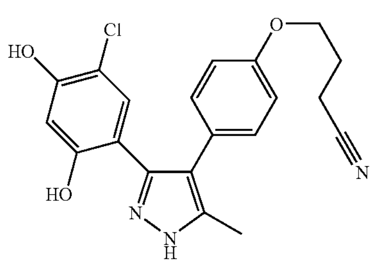 | 384 | A | |
| 71 | 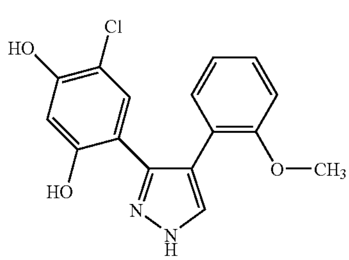 | 316 | B | |

-continued

| Example | Structure | MWt | Hsp90 IC50 | Comment |
|---|---|---|---|---|
| 72 | 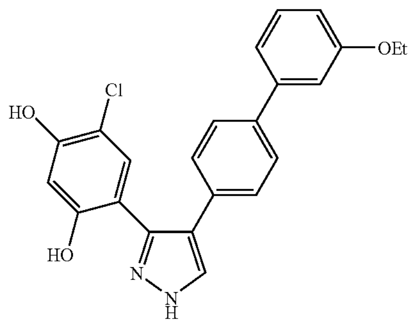 | 407 | A | |
| 73 | 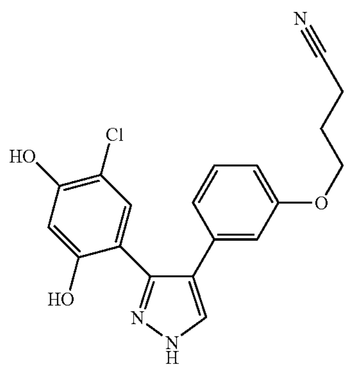 | 370 | A | |
| 74 | 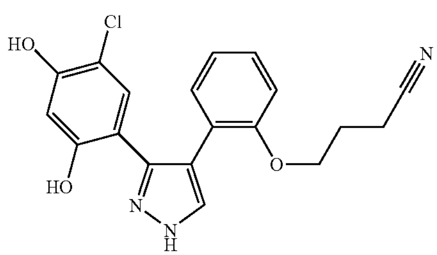 | 370 | A | |
| 75 | 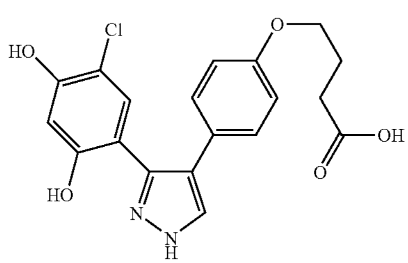 | 389 | A | |
| 76 | 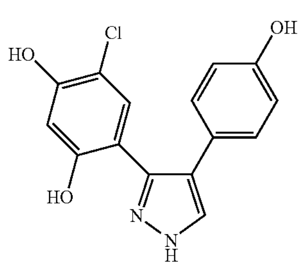 | 302 | A | |

-continued

| Example | Structure | MWt | Hsp90 IC50 | Comment |
|---------|-----------|-----|------------|---------|
| 77 | 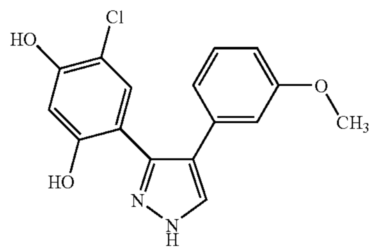 | 317 | A | |
| 78 | 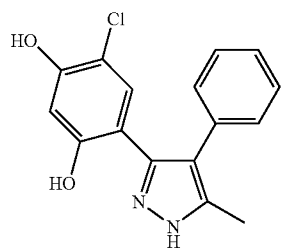 | 301 | A | |
| 79 | 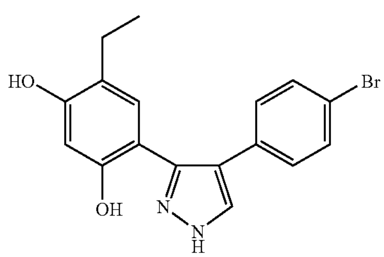 | 359 | A | |
| 80 | 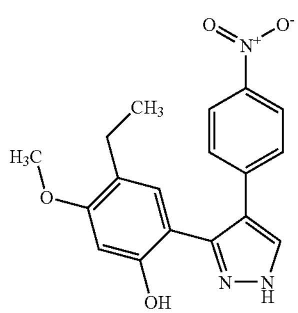 | 339 | B | MH+ = 340 |
| 81 | 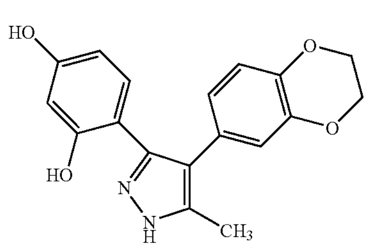 | 324 | B | MH+ = 325 |

-continued

| Example | Structure | MWt | Hsp90 IC50 | Comment |
|---|---|---|---|---|
| 82 | 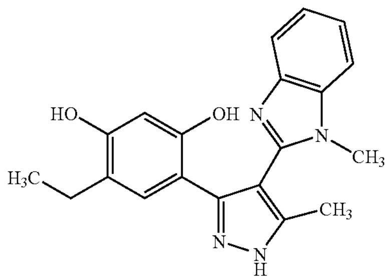 | 348 | B | MH+ = 349 |
| 83 | 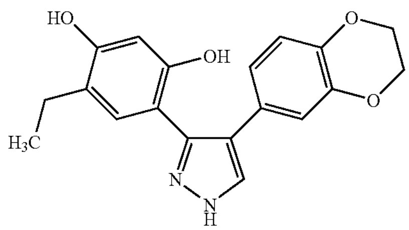 | 338 | A | MH+ = 339 |
| 84 | 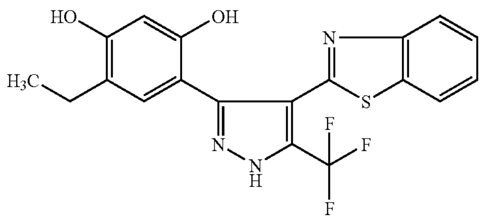 | 405 | B | MH+ = 406 |
| 85 | 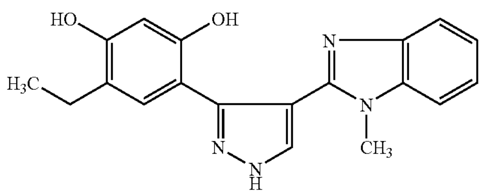 | 377 | B | MH+ = 377 |
| 86 | 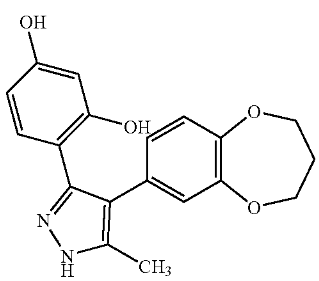 | 338 | C | MH+ = 339 |
| 87 | 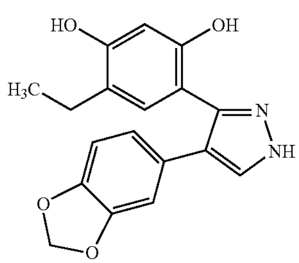 | 324 | A | MH+ = 325 |

-continued

| Example | Structure | MWt | Hsp90 IC50 | Comment |
|---|---|---|---|---|
| 88 | 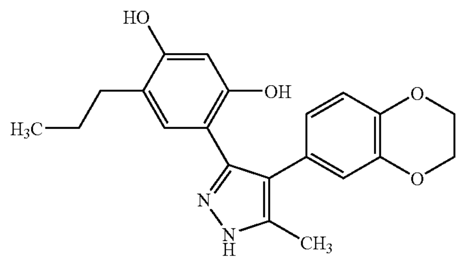 | 366 | B | MH+ = 367 |
| 89 | 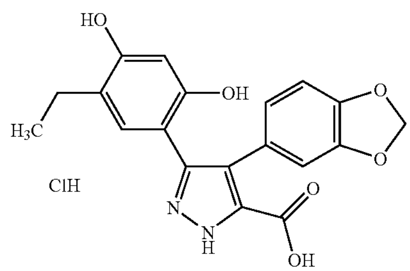 | 404 | A | MH+ = 405 |
| 90 | 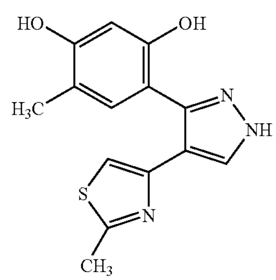 | 287 | B | MH+ = 288 |
| 91 | 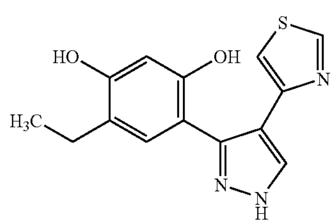 | 287 | B | MH+ = 288 |
| 92 | 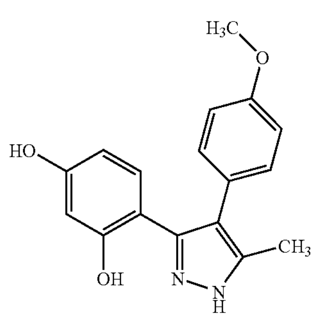 | 296 | B | |

-continued

| Example | Structure | MWt | Hsp90 IC50 | Comment |
|---|---|---|---|---|
| 93 | 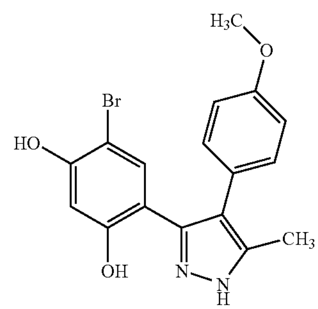 | 375 | A | |
| 94 | 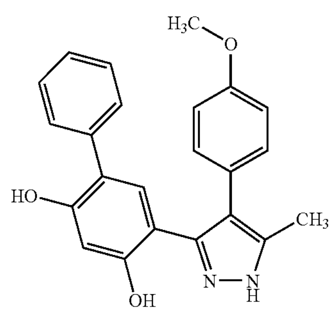 | 372 | A | |
| 95 | 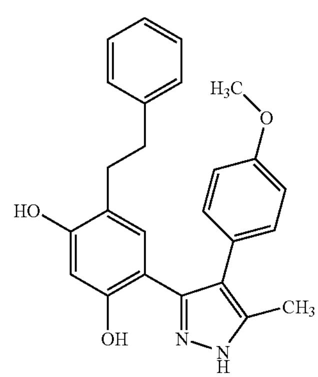 | 400 | A | |
| 96 | 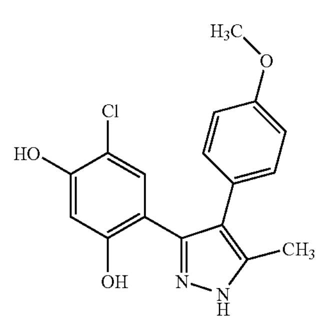 | 330 | A | |

-continued

| Example | Structure | MWt | Hsp90 IC50 | Comment |
| --- | --- | --- | --- | --- |
| 97 | 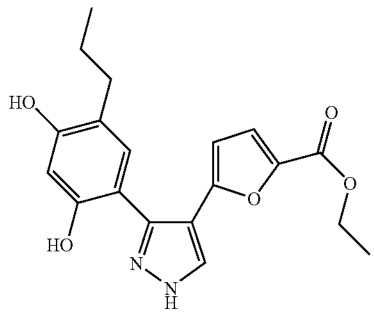 | 356 | B | MH+ = 357 |
| 98 | 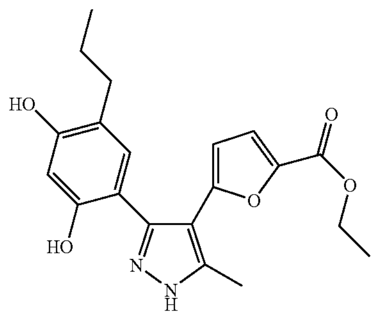 | 370 | B | MH+ = 371 |
| 99 | 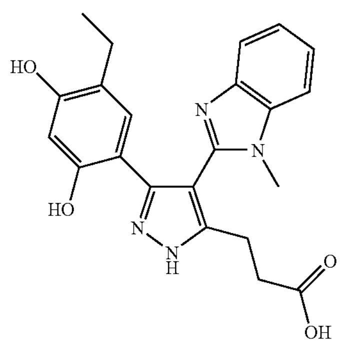 | 406 | B | MH+ = 407 |
| 100 | 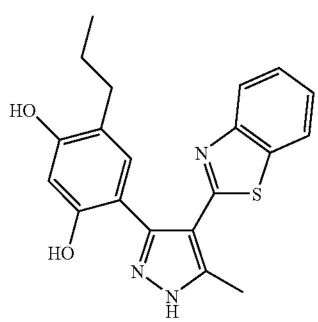 | 365 | B | MH+ = 366 |
| 101 | 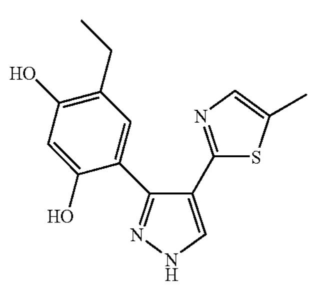 | 301 | B | MH+ = 302 |

-continued

| Example | Structure | MWt | Hsp90 IC50 | Comment |
|---------|-----------|-----|------------|---------|
| 102 | 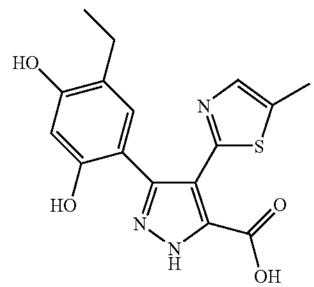 | 345 | B | MH+ = 346 |
| 103 | 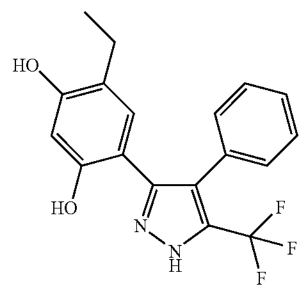 | 348 | B | MH+ = 349 |
| 104 | 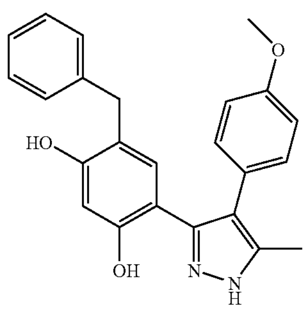 | 386 | A | |
| 105 | 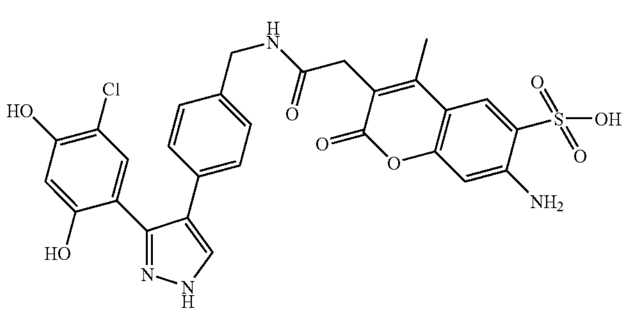 | 611 | A | |

-continued

| Example | Structure | MWt | Hsp90 IC50 | Comment |
|---|---|---|---|---|
| 106 | 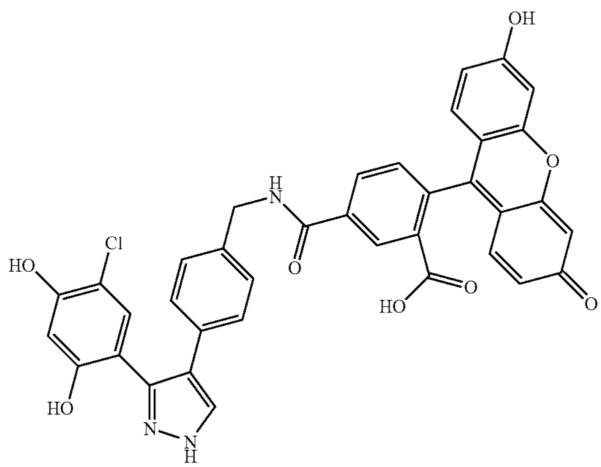 | 674 | A | |
| 107 | 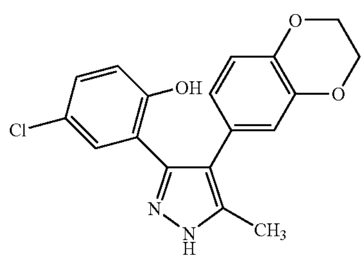 | 343 | B | |
| 108 | 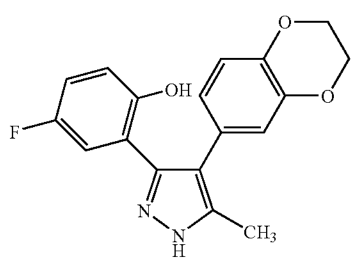 | 326 | A | |
| 109 | 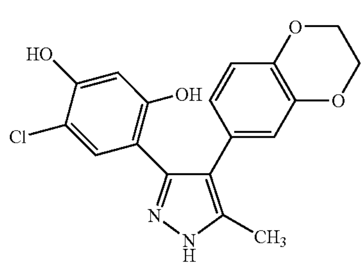 | 359 | A | |
| 110 | 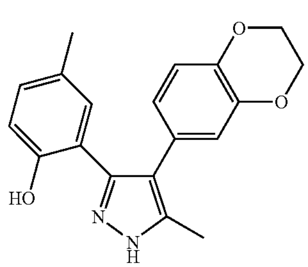 | 322 | C | |

| Example | Structure | MWt | Hsp90 IC50 | Comment |
|---|---|---|---|---|
| 111 | 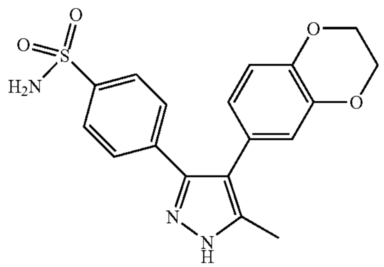 | 371 | C | |
| 112 | 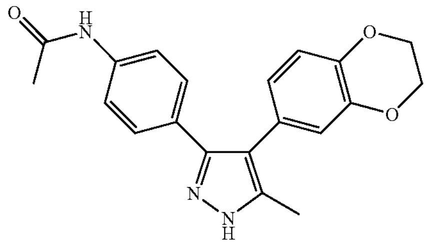 | 349 | C | |
| 113 | 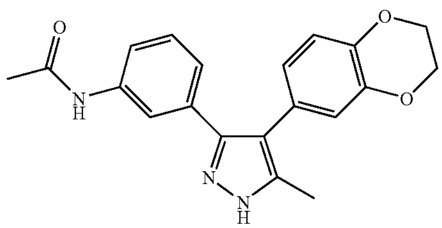 | 349 | C | |
| 114 | 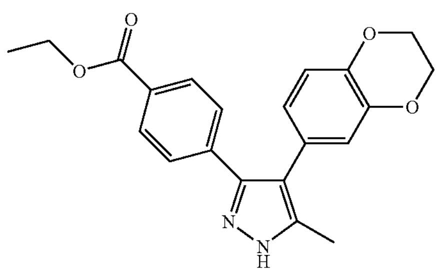 | 364 | C | |
| 115 | 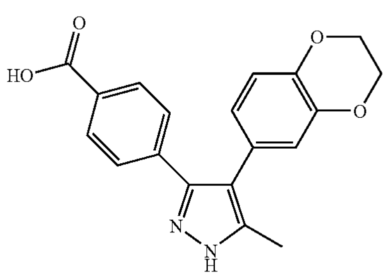 | 336 | C | |
| 116 | 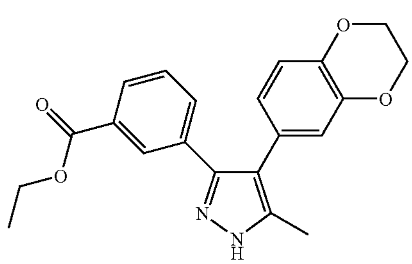 | 364 | C | |

-continued

| Example | Structure | MWt | Hsp90 IC50 | Comment |
|---|---|---|---|---|
| 117 | 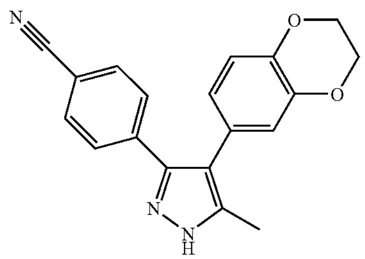 | 317 | C | |
| 118 | 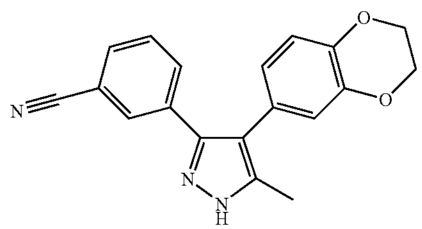 | 317 | C | |
| 119 | 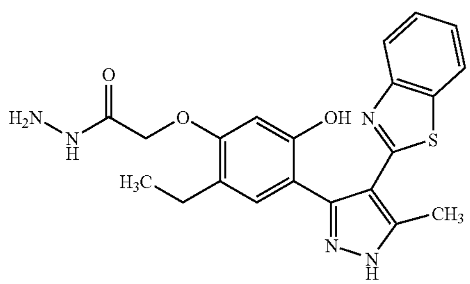 | 423 | C | |
| 120 | 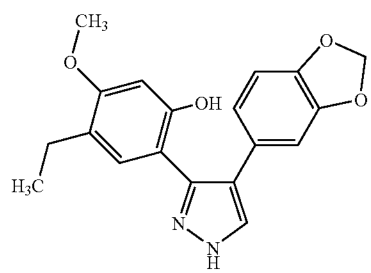 | 338 | C | MH+ = 339 |
| 121 | 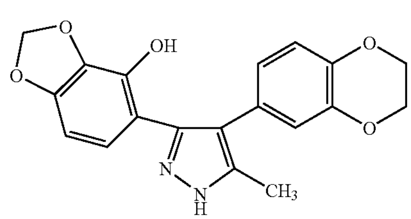 | 352 | C | MH+ = 353 |
| 122 | 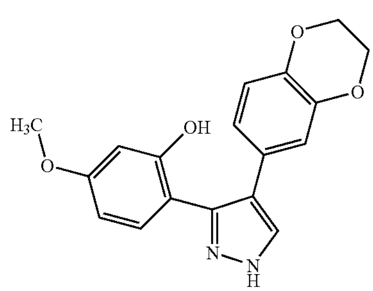 | 324 | C | MH+ = 325 |

-continued

| Example | Structure | MWt | Hsp90 IC50 | Comment |
|---|---|---|---|---|
| 123 | 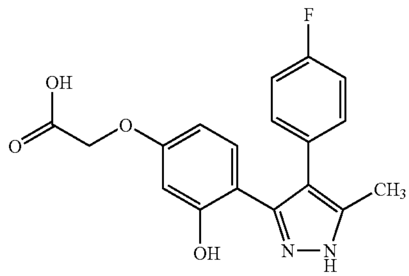 | 342 | C | MH+ = 343 |
| 124 | 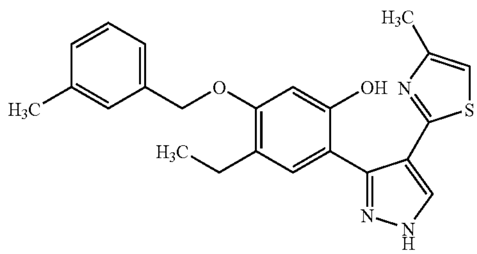 | 405 | C | MH+ = 406 |
| 125 | 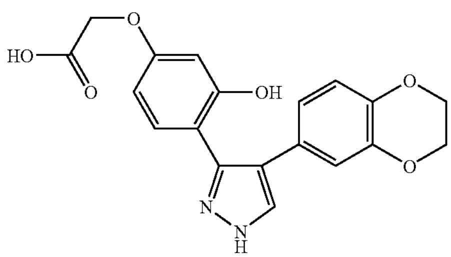 | 368 | C | MH+ = 369 |
| 126 | 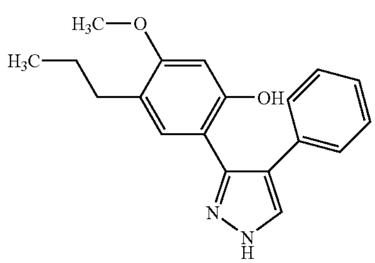 | 308 | C | |
| 127 | 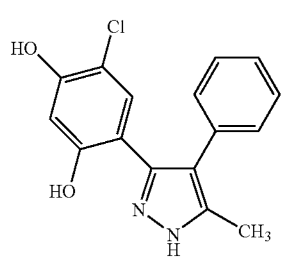 | 301 | C | |
| 128 | 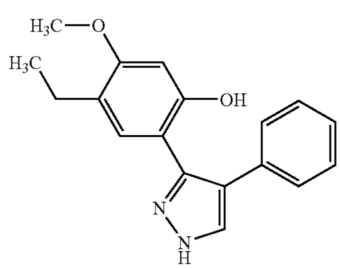 | 294 | C | MH+ = 295 |

US 7,247,734 B2

| Example | Structure | MWt | Hsp90 IC50 | Comment |
|---|---|---|---|---|
| 129 | 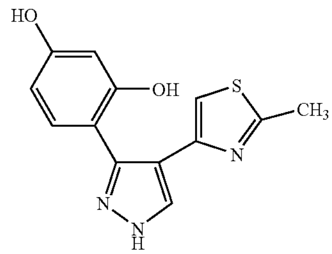 | 273 | C | MH+ = 274 |
| 130 | 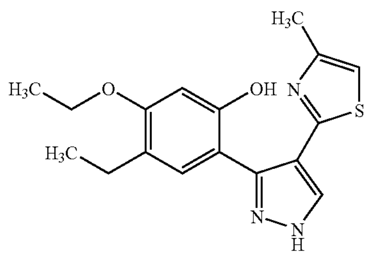 | 329 | C | MH+ = 330 |
| 131 | 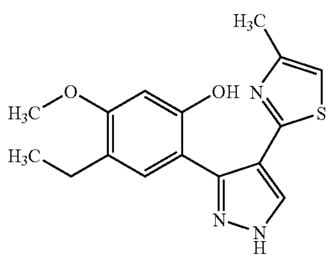 | 315 | C | MH+ = 316 |
| 132 | 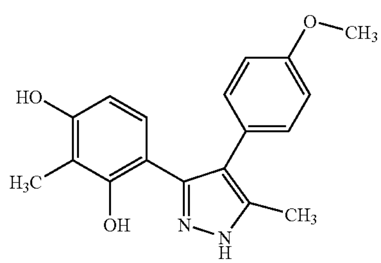 | 310 | C | |
| 133 | 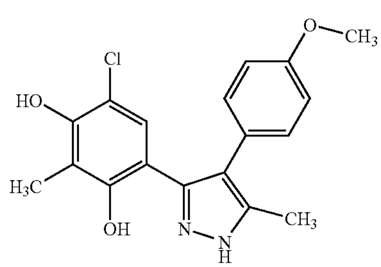 | 344 | C | |
| 134 | 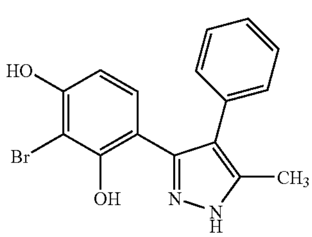 | 345 | C | |

-continued

| Example | Structure | MWt | Hsp90 IC50 | Comment |
|---|---|---|---|---|
| 135 | 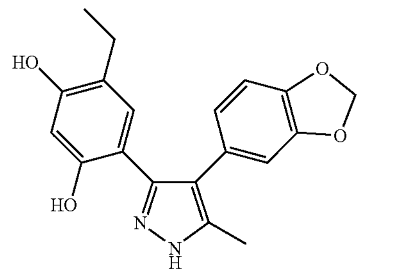 | 338 | C | MH+ = 339 |
| 136 | 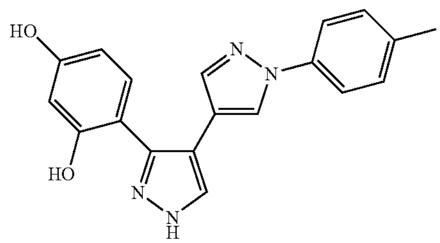 | 332 | C | |
| 137 | 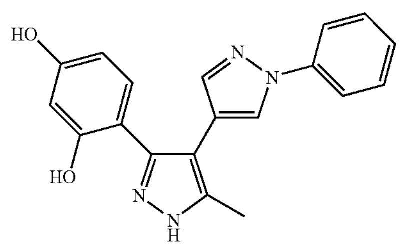 | 332 | C | |
| 138 | 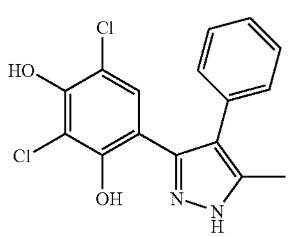 | 335 | C | |
| 139 | 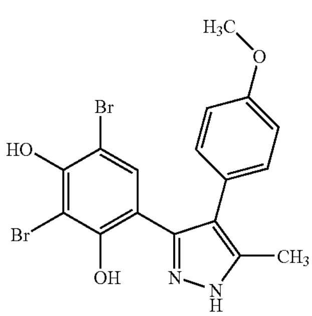 | 454 | C | |

-continued

| Example | Structure | MWt | Hsp90 IC50 | Comment |
| --- | --- | --- | --- | --- |
| 140 | 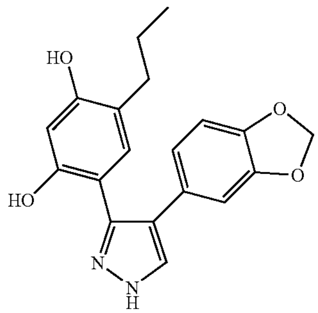 | 338 | C | MH+ = 339 |
| 141 | 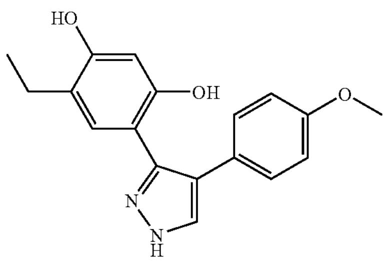 | 310 | B | MH+ = 311 |
| 142 | 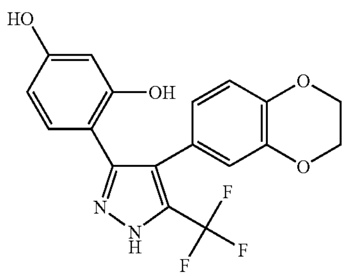 | 378 | C | MH+ = 379 |
| 143 | 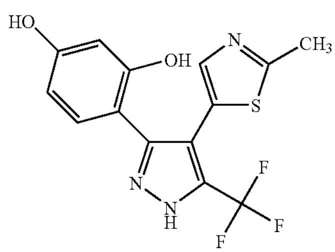 | 341 | C | MH+ = 342 |
| 144 | 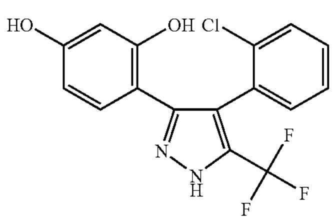 | 355 | C | |
| 145 | 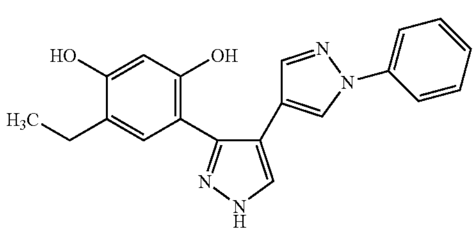 | 346 | C | MH+ = 347 |

-continued

| Example | Structure | MWt | Hsp90 IC50 | Comment |
|---|---|---|---|---|
| 146 | 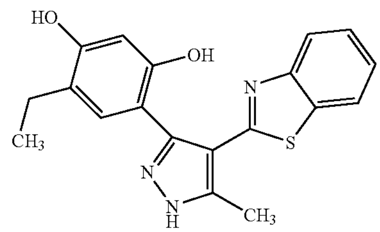 | 351 | C | MH+ = 352 |
| 147 | 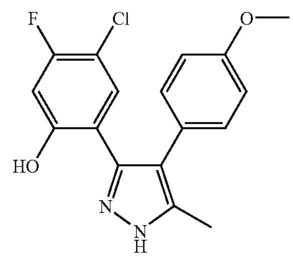 | 333 | C | |
| 148 | 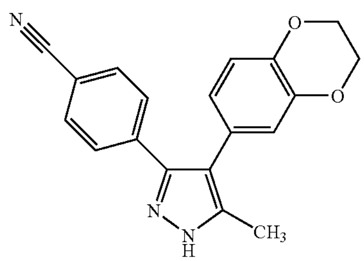 | 317 | C | |
| 149 | 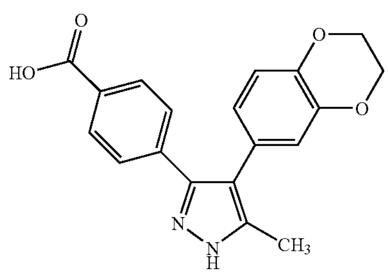 | 336 | C | |
| 150 | 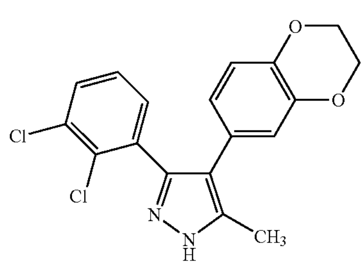 | 361 | C | |
| 151 | 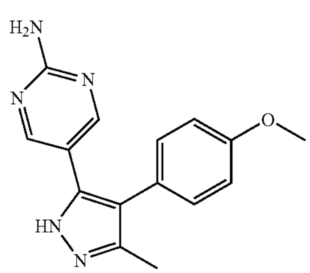 | 281 | C | |

-continued

| Example | Structure | MWt | Hsp90 IC50 | Comment |
|---|---|---|---|---|
| 152 | 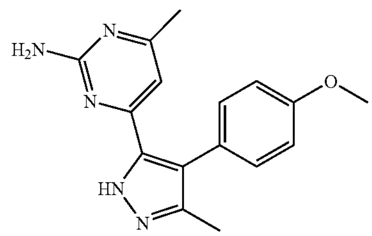 | 295 | C | |
| 153 | 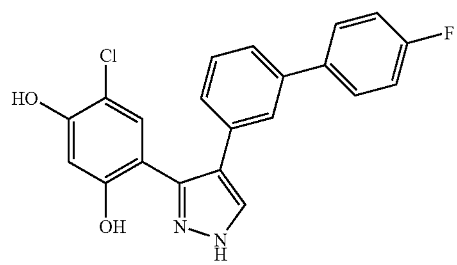 | 380 | | |
| 154 | 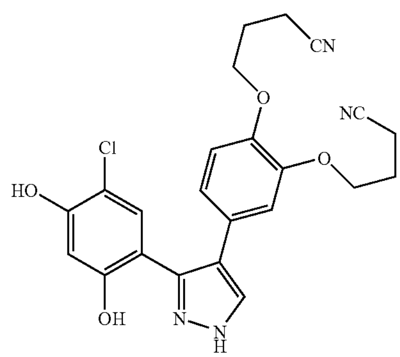 | 452.9 | | |
| 155 | 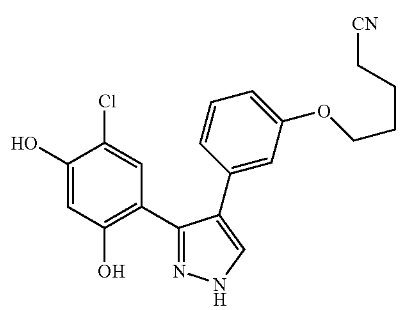 | 385 | A | |
| 156 | 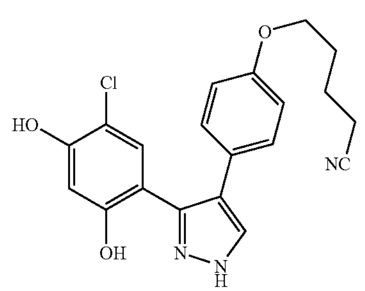 | 385 | A | |

| Example | Structure | MWt | Hsp90 IC50 | Comment |
|---|---|---|---|---|
| 157 | 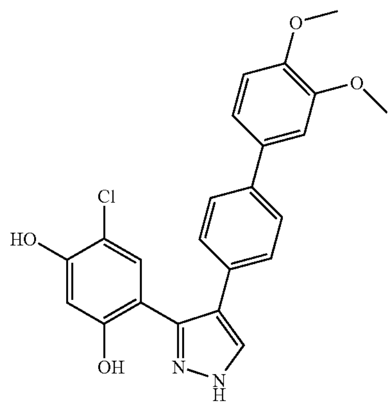 | 424 | A | |

The following Table summarises the structures of further compounds of the invention prepared as Examples 158–183, and the synthetic route by which they were prepared, together with the results obtained in the ATPase assay described in the "Assay" section below. In some cases, further experimental and characterisation details follow in the "Examples" section below. In connection with the ATPase assay results, the compounds tested were assigned to one of two activity ranges, namely A=<50 μM; B=>50 μM, and it is those assignments which are reported.

| Example | Structure | ATPase IC50 | MH+ | Scheme Used |
|---|---|---|---|---|
| 158 | 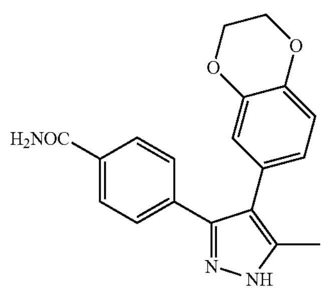 | B | 336 | 14, 24 |
| 159 | 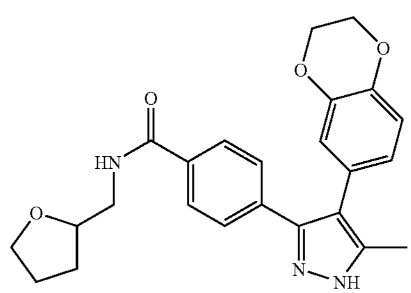 | B | 420 | 14, 24 |
| 160 | 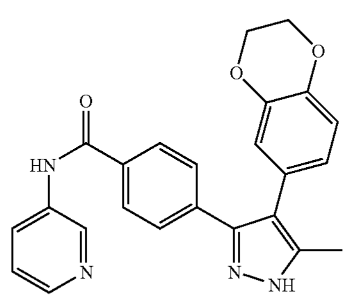 | B | 413 | 14, 24 |

-continued
| Example | Structure | ATPase IC50 | MH+ | Scheme Used |
|---|---|---|---|---|
| 161 | 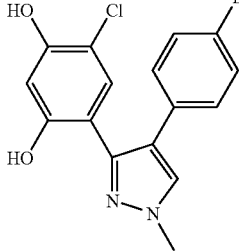 | B | 379,381 | 13 |
| 162 | 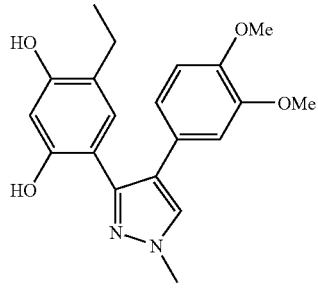 | B | 355 | 13 |
| 163 | 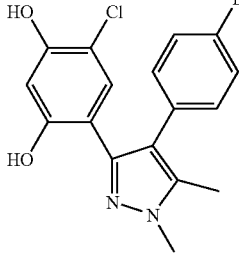 | B | 393,395 | 13 |
| 164 | 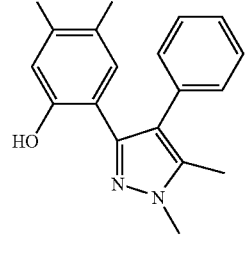 | B | 315 | 13 |
| 165 | 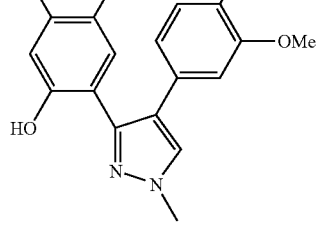 | B | 361 | 13 |

-continued

| Example | Structure | ATPase IC50 | MH+ | Scheme Used |
|---|---|---|---|---|
| 166 | 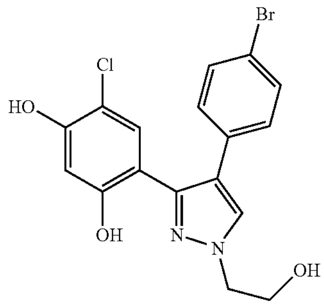 | B | 409,411 | 13 |
| 167 | 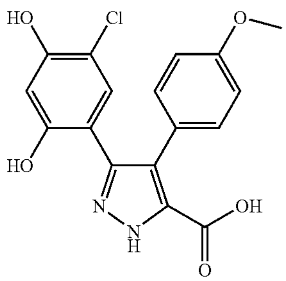 | A | 361,363 | 25 |
| 168 | 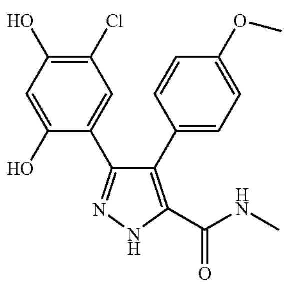 | A | 374,376 | 25 |
| 169 | 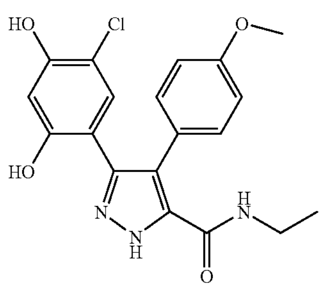 | A | 388,390 | 25 |
| 170 | 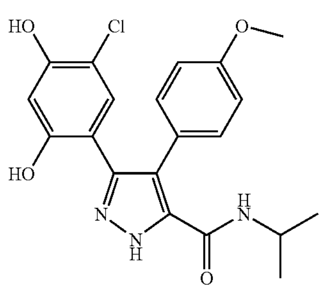 | A | 402,404 | 25 |

-continued

| Example | Structure | ATPase IC50 | MH+ | Scheme Used |
|---|---|---|---|---|
| 171 | 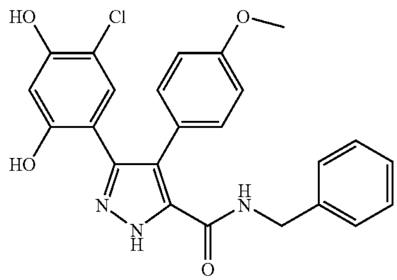 | A | 450,452 | 25 |
| 172 | 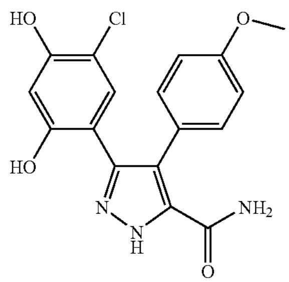 | A | 360,362 | 10, 11, 13 |
| 173 | 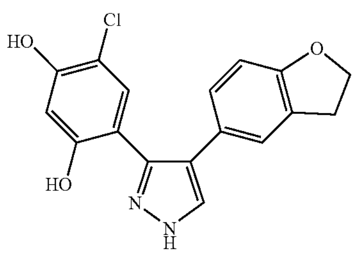 | A | 329 | 10, 11, 13 |
| 174 | 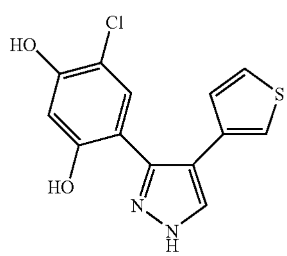 | A | 293 | 14 |
| 175 | 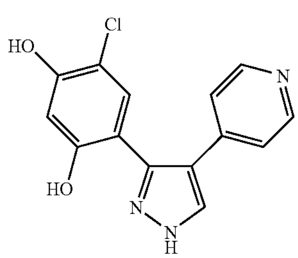 | A | 288 | 14 |
| 176 | 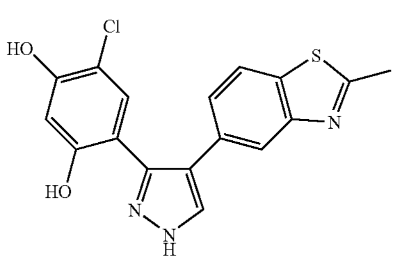 | A | 358 | 14 |

-continued
| Example | Structure | ATPase IC50 | MH+ | Scheme Used |
|---|---|---|---|---|
| 177 | 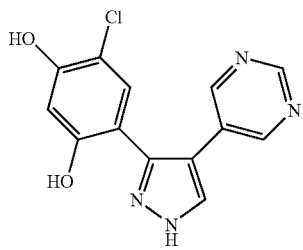 | A | 289 | 14 |
| 178 | 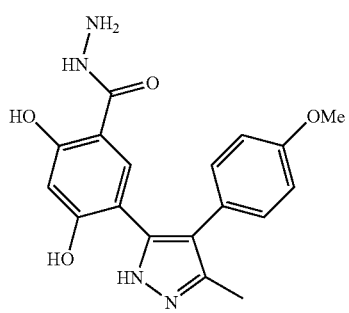 | B | 355 | 10, 11, 13 |
| 179 | 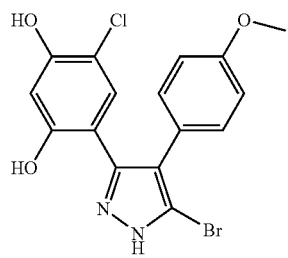 | A | 394, 396 | 10, 11, 13 |
| 180 | 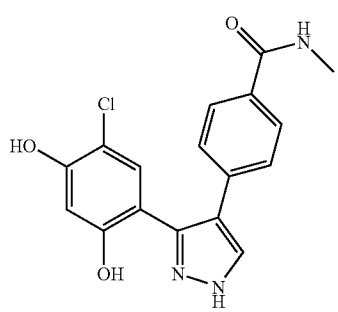 | A | 344 | 10, 11, 13 |
| 181 | 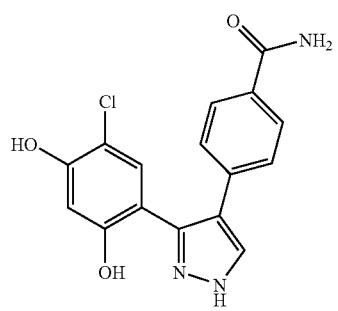 | A | 330 | 10, 11, 13 |

-continued

| Example | Structure | ATPase IC50 | MH+ | Scheme Used |
|---------|-----------|-------------|-----|-------------|
| 182 | 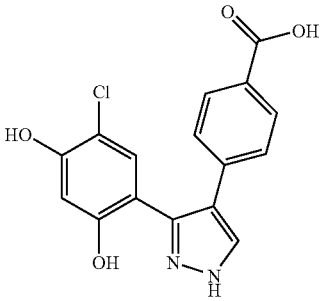 | A | 331 | 10, 11, 13 |
| 183 | 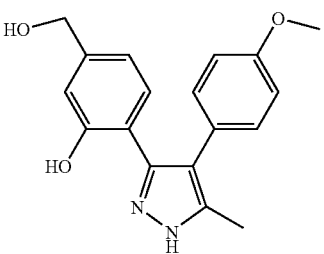 | B | 311 | 10, 11, 13 |

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alkidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($C_{12}$), tridecyl ($C_{13}$), tetradecyl ($C_{14}$), pentadecyl ($C_{1-5}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), norcarane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl, menthane, thujane, carane, pinane, bornane, norcarane, and camphene.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), aceanthrene ($C_{16}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH═$CH_2$), 1-propenyl (—CH═CH—$CH_3$), 2-propenyl (allyl, —CH—CH═$CH_2$), isopropenyl (—C($CH_3$)═$CH_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —$CH_2$—C—CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated.

Examples of groups of alkylidene groups include $C_{1-4}$alkylidene, $C_{1-7}$alkylidene, $C_{1-20}$alkylidene.

Examples of alkylidene groups include, but are not limited to, methylidene (═$CH_2$), ethylidene (═CH—$CH_3$), vinylidene (═C═$CH_2$), and isopropylidene (═C($CH_3$)$_2$). An example of a substituted alkylidene is benzylidene (═CH-Ph).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne (≡CH) and ethylidyne (≡C—$CH_3$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{3-12}$aryl, $C_{5-12}$aryl, $C_{5-7}$aryl, and $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), pyrene ($C_{16}$), and naphthacene ($C_{18}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl).

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substituents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)=(also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:

$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above groups (e.g., alkyl, alkylidene, alkylidyne, heterocyclyl, aryl), whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$, R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom, Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a $C_{1-7}$alkyl group, a $C_{3-20}$heterocyclyl group, or a $C_{5-20}$aryl group, preferably H or a $C_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH$_3$ and —SCH$_2$CH$_3$.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$alkyl group, a $C_{3-20}$heterocyclyl group, or a $C_{5-20}$aryl group, preferably a $C_{1-7}$alkyl group, including, for example, a fluorinated or perfluorinated $C_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$alkyl group, a $C_{3-20}$heterocyclyl group, or a $C_{5-20}$aryl group, preferably a $C_{1-7}$alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.

In many cases, substituents may themselves be substituted. For example, a $C_{1-7}$alkyl group may be substituted with, for example, hydroxy (e.g., a $C_{1-7}$hydroxyalkyl group), $C_{1-7}$alkoxy (e.g., a $C_{1-7}$alkoxyalkyl group), amino (e.g., a $C_{1-7}$aminoalkyl group), halo (e.g., a $C_{1-7}$haloalkyl group), carboxy (e.g., a $C_{1-7}$carboxyalkyl group), and $C_{5-20}$aryl (e.g., a $C_{5-20}$aryl-$C_{1-7}$alkyl group).

Similarly, a $C_{5-20}$aryl group may be substituted with, for example, hydroxy (e.g., a $C_{5-20}$hydroxyaryl group), halo (e.g., a $C_{5-20}$haloaryl group), amino (e.g., a $C_{5-20}$aminoaryl group, e.g., as in aniline), $C_{1-7}$alkyl (e.g., a $C_{1-7}$alkyl-$C_{5-20}$aryl group, e.g., as in toluene), and $C_{1-7}$alkoxy (e.g., a $C_{1-7}$alkoxy-$C_{5-20}$aryl group, e.g., as in anisole).

These and other specific examples of such substituted-substituents are described below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group." Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

$C_{1-7}$haloalkoxy: —OR, wherein R is a $C_{1-7}$haloalkyl group. Examples of $C_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$aminoalkylamino: The term "$C_{1-7}$aminoalkylamino," as used herein, pertains to an amino group, —NR$^1$R$^2$, in which one of the substituents, R$^1$ or R$^2$, is itself a $C_{1-7}$aminoalkyl group (—$C_{1-7}$alkyl-NR$^1$R$^2$). The $C_{1-7}$aminoalkylamino may be represented, for example, by the formula —NR$^1$—$C_{1-7}$alkyl-NR$^1$R$^2$. Examples of amino-$C_{1-7}$alkylamino groups include, but are not limited to, groups of the formula —NR$^1$(CH$_2$)$_n$NR$^1$R$^2$, where n is 1 to 6, for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (from toluene), xylyl (from xylene), mesityl (from mesitylene), and cumenyl (or cumyl, from cumene), and duryl (from durene).

$C_{1-7}$alkyl-$C_{5-20}$aryloxy: The term "$C_{1-7}$alkyl-$C_{5-20}$aryloxy," as used herein, describes certain $C_{5-20}$aryloxy groups which have been substituted with a $C_{1-7}$alkyl group. Examples of such groups include, but are not limited to, tolyloxy, xylyloxy, mesityloxy, cumenyloxy, and duryloxy.

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—), cinnamyl (Ph-CH=CH—CH$_2$—).

$C_{5-20}$aryl-$C_{1-7}$alkoxy: The term "$C_{5-20}$aryl-$C_{1-17}$alkoxy," as used herein, describes certain $C_{1-7}$alkoxy groups which have been substituted with a $C_{5-20}$aryl group. Examples of such groups include, but are not limited to, benzyloxy, benzhydryloxy, trityloxy, phenethoxy, styryloxy, and cimmamyloxy.

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

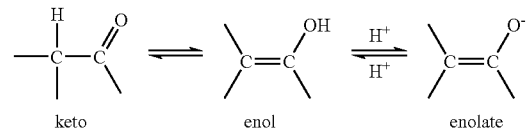

keto    enol    enolate

It will be appreciated that when R$^N$ is hydrogen, the pyrazoles of the present invention may exist in tautomeric forms as illustrated below. For the avoidance of doubt, both tautomeric forms are encompassed by the present invention and reference to one tautomeric form includes reference to the other.

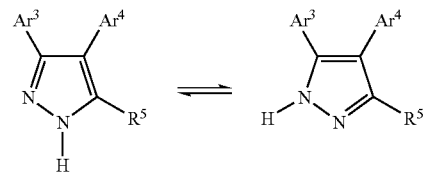

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4$+.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyidimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

General Synthesis

The 3,4-diarylpyrazoles of the present invention may be prepared, for example, by the methods described herein, or by adapting these or other well known methods in well known ways.

In one method, isoflavones are reacted with hydrazine to yield the corresponding pyrazole, for example, as illustrated in the following scheme. See, for example, Bass, 1976; Nakano et al., 1979; Baker et al., 1953; and Khilya et al., 1994.

Scheme 1

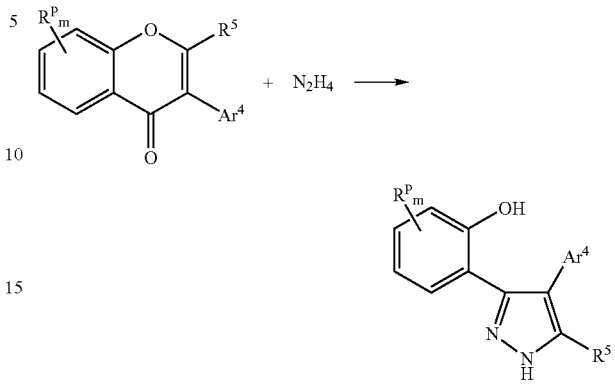

More generally, 3,4-diarylpyrazoles can be prepared by reaction of a suitably substituted dicarbonyl compound with hydrazine, for example, as illustrated in the following scheme. See, for example, Terrett et al., 1996 and Leigh et al., 1979.

Scheme 2

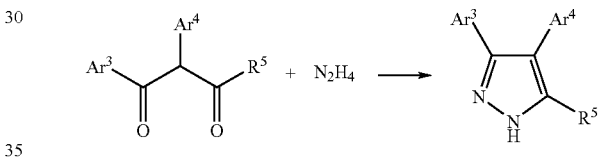

The required dicarbonyl compounds can be obtained by various synthetic approaches including the following.

In one method, the dicarbonyl compound is prepared by acylation of an aryl benzyl ketone, for example, as illustrated in the following scheme. See, for example, Berk et al., 1988, and Le et al., 1997.

Scheme 3

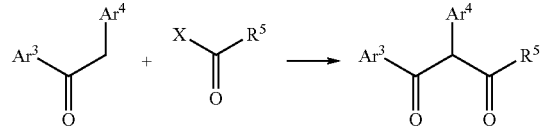

Examples of acylating agent, $R^5COX$, include esters, acid chlorides, anhydrides, and the like, and reactions may be catalysed, for example, by bases such as metal alkoxides, or by prior formation of an enolate anion, using, for example, lithium di-isopropylamide in tetrahydrofuran at low temperature. Alternatively the acylating agent may be a formamide or an orthoformate, used in the presence of a Lewis acid catalyst, such as $BF_3$.

The aryl benzyl ketone, $Ar^3C(=O)CH_2Ar^4$, may be replaced by related substrates, such as enol ethers, shown below, where R is, for example, alkyl, trialkylsilyl, and the like.

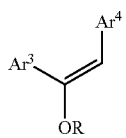

In another method, the dicarbonyl compound is prepared by acylation of an alkyl benzyl ketone, for example, as illustrated in the following scheme. See, for example, Berk et al., 1988.

Scheme 4

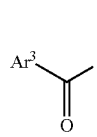 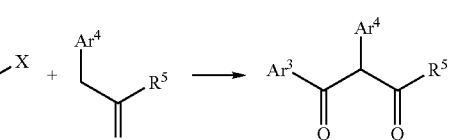

Again, examples of acylating agent, $R^5COX$, include esters, acid chlorides, anhydrides, and the like, and reactions may be catalysed, for example, by bases such as metal alkoxides, or by prior formation of an enolate anion, using, for example, lithium di-isopropylamide in tetrahydrofuran at low temperature. Alternatively the acylating agent may be a formamide or an orthoformate, used in the presence of a Lewis acid catalyst, such as $BF_3$.

Again, the alkyl benzyl ketone, $R^5C(=O)CH_2Ar^4$, may be replaced by related substrates, such as enol ethers, shown below, where R is, for example, alkyl, trialkylsilyl, and the like.

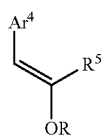

In another method, the dicarbonyl compound is prepared by arylation of a 1,3-dicarbonyl compound, for example, as illustrated in the following scheme. See, for example, Scheme 5

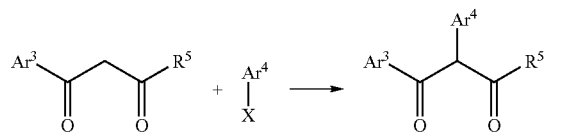

In favourable cases, anions derived from 1,3-diketones may be arylated directly by reaction with a haloaromatic compound, $Ar_2X$, where X is, for example, F, Cl, or Br. This method is especially useful when the aromatic ring, $Ar^4$, is electron deficient, as in, for example, groups such as 4-nitrophenyl and heteroraryl groups such as 4-pyridyl and 2-pyrimidinyl.

The required benzyl aryl ketones can be obtained by various synthetic approaches including, for example, the ones illustrated in the following schemes. See, for example, Berk et al., 1988; Hajipour et al., 1998; Anderson et al., 1997; Farkas et al., 2000; Wahala et al., 1991; Knchel et al., 1988; and Zhu et al., 1991.

Scheme 6

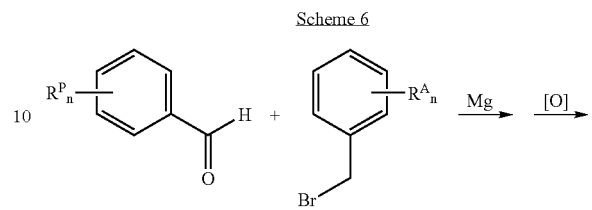

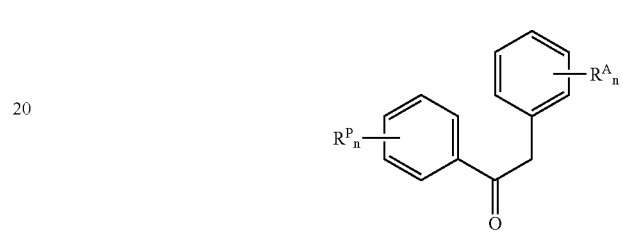

Scheme 7

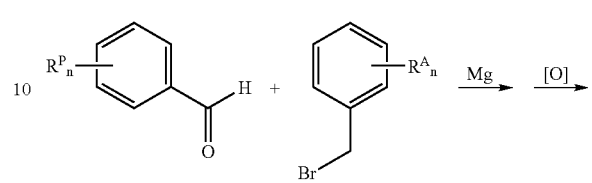

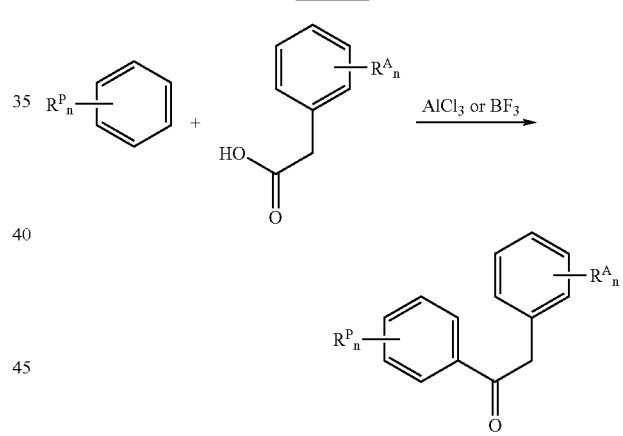

Scheme 8

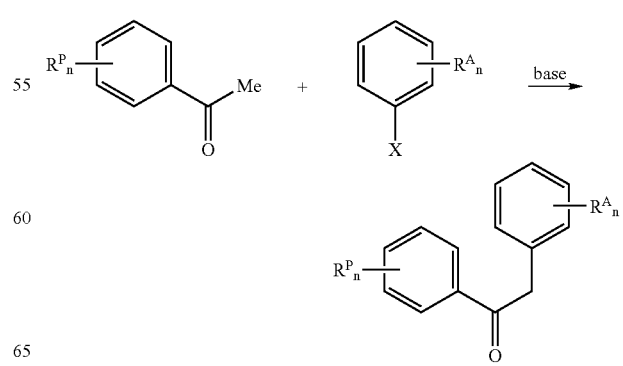

105
Scheme 9
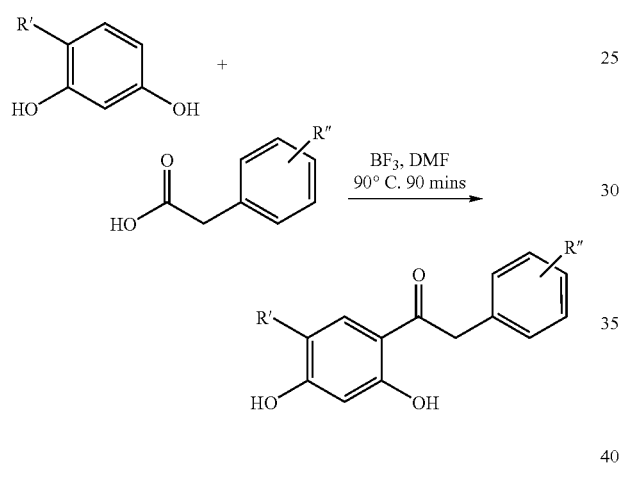
Scheme 10. General synthesis of dihydroxyphenyl ketones
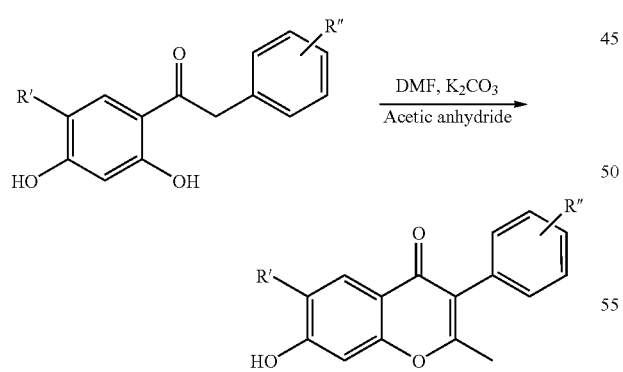
Scheme 11. General synthesis of
7-hydroxy-2-methyl-3-phenyl-chromen-4-ones.
Scheme 12. One pot synthesis of isoflavones.
106
-continued
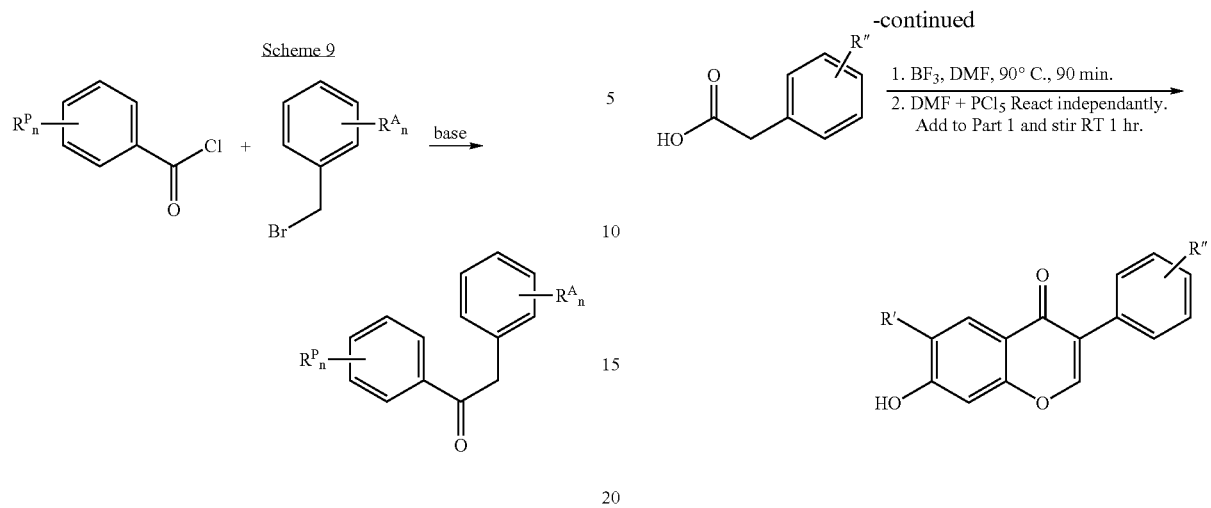
Scheme 13. Pyrazole synthesis
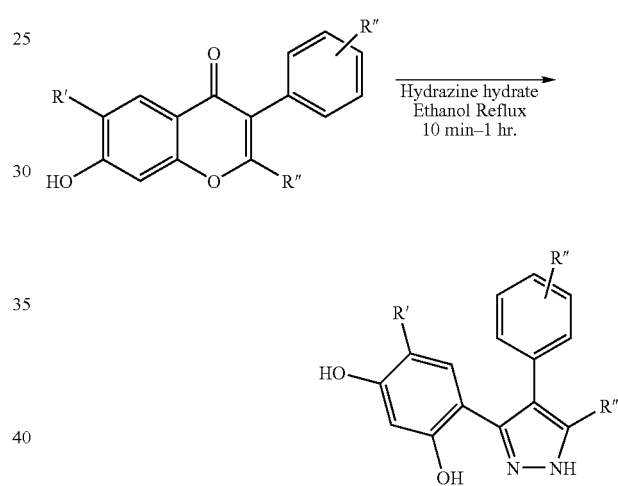
Scheme 14: Synthesis of Non-Resorcinols
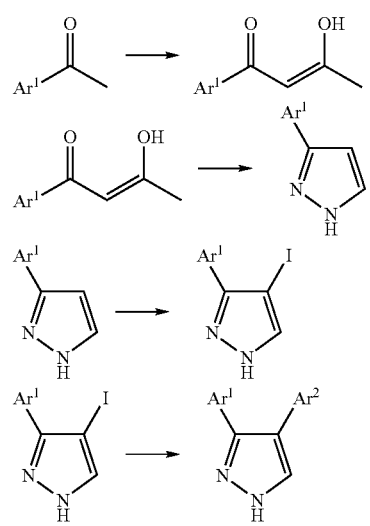

Scheme 15: Synthesis of Benzyl Intermediate:
then chemistry as for "Synthesis of Resorcinols", above
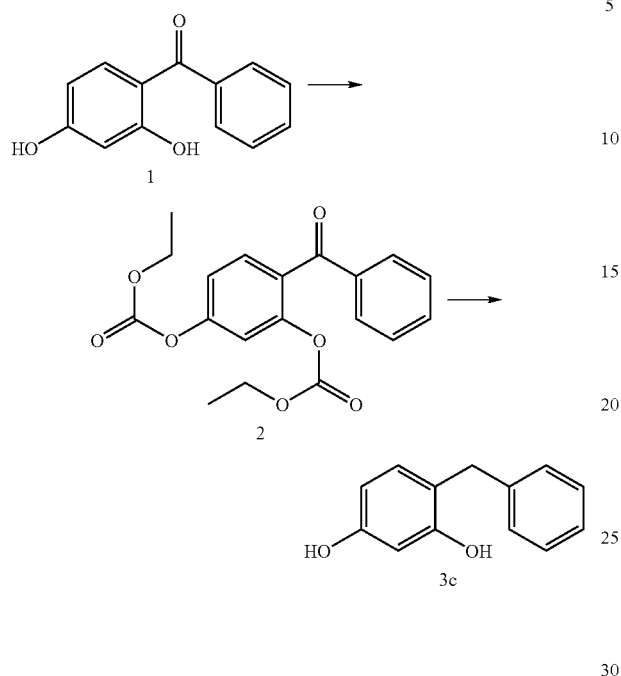
Scheme 16: Synthesis of Dichloro
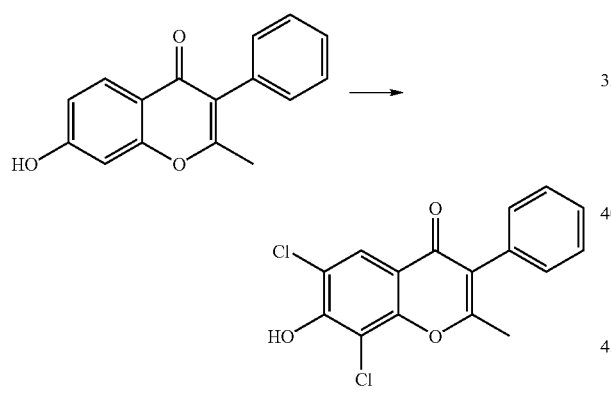
Scheme 17: Synthesis of Bromo Flavone
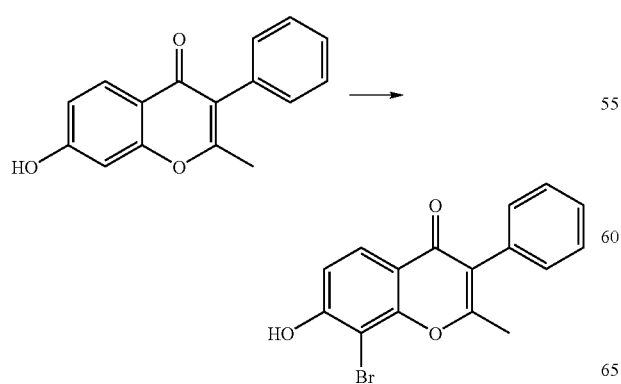
Scheme 18: Synthesis of Bromo Resorcinols
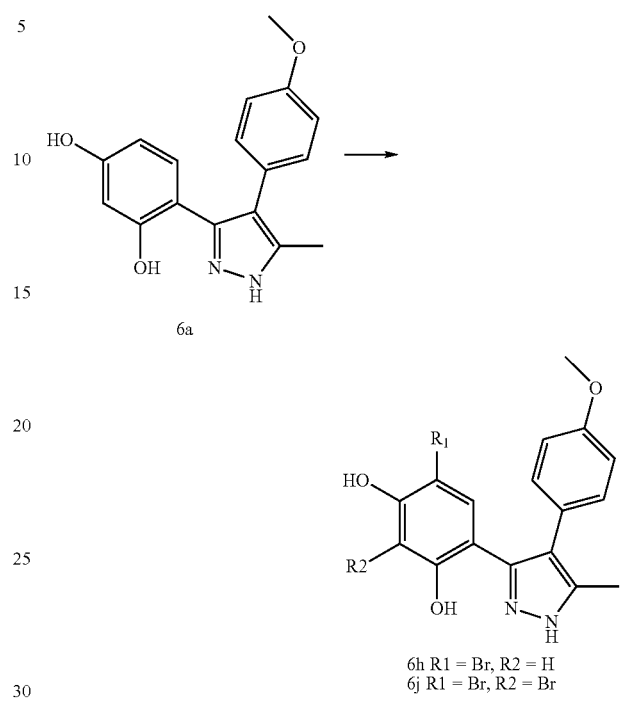
Scheme 19: Synthesis of 2-methyl resorcinol
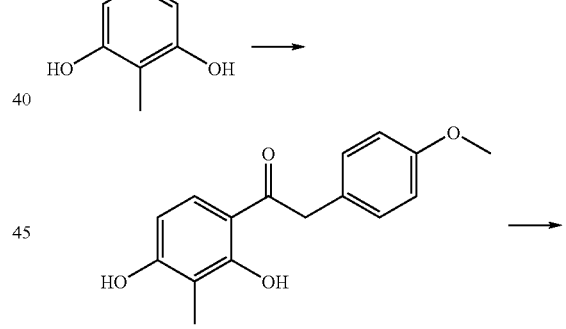
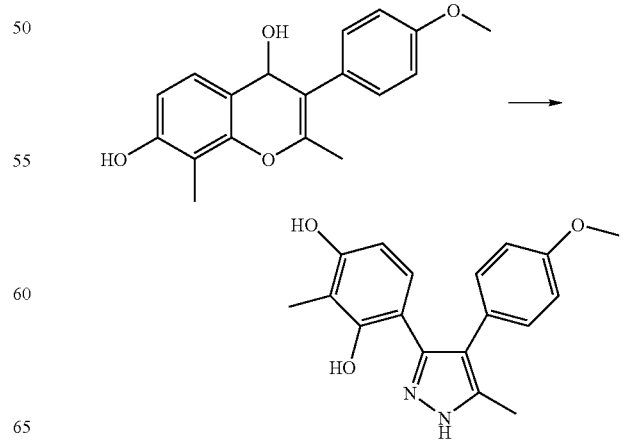

Scheme 20: Synthesis of 4'fluoro-2'-phenol
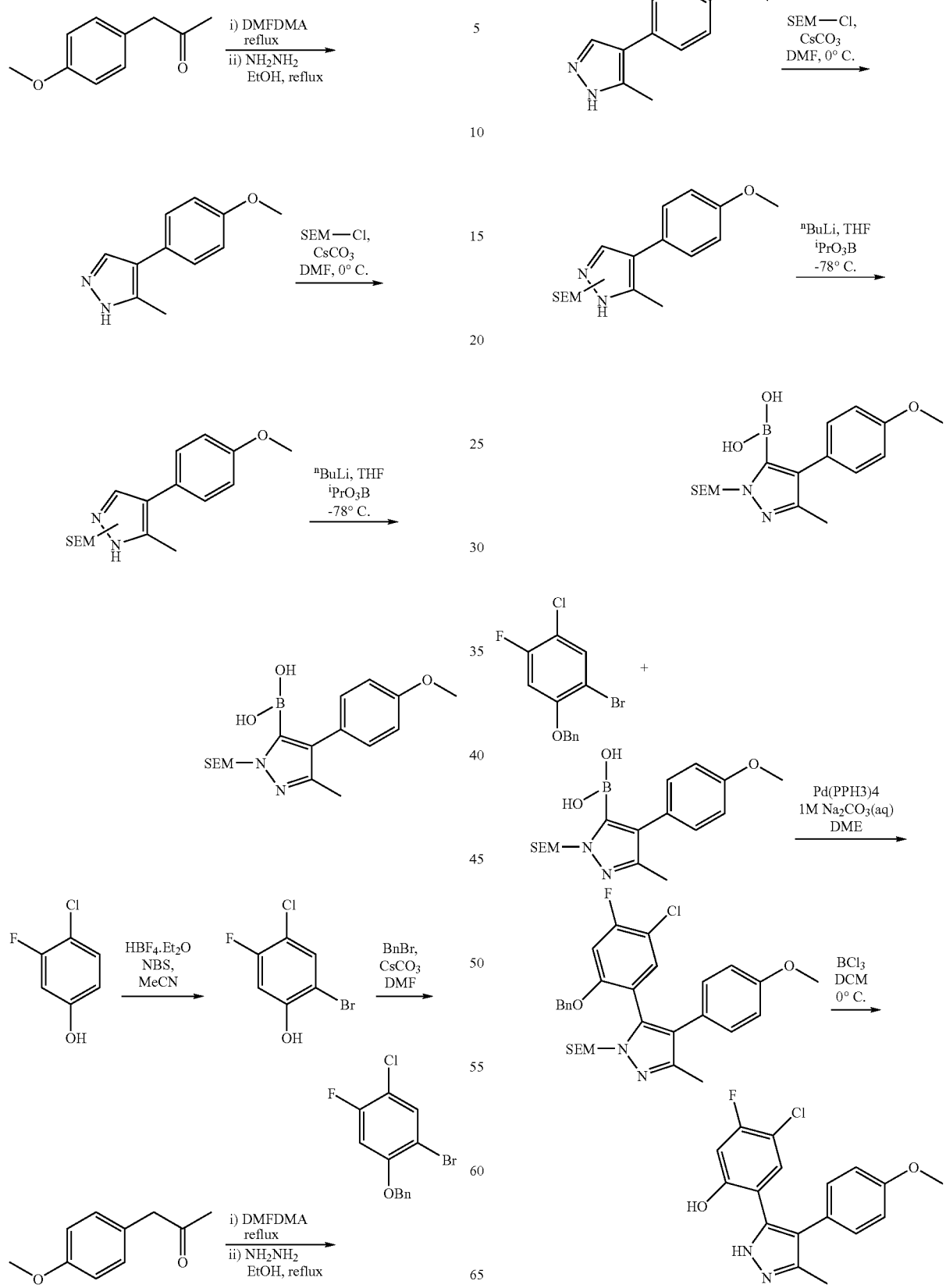

Scheme 21: Synthesis of Fluorescence Probes
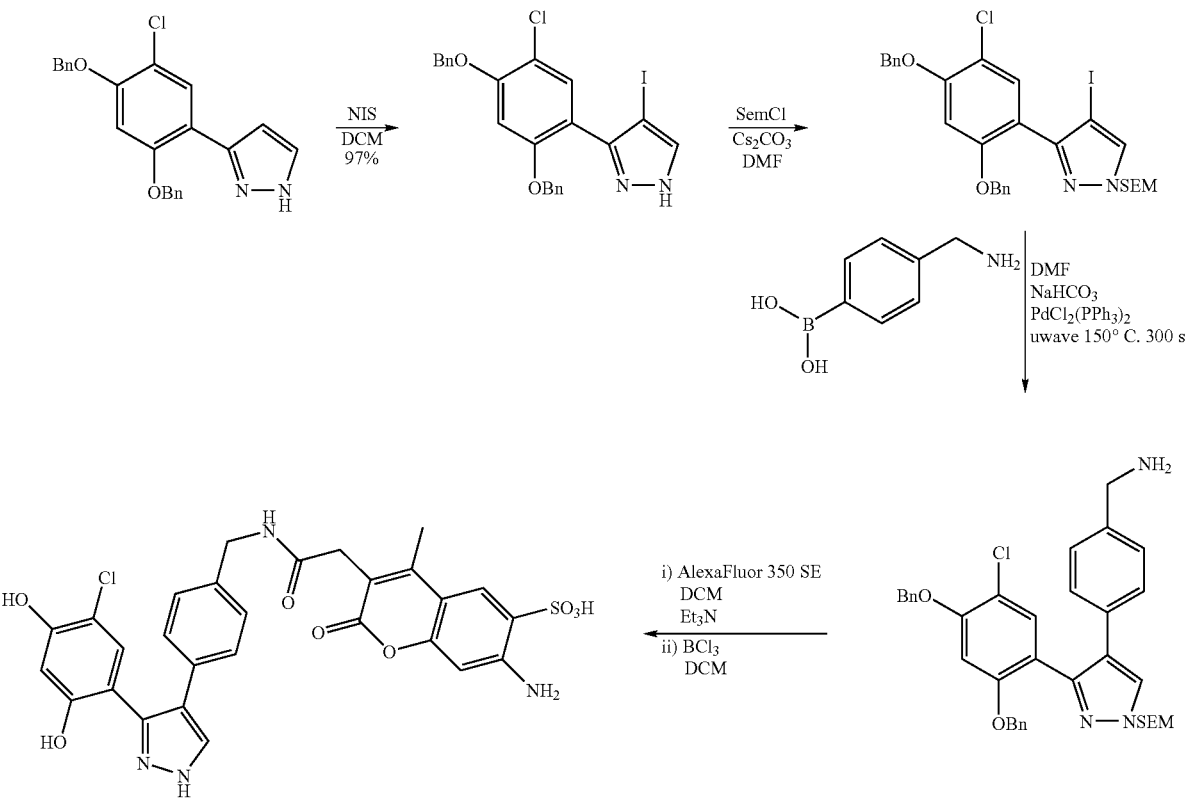
Scheme 22: Synthesis of methyl-aminopyrimidine
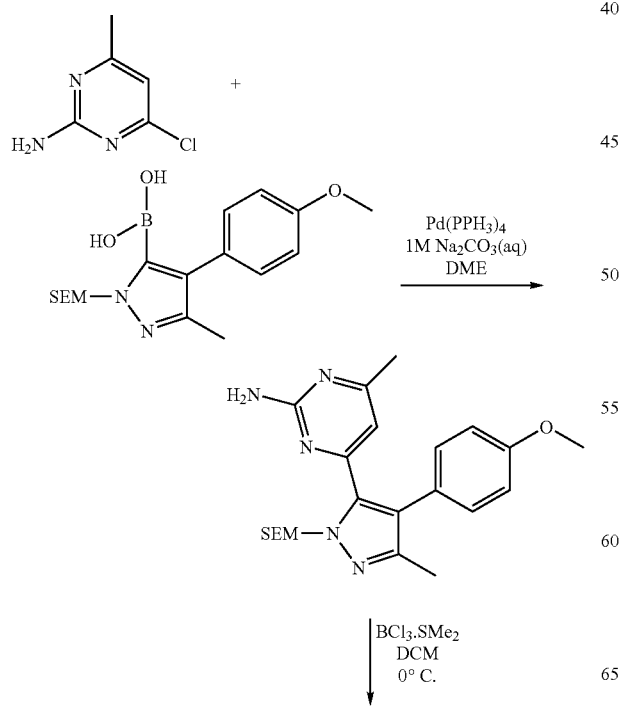
Scheme 23: Synthesis of aminopyrimidine
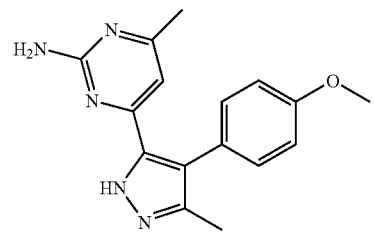

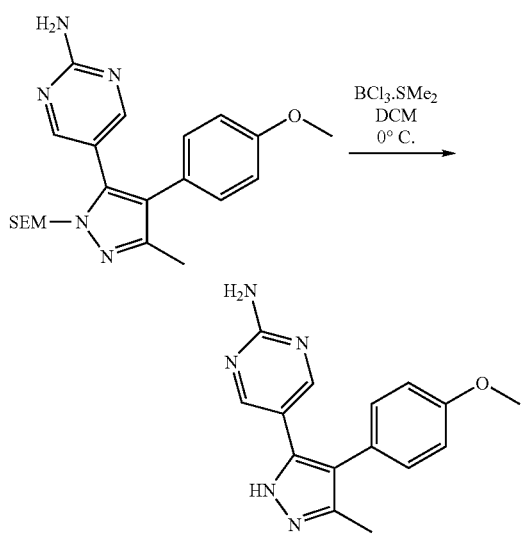

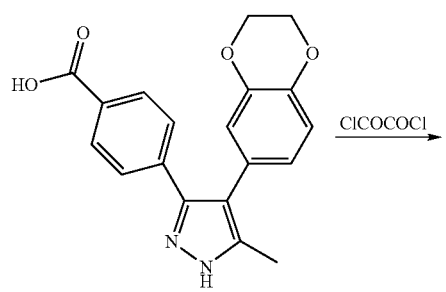

Example 149

Scheme 24:

General Procedure of the Preparation of the Corresponding Acetyl Chlorides

The acid (e.g. Example 149) (ca. 5 mg) was dissolved in dried THF (2 mL); oxalyl chloride (2 mole-equiv) was added and followed by a drop of DMF. The solution was stirred at rt for a hour and then ready to be used.

General Procedure of the Preparation of the Corresponding Acetamides

To the solution of the acid chloride in THF, conc. $NH_3$ (½ mL) or the corresponding amines (1.5 mole-equiv), triethylamine (1.5 mole-equiv) and few crystals of DMAP were added. The solution was refluxed for one hour. It was then diluted with water (3 mL) and extracted with EtOAC (3×3 mL). The combined organic layers were washed with NaCl solution and dried with $Na_2SO_4$. After evaporation of the solvent, an oil was obtained which then was purified by chromatography; eluted with EtOAc:MeOH (7:1).

Scheme 25: Synthesis of 5-position analogues

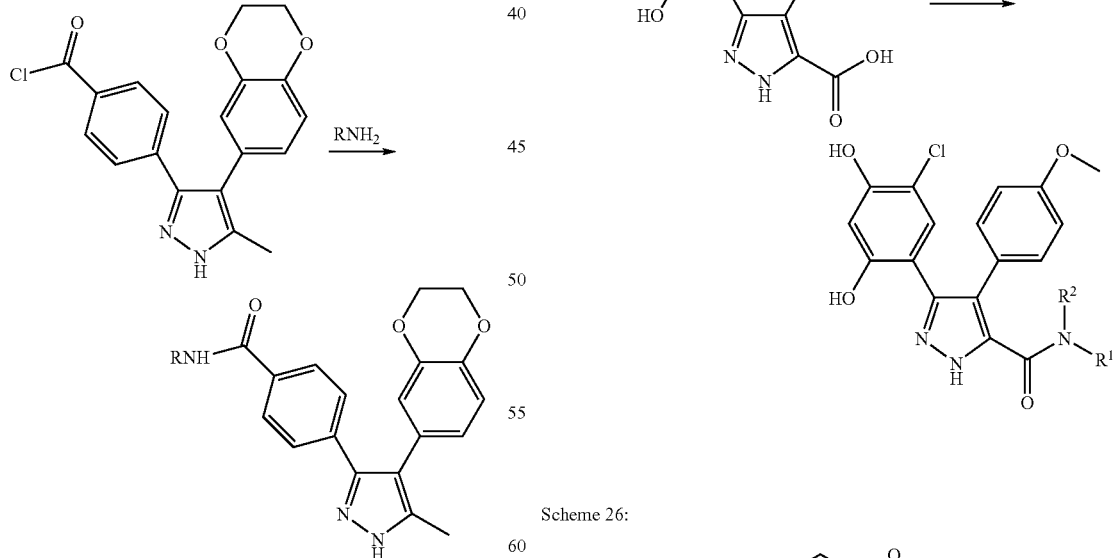

Scheme 26:

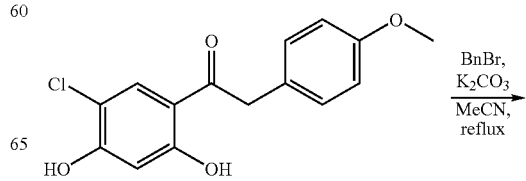

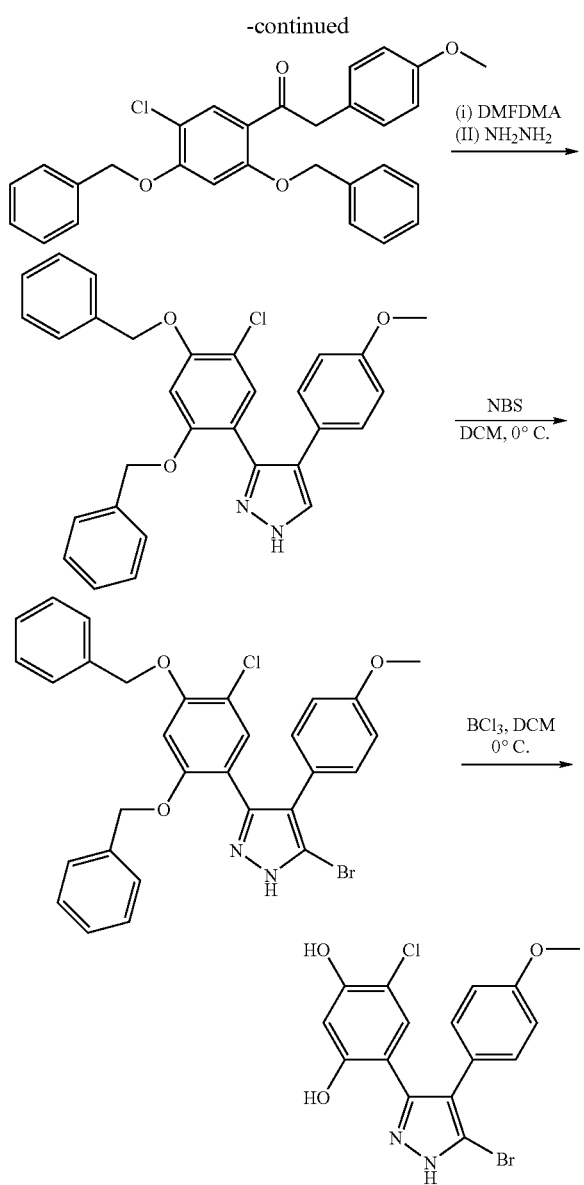

Uses

The present invention provides active compounds, specifically, active 3,4-diarylpyrazoles, as described herein, which are capable of inhibiting HSP90.

The present invention also provides methods of inhibiting HSP90, in vitro or in vivo, comprising contacting a cell with an effective amount of an active compound, as described herein. In one embodiment, the method is performed in vitro. In one embodiment, the method is performed in vivo.

The term "inhibiting HSP90," as used herein, includes: inhibiting HSP90 activity; inhibiting the formation of HSP90 complexes; inhibiting the activity of HSP90 complexes; inhibiting the ability of HSP90 to act upon a client protein; inhibiting the ability of HSP90 to act as a chaperone to a client protein; inhibiting the ability of HSP90 to facilitate conformational change (e.g., folding) of a client protein.

For example, one mode of HSP90 inhibition involves compounds which bind (e.g., competitively) at an HSP90 ATP binding site. Another mode involves compounds which instead, or in addition, bind elsewhere on the HSP90 molecule, on a client protein, on a co-chaperone, or a combination thereof.

The term "active," as used herein, pertains to compounds which are capable of inhibiting HSP90, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound inhibits HSP90 activity. For example, assays which may conveniently be used in order to assess the HSP90 inhibition offered by a particular compound are described in the examples below.

The present invention also provides active compounds which inhibit the ATPase activity of HSP90.

The present invention also provides methods of inhibiting the ATPase activity of HSP90, in vitro or in vivo, comprising contacting a cell with an effective amount of an active compound, as described herein. In one embodiment, the method is performed in vitro. In one embodiment, the method is performed in vivo.

One of ordinary skill in the art is readily able to determine whether or not a candidate compound inhibits the ATPase activity of HSP90. For example, assays which may conveniently be used in order to assess the inhibition offered by a particular compound are described in the examples below.

The present invention also provides methods of inhibiting HSP90 in a cell, comprising contacting said cell with an effective amount of an active compound, preferably in the form of a pharmaceutically acceptable composition. Such a method may be practised in vitro or in vivo.

The present invention also provides active compounds which (a) inhibit cell proliferation; (b) inhibit cell cycle progression; (c) promote apoptosis; or (d) a combination of one or more of these.

Thus, the present invention also provides methods of (a) inhibiting cell proliferation; (b) inhibiting cell cycle progression; (c) promoting apoptosis; or (d) a combination of one or more of these, in vitro or in vivo, comprising contacting a cell with an effective amount of an active compound, as described herein.

The present invention also provides active compounds which are useful in the treatment of a condition mediated by HSP90.

The term "a condition mediated by HSP90," as used herein pertains to a condition in which HSP90 and/or the action of HSP90 is important or necessary, e.g., for the onset, progress, expression, etc. of that condition. Examples of conditions mediated by HSP90 include, but are not limited to, a condition characterised by HSP90 action upon a client protein which drives that condition; a condition characterised by one or more client proteins which are acted upon by HSP90; a condition driven by one or more proteins, which proteins are HSP90 client proteins, and which proteins could not drive the condition in the absence of action (e.g., chaperoning) by HSP90; a condition driven by one or more proteins, which proteins are HSP90 client proteins, and the action (e.g., chaperoning) by HSP90 in order to drive the condition.

Examples of such conditions include, but are not limited to: cancer; immunosuppressive applications such auto-immune disease; arthritis; prion diseases (e.g., Creutzfeld Jacob Disease (CJD), variant CJD); other diseases associated with defects in protein folding and aggregation (e.g., Alzheimer's disease, Huntingdon's disease).

For example, many oncoproteins are HSP90 client proteins. In the absence of the chaperoning action of HSP90, these proteins are degraded, for example, by ubiquitin dependent proteasome degradation. Similarly, LCK protein, characteristic of many autoimmune diseases, is also an HSP90 client protein. In the absence of the chaperoning action of HSP90, LCK levels are reduced.

Thus, in one embodiment, the present invention provides active compounds which are anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

One of ordinary skill in the art is readily able to determine whether or not a candidate compound treats a cancerous condition for any particular cell type. For example, assays which may conveniently be used to assess the activity offered by a particular compound are described in the examples below.

The present invention also provides active compounds which are antiproliferative agents. The term "antiproliferative agent" as used herein, pertain to a compound which treats a proliferative condition (i.e., a compound which is useful in the treatment of a proliferative condition).

One of ordinary skill in the art is readily able to determine whether or not a candidate compound treats a proliferative condition for any particular cell type. For example, assays which may conveniently be used to assess the activity offered by a particular compound are described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

Any type of cell may be treated, including but not limited to, lung, gastrointestinal (including, e.g., bowel, colon), breast, ovarian, prostate, liver (hepatic), kidney (renal), bladder, pancreas, brain, and skin.

The invention further provides a method of treatment of the human or animal body, the method comprising administering to a subject in need of treatment a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

The invention further provides active compounds for use in a method of treatment of the human or animal body, for example, in the treatment of a condition mediated by HSP90, such as cancer or other condition as described above.

The invention further provides the use of an active compound for the manufacture of a medicament, for example, for the treatment of a condition mediated by HSP90, such as cancer or other condition as described above.

Active compounds may also be used as cell culture additives to inhibit HSP90.

Active compounds may also be used, as described above, in combination therapies, that is, in conjunction with other agents, for example, cytotoxic agents.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other HSP90 inhibitors, other anticancer agents, etc.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fern, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one preferred embodiment, the subject is a human.

Formulations

While it is possible for the active ingredient to be administered alone, it is preferable to present it as a pharmaceutical composition (e.g., formulation) comprising at least one active ingredient, as defined above, together with one or more pharmaceutically acceptable carriers, excipients, buffers, adjuvants, stabilisers, or other materials well known to those skilled in the art and optionally other therapeutic agents.

Thus, the present invention further provides pharmaceutical compositions, as defined above, and methods of making a pharmaceutical composition comprising admixing at least one active ingredient, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations may be in the form of liquids, solutions, suspensions, emulsions, tablets, lozenges, granules, powders, capsules, cachets, pills, ampoules, suppositories, pessaries, ointments, gels, pastes, creams, sprays, foams, lotions, oils, boluses, electuaries, or aerosols.

Formulations suitable for oral administration (e.g., by ingestion) may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, paste, gel, spray, aerosol, or oil. Alternatively, a formulation may comprise a patch or a dressing such as a bandage or adhesive plaster impregnated with active ingredients and optionally one or more excipients or diluents.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active ingredient.

Formulations suitable for topical administration via the skin include ointments, creams, and emulsions. When formulated in an ointment, the active ingredient may optionally be employed with either a paraffinic or a water-miscible ointment base. Alternatively, the active ingredients may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active ingredient in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freese-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active ingredient is a salt, an ester, prodrug, or the like, the amount administered is calculated on the basis the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound, etc.

The written instructions may also include a list of indications for which the active ingredient is a suitable treatment.

EXAMPLES

The following are examples are provided solely to illustrate the present invention and are not intended to limit the scope of the invention, as described herein. Some examples were purchased from commercial sources. Mass spec data are given in the above table for those examples.

Preparation of Compounds of the Invention

General procedures All reagents obtained from commercial sources were used without further purification. Anhydrous solvents were obtained from commercial sources and used without further drying. Flash chromatography was carried out with silica gel 60, 0.015–0.040 mm, (MERCK). Thin layer chromatography was carried out on silica gel 60 $F_{254}$ aluminium plates (MERCK). Compounds of the invention were characterised by LC/MS using a supelco DISCOVERY $C_{18}$ 5 cm×4.6 mm i.d, 5 μm column, gradient A: MeOH, C: 0.1% Formic acid in $H_2O$ [0 min 10% A 90% C, 0.5 min 10% A 90% C, 6.5 min 90% A 10% C, 10 min 90% A 10% C, 10.5 min 10% A 90% C, 12 min 10% A 90% C], flow rate 1 ml/min, electrospray ionisation, scanning 20–850 m/z, UV λ: 254 nm or a HP1100 machine using a Luna 3 μm, C18(2), 30 mm×4.6 mm i.d. column from Phenomenex, temperature 22° C., using the following solvents: A—Water+10 mmol ammonium acetate+0.08% (v/v) formic acid and B—Acetonitrile+0.08% (v/v) formic acid, flow rate 2 mL/min.

Gradient:

| Time (mins) | % Solvent A | % Solvent B |
|---|---|---|
| 0 | 95 | 5 |
| 0.25 | 95 | 5 |
| 2.50 | 5 | 95 |
| 3.65 | 5 | 95 |
| 3.75 | 95 | 5 |

Total acquisition time is 3.75 minutes

Detection: UV detection at 230 nm, 254 nm and 270 nm

Mass spec: HP1100 MSD, Series A

Ionisation is positive ion electrospray

Molecular weight scan range is 120–1000

Nuclear magnetic resonance spectroscopy (NMR) was carried out using a 300 or 400 MHz Bruker and were recorded in deuteriated solvents.

Microwave experiments were conducted using a CEM Discover Synthesis Unit or Smith Personal Synthesiser. These machines provide a continuous focused microwave delivery system.

For the CEM system the power output can be varied from 0 to 300 W. Reactions were performed in glass vessels (ca. 10 ml) sealed with a septum. The pressure was monitored by a gauge needle penetrated through the septum, and the temperature by an infrared probe at the bottom of the glass vessel. All experiments were performed under stirring option. Melting points were determined with an Electrothermal apparatus and are uncorrected. All the yields have not been optimised.

EXAMPLES

Preparation of Phenylacetic Acids for Examples 49, 61, 62, 63, 68, 70, 71, 153–157

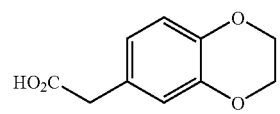

2,3-Dihydro-benzo[1,4]dioxin-6-yl)-acetic acid—3,4-Dihydroxyphenyl acetic acid (5.08 g, 30.2 mmol) and potassium carbonate (12.5 g, 3.0 equiv) were dissolved in a mixture of acetone (80 ml) and water (80 ml) and refluxed for 1 hour before 1,2-dibromoethane (3.4 ml, 1.3 equiv) was added. The mixture was then refluxed for 36 hrs with rapid stirring. After cooling the acetone was removed under vacuum and the neutrals extracted with ether (1×50 ml). The aqueous layer was acidified with 3M HCl and extracted with EtOAc (40 ml×3), the last extraction being performed after the aqueous layer had been saturated with NaCl. The EtOAc extractions were combined, dried over $Na_2SO_4$ and the solvent removed to leave a brown viscous oil. This was dissolved in a small amount of DCM and purified by column chromatography using a 95/5 DCM/EtOH mixture as the elution solvent. The appropriate fractions provided 2.8 g (48% yield) of the product as an off white coloured powder.

$\delta_H$ ($CDCl_3$), 8.86 (1H, broad, $CO_2H$), 6.67 (3H, m, Ar—H), 4.16 (4H, s, O—$CH_2CH_2$—O), 3.45 (2H, s, $CH_2CO_2H$). LCMS $t_R$=5.38, MS m/z 193.3 [M–H]⁻.

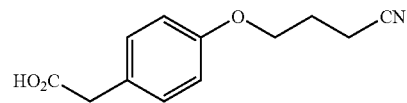

[4-(3-Cyano-propoxy)-phenyl]-acetic acid—4-hydroxyphenyl acetic acid (3.5 g, 23 mmol) and potassium hydroxide (3.9 g, 3.0 equiv.) were dissolved in MeOH (100 ml) and stirred for 1 hour before the 4-bromobutyronitrile (10 g, 3 equiv.) was added. The mixture was refluxed overnight before more KOH (3.7 g) in MeOH was added and refluxed for a further hour before cooling. The mixture was poured into water (100 ml), washed with EtOAc (2×20 ml), acidified using 5M HCl. The resulting white preciptate was filtered off and the filtrate extracted with DCM (2×30 ml). The DCM extractions were combined, washed with brine, dried over $Na_2SO_4$ and evaporated to dryness provided 3.78 g (75% yield) of the pure product as a white powder.

$\delta_H$ ($CDCl_3$), 7.24 (2H, d, Ar—H), 6.86 (2H, d, Ar—H), 4.11 (2H, t, $OCH_2$), 3.61 (2H, s, $CH_2CO_2H$), 2.60 (2H, t, $CH_2CN$), 2.10 (2H, m, $CH_2$ $CH_2CH_2$). LCMS $t_R$=5.54, MS m/z 218.2 [M–H]⁻, 220.3 [M+H]⁺.

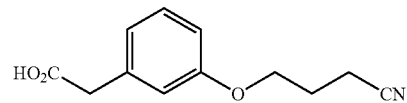

[3-(3-Cyano-propoxy)-phenyl]-acetic acid—3-Hydroxyphenyl acetic acid (0.74 g, 4.9 mmol) and potassium hydroxide (0.76 g, 2.8 equiv.) were dissolved in MeOH (30 ml) and stirred for 1 hour before the 4-bromobutyronitrile (2.45 g, 3.4 equiv.) was added. The mixture was refluxed overnight before more KOH (4 g) in MeOH was added and refluxed for a further hour before cooling. The mixture was poured into water (100 ml), extracted with EtOAc (2×20 ml), acidified using 5M HCl and extracted again this time with DCM (2×30 ml). The DCM extractions were combined, washed with brine, dried using sodium sulfate and evaporated to dryness to provide 0.65 g (61% yield) the product as a white powder that required no further purification.

$\delta_H$ (CDCl$_3$), 7.18 (1H, m, Ar—H), 6.76 (3H, m, Ar—H), 4.00 (2H, t, OCH$_2$), 3.55 (2H, s, CH$_2$CO$_2$H), 2.51 (2H, t, CH$_2$CN), 2.06 (2H, m, CH$_2$ CH$_2$CH$_2$).

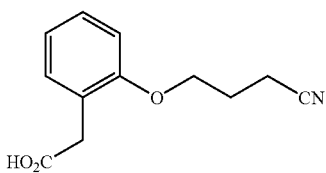

[2-(3-Cyano-propoxy)-phenyl]-acetic acid—The same method was used as above except that 2-hydroxyphenyl acetic acid (2.48 g, 16.8 mmol) was used. The DCM extracts provided 0.19 g (18%) of the product as a light yellow coloured oil.

$\delta_H$ (CDCl$_3$), 7.18 (2H, m, Ar—H), 6.85 (2H, m, Ar—H), 4.03 (2H, t, OCH$_2$), 3.58 (2H, s, CH$_2$CO$_2$H), 2.51 (2H, t, CH$_2$CN), 2.05 (2H, m, CH$_2$ CH$_2$CH$_2$).

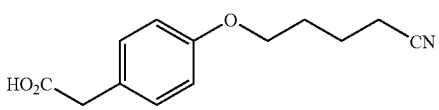

[4-(4-Cyano-butoxy)-phenyl]-acetic acid—The same method was used as described above except that 4-hydroxyphenyl acetic acid (1.0 g, 6.6 mmol), potassium hydroxide (0.77 g, 2.1 equiv.) and 5-bromovaleronitrile (3.0 ml, 3.8 equiv.) were used. The DCM extracts provided 1.18 g (77%) of the product as a bright white crystalline powder.

$\delta_H$ (CDCl$_3$), 7.23 (2H, d, Ar—H), 6.86 (2H, d, Ar—H), 4.02 (2H, t, OCH$_2$), 3.61 (2H, s, CH$_2$CO$_2$H), 2.47 (2H, t, CH$_2$CN), 1.94 (2H, m, CH$_2$ CH$_2$CH$_2$) 1.78 (2H, m, CH$_2$ CH$_2$CH$_2$). LCMS t$_R$=6.04, MS m/z 232.1 [M–H]$^-$.

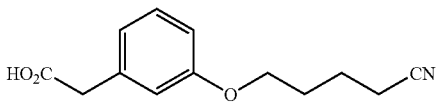

[3-(4-Cyano-butoxy)-phenyl]-acetic acid—The same method was used as described above except that 3-hydroxyphenyl acetic acid (1.0 g, 6.6 mmol), potassium hydroxide (0.77 g, 2.1 equiv.) and 5-bromovaleronitrile (0.79 ml, 1 equiv.) were used. The DCM extracts provided 0.98 g (63%) of the product as a bright white crystalline powder.

$\delta_H$ (CDCl$_3$), 7.17 (1H, m, Ar—H), 6.75 (3H, m, Ar—H), 3.93 (2H, t, OCH$_2$), 3.54 (2H, s, CH$_2$CO$_2$H), 2.37 (2H, t, CH$_2$CN), 1.84 (4H, m, CH$_2$ CH$_2$CH$_2$). LCMS t$_R$=5.98, MS m/z 232.1 [M–H]$^-$.

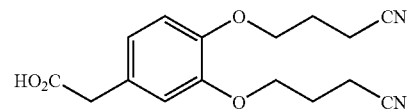

[3,4-Bis-(3-cyano-propoxy)-phenyl]-acetic acid—3,4-Dihydroxyphenylacetic acid (2.4 g, 14 mmol) and potassium carbonate (5.9 g, 3.3 equiv.) were dissolved in a 1:1 acetone/water solvent mixture and refluxed for 1 Hr before the 4-bromobutyronitrile (4.9 g, 2.3 equiv.) was added and the mixture refluxed for a further 35 Hours with vigorous stirring. After cooling the acetone was removed by evaporation under vacuum and more water (20 ml) was added. The solution was washed with ether (2×20 ml), acidified using 5M HCl, and extracted with EtOAc (2×25 ml). The aqueous layer was saturated with solid NaCl and extracted again with EtOAc (20 ml). These extracts were combined, washed with brine, dried over Na$_2$SO$_4$, and evaporated to dryness and the residue purified by column chromatography using a mixture of DCM:EtOH (95/5) as the elution solvent. The appropriate fractions provided 2.35 g (54% yield) of the product as a white crystalline solid.

$\delta_H$ (CDCl$_3$), 6.78 (3H, s, Ar—H), 4.03 (4H, t, OCH$_2$), 3.51 (2H, s, CH$_2$CO$_2$H), 2.54 (4H, t, CH$_2$CN), 2.11 (4H, m, CH$_2$ CH$_2$CH$_2$). LCMS t$_R$=5.42, MS m/z 301.0 [M–H]$^-$.

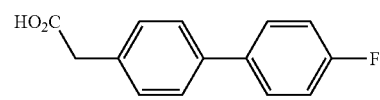

(4'-Fluoro-biphenyl-4-yl)-acetic acid (Adapted from Gala, D., Stamford, A., Jenkins, J. & Kugelman M., *Org. Proc. Res. & Dev,* 1997, 1, 163–164.)-4-Bromophenylacetic acid (0.7 g, 3.3 mmol) and 4-fluoroboronic acid (0.5 g, 1.1 equiv) were dissolved in a mixture of EtOH (2 ml) and H$_2$O (5 ml) before 5% Palladium on carbon (0.16 g) was added to the stirred solution (Slightly more EtOH may be added to aid dissolution of the acids). Sodium carbonate (0.4 g, 1.3 equiv.) was dissolved in a minimum amount of water and added to the reaction mixture which was then split into to equal measures and sealed, with a magnetic stirring bar into two microwave reactor tubes. These were heated to, and held at 65° C. for 25 minutes using a power of 15 W, whilst under vigorous stirring. After cooling the two solutions were combined, filtered and the tubes and solid washed with a 1:1 mixture of EtOH/0.1M NaOH. The volatile components of the filtrate were evaporated off and the reminaing aqueous solution acidified where upon a precipitate formed. This was filtered off, washed with a small amount of water and dried under vacuum in the presence of P$_2$O$_5$ to provide 0.59 g (79% yield) of the product as a white powder.

$\delta_H$ (d$_6$-DMSO), 7.69 (2H, m, Ar—H), 7.55 (2H, d, Ar—H), 7.27 (4H, m, Ar—H), 3.56 (2H, s, CH$_2$CO$_2$H). LCMS t$_R$=7.43, MS m/z 228.8 [M–H]$^-$.

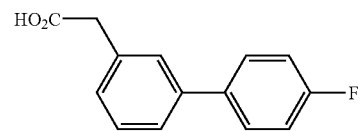

(4'-Fluoro-biphenyl-3-yl)-acetic acid—The procedure as described in the preceding reaction using 3-bromophenyl acetic acid (0.5 g, 2.3 mmol) was employed to provide 0.42 g (78% yield) as white crystals.

$\delta_H$ (d$_6$-DMSO), 7.67 (2H, m, Ar—H), 7.49 (2H, m, Ar—H), 7.33 (4H, m, Ar—H), 3.56 (2H, s, CH$_2$CO$_2$H). LCMS t$_R$=7.37, MS m/z 229.1 [M–H]$^-$.

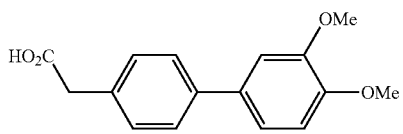

(3',4'-Dimethoxy-biphenyl-4-yl)-acetic acid—The procedure as describe above using 4-bromophenylacetic acid (0.5 g, 2.3 mmol) and 3,4-dimethoxyphenyl boronic acid (0.55 g, 1.3 equiv.) was employed to provide 0.47 g (74% yield) as a white powder.

$\delta_H$ (d$_6$-DMSO), 7.57 (2H, d, Ar—H), 7.31 (2H, d, Ar—H), 7.16 (2H, d, Ar—H), 7.02 (1H, d, Ar—H), 3.84 (3H, s, OCH$_3$), 3.79 (3H, s, OCH$_3$), 3.58 (2H, s, CH$_2$CO$_2$H). LCMS t$_R$=6.83, MS m/z 270.9 [M–H]$^-$.

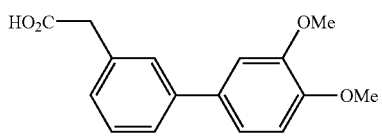

(3',4'-Dimethoxy-biphenyl-3-yl)-acetic acid—The procedure as described above using 3-bromophenylacetic acid (0.5 g, 2.3 mmol) was employed to provide 0.29 g (45% yield) as a white powder.

$\delta_H$ (d$_6$-DMSO), 7.51 (2H, d, Ar—H), 7.34 (1H, t, Ar—H), 7.15 (3H, m, Ar—H), 7.00 (1H, m, Ar—H), 3.84 (3H, s, OCH$_3$), 3.79 (3H, s, OCH$_3$), 3.58 (2H, s, CH$_2$CO$_2$H). LCMS t$_R$=6.83, MS m/z 271.0 [M–H]$^-$.

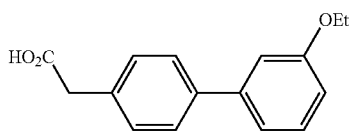

(3'-Ethoxy-biphenyl-4-yl)-acetic acid—The procedure as described above using 4-bromophenyl acetic acid (0.6 g, 2.8 mmol) and 3-ethoxyphenyl boronic acid (0.51 g, 1.1 equiv.) was employed to provide 0.47 g (66% yield) as a white powder.

$\delta_H$ (d$_6$-DMSO), 7.59 (2H, d, Ar—H), 7.33 (2H, d, Ar—H), 7.17 (2H, m, Ar—H), 6.90 (1H, m, Ar—H), 4.08 (2H, q, CH$_3$CH$_2$), 3.58 (2H, s, CH$_2$CO$_2$H), 1.35 (3H, t, CH$_3$CH$_2$).

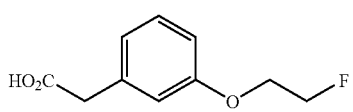

[3-(2-Fluoro-ethoxy)-phenyl]-acetic acid—The procedure as described above using 3-hydroxyphenyl acetic acid (1.0 g, 6.6 mmol) and 1-bromo-2-fluoroethane (1.1 mL, 2.3 equiv.) was employed to provide 0.61 g (47% yield) as a white powder.

$\delta_H$ (d$_6$-Acetone), 10.76 (1H, s broad, CO$_2$H), 7.27 (1H, t, Ar—H), 6.90 (3H, m, Ar—H), 4.76 (2H, 2t, J=4 Hz, J$_{H-F}$=48 Hz, CH$_2$CH$_2$F), 4.27 (2H, 2t, J=4 Hz, J$_{H-F}$=26 Hz, CH$_2$CH$_2$F), 3.63 (2H, s, CH$_2$CO$_2$H). LCMS t$_R$=5.37, MS m/z (Parent ion not observed).

The Following Reactions Refer to Scheme 10:
General Synthesis of Dihydroxyphenyl Ketones for Examples 49, 53–63, 69, 70, 73, 78, 79

Synthesis of 1-(2,4-Dihydroxy-phenyl)-2-phenyl-ethanone

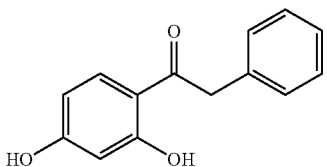

Phenylacetic acid (0.82 g, 6 mmol), resorcinol (0.66 g, 6 mmol), and boron trifluoride etherate (4 ml, 33 mmol) were mixed together and heated to 80° C. under argon. The mixture was then poured into 10% NaOAc (100 ml) and after standing for two hours a brown solid precipitate formed. This was purified by flash chromatography to give the required compound as a white solid (1.19 g, 87%); R$_f$ 0.5 hexane/ethyl acetate (70/30).

$\nu_{(max)}$ (Film) cm-1: 3349 (OH), 1700 (C=O). $\delta_H$ (DMSO): 10.71 (1H, s, OH), 8.26 (2H, d, J=8 Hz, ArH), 7.27 (5H, m, ArH), 6.42 (1H, dd, ArH), 6.27 (1H, s, ArH), 4.29 (2H, s, CH$_2$). LCMS t$_R$ 6.98, m/z 227 [M–H]$^-$.

Synthesis of 1-(5-Chloro-2,4-dihydroxy-phenyl)-2-phenyl-ethanone

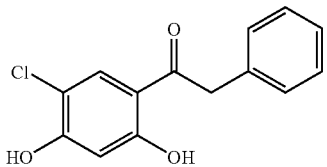

This compounds was synthesised in the same manner as described above. Phenylacetic acid (4.71 g, 34.6 mmol), 4-chlororesorcinol (5 g, 34.6 mmol), boron trifluoride etherate (30 ml). After standing for two hours an orange precipitate formed. This was purified by flash chromatography to give the required compound as a white solid (7.2 g, 79.3%); R$_f$ 0.9 hexane/ethyl acetate (20/80)].

$\delta_H$ (DMSO): 8.01 (1H, s, ArH), 7.28 (5H, m, ArH), 6.47 (1H, s, ArH), 4.33 (2H, s, CH$_2$). $\delta_c$ (DMSO): 201.6 (C=O), 162.8, 160.6, 135.3, 132.5, 129.8, 128.7, 126.9, 113.3, 112.1, 104.1 (CAr), 44.8 (CH$_2$). LCMS t$_R$ 7.55, m/z 261 [M–H]$^-$.

Synthesis of 2-(4-Bromo-phenyl)-1-(5-chloro-2,4-dihydroxy-phenyl)-ethanone

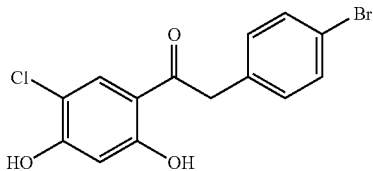

This compounds was synthesised in the same manner as described above. 4-Bromophenylacetic acid (7.44 g, 34.6 mmol), 4-chlororesorcinol (5 g, 34.6 mmol), boron trifluoride etherate (30 ml). After standing for two hours an orange precipitate formed. This was purified by flash chromatography to give the required compound as an off white solid (10.5 g, 89%); $R_f$ 0.9 hexane/ethyl acetate (20/80).

$\delta_H$ (DMSO): 8.01 (1H, s, ArH), 7.49 (2H, d, J=8 Hz, ArH), 7.22 (2H, d, J=8 Hz, ArH), 6.45 (1H, s, ArH), 4.29 (2H, s, CH$_2$). $\delta_c$ (CDCl$_3$): 200.9 (C=O), 162.5, 160.3, 134.7, 132.4, 132.0, 131.4, 120.2, 113.6, 112.0, 104.1 (CAr), 44.3 (CH$_2$). LCMS $t_R$ 8.12, m/z 339/341/343 [M−H]$^-$.

Synthesis of 2-(2-Bromo-phenyl)-1-(5-chloro-2,4-dihydroxy-phenyl)-ethanone

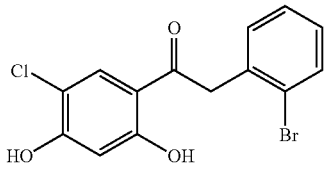

This compounds was synthesised in the same manner as described above. 2-Bromophenylacetic acid (5 g, 23.3 mmol), 4-chlororesorcinol (3.36 g, 23.3 mmol), boron trifluoride etherate (20 ml). After standing for two hours a brown precipitate formed (7.4 g, 93.3%); $R_f$ 0.4 hexane/ethyl acetate (70/30). This was shown to be the required product.
LCMS $t_R$ 7.92, m/z 339/341 [M−H]$^-$.

Synthesis of 1-(5-Chloro-2,4-dihydroxy-phenyl)-2-(2,3-dihydro-benzo[1,4]dioxin-6-yl)-ethanone

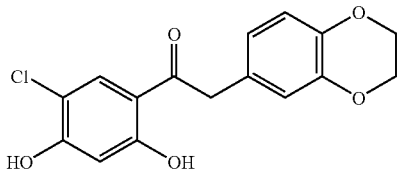

This compounds was synthesised in the same manner as described above. (2,3-Dihydro-benzo[1,4]dioxin-6-yl)-acetic acid (0.3 g, 1.55 mmol), 4-chlororesorcinol (0.22 g, 1.55 mmol), boron trifluoride etherate (3 ml). After standing for two hours a precipitate formed which was filtered, washed (water), and dried to give 1-(5-Chloro-2,4-dihydroxy-phenyl)-2-(2,3-dihydro-benzo[1,4]dioxin-6-yl)-ethanone as a white solid (0.34 g, 68.3%); $R_f$ 0.9 hexane/ethyl acetate (20/80).

$\delta_H$ (DMSO): 8.02 (1H, s, ArH), 6.80 (3H, m, ArH), 6.01 (1H, s, ArH), 4.20 (4H, s, (CH$_2$)$_2$), 4.00 (2H, s, CH$_2$). $\delta_c$ (CDCl$_3$): 198.7 (C=O), 173.0, 168.8, 164.6, 143.4, 131.3, 129.2, 122.3, 118.1, 117.2, 115.8, 108.3, 104.0 (CAr), 64.3, 43.1, 22.1. LCMS $t_R$ 7.46, m/z 319/321 [M−H]$^-$.

Synthesis of 2-(2,3-Dihydro-benzo[1,4]dioxin-6-yl)-1-(5-ethyl-2,4-dihydroxy-phenyl)-ethanone

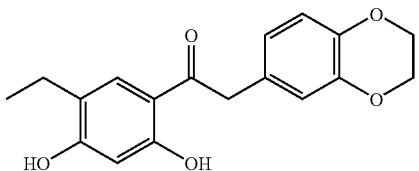

This compounds was synthesised in the same manner as described above. (2,3-Dihydro-benzo[1,4]dioxin-6-yl)-acetic acid (1.0 g, 5.15 mmol), ethyl resorcinol (0.71 g, 5.15 mmol), boron trifluoride etherate (6 ml). After standing for two hours an oil separated out. This was extracted into ethyl acetate, washed (water), dried (MgSO$_4$), and the solvent removed to give a sticky orange solid. LC-MS showed that this contained 2-(2,3-Dihydro-benzo[1,4]dioxin-6-yl)-1-(5-ethyl-2,4-dihydroxy-phenyl)-ethanone as the major component. The product was taken onto the next stage without further purification.
LCMS $t_R$ 7.69, m/z 313/315 [M−H]$^-$.

Synthesis of 4-{4-[2-(5-Chloro-2,4-dihydroxy-phenyl)-2-oxo-ethyl]-phenoxy}-butyronitrile

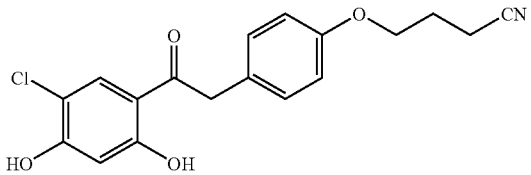

This compounds was synthesised in the same manner as described above. [4-(3-Cyano-propoxy)-phenyl]-acetic acid (0.5 g, 2.28 mmol), 4-chlororesorcinol (0.33 g, 2.28 mmol), boron trifluoride etherate (5 ml). After standing for two hours a precipitate formed which was filtered, washed (water), and dried to give 4-{4-[2-(5-Chloro-2,4-dihydroxy-phenyl)-2-oxo-ethyl]-phenoxy}butyronitrile as a white solid (0.62 g, 78.7%); $R_f$ 0.6 hexane/ethyl acetate (20/80).
LCMS $t_R$ 7.24, m/z 344/346 [M−H]$^-$.

The following reactions refer to scheme 11.
General synthesis of
7-hydroxy-2-methyl-3-phenyl-chromen-4-ones for Examples 49, 59, 69, 70

Synthesis of 7-Hydroxy-2-methyl-3-phenyl-chromen-4-one

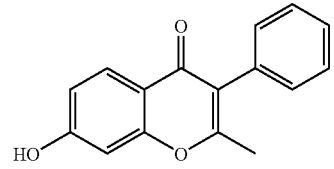

1-(2,4-Dihydroxy-phenyl)-2-phenyl-ethanone (0.5 g, 3.2 mmol) was refluxed in anhydrous DMF with acetic anhydride (1.5 ml), and anhydrous potassium carbonate (1.4 g 10.1 mmol) for 3 hrs. The solution was then poured into water and the precipitate filtered to give 7-hydroxy-2-methyl-3-phenyl-chromen-4-one as white solid (0.62 g, 66%); $R_f$ 0.75 cf SM 0.9 ethyl acetate/hexane (75/25).

$\delta_H$ (DMSO): 10.72 (1H, s, OH), 7.88 (1H, d, J=9 Hz, ArH), 7.37 (3H, m, ArH), 7.27 (2H, m, ArH), 6.92 (1H, d, J=9 Hz, ArH), 6.73 (1H, s, ArH), 2.22 (3H, s, $CH_3$). $\delta_c$ (DMSO): 175.1 (C=O), 162.9, 162.8, 157.4, 133.8, 130.9, 128.3, 127.7, 127.4, 122.5, 115.9, 115.1, 102.3 (unsaturated), 19.5 ($CH_3$). LCMS $t_R$ 7.02, MS m/z 295 $[M+H]^+$.

Synthesis of 6-Chloro-7-hydroxy-2-methyl-3-phenyl-chromen-4-one

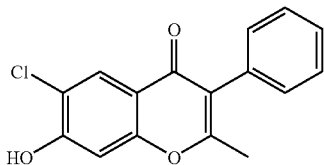

This compounds was synthesised in the same manner as described above. 1-(5-Chloro-2,4-dihydroxy-phenyl)-2-phenyl-ethanone (1.5 g, 5.7 mmol), acetic anhydride (2.0 ml), Potassium carbonate (2.1 g 15.2 mmol). 6-Chloro-7-hydroxy-2-methyl-3-phenyl-chromen-4-one was obtained as white solid (1.4 g, 85.8%).

LCMS $t_R$ 7.26, MS m/z 287 $[M+H]^+$.

Synthesis of 3-(4-Bromo-phenyl)-6-chloro-7-hydroxy-2-methyl-chromen-4-one

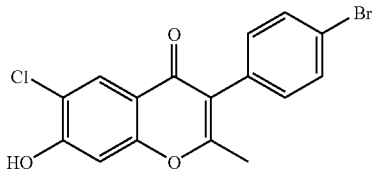

This compounds was synthesised in the same manner as described above. 2-(4-Bromo-phenyl)-1-(5-chloro-2,4-dihydroxy-phenyl)-ethanone (1.5 g, 4.4 mmol), Acetic anhydride (2.0 ml), Potassium carbonate (2.1 g 15.2 mmol). 3-(4-Bromo-phenyl)-6-chloro-7-hydroxy-2-methyl-chromen-4-one was obtained an off white solid (1.2 g, 74.5%).

LCMS $t_R$ 7.88, MS m/z 365 $[M-H]^-$.

Synthesis of 3-(2-Bromo-phenyl)-6-chloro-7-hydroxy-2-methyl-chromen-4-one

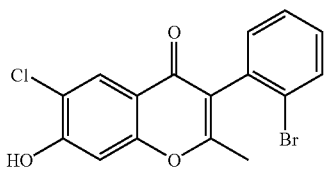

This compounds was synthesised in the same manner as described above. 2-(2-Bromo-phenyl)-1-(5-chloro-2,4-dihydroxy-phenyl)-ethanone (2.0 g, 5.88 mmol), acetic anhydride (2.0 ml), potassium carbonate (2.5 g 18.1 mmol). The white precipitate formed was shown to contain the required compound and was taken directly onto the next stage.

LCMS $t_R$ 7.51, MS m/z 365/367/369 $[M+H]^+$.

6-Chloro-3-(2,3-dihydro-benzo[1,4]dioxin-6-yl)-7-hydroxy-2-methyl-chromen-4-one

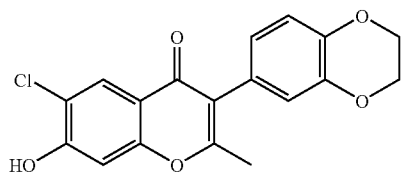

This compounds was synthesised in the same manner as described above. 1-(5-Chloro-2,4-dihydroxy-phenyl)-2-(2,3-dihydro-benzo[1,4]dioxin-6-yl)-ethanone (1.1.2.5) (0.3 g, 0.9 mmol), acetic anhydride (0.5 ml), potassium carbonate (0.5 g 3.6 mmol). 6-Chloro-3-(2,3-dihydro-benzo[1,4]dioxin-6-yl)-7-hydroxy-2-methyl-chromen-4-one was obtained an off white solid (0.3 g, 96.8%).

LCMS $t_R$ 7.16, MS m/z 343 $[M-H]^-$.

3-(2,3-Dihydro-benzo[1,4]dioxin-6-yl)-6-ethyl-7-hydroxy-2-methyl-chromen-4-one

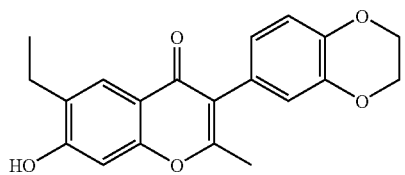

This compounds was synthesised in the same manner as described above. 2-(2,3-Dihydro-benzo[1,4]dioxin-6-yl)-1-(5-ethyl-2,4-dihydroxy-phenyl)-ethanone (1.0 g, 3.2 mmol), acetic anhydride (2.0 ml), potassium carbonate (2.1 g, 15.2 mmol). 3-(2,3-Dihydro-benzo[1,4]dioxin-6-yl)-6-ethyl-7-hydroxy-2-methyl-chromen-4-one was shown to be present in the oil product by LCMS, $R_f$ 0.8 ethyl acetate/hexane (70/30). The product was taken on to the next stage without further purification.

LCMS $t_R$ 7.41, m/z 337/339 $[M-H]^-$

4-[4-(6-Chloro-7-hydroxy-2-methyl-4-oxo-4H-chromen-3-yl)-phenoxy]-butyronitrile

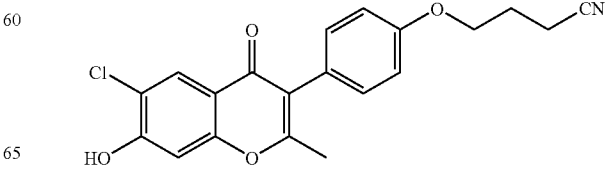

This compounds was synthesised in the same manner as described above. 4-{4-[2-(5-Chloro-2,4-dihydroxy-phenyl)-2-oxo-ethyl]-phenoxy}-butyronitrile (0.62 g, 1.8 mmol), acetic anhydride (1.0 ml), potassium carbonate (1 g, 7.2 mmol). 4-[4-(6-Chloro-7-hydroxy-2-methyl-4-oxo-4H-chromen-3-yl)-phenoxy]-butyronitrile was obtained as a white solid (0.55 g, 82.7%) R$_f$ 0.6 ethyl acetate/hexane (70/30).

LCMS t$_R$ 7.07, m/z 368/371 [M+H]$^+$.

The Following Reactions Refer to Scheme 12. One pot Synthesis of Isoflavones for Examples 50–57, 60, 62, 63, 65–68, 72–74, 77, 79, 153–157

Synthesis of 7-Hydroxy-3-phenyl-chromen-4-one

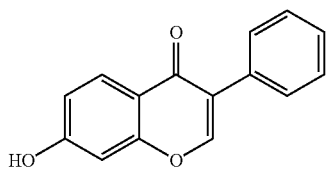

Resorcinol (0.66 g, 6 mmol), phenylacetic acid (0.816 g, 6 mmol), and boron triflouride diethyletherate (5 ml) were heated to 85° C. for 90 mins. After this time the reaction was cooled and DMF (4 ml) was added. 30 min prior to the completion of the first stage, PCl$_5$ (1.878 g, 9 mmol) was added to cool DMF (8 ml) and the mixture heated (60° C.) for 20 minutes. This was added to the solution from stage one, and the combined solution allowed to stir at room temperature for 1 hour. The reaction mixture was then poured into 1MHCl (100 ml). The precipitate formed was filtered and re-crystallized from methanol to give 7-Hydroxy-3-phenyl-chromen-4-one as a white solid (1.3 g, 91.0%); R$_f$ 0.25 ethyl acetate/hexane (30/70)].

ν$_{(max)}$ (Film) cm-1: 3195 (OH), 1621 (C═O). δ$_H$ (DMSO): 10.84 (1H, s, OH), 8.37 (1H, s, ═CH), 8.0 (1H, d, J=8 Hz, ArH), 7.55 (2H, m, ArH), 7.39 (3H, m, ArH), 6.94 (1H, d, J=8 Hz, ArH), 6.63 (1H, s, ArH). δ$_c$ (CDCl$_3$): 174.7 (C═O), 163.0, 157.8, 154.1, 132.5, 129.3, 128.4, 128.1, 127.7, 123.9, 117.0, 115.6, 102.5. LCMS t$_R$ 6.94, MS m/z 239 [M+H]$^+$.

Synthesis of 3-(4-Bromo-phenyl)-7-hydroxy-chromen-4-one

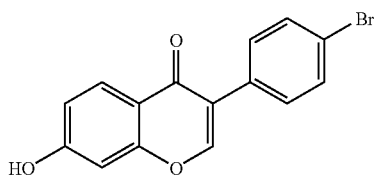

This compounds was synthesised in the same manner as described above. Resorcinol (0.66 g, 6 mmol), 4-bromophenylacetic acid (1.29 g, 6 mmol), BF$_3$Et$_2$O (4 ml), PCl$_5$ (1.9 g, 9.1 mmol), DMF (5 ml and 10 ml). The precipitate formed was filtered and re-crystallized from methanol to give 3-(4-bromo-phenyl)-7-hydroxy-chromen-4-one as a white crystalline solid (1.1 g, 57.8%); R$_f$ 0.85 ethyl acetate.

δ$_H$ (DMSO): 10.84 (1H, s, OH), 8.43 (1H, s, ═CH), 7.97 (1H, d, J=8 Hz, ArH), 7.58 (4H, m, ArH), 6.97 (1H, d, J=8 Hz, ArH), 6.88 (1H, s, ArH). δ$_c$ (DMSO): 174.5 (C═O), 163.1, 157.8, 154.4, 131.7, 131.4, 131.3, 127.7, 122.7, 121.4, 116.9, 115.7, 102.6. LCMS t$_R$ 7.63, MS m/z 317 [M+H]$^+$.

Synthesis of 3-(3,4-Dimethoxy-phenyl)-7-hydroxy-chromen-4-one

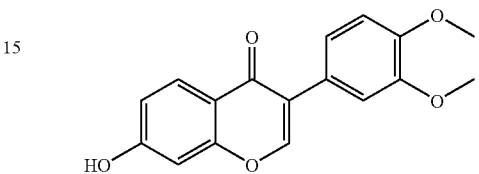

This compounds was synthesised in the same manner as described above. Resorcinol (0.66 g, 6 mmol), 3,4-dimethoxy-phenylacetic acid (1.18 g, 6 mmol), BF$_3$Et$_2$O (4 ml), PCl$_5$ (1.9 g, 9.1 mmol), DMF (5 ml and 10 ml). The precipitate formed was filtered and re-crystallized from methanol to give 3-(3,4-Dimethoxy-phenyl)-7-hydroxy-chromen-4-one as a pale orange solid (1.43 g, 80%); R$_f$ 0.9 ethyl acetate/hexane (75/25).

δ$_H$ (DMSO): 10.78 (1H, s, OH), 8.56 (1H, s, ═CH), 7.99 (1H, d, J=9 Hz, ArH), 7.00 (5H, m, ArH), 3.78 (6H, s, 2×CH$_3$). δ$_c$ (DMSO): 174.9 (C═O), 162.9, 157.7, 153.7, 148.6, 149.0, 127.6, 124.9, 123.6, 121.6, 117.0, 115.5, 113.2, 111.9, 102.5 (Unsaturated), 55.9 (CH$_3$). LCMS t$_R$ 6.51, MS m/z 299 [M+H]$^+$.

Synthesis of 6-Ethyl-7-hydroxy-3-phenyl-chromen-4-one

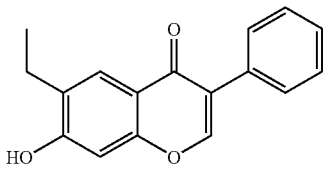

This compounds was synthesised in the same manner as described above. Ethyl resorcinol (0.83 g, 6 mmol), phenylacetic acid (0.82 g, 6 mmol), BF$_3$Et$_2$O (3.88 ml, 31.5 mmol), PCl$_5$ (1.88 g, 9 mmol), DMF (4.6 ml and 10 ml). The precipitate formed was filtered and re-crystallized from methanol to give 6-Ethyl-7-hydroxy-3-phenyl-chromen-4-one as a pale brown solid (1.4 g, 87.7%); R$_f$ 0.4 cf SM 0.5 ethyl acetate/hexane (40/60).

δ$_H$ (DMSO): 10.84 (1H, s, OH), 8.35 (1H, s, ═CH), 7.97 (1H, s, ArH), 7.54 (2H, m, ArH), 7.40 (3H, m, ArH), 6.90 (1H, s, ArH), 2.50 (2H, q, J=7 Hz, CH$_2$), 1.18 (3H, t, J=7 Hz, CH$_3$). δ$_c$ (DMSO): 174.7 (C═O), 161.0, 156.1, 153.9, 132.7, 130.5, 129.3, 128.4, 128.0, 125.3, 123.8, 116.7, 101.8 (Unsaturated carbons), 22.7 (CH$_2$), 14.1 (CH$_3$). LCMS t$_R$ 7.48, MS m/z 267 [M+H]$^+$.

Synthesis of 3-(4-Bromo-phenyl)-6-ethyl-7-hydroxy-chromen-4-one

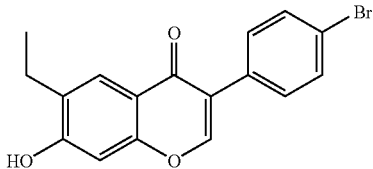

This compounds was synthesised in the same manner as described above. Ethyl resorcinol (0.83 g, 6 mmol), 4-bromophenylacetic acid (1.29 g, 6 mmol), BF$_3$Et$_2$O (5 ml), PCl$_5$ (1.99, 9.1 mmol), DMF (5 ml and 10 ml). The precipitate formed was filtered and re-crystallized from methanol to give 3-(4-bromo-phenyl)-6-ethyl-7-hydroxy-chromen-4-one as a pale pink solid (1.7 g, 82.3%); R$_f$ 0.84 ethyl acetate.

$\delta_H$ (DMSO): 10.76 (1H, s, OH), 8.30 (1H, s, =CH), 7.73 (1H, s, ArH), 7.52 (4H, m, ArH), 6.80 (1H, s, ArH), 2.53 (2H, q, J=7 Hz, CH$_2$), 1.09 (3H, t, J=7 Hz, CH$_3$). $\delta_c$ (DMSO): 174.4 (C=O), 161.1, 156.1, 154.1, 131.9, 131.4, 131.3, 130.7, 125.3, 122.6, 121.3, 116.6, 101.8, (Unsaturated carbons), 22.7 (CH$_2$), 14.1 (CH$_3$). LCMS t$_R$ 8.16, MS m/z 347 [M+H]$^+$.

Synthesis of 3-(3,4-Dimethoxy-phenyl)-6-ethyl-7-hydroxy-chromen-4-one

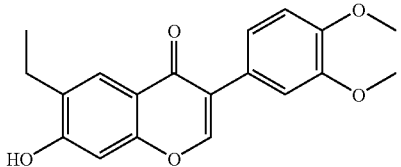

This compounds was synthesised in the same manner as described above. Ethyl resorcinol (0.83 g, 6 mmol), 3,4-dimethoxyphenylacetic acid (0.83 g, 6 mmol), BF$_3$Et$_2$O (4 ml), PCl$_5$ (1.9 g, 9.1 mmol), DMF (5 ml and 10 ml). The precipitate formed was filtered and re-crystallized from methanol to give 3-(3,4-dimethoxy-phenyl)-6-ethyl-7-hydroxy-chromen-4-one as a pale brown solid (1.8 g, 92%); R$_f$ 0.4 cf SM 0.5 ether/petroleum ether [40–60° C.] (50/50).

$\delta_H$ (DMSO): 10.70 (1H, s, OH), 8.42 (1H, s, =CH), 7.73 (1H, s, ArH), 7.10 (1H, s, ArH), 6.91 (1H, d, J=8 Hz, ArH), 6.83 (1H, d, J=8 Hz, ArH), 6.70 (1H, s, ArH), 3.69 (6H, s, OCH$_3$), 2.50 (2H, q, J=7 Hz, CH$_2$), 1.07 (3H, t, J=7 Hz, CH$_3$). $\delta_c$ (DMSO): 174.9 (C=O), 160.0, 156.0, 153.4, 148.9, 148.6, 130.4, 125.2, 125.1, 123.5, 121.5, 116.7, 113.2, 111.9, 101.7, (Unsaturated carbons), 55.9 (OCH$_3$), 22.7 (CH$_2$), 14.1 (CH$_3$). LCMS t$_R$ 7.14, MS m/z 327 [M+H]$^+$.

Synthesis of 6-Chloro-7-hydroxy-3-phenyl-chromen-4-one

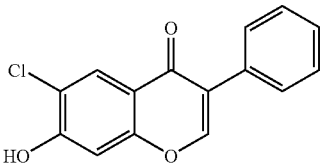

This compounds was synthesised in the same manner as described above. Chlororesorcinol (0.87 g, 6 mmol), phenylacetic acid (0.82 g, 6 mmol), BF$_3$Et$_2$O (4 ml), PCl$_5$ (1.9 g, 9.1 mmol), DMF (5 ml and 10 ml). The pink precipitate formed was filtered and re-crystallized from methanol to give 6-Chloro-7-hydroxy-3-phenyl-chromen-4-one as fine light pink crystals (1.4 g, 85%); R$_f$ 0.6 ethyl acetate/hexane (75/25).

$\delta_H$ (DMSO): 8.33 (1H, s, =CH), 7.98 (1H, s, ArH), 7.54 (2H, m, ArH), 7.43 (3H, m, ArH), 7.07 (1H, s, ArH). $\delta_c$ (DMSO): 173.9 (C=O), 158.3, 155.9, 154.5, 132.1, 129.3, 128.5, 128.2, 126.5, 123.8, 120.1, 117.5, 104.0. LCMS t$_R$ 7.25, MS m/z 273 [M+H]$^+$.

Synthesis of 3-(4-Bromo-phenyl)-6-chloro-7-hydroxy-chromen-4-one

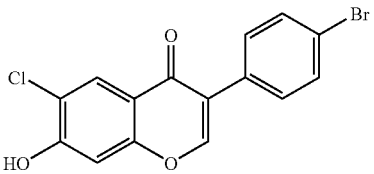

This compounds was synthesised in the same manner as described above. 4-Chlororesorcinol (0.87 g, 6 mmol), 4-bromophenyl acetic acid (1.29 g, 6 mmol), BF$_3$Et$_2$O (4 ml), PCl$_5$ (1.9 g, 9.1 mmol), DMF (5 ml and 10 ml). The precipitate formed was filtered and re-crystallized from methanol to give 3-(4-Bromo-phenyl)-6-chloro-7-hydroxy-chromen-4-one a flakey white solid (1.2 g, 56.8%); R$_f$ 0.81 ethyl acetate.

$\delta_H$ (DMSO): 8.47 (1H, s, =CH), 8.00 (1H, s, ArH), 7.60 (4H, dd, ArH), 7.07 (1H, s, ArH), $\delta_c$ (DMSO): 174.1 (C=O), 158.4, 155.9, 154.7, 131.4, 131.4, 131.3, 126.5, 122.7, 121.5, 120.2, 117.3, 104.0 (Unsaturated). LCMS t$_R$ 8.02, MS m/z 351/353 [M+H]$^+$.

Synthesis of 6-Chloro-3-(3,4-dimethoxy-phenyl)-7-hydroxy-chromen-4-one

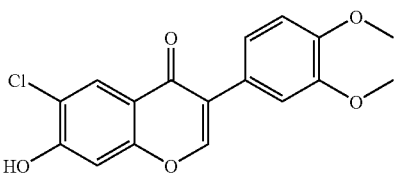

This compounds was synthesised in the same manner as described above. 4-Chlororesorcinol (0.87 g, 6 mmol), 3,4-dimethoxy-phenylacetic acid (1.18 g, 6 mmol), BF$_3$Et$_2$O (4 ml), PCl$_5$ (1.9 g, 9.1 mmol), DMF (5 ml and 10 ml). The precipitate formed was filtered and re-crystallized from methanol to give 6-Chloro-3-(3,4-dimethoxy-phenyl)-7-hydroxy-chromen-4-one an off white solid (1.4 g, 70.20%); R$_f$ 0.72 ethyl acetate.

$\delta_H$ (DMSO): 8.78 (1H, s, =CH), 7.99 (1H, s, ArH), 7.00 (4H, m, ArH), 3.78 (6H, s, 2×CH$_3$). $\delta_c$ (DMSO): 174.1 (C=O), 158.21, 155.86, 154.0, 149.0, 148.7, 126.5, 124.5, 123.5, 121.6, 120.0, 117.4, 113.1, 111.9, 103.9 (Unsaturated), 55.9 (CH$_3$). LCMS t$_R$ 6.91, MS m/z 333 [M+H]$^+$.

Synthesis of 6-Chloro-3-(2,3-dihydro-benzo[1,4]dioxin-6-yl)-7-hydroxy-chromen-4-one

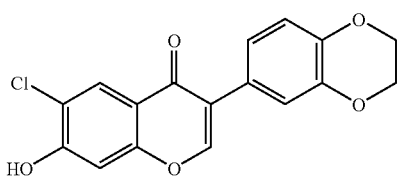

This compounds was synthesised in the same manner as described above. Chlororesorcinol (0.075 g, 0.52 mmol), 2,3-dihydro-benzo[1,4]dioxin-6-yl)acetic acid (0.1 g, 0.52 mmol), BF$_3$Et$_2$O (4 ml), PCl$_5$ (0.16 g, 0.77 mmol), DMF (5 ml and 8 ml). The quenched solution was extracted into ethyl acetate (2×30 ml), washed (2×50 ml water), dried (MgSO4), and the solvent remove to give the crude product which was purified by column chromatography to give 6-chloro-3-(2,3-dihydro-benzo[1,4]dioxin-6-yl)-7-hydroxy-chromen-4-one as a powdery white solid (0.1 g, 58%); R$_f$ 0.8 cf SMs 0.85, 0.82 ethyl acetate/hexane (75/25).

$\delta_H$ (DMSO): 8.40 (1H, s, =CH), 8.05 (1H, s, ArH), 7.10 (4H, m, ArH), 6.89 (1H, d, J=8 Hz, ArH), 4.32 (4H, s, CH$_2$CH$_2$). LCMS t$_R$ 7.20, MS m/z 331/333 [M+H]$^+$.

Synthesis of 3-(2-Bromo-phenyl)-6-chloro-7-hydroxy-chromen-4-one

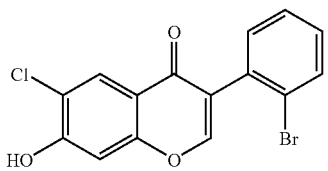

This compounds was synthesised in the same manner as described above. 4-Chlororesorcinol (2.0 g, 13.8 mmol), 2-bromophenyl acetic acid (2.98 g, 13.8 mmol), BF$_3$Et$_2$O (8 ml), PCl$_5$ (4.3 g, 20.6 mmol), DMF (8 ml and 12 ml). The precipitate formed was filtered and re-crystallized from methanol to give 3-(2-Bromo-phenyl)-6-chloro-7-hydroxy-chromen-4-one as a white solid (1.9 g, 39.1%); R$_f$ 0.85 ethyl acetate/hexane (75/25).

$\delta_H$ (DMSO): 8.32 (1H, s, =CH), 7.99 (1H, s, ArH), 7.70 (1H, d, J=8 Hz, ArH), 7.39 (3H, m, ArH), 7.11 (1H, s, ArH), $\delta_c$ (DMSO): 173.1 (C=O), 158.5, 156.2, 155.2, 133.6, 132.9, 132.7, 130.6, 127.9, 126.4, 125.12, 124.9, 120.2, 117.2, 104.2. LCMS t$_R$ 7.23, MS m/z 351/353/355 [M+H]$^+$.

Synthesis of 4-[4-(6-Chloro-7-hydroxy-4-oxo-4H-chromen-3-yl)-phenoxy]-butyronitrile

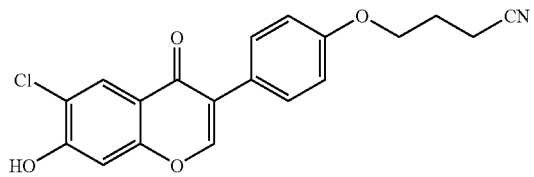

This compounds was synthesised in the same manner as described above. 4-Chlororesorcinol (0.33 g, 2.28 mmol), [4-(3-cyanopropyxy)-phenyl]acetic acid (0.5 g, 2.28 mmol), BF$_3$Et$_2$O (5 ml), PCl$_5$ (0.94 gg, 4.5 mmol), DMF (8 ml and 12 ml). The precipitate formed was filtered and re-crystallized from methanol to give 4-[4-(6-Chloro-7-hydroxy-4-oxo-4H-chromen-3-yl)-phenoxy]-butyronitrile as a white solid (0.55 g, 67.9%); R$_f$ 0.75 ethyl acetate/hexane (80/20)]. LCMS t$_R$ 7.10, m/z 356/358 [M+H]$^+$.

Synthesis of 6-Chloro-3-(4'-fluoro-biphenyl-4-yl)-7-hydroxy-chromen-4-one

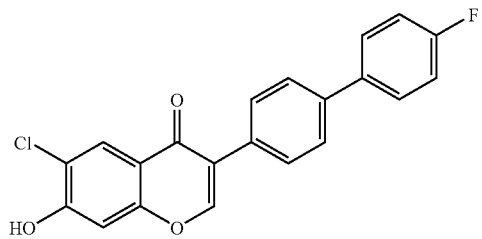

This compounds was synthesised in the same manner as described above. 4-Chlororesorcinol (0.31 g, 2.17 mmol), (4'-fluorobiphenyl-4-yl)-acetic acid (0.5 g, 2.17 mmol), BF$_3$Et$_2$O (5 ml), PCl$_5$ (0.68 g, 3.3 mmol), DMF (8 ml and 5 ml). 6-chloro-3-(4'-fluoro-biphenyl-4-yl)-7-hydroxy-chromen-4-one precipitated out as a white solid (0.45 g, 68.6%).

LCMS t$_R$ 8.41, MS m/z 365/367 [M−H]$^-$.

Synthesis of 6-Chloro-7-hydroxy-3-(3-methoxy-phenyl)-chromen-4-one

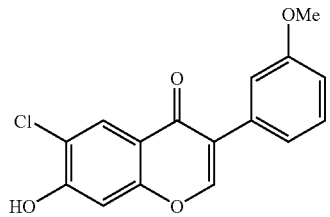

This compounds was synthesised in the same manner as described above. 4-Chlororesorcinol (1.74 g, 12 mmol), 3-methoxyphenylacetic acid (2.0 g, 12 mmol), BF$_3$Et$_2$O (5 ml), PCl$_5$ (3.75 g, 18 mmol), DMF (15 ml and 10 ml). 6-Chloro-7-hydroxy-3-(3-methoxy-phenyl)-chromen-4-one precipitated out as a white solid (1.6 g, 44%).

$\delta_H$ (DMSO): 8.45 (1H, s, =CH), 8.02 (1H, s, ArH), 6.98 (5H, m, ArH), 3.79 (3H, s, CH$_3$). LCMS $t_R$ 7.32, MS m/z 301 [M–H]$^-$.

Synthesis of 6-Chloro-3-(3'-ethoxy-biphenyl-4-yl)-7-hydroxy-chromen-4-one

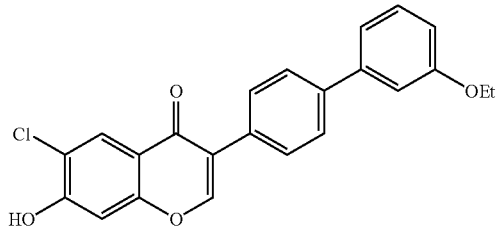

This compounds was synthesised in the same manner as described above. 4-Chlororesorcinol (0.26 g, 1.8 mmol), (3'-Ethoxybiphenyl-4-yl)-acetic acid (0.44 g, 1.8 mmol), BF$_3$Et$_2$O (5 ml), PCl$_5$ (0.56 g, 2.69 mmol), DMF (8 ml and 5 ml). The crude oil product (0.39 g, 55.2%) was taken onto the next stage. R$_f$ 0.8 ethyl acetate/hexane (70/30)].
LCMS $t_R$ 8.34, MS m/z 391/393 [M–H]$^-$.

Synthesis of 6-Chloro-3-(4'-fluoro-biphenyl-3-yl)-7-hydroxy-chromen-4-one

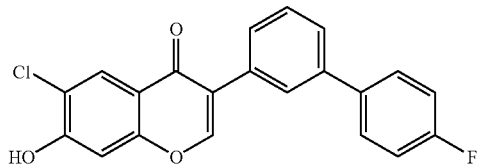

This compounds was synthesised in the same manner as described above. 4-Chlororesorcinol (0.25 g, 1.7 mmol), (4'-Fluorobiphenyl-3-yl)-acetic acid (0.4 g, 1.7 mmol), BF$_3$Et$_2$O (5 ml), PCl$_5$ (0.54 g, 2.59 mmol), DMF (8 ml and 5 ml). 6-Chloro-3-(4'-fluoro-biphenyl-3-yl)-7-hydroxy-chromen-4-one precipitated out as a white solid (0.36 g, 57.8%). This was taken onto the next stage without further purification. R$_f$ 0.6 ethyl acetate/hexane (70/30)].
LCMS $t_R$ 8.33, MS m/z 365/367 [M–H]$^-$.

Synthesis of 6-Chloro-3-[3-(2-fluoro-ethoxy)-phenyl]-7-hydroxy-chromen-4-one

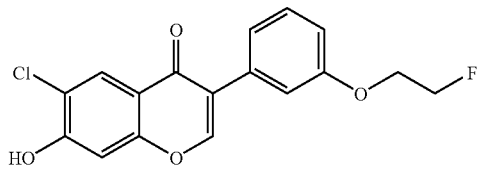

This compounds was synthesised in the same manner as described above. 4-Chlororesorcinol (0.36 g, 2.5 mmol), [3-(2-Fluoro-ethoxy)-phenyl]-acetic acid (0.5 g, 2.5 mmol), BF$_3$Et$_2$O (5 ml), PCl$_5$ (0.79 g, 3.79 mmol), DMF (8 ml and 5 ml). 6-Chloro-3-[3-(2-fluoro-ethoxy)-phenyl]-7-hydroxy-chromen-4-one precipitated out as a white solid (0.49 g, 58.6%). This was taken onto the next stage without further purification. R$_f$ 0.6 ethyl acetate/hexane (70/30)].
LCMS $t_R$ 7.16, MS m/z 333/335 [M–H]$^-$.

Synthesis of 3-(3-Bromo-phenyl)-6-chloro-7-hydroxy-chromen-4-one

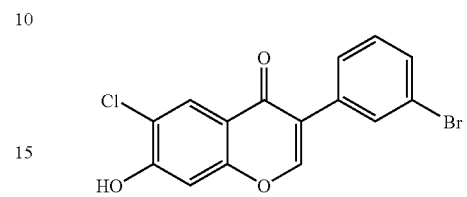

This compounds was synthesised in the same manner as described above. 4-Chlororesorcinol (0.34 g, 2.4 mmol), 3-bromophenyl acetic acid (0.51 g, 2.4 mmol), BF$_3$Et$_2$O (5 ml), PCl$_5$ (0.74 g, 3.6 mmol), DMF (5 ml and 10 ml). The precipitate formed was filtered and re-crystallized from methanol to give 3-(3-Bromo-phenyl)-6-chloro-7-hydroxy-chromen-4-one a flakey white solid (0.64 g, 76%).
LCMS $t_R$ 7.96, MS m/z 349/351 [M–H]$^-$.

Synthesis of 6-Chloro-3-(3',4'-dimethoxy-biphenyl-3-yl)-7-hydroxy-chromen-4-one

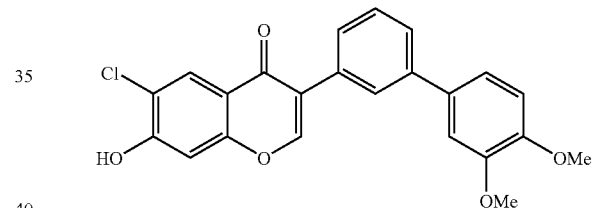

This compounds was synthesised in the same manner as described above. 4-Chlororesorcinol (0.15 g, 1.0 mmol), (3',4'-dimethoxy-biphenyl-3-yl)-acetic acid (0.28 g, 1 mmol), BF$_3$Et$_2$O (5 ml), PCl$_5$ (0.32 g, 1.5 mmol), DMF (6 ml and 4 ml). The white precipitate formed was shown to contain the required compound and was taken directly onto the next stage.
LCMS $t_R$ 7.86, MS m/z 407/409 [M–H]$^-$.

Synthesis of 6-Chloro-7-hydroxy-3-(2-methoxy-phenyl)-chromen-4-one

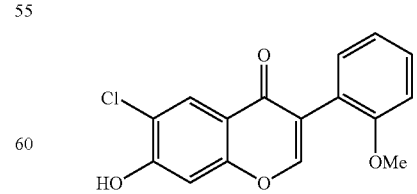

This compounds was synthesised in the same manner as described above. 4-Chlororesorcinol (1.74 g, 12.0 mmol), 2-methoxyphenylacetic acid (2.0 g, 12.0 mmol), BF$_3$Et$_2$O (10 ml), PCl$_5$ (3.76 g, 18.1 mmol), DMF (20 ml and 10 ml).

The pale brown solid precipitate was taken directly onto the next stage without further purification.

Synthesis of 4-[3-(6-Chloro-7-hydroxy-4-oxo-4H-chromen-3-yl)-phenoxy]-butyronitrile

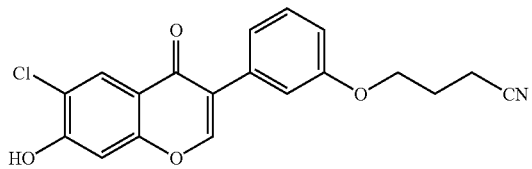

This compounds was synthesised in the same manner as described above. 4-Chlororesorcinol (0.33 g, 2.28 mmol), [3-(3-Cyano-propoxy)-phenyl]-acetic acid (0.5 g, 2.28 mmol), $BF_3Et_2O$ (5 ml), $PCl_5$ (0.71 g, 3.4 mmol), DMF (8 ml and 5 ml). Crude 4-[3-(6-Chloro-7-hydroxy-4-oxo-4H-chromen-3-yl)-phenoxy]-butyronitrile was obtained as an oil which was taken onto the next stage without further purification.

LCMS $t_R$ 7.10, MS m/z 354/356 [M–H]−.

Synthesis of 4-[2-(6-Chloro-7-hydroxy-4-oxo-4H-chromen-3-yl)-phenoxy]-butyronitrile

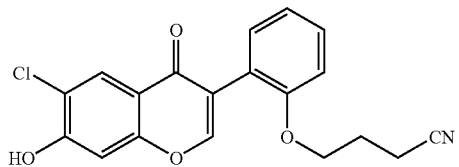

This compounds was synthesised in the same manner as described above. 4-Chlororesorcinol (0.125 g, 0.87 mmol), [2-(3-Cyano-propoxy)-phenyl]-acetic acid (0.19 g, 0.87 mmol), $BF_3Et_2O$ (5 ml), $PCl_5$ (0.27 g, 1.3 mmol), DMF (8 ml and 5 ml). Crude 4-[2-(6-Chloro-7-hydroxy-4-oxo-4H-chromen-3-yl)-phenoxy]-butyronitrile was obtained as an oil which was taken onto the next stage without further purification.

LCMS $t_R$ 6.76, MS m/z 354/356 [M–H]−.

Synthesis of 6-Chloro-3-(2-fluoro-phenyl)-7-hydroxy-chromen-4-one

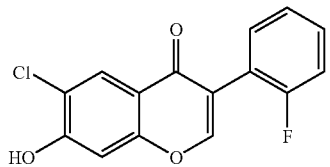

This compounds was synthesised in the same manner as described above. 4-Chlororesorcinol (1.889, 13.0 mmol), 2-fluorophenylacetic acid (2.0 g, 13 mmol), $BF_3Et_2O$ (10 ml), $PCl_5$ (4.0 g, 19.2 mmol), DMF (20 ml and 10 ml). The pale white precipitate formed was shown to contain the required compound and was taken directly onto the next stage.

LCMS $t_R$ 7.01, MS m/z 289/291 [M–H]−.

4-[4-(6-Chloro-7-hydroxy-4-oxo-4H-chromen-3-yl)-2-(3-cyano-propoxy)-phenoxy]-butyronitrile

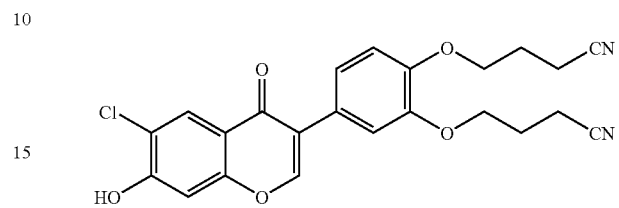

This compounds was synthesised in the same manner as described above. 4-Chlororesorcinol (0.48 g, 3.31 mmol), [3,4-Bis-(3-cyano-propoxy)-phenyl]-acetic acid (1 g, 3.31 mmol), $BF_3Et_2O$ (8 ml), $PCl_5$ (1.03 g, 4.97 mmol), DMF (8 ml and 12 ml). The precipitate formed was filtered and re-crystallized from methanol to give 4-[4-(6-Chloro-7-hydroxy-4-oxo-4H-chromen-3-yl)-2-(3-cyano-propoxy)-phenoxy]-butyronitrile as a white solid (1.05 g, 72.5%); $R_f$ 0.6 ethyl acetate/hexane (80/20)].

LCMS $t_R$ 6.847.10, m/z 439/441 [M+H]+.

Synthesis of 5-[3-(6-Chloro-7-hydroxy-4-oxo-4H-chromen-3-yl)-phenoxy]-pentanenitrile

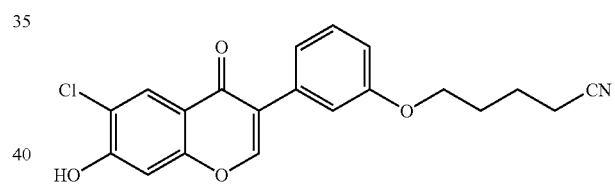

This compound was synthesised in the same manner as described above. 4-Chlororesorcinol (0.37 g, 2.58 mmol), [3-(4-Cyano-butoxy)-phenyl]-acetic acid (0.6 g, 2.58 mmol), $BF_3Et_2O$ (8 ml), $PCl_5$ (0.81 g, 3.89 mmol), DMF (8 ml and 12 ml). The precipitate formed was filtered and re-crystallized from methanol to give 5-[3-(6-Chloro-7-hydroxy-4-oxo-4H-chromen-3-yl)-phenoxy]-pentanenitrile as a white solid (0.59 g, 59.1%); $R_f$ 0.7 ethyl acetate/hexane (80/20)].

LCMS $t_R$ 7.26, m/z 368/370 [M–H]−.

Synthesis of 5-[4-(6-Chloro-7-hydroxy-4-oxo-4H-chromen-3-yl)-phenoxy]-pentanenitrile

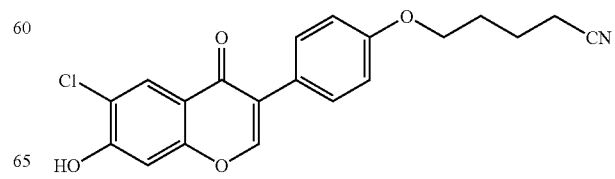

This compounds was synthesised in the same manner as described in Section 1.1.4.1. 4-Chlororesorcinol (0.37 g, 2.58 mmol), [[4-(4-Cyano-butoxy)-phenyl]-acetic acid (0.6 g, 2.28 mmol), BF₃Et₂O (5 ml), PCl₅ (0.81 g, 3.89 mmol), DMF (8 ml and 12 ml). The precipitate formed was filtered and re-crystallized from methanol to give 5-[4-(6-Chloro-7-hydroxy-4-oxo-4H-chromen-3-yl)-phenoxy]-pentanenitrile as a white solid (0.63 g, 66.2%); $R_f$ 0.65 ethyl acetate/hexane (80/20)].

LCMS $t_R$ 7.29, m/z 368/370 [M–H]⁻.

The Following Reactions Refer to Scheme 13.
Pyrazole Synthesis for Examples 49–63, 65–79, 109, 153–157

Synthesis of 4-(4-Phenyl-1H-pyrazol-3-yl)-benzene-1,3-diol

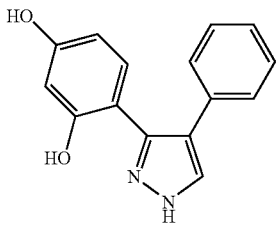

7-Hydroxy-3-phenyl-chromen-4-one (0.2 g, 0.84 mmol) was dissolved in ethanol (5 ml) and heated to ~60° C. Hydrazine hydrate (5 ml) was added, and the solution refluxed until no starting material was visible by TLC (45 mins). After this time the majority of the ethanol was remove under vacuum and the residue quenched with cold water. The residue was extracted into ethyl acetate, washed (water), and the solvent removed under vacuum to give 4-(4-Phenyl-1H-pyrazol-3-yl)-benzene-1,3-diol as a white solid (0.17 g, 80.3%); $R_f$ 0.65 ethyl acetate/hexane (70/30)].

$\delta_H$ (DMSO): 9.63, 9.43 (2H, s, OH), 7.81 (1H, s, =CH), 7.25 (6H, m, ArH), 6.87 (1H, d, J=8 Hz, ArH), 6.38 (1H, s, ArH), 6.19 (1H, d, J=8 Hz, ArH). LCMS $t_R$ 6.29, MS m/z 253 [M+H]⁺.

Synthesis of 4-[4-(4-Bromo-phenyl)-1H-pyrazol-3-yl]-benzene-1,3-diol

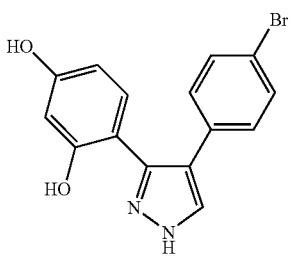

This compounds was synthesised in the same manner as described in the preceding experiment. 3-(4-Bromo-phenyl)-7-hydroxy-chromen-4-one (0.1 g, 0.3 mmol), hydrazine hydrate (4 ml), ethanol (10 ml). The crude solid product was washed in hot ether to give 4-[4-(4-Bromo-phenyl)-1H-pyrazol-3-yl]-benzene-1,3-diol as a white solid (0.069, 60.6%); $R_f$ 0.44 Cf SM 0.79 ethyl acetate/hexane (75/25).

$\delta_H$ (DMSO): 9.47, 8.92 (2H, s, OH), 7.81 (1H, s, =CH), 7.43 (2H, d, J=9 Hz, ArH), 7.24 (2H, d, J=9 Hz, ArH), 6.89 (1H, d, J=9 Hz, ArH), 6.37 (1H, s, ArH), 6.26 (1H, d, J=9 Hz, ArH). LCMS $t_R$ 7.12, MS m/z 331/333 [M+H]⁺.

Synthesis of 4-[4-(3,4-Dimethoxy-phenyl)-1H-pyrazol-3-yl]-benzene-1,3-diol

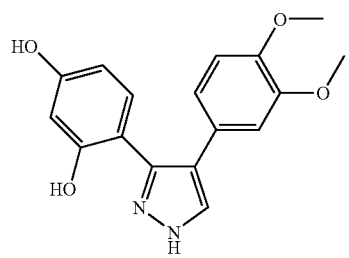

This compounds was synthesised in the same manner as described above. 3-(3,4-Dimethoxy-phenyl)-7-hydroxy-chromen-4-one (0.5 g, 1.68 mmol), hydrazine hydrate (4 ml), ethanol (10 ml). The crude product was columned to give 4-[4-(3,4-Dimethoxy-phenyl)-1H-pyrazol-3-yl]-benzene-1,3-diol as a pale yellow solid (0.29 g, 55.3%); $R_f$ 0.2 Cf SM 0.7 ethyl acetate/hexane (75/25).

$\delta_H$ (DMSO): 10.18, 9.42 (2H, s, OH), 7.77 (1H, s, =CH), 6.90 (4H, m, ArH), 6.38 (1H, s, ArH), 6.24 (1H, s, ArH), 3.71 (3H, s, CH₃), 3.59 (3H, s, CH₃). LCMS $t_R$ 5.71, MS m/z 313 [M+H]⁺.

Synthesis of 4-Ethyl-6-(4-phenyl-1H-pyrazol-3-yl)-benzene-1,3-diol

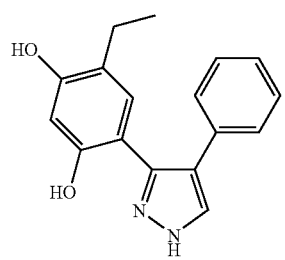

This compounds was synthesised in the same manner as described above. 6-Ethyl-7-hydroxy-3-phenyl-chromen-4-one (0.29 g, 1.1 mmol), hydrazine hydrate (4 ml), ethanol (20 ml). The crude product was columned to give 4-Ethyl-6-(4-phenyl-1H-pyrazol-3-yl)-benzene-1,3-diol as a off white solid (0.23 g, 74.73%); $R_f$ 0.7 Cf SM 0.9 ethyl acetate/hexane (70/30).

$\delta_H$ (DMSO): 9.63, 9.43 (2H, s, OH), 7.62 (1H, s, =CH), 7.23 (5H, m, ArH), 6.96 (1H, s, ArH), 6.24 (1H, s, ArH), 2.36 (2H, q, J=7 Hz, CH₂), 0.78 (3H, t, J=7 Hz, CH₃). LCMS $t_R$ 7.29, MS m/z 281 [M+H]⁺.

Synthesis of 4-[4-(4-Bromo-phenyl)-1H-pyrazol-3-yl]-6-ethyl-benzene-1,3-diol

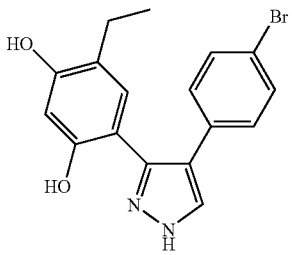

This compounds was synthesised in the same manner as described above. 3-(4-Bromo-phenyl)-6-ethyl-7-hydroxy-chromen-4-one (0.13 g, 0.38 mmol), hydrazine hydrate (4 ml), ethanol (10 ml). The crude solid product was columned to give 4-[4-(4-bromo-phenyl)-1H-pyrazol-3-yl]-6-ethyl-benzene-1,3-diol as a white solid (0.0969 g, 71%); $R_f$ 0.44 Cf SM 0.79 ethyl acetate/hexane (75/25).

$\delta_H$ (DMSO): 9.48 (2H, s, OH), 8.27 (1H, s, =CH), 7.53 (2H, d, J=9 Hz, ArH), 7.34 (2H, d, J=9 Hz, ArH), 6.91 (1H, s, ArH), 6.54, (1H, s, ArH), 2.49 (2H, q, J=7 Hz, CH$_2$), 1.11 (3H, t, J=7 Hz, CH$_3$). LCMS $t_R$ 7.89, MS m/z 359/361 [M+H]$^+$.

Synthesis of 4-[4-(3,4-Dimethoxy-phenyl)-1H-pyrazol-3-yl]-6-ethyl-benzene-1,3-diol

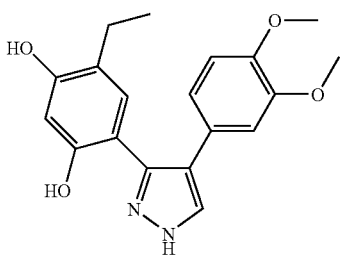

This compounds was synthesised in the same manner as described above. 3-(3,4-Dimethoxy-phenyl)-6-ethyl-7-hydroxy-chromen-4-one (0.25 g, 0.77 mmol), hydrazine hydrate (4 ml), ethanol (10 ml). The crude solid product was columned to give 4-[4-(3,4-Dimethoxy-phenyl)-1H-pyrazol-3-yl]-6-ethyl-benzene-1,3-diol as a white solid (0.16 g, 61.1%); $R_f$ 0.33 Cf SM 0.71 ethyl acetate/hexane (75/25).

$\delta_H$(DMSO): 10.06, 9.36 (2H, s, OH), 7.81 (1H, s, =CH), 7.19 (4H, m, ArH), 6.47 (1H, s, ArH), 3.72 (3H, s, CH$_3$), 3.60 (3H, s, CH$_3$), 2.39 (2H, q, J=7 Hz, CH$_2$), 1.01 (3H, t, J=7 Hz, CH$_3$). LCMS $t_R$ 6.57, MS m/z 341 [M+H]$^+$.

Synthesis of 4-Chloro-6-(4-phenyl-1H-pyrazol-3-yl)-benzene-1,3-diol

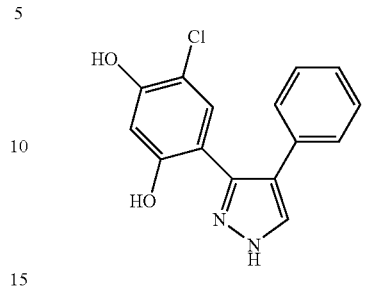

This compounds was synthesised in the same manner as described above. 6-Chloro-7-hydroxy-3-phenyl-chromen-4-one (0.4 g, 1.47 mmol), hydrazine hydrate (4 ml), ethanol (10 ml). 4-Chloro-6-(4-phenyl-1H-pyrazol-3-yl)-benzene-1,3-diol precipitated out on quenching as a pale yellow (0.37 g, 88%); $R_f$ 0.3 Cf SM 0.7 ethyl acetate/hexane (75/25).

$\delta_H$ (DMSO): 10.16 (2H, 2×s, OH), 7.86 (1H, s, =CH), 7.24 (5H, m, ArH), 7.03 (1H, s, ArH), 6.41 (1H, s, ArH). LCMS $t_R$ 6.89, MS m/z 287/289 [M+H]$^+$.

Synthesis of 4-[4-(4-Bromo-phenyl)-1H-pyrazol-3-yl]-6-chloro-benzene-1,3-diol

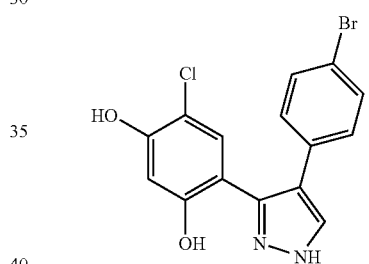

This compounds was synthesised in the same manner as described above. 3-(4-Bromo-phenyl)-6-chloro-7-hydroxy-chromen-4-one (0.1 g, 0.28 mmol), hydrazine hydrate (4 ml), ethanol (10 ml). 4-[4-(4-Bromo-phenyl)-1H-pyrazol-3-yl]-6-chloro-benzene-1,3-diol precipitated out on quenching as a white solid (0.073 g, 71.2%); $R_f$ 0.34 Cf SM 0.55 ethyl acetate/hexane (75/25).

$\delta_H$ (DMSO): 10.47 (2H, 2×s, OH), 7.88 (1H, s, =CH), 7.46 (2H, d, J=9 Hz, ArH), 7.21 (2H, d, J=9 Hz, ArH), 7.05 (1H, s, ArH), 6.5 (1H, s, ArH). LCMS Single peak $t_R$ 7.56, MS m/z 365/367 [M+H]$^+$.

Synthesis of 4-Chloro-6-[4-(3,4-dimethoxy-phenyl)-1H-pyrazol-3-yl]-benzene-1,3-diol

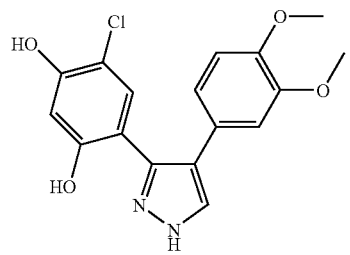

This compounds was synthesised in the same manner as described above. 6-Chloro-3-(3,4-dimethoxy-phenyl)-7-hydroxy-chromen-4-one (0.2 g, 0.62 mmol), hydrazine hydrate (4 ml), ethanol (10 ml). The crude solid product was columned to give 4-Chloro-6-[4-(3,4-dimethoxy-phenyl)-1H-pyrazol-3-yl]-benzene-1,3-diol as a white solid (0.139 g, 65.1%); $R_f$ 0.36 Cf SM 0.56 ethyl acetate/hexane (75/25).

$\delta_H$ (DMSO): 10.19, 10.02 (2H, 2×s, OH), 7.83 (1H, s, =CH), 7.05 (1H, s, ArH), 6.84 (4H, m, ArH), 6.59 (1H, s, ArH), 3.72 (3H, s, CH$_3$), 3.61 (3H, s, CH$_3$). $\delta_c$ (DMSO): 115.8, 154.0, 148.8, 147.6, 137.2, 131.4, 126.7, 120.1, 119.4, 112.4, 111.5, 110.9, 109.9, 104.2 (Unsaturated), 55.8, 55.5 (CH$_3$). LCMS $t_R$ 6.24, MS m/z 347/349 [M+H]$^+$.

Synthesis of 4-Chloro-6-[4-(2,3-dihydro-benzo[1,4] dioxin-6-yl)-1H-pyrazol-3-yl]-benzene-1,3-diol

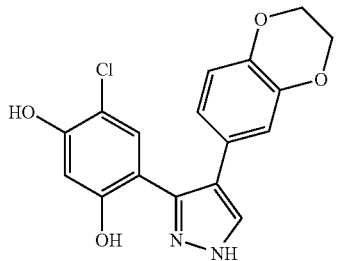

This compounds was synthesised in the same manner as described above. 6-Chloro-3-(2,3-dihydro-benzo[1,4]dioxin-6-yl)-7-hydroxy-chromen-4-one (0.1 g, 0.30 mmol), hydrazine hydrate (4 ml), ethanol (10 ml). The quenched reaction was extracted into ethyl acetate (2×30 ml), washed (water), dried (MgSO$_4$), and the solvent remove to give 4-Chloro-6-[4-(2,3-dihydro-benzo[1,4]dioxin-6-yl)-1H-pyrazol-3-yl]-benzene-1,3-diol as an off white solid (0.031 g, 30%); $R_f$ 0.6 Cf SM 0.8 ethyl acetate/hexane (75/25).

$\delta_H$ (DMSO): 10.19, 9.91 (2H, 2×s, OH), 7.78 (1H, s, =CH), 7.02 (1H, s, ArH), 6.75 (3H, m, ArH), 6.52 (1H, s, ArH). LCMS $t_R$ 6.56, MS m/z 345/347 [M+H]$^+$.

Synthesis of 4-[4-(2-Bromo-phenyl)-1H-pyrazol-3-yl]-6-chloro-benzene-1,3-diol

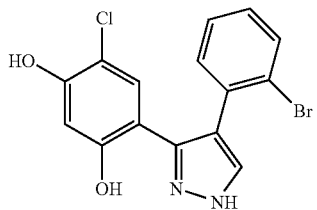

This compounds was synthesised in the same manner as described above. 3-(2-Bromo-phenyl)-6-chloro-7-hydroxy-chromen-4-one (0.4 g, 1.1 mmol), hydrazine hydrate (10 ml), ethanol (10 ml). The quenched solution was extracted into ethyl acetate, washed (water), dried (MgSO$_4$), and the solvent removed under vacuum to give a yellow oil which was purified by column chromatography to give 4-[4-(2-Bromo-phenyl)-1H-pyrazol-3-yl]-6-chloro-benzene-1,3-diol as a white solid (0.28 g, 70%); $R_f$ 0.6 ethyl acetate/hexane (80/20).

$\delta_H$ (DMSO): 10.17, 9.93 (2H, 2×s, OH), 7.94 (1H, s, C=H), 7.54 (4H, m, ArH), 6.76 (1H, s, ArH), 6.51 (1H, s, ArH). LCMS $t_R$ 7.02, MS m/z 263/365 [M–H]$^-$.

Synthesis of 4-(4-[3-(5-Chloro-2,4-dihydroxy-phenyl)-1H-pyrazol-4-yl]-phenoxy}-butyronitrile

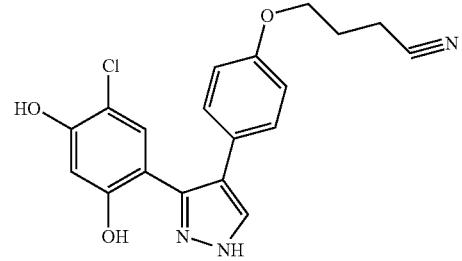

This compounds was synthesised in the same manner as described above. 4-[4-(6-Chloro-7-hydroxy-4-oxo-4H-chromen-3-yl)-phenoxy]-butyronitrile (0.12 g, 0.34 mmol), Hydrazine hydrate (5 ml). The precipitate formed on quenching was filtered to give 4-{4-[3-(5-Chloro-2,4-dihydroxy-phenyl)-1H-pyrazol-4-yl]-phenoxy}-butyronitrile as a white solid (0.09 g, 71.6%); $R_f$ 0.6 ethyl acetate/hexane (70/30)].

$\delta_H$ (DMSO): 10.19 (2H, s, OH), 7.78 (1H, s, =CH), 7.20 (2H, d, J=9 Hz, ArH), 7.01 (1H, s, ArH), 6.88 (2H, d, J=9 Hz, ArH), 6.43 (1H, s, ArH), 4.01 (2H, t, J=7 Hz, CH$_2$), 2.64 (2H, t, J=7 Hz, CH$_2$), 2.06 (2H, m, CH$_2$). LCMS $t_R$ 6.47, m/z 370/372 [M+H]$^+$.

Synthesis of 4-Chloro-6-[4-(4'-fluoro-biphenyl-4-yl)-1H-pyrazol-3-yl]-benzene-1,3-diol

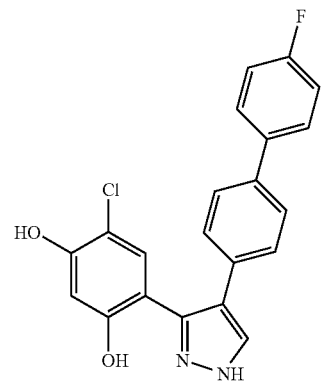

This compounds was synthesised in the same manner as described above. 6-Chloro-3-(4'-fluorobiphenyl-4-yl)-7-hydroxy-chromen-4-one (0.12 g, 0.33 mmol), Hydrazine hydrate (5 ml). The quenched reaction was extracted into ethyl acetate, washed (water), dried (MgSO$_4$), and the solvent removed under vacuum to give 4-Chloro-6-[4-(4'-fluoro-biphenyl-4-yl)-1H-pyrazol-3-yl]-benzene-1,3-diol as a white solid (0.08 g, 63.7%).

$\delta_H$ (DMSO): 10.02, 9.88 (2H, 2×s, OH), 7.90 (1H, s, =CH), 7.70 (2H, d, J=9 Hz, ArH), 7.56 (2H, d, J=9 Hz, ArH), 7.29 (2H, d, J=9 Hz, ArH), 7.22 (2H, d, J=9 Hz, ArH), 7.09 (1H, s, ArH), 6.63 (1H, s, ArH). LCMS $t_R$ 7.96, m/z 379/381 [M–H]$^-$.

Synthesis of 4-Chloro-6-[4-(3-methoxy-phenyl)-1H-pyrazol-3-yl]-benzene-1,3-diol

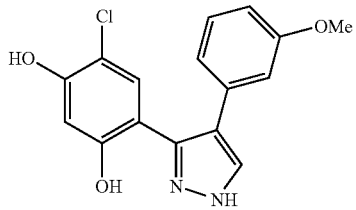

This compounds was synthesised in the same manner as described above. 6-Chloro-7-hydroxy-3-(3-methoxy-phenyl)-chromen-4-on (1.0 g, 3.3 mmol), Hydrazine hydrate (8 ml). The quenched reaction was extracted into ethyl acetate, washed (water), dried (MgSO$_4$), and the solvent removed under vacuum to give 4-Chloro-6-[4-(3-methoxy-phenyl)-1H-pyrazol-3-yl]-benzene-1,3-diol as a white solid (0.48 g, 46%); R$_f$ 0.5 ethyl acetate/hexane (80/20)].

$\delta_H$ (DMSO): 10.23, 9.94 (2H, 2×s, OH), 7.88 (1H, s, C═CH), 7.22 (1H, t, ArH), 7.16 (1H, s, ArH), 6.91 (1H, d, ArH), 6.85 (1H, s, ArH), 6.73 (1H, d, ArH), 6.49 (1H, s, ArH), 3.66 (3H, s, OCH$_3$). $\delta_c$ (DMSO). LCMS t$_R$ 6.72, m/z 317/319 [M+H]$^+$.

Synthesis of 4-Chloro-6-[4-(3'-ethoxy-biphenyl-4-yl)-1H-pyrazol-3-yl]-benzene-1,3-diol

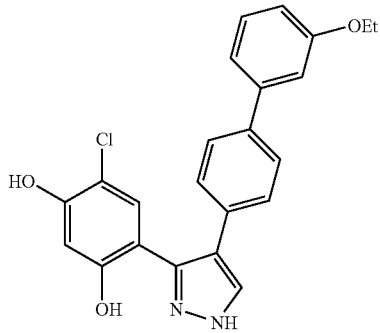

This compounds was synthesised in the same manner as described above. 6-Chloro-3-(3'-ethoxy-biphenyl-4-yl)-7-hydroxy-chromen-4-on (0.2 g, 0.69 mmol), hydrazine hydrate (5 ml), ethanol (10 ml). The quenched solution was extracted into ethyl acetate, washed (water), dried (MgSO$_4$), and the solvent removed under vacuum to give an oil. MS m/z 407 [M–H]$^-$.

Synthesis of 4-Chloro-6-[4-(4'-fluoro-biphenyl-3-yl)-1H-pyrazol-3-yl]-benzene-1,3-diol

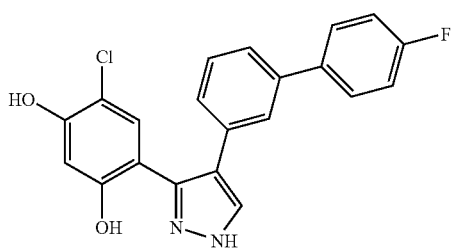

This compounds was synthesised in the same manner as described above. 6-Chloro-3-(4'-fluoro-biphenyl-3-yl)-7-hydroxy-chromen-4-one (0.2 g, 0.54 mmol), hydrazine hydrate (2.5 ml), ethanol (10 ml). The quenched solution was extracted into ethyl acetate, washed (water), dried (MgSO$_4$), and the solvent removed under vacuum to give an oil which was purified by column chromatography to give 4-Chloro-6-[4-(4'-fluoro-biphenyl-3-yl)-1H-pyrazol-3-yl]-benzene-1,3-diol as an off white solid (0.13 g, 63.3%); R$_f$ 0.2 cf SM 0.7 ethyl acetate/hexane (80/20).

$\delta_H$ (DMSO): 10.24, 9.98 (2H, 2×s, OH), 7.99 (1H, s, C═CH), 7.39 (8H, m, ArH), 7.10 (1H, s, ArH), 6.63 (1H, s, ArH). LCMS t$_R$ 7.86, MS m/z 381/383 [M–H]$^-$.

Synthesis of 4-Chloro-6-{4-[3-(2-fluoro-ethoxy)-phenyl]-1H-pyrazol-3-yl}-benzene-1,3-diol

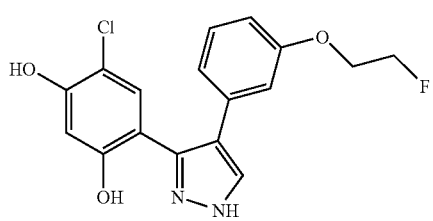

This compounds was synthesised in the same manner as described above. 6-Chloro-3-[3-(2-fluoro-ethoxy)-phenyl]-7-hydroxy-chromen-4-one (0.2 g, 0.6 mmol), hydrazine hydrate (2.5 ml), ethanol (10 ml). The quenched solution was extracted into ethyl acetate, washed (water), dried (MgSO$_4$), and the solvent removed under vacuum to give an oil which was purified by column chromatography to give 4-Chloro-6-{4-[3-(2-fluoro-ethoxy)-phenyl]-1H-pyrazol-3-yl}-benzene-1,3-diol as an off white solid (0.12 g, 57.3%); R$_f$ 0.5 cf SM 0.85 ethyl acetate/hexane (80/20).

$\delta_H$ (DMSO): 10.21, 9.92 (2H, 2×s, OH), 7.87 (1H, s, C═CH), 7.02 (1H, s, ArH), 6.87 (4H, m, ArH), 6.60 (1H, s, ArH), 4.66 (2H, dt, CH$_2$), 4.15 (2H, dt, CH$_2$). LCMS t$_R$ 6.72, MS m/z 347/349 [M–H]$^-$.

Synthesis of 4-[4-(3-Bromo-phenyl)-1H-pyrazol-3-yl]-6-chloro-benzene-1,3-diol

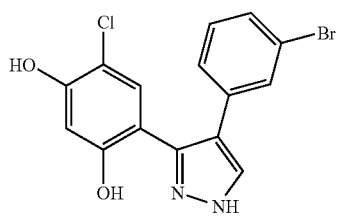

This compounds was synthesised in the same manner as described above. 3-(3-Bromo-phenyl)-6-chloro-7-hydroxy-chromen-4-one (0.25 g, 0.71 mmol), hydrazine hydrate (5 ml), ethanol (10 ml). The quenched solution was extracted into ethyl acetate, washed (water), dried (MgSO$_4$), and the solvent removed under vacuum to give a yellow oil which was purified by column chromatography to give 4-[4-(3-Bromo-phenyl)-1H-pyrazol-3-yl]-6-chloro-benzene-1,3-diol as a white solid (0.21 g, 80.8%); R$_f$ 0.8 ethyl acetate/hexane (70/30).

$\delta_H$ (DMSO): 10.29, 9.84 (2H, 2×s, OH), 7.90 (1H, s, C=H), 7.48 (1H, s, ArH), 7.26 (3H, m, ArH), 7.07 (1H, s, ArH), 6.62 (1H, s, ArH). LCMS t$_R$ 7.40, MS m/z 265/367/369 [M+H]$^+$.

Synthesis of 4-Chloro-6-[4-(3',4'-dimethoxy-biphenyl-3-yl)-1H-pyrazol-3-yl]-benzene-1,3-diol

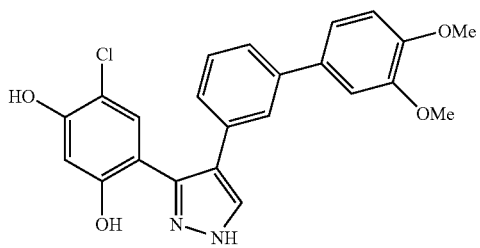

This compounds was synthesised in the same manner as described above. 6-Chloro-3-(3',4'-dimethoxy-biphenyl-3-yl)-7-hydroxy-chromen-4-one (0.1 g, 0.24 mmol), hydrazine hydrate (2.5 ml), ethanol (10 ml). The quenched solution was extracted into ethyl acetate, washed (water), dried (MgSO$_4$), and the solvent removed under vacuum to give an oil which was purified by column chromatography to give 4-Chloro-6-[4-(3',4'-dimethoxy-biphenyl-3-yl)-1H-pyrazol-3-yl]-benzene-1,3-diol as an off white solid (0.05 g, 49.3.3%); R$_f$ 0.3 cf SM 0.6 ethyl acetate/hexane (70/30).

LCMS tR 6.27, MS m/z 423/425 [M+H]$^+$.

Synthesis of 4-Chloro-6-[4-(2-methoxy-phenyl)-1H-pyrazol-3-yl]-benzene-1,3-diol

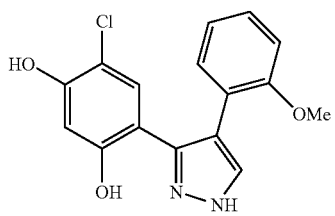

This compounds was synthesised in the same manner as described above. 6-Chloro-7-hydroxy-3-(2-methoxy-phenyl)-chromen-4-one (2.0 g, 6.6 mmol), hydrazine hydrate (5 ml), ethanol (10 ml). The quenched solution was extracted into ethyl acetate, washed (water), dried (MgSO$_4$), and the solvent removed under vacuum to give 4-chloro-6-[4-(2-methoxy-phenyl)-1H-pyrazol-3-yl]-benzene-1,3-diol as a white solid. R$_f$ 0.8 ethyl acetate/hexane (70/30).

LCMS t$_R$ 6.74, MS m/z 317/319 [M+H]$^+$.

Synthesis of 4-{3-[3-(5-Chloro-2,4-dihydroxy-phenyl)-1H-pyrazol-4-yl]-phenoxy}-butyronitrile

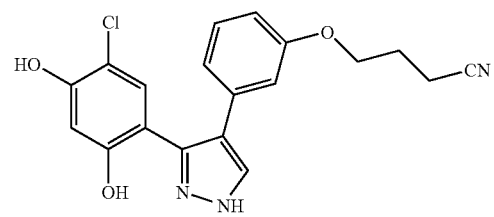

This compounds was synthesised in the same manner as described above. 4-[3-(6-Chloro-7-hydroxy-4-oxo-4H-chromen-3-yl)-phenoxy]-butyronitrile (0.3 g, 0.84 mmol), Hydrazine hydrate (6 ml). The quenched reaction was extracted into ethyl acetate, washed (water), dried (MgSO$_4$), and the solvent removed under vacuum to give a clear oil which was purified by column chromatograpy to give 4-{3-[3-(5-chloro-2,4-dihydroxy-phenyl)-1H-pyrazol-4-yl]-phenoxy}-butyronitrile as a white soild R$_f$ 0.6 ethyl acetate/hexane (70/30).

$\delta_H$ (DMSO): 10.14, 9.82 (2H, 2×s, OH), 7.80 (1H, s, =CH), 6.67 (6H, m, ArH), 3.89 (2H, t, J=7 Hz, CH$_2$), 2.53 (2H, t, J=7 Hz, CH$_2$), 1.93 (2H, m, CH$_2$). LCMS t$_R$ 6.64, m/z 370/372 [M+H]$^+$.

Synthesis of 4-{2-[3-(5-Chloro-2,4-dihydroxy-phenyl)-1H-pyrazol-4-yl]-phenoxy}-butyronitrile

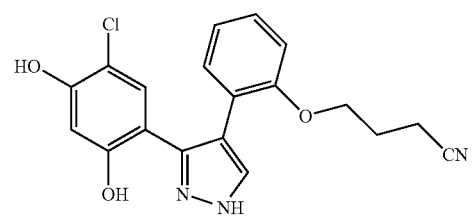

This compounds was synthesised in the same manner as described above. 4-[2-(6-Chloro-7-hydroxy-4-oxo-4H-chromen-3-yl)-phenoxy]-butyronitrile (0.1 g, 0.28 mmol), Hydrazine hydrate (6 ml). The quenched reaction was extracted into ethyl acetate, washed (water), dried (MgSO$_4$), and the solvent removed under vacuum to give a clear oil which was purified by column chromatograpy to give 4-{2-[3-(5-chloro-2,4-dihydroxy-phenyl)-1H-pyrazol-4-yl]-phenoxy}-butyronitrile as an off white soild R$_f$ 0.65 ethyl acetate/hexane (70/30).

$\delta_H$ (DMSO): 10.13 (2H, 2×s, OH), 7.86 (1H, s, =CH), 6.89 (6H, m, ArH), 3.90 (2H, t, J=7 Hz, CH$_2$), 2.24 (2H, t, J=7 Hz, CH$_2$), 1.75 (2H, m, CH$_2$). LCMS t$_R$ 6.71, m/z 370/372 [M+H]$^+$.

Synthesis of 4-Chloro-6-[4-(2-fluoro-phenyl)-1H-pyrazol-3-yl]-benzene-1,3-diol

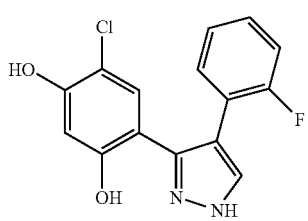

This compounds was synthesised in the same manner as described above. 6-Chloro-3-(2-fluoro-phenyl)-7-hydroxy-chromen-4-one (0.37 g, 1.27 mmol), hydrazine hydrate (5 ml), ethanol (15 ml). The quenched solution was extracted into ethyl acetate, washed (water), dried (MgSO$_4$), and the solvent removed under vacuum to give a yellow oil which was purified by column chromatography to give 4-chloro-6-[4-(2-fluoro-phenyl)-1H-pyrazol-3-yl]-benzene-1,3-diol as a white solid (0.28 g, 72.4%); Rf 0.8 cf SM 0.9 ethyl acetate/hexane (70/30).

$\delta_H$ (DMSO): 10.21, 9.86 (2H, 2×s, OH), 7.90 (1H, s, C=H), 7.17 (4H, m, ArH), 6.98 (1H, s, ArH), 6.57 (1H, s, ArH). LCMS tR 6.84, MS m/z 303/305 [M−H]$^-$.

Synthesis of 4-(5-Methyl-4-phenyl-1H-pyrazol-3-yl)-benzene-1,3-diol

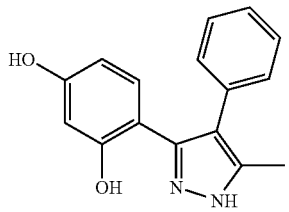

This compounds was synthesised in the same manner as described above. 7-Hydroxy-2-methyl-3-phenyl-chromen-4-one (0.5 g, 1.70 mmol), hydrazine hydrate (5 ml), ethanol (10 ml). The quenched solution was extracted into ethyl acetate, washed (water), dried (MgSO$_4$), and the solvent removed under vacuum to give a yellow oil which was purified by column chromatography to give 4-(5-Methyl-4-phenyl-1H-pyrazol-3-yl)-benzene-1,3-diol as an off white solid (0.37 g, 88%); R$_f$ 0.7 Cf SM 0.8 ethyl acetate/hexane (80/20).

$\delta_H$ (DMSO): 10.53, 9.37 (2H, 2×s, OH), 7.29 (5H, m, ArH), 7.76 (1H, d, J=8 Hz, ArH), 6.32 (1H, s, ArH), 6.06 (1H, d, J=8 Hz, ArH), 2.18 (3H, s, CH$_3$). $\square_c$ (DMSO): 170.7, 158.4, 157.3, 134.6, 129.9, 128.7, 126.7, 116.8, 109.5, 106.5, 103.2 (only 11 unsaturated C peaks observed), 21.1 (CH$_3$). LCMS t$_R$ 6.54, MS m/z 267 [M+H]$^+$.

Synthesis of 4-Chloro-6-(5-methyl-4-phenyl-1H-pyrazol-3-yl)-benzene-1,3-diol

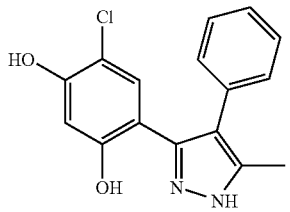

This compounds was synthesised in the same manner as described above. 6-Chloro-7-hydroxy-2-methyl-3-phenyl-chromen-4-one (0.5 g, 1.75 mmol), Hydrazine hydrate (5 ml). The quenched reaction was extracted into ethyl acetate, washed (water), dried (MgSO$_4$), and the solvent removed under vacuum to give 4-Chloro-6-(5-methyl-4-phenyl-1H-pyrazol-3-yl)-benzene-1,3-diol as a white solid (0.27 g, 51.4%); R$_f$ 0.55 ethyl acetate/hexane (80/20)].

$\delta_H$ (DMSO): 10.84, 10.13 (2H,2×s, OH), 7.33 (5H, m, ArH), 6.78 (1H, s, ArH), 6.52 (1H, s, ArH), 2.19 (3H, s, CH$_3$). LCMS t$_R$ 7.16, m/z 301/303 [M+H]$^+$.

Synthesis of 4-[4-(4-Bromo-phenyl)-5-methyl-1H-pyrazol-3-yl]-6-chloro-benzene-1,3-diol

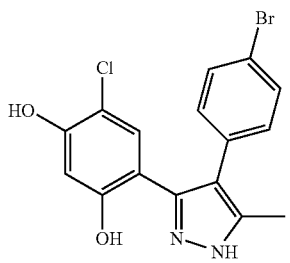

This compounds was synthesised in the same manner as described above. 3-(4-Bromo-phenyl)-6-chloro-7-hydroxy-2-methyl-chromen-4-one (0.5 g, 1.4 mmol), Hydrazine hydrate (5 ml). 4-[4-(4-Bromo-phenyl)-5-methyl-1H-pyrazol-3-yl]-6-chloro-benzene-1,3-diol precipitated out as a pale orange solid (0.08 g, 63.7%); R$_f$ 0.48 cf SM 0.8 [ethyl acetate/petroleum ether 40–60° C. (80/20)].

$\delta_H$ (DMSO): 7.53 (2H, d, J=8 Hz, ArH), 7.14 (2H, d, J=8 Hz, ArH), 6.90 (1H, s, ArH), 6.49 (1H, s, ArH), 2.20 (3H, s, CH$_3$). LCMS t$_R$ 7.75, m/z 379/381 [M+H]$^+$.

Synthesis of 4-[4-(2-Bromo-phenyl)-5-methyl-1H-pyrazol-3-yl]-6-chloro-benzene-1,3-diol

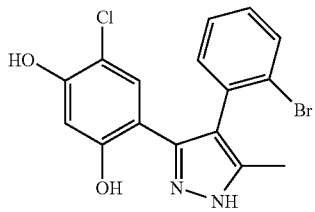

This compounds was synthesised in the same manner as described above. 3-(2-Bromo-phenyl)-6-chloro-7-hydroxy- 2-methyl-chromen-4-one (2.5 g, 6.9 mmol), Hydrazine hydrate (10 ml). 4-[4-(2-Bromo-phenyl)-5-methyl-1H-pyrazol-3-yl]-6-chloro-benzene-1,3-diol precipitated out as an off white solid (0.53 g, 20.2%); R$_f$ 0.5 cf SM 0.85 [ethyl acetate/petroleum ether 40–60° C. (80/20)].

δ$_H$ (DMSO): 10.21, 9.23 (2H, 2×s, OH), 7.77 (1H, d, J=8 Hz, ArH), 7.38 (3H, m, ArH), 6.69 (1H, s, ArH), 6.50 (1H, s, ArH), 2.06 (3H, s, CH$_3$). LCMS t$_R$ 7.28, m/z 379/381 [M+H]$^+$.

Synthesis of 4-Chloro-6-[4-(2,3-dihydro-benzo[1,4]dioxin-6-yl)-5-methyl-1H-pyrazol-3-yl]-benzene-1,3-diol

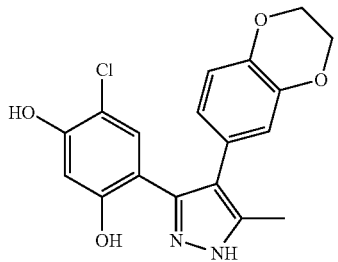

This compounds was synthesised in the same manner as described above. 6-Chloro-3-(2,3-dihydro-benzo[1,4]dioxin-6-yl)-7-hydroxy-2-methyl-chromen-4-one (0.2 g, 0.58 mmol), Hydrazine hydrate (5 ml). The quenched reaction was extracted into ethyl acetate, washed (water), dried (MgSO$_4$), and the solvent removed under vacuum to give 4-Chloro-6-[4-(2,3-dihydro-benzo[1,4]dioxin-6-yl)-5-methyl-1H-pyrazol-3-yl]-benzene-1,3-diol as a white solid (0.08 g, 63.7%).

δ$_H$ (CDCl$_3$): 6.97 (1H, s, ArH), 6.88 (1H, d, J=8 Hz, ArH), 6.69 (1H, d, J=8 Hz, ArH), 6.62 (1H, s, ArH), 6.58 (1H, s, ArH), 4.25 (4H, s, 2×CH$_2$), 2.10 (3H, s, CH$_3$). LCMS t$_R$ 6.85, m/z 357/359 [M−H]$^-$.

Synthesis of 4-[4-(2,3-Dihydro-benzo[1,4]dioxin-6-yl)-5-methyl-1H-pyrazol-3-yl]-6-ethyl-benzene-1,3-diol

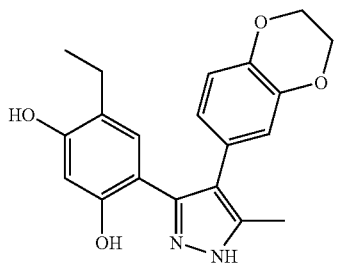

This compounds was synthesised in the same manner as described above. 3-(2,3-Dihydro-benzo[1,4]dioxin-6-yl)-6-ethyl-7-hydroxy-2-methyl-chromen-4-one (0.6 g, 1.77 mmol), hydrazine hydrate (6 ml). The quenched reaction was extracted into ethyl acetate, washed (water), dried (MgSO$_4$), and the solvent removed under vacuum to give a yellow oil which was purified by column chromatography to give 4-[4-(2,3-Dihydro-benzo[1,4]dioxin-6-yl)-5-methyl-1H-pyrazol-3-yl]-6-ethyl-benzene-1,3-diol as a clear oil which solidified over a period of 1 month (0.38 g, 60.9%); R$_f$ 0.4 cf SM 0.6 Hexane/Ethyl acetate/MeOH (8/4/1).

δ$_H$ (DMSO): 10.85, 9.24 (2H, 2×s, OH), 6.76 (5H, m, ArH), 4.23 (4H, s, 2×CH$_2$), 2.05 (3H, s, CH$_3$). LCMS t$_R$ 6.46, m/z 353/355 [M+H]$^-$.

Synthesis of 4-{4-[3-(5-Chloro-2,4-dihydroxy-phenyl)-5-methyl-1H-pyrazol-4-yl]-phenoxy}-butyronitrile

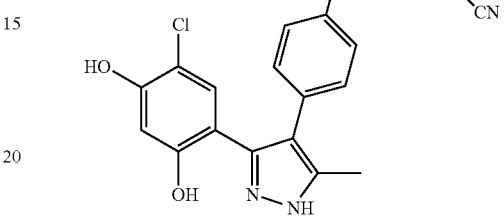

This compound was synthesised in the same manner as described above. 4-[4-(6-Chloro-7-hydroxy-2-methyl-4-oxo-4H-chromen-3-yl)-phenoxy]-butyronitrile (0.55, 1.49 mmol), hydrazine hydrate (6 ml). The quenched reaction was extracted into ethyl acetate, washed (water), dried (MgSO$_4$), and the solvent removed under vacuum to give a brown oil which was purified by column chromatography to give 4-{4-[3-(5-Chloro-2,4-dihydroxy-phenyl)-5-methyl-1H-pyrazol-4-yl]-phenoxy}-butyronitrile as a white solid (0.18 g, 31.5%); R$_f$ 0.5 Ethyl acetate/Hexane (70/30).

δ$_H$ (DMSO): 10.98, 10.13 (2H, 2×s, OH), 7.13 (2H, d, J=8 Hz, ArH), 7.04 (2H, d, J=8 Hz, ArH), 6.90 (41, s, ArH), 6.24 (1H, s, ArH), 4.05 (2H, t, J=7 Hz, CH$_2$), 2.66 (2H, t, J=7 Hz, CH$_2$), 2.01 (2H, m, CH$_2$). LCMS t$_R$ 6.72, m/z 384/386 [M+H]$^-$.

4-{4-[3-(5-Chloro-2,4-dihydroxy-phenyl)-1H-pyrazol-4-yl]-phenoxy}-butyric acid and 4-Chloro-6-[4-(4-hydroxy-phenyl)-1H-pyrazol-3-yl]-benzene-1,3-diol

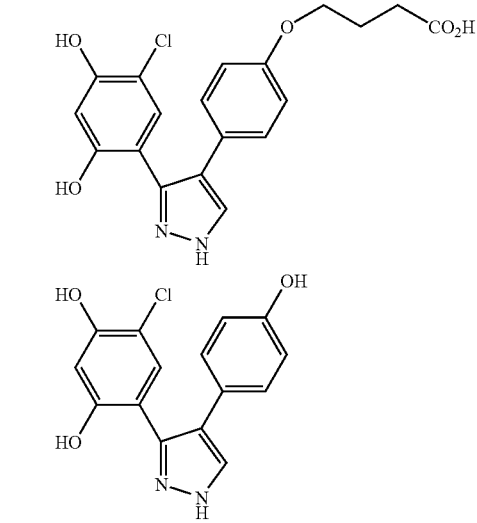

4-{4-[3-(5-Chloro-2,4-dihydroxy-phenyl)-1H-pyrazol-4-yl]-phenoxy}butyronitrile (11 mg, 0.03 mmol) dissolved in 5M HCl (2 ml) and refluxed for 20 hrs before being poured into water and extracted with EtOAc (2×15 ml). The extracts were combined, washed with brine, dried over $Na_2SO_4$ and evaporated off to leave a grey coloured solid. The solid contained the two products which were isolated using preparative TLC, eluting with EtOAc/Hexane/Acetic acid (70:30:1) providing 0.9 mg (12% yield) and 1.1 mg (12% yield) of the products respectively as white crystalline solids.

4-{4-[3-(5-Chloro-2,4-dihydroxy-phenyl)-1H-pyrazol-4-yl]-phenoxy}-butyric acid $δ_H$ ($d_6$-Acetone) 10.59, 8.64 (2H, 2×broad s, OH), 7.71 (1H, s, Het-H), 7.17 (2H d, J=8.8 Hz, Ar—H), 7.07 (1H, s, Ar—H, 6.88 (2H, d, J=8.8 Hz, Ar—H), 6.46 (1H, s, Ar—H), 3.99 (2H, t, J=6.4 Hz, $OCH_2CH_2H$), 2.41 (2H, t, J=6.3 Hz, $CH_2CO_2H$), 21.97 (2H, t, $CH_2CH_2CH_2$). LCMS $t_R$=6.53, MS m/z 389.3 $[M+H]^+$.

4-Chloro-6-[4-(4-hydroxy-phenyl)-1H-pyrazol-3-yl]-benzene-1,3-diol $δ_H$ ($d_6$-Acetone) 10.85, 8.59, 8.33 (3H, 2×broad s, OH), 7.69 (1H, s, Het-H), 7.08 (3H, m Ar—H), 6.78 (2H, d, Ar—H), 6.44 (1H, s, Ar—H). LCMS $t_R$=5.65, MS m/z 303.3 $[M+H]^+$.

4-[4-[3-(5-Chloro-2,4-dihydroxy-phenyl)-1H-pyrazol-4-yl]-2-(3-cyano-propoxy)-phenoxy]-butyronitrile

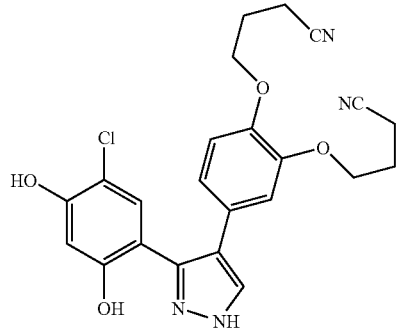

This compound was synthesised in the same manner as described above. 4-[4-(6-Chloro-7-hydroxy-4-oxo-4H-chromen-3-yl)-2-(3-cyano-propoxy)-phenoxy]-butyronitrile (0.12 g, 0.27 mmol), Hydrazine hydrate (5 ml). The precipitate formed on quenching was filtered to give 4-[4-[3-(5-Chloro-2,4-dihydroxy-phenyl)-1H-pyrazol-4-yl]-2-(3-cyano-propoxy)-phenoxy]-butyronitrile as a white solid (0.11 g, 90.1%); $R_f$ 0.6 ethyl acetate/hexane (70/30)]. LCMS $t_R$ 6.21, m/z 453/455 $[M+H]^+$.

5-{3-[3-(5-Chloro-2,4-dihydroxy-phenyl)-1H-pyrazol-4-yl]-phenoxy}-pentanenitrile

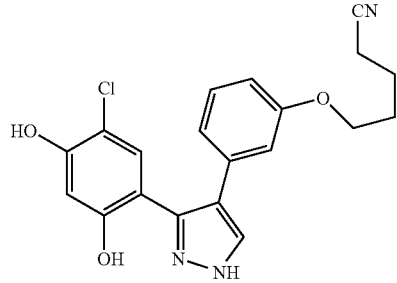

This compound was synthesised in the same manner as described above. 5-[3-(6-Chloro-7-hydroxy-4-oxo-4H-chromen-3-yl)-phenoxy]-pentanenitrile (0.1 g, 0.27 mmol), Hydrazine hydrate (5 ml). The precipitate formed on quenching was filtered to give 5-{3-[3-(5-Chloro-2,4-dihydroxy-phenyl)-1H-pyrazol-4-yl]-phenoxy}-pentanenitrile as a white solid (0.09 g, 87.0%); $R_f$ 0.6 ethyl acetate/hexane (70/30)].

$δ_H$ (DMSO): 10.14 (2H, s, OH), 7.72 (1H, s, =CH), 6.96 (6H, m, ArH), 3.90 (2H, t, J=7 Hz, $CH_2$), 2.45 (2H, t, J=7 Hz, $CH_2$), 1.68 (4H, m, —$(CH_2)_2$—). LCMS $t_R$ 6.63, m/z 384/386 $[M+H]^+$.

5-{4-[3-(5-Chloro-2,4-dihydroxy-phenyl)-1H-pyrazol-4-yl]-phenoxy}-pentanenitrile

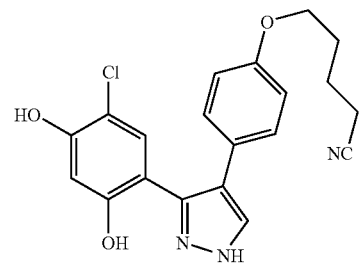

This compounds was synthesised in the same manner as described in Section 1.1.5.1. 5-[4-(6-Chloro-7-hydroxy-4-oxo-4H-chromen-3-yl)-phenoxy]-pentanenitrile (0.1 g, 0.27 mmol), Hydrazine hydrate (5 ml). The precipitate formed on quenching was filtered to give 5-{3-[3-(5-Chloro-2,4-dihydroxy-phenyl)-1H-pyrazol-4-yl]-phenoxy}pentanenitrile as a white solid (0.08 g, 77%); $R_f$ 0.65 ethyl acetate/hexane (70/30)].

$δ_H$ (DMSO): 10.16 (2H, s, OH), 7.80 (1H, s, =CH), 6.90 (6H, m, ArH), 3.84 (2H, t, J=7 Hz, $CH_2$), 2.46 (2H, t, J=7 Hz, $CH_2$), 1.65 (4H, m, —$(CH_2)_2$—). LCMS $t_R$ 6.83, m/z 384/386 $[M+H]^+$.

4-Chloro-6-[4-(3',4'-dimethoxy-biphenyl-4-yl)-1H-pyrazol-3-yl]-benzene-1,3-diol

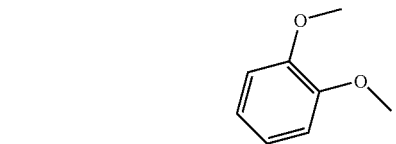

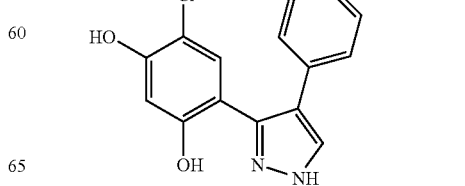

This compound was made as described above.

δ$_H$ (DMSO): 10.23, 9.89 (2H, 2×s, OH), 7.78 (1H, s, =CH), 7.17 (9H, m, ArH), 3.83, 3.78 (6H, 2×s, 2×CH$_3$). LCMS t$_R$ 7.33, m/z 423/425 [M+H]$^+$.

The Following Reactions Refer to Scheme 15:
Synthesis of Benzyl Intermediate for Example 104

Carbonic acid 2-benzoyl-5-ethoxycarbonyloxy-phenyl ester ethyl ester

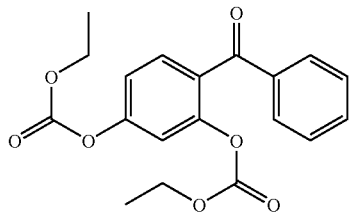

Triethyl amine (10 ml, 72.2 mmol) was added to a solution of 2,4-dihydroxybenzophenone (1) (5.4 g, 23.3 mmol) in THF (50 ml) and the solution cooled to 0° C. Ethyl chloroformate (6.9 ml, 72.2 mmol) was added slowly and the suspension stirrred for ~30 mins at 0° C., and for ~3 hrs at room temperature. Water (150 ml) was added and the mixture extracted with diethyl ether (150 ml). The extracts were washed with water (2×150 ml) and saturated aqueous sodium chloride solution (100 ml). The solution was dried over anhydrous magnesium sulphate and concentrated to give 4-benzyl-benzene-1,3-diol as a pale green gum, solidified on standing, (8.2 g).

LC retention time 2.73 minutes [M+H]$^+$ 359.2 (Run time 3.75 mins) δ (Chloroform-d) 7.7(m 2ArH) 7.5(m 2ArH) 7.35(m 2ArH) 7.15(m 2ArH) 4.25(q J 7.1 Hz 2CH$_2$) 4.05(q J 7.1 Hz 2 CH$_2$) 1.35(t J 7.1 Hz 3CH$_3$) 1.15(t J 7.1 Hz 3 CH$_3$)

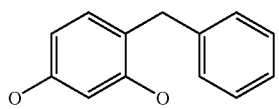

4-benzyl-benzene-1,3-diol

A solution of sodium borohydride (1.85 g, 49 mmol) in water (30 ml) was added to an ice cooled solution of carbonic acid 2-benzoyl-5-ethoxycarbonyloxy-phenyl ester ethyl ester (3.6 g, 10 mmol) in THF (30 ml). The mixture was stirred for ~60 mins. at 0° C., and for ~60 hrs. at room temperature, to give a pale red suspension. Water (150 ml) was added and the mixture extracted with diethyl ether (150 ml). The extracts were washed with water (2×100 ml) and saturated aqueous sodium chloride solution (50 ml). The solution was dried over anhydrous magnesium sulphate and concentrated to give a pale yellow gum. The gum was taken up in aqueous sodium hydroxide (20 ml, 10%), and the solution heated under reflux for ~60 mins. The solution was allowed to cool and acidified with hydochloric acid (5 ml, 37%). The mixture was extracted with diethyl ether (50 ml).

The extracts were washed with water (3×40 ml) and saturated aqueous sodium chloride solution (30 ml). The solution was dried over anhydrous magnesium sulphate and concentrated to give 4-benzyl-benzene-1,3-diol as a dark red gum, (2.1 g).

LC retention time 2.28 minutes [M+H]$^+$ no ion (Run time 3.75 mins) δ (Chloroform-d) 7.2(m 3ArH) 7.1(m 2ArH) 6.85(d J 8.1 Hz ArH) 6.3(d J 8.1 Hz ArH) 6.2(s ArH) 3.85(s 2CH$_2$)

The Following Reactions Refer to Scheme 10:
General Synthesis of Dihydroxyphenyl Ketones for Example 64, 92–96, 104, 140

1-(2,4-Dihydroxy-phenyl)-2-(4-methoxy-phenyl)-ethanone

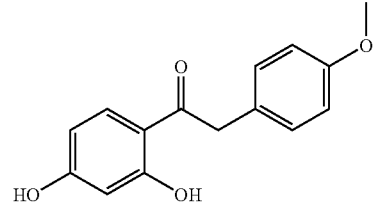

Resorcinol (4.4 g, 40 mmol) and 4-methoxyphenylacetic acid (6.6 g, 40 mmol) in boron trifluoride.etherate (25 ml, 0.2 mol) was heated, under a nitrogen atmosphere, at 90° C. for ~90 mins. to give a pale red solution. The solution was allowed to cool and poured into aqueous sodium acetate (200 ml, 10%) and the mixture stirred to give a pale yellow precipitate. The solids were removed by filtration and washed with water (200 ml). Solids were taken up in ethyl acetate (250 ml) and washed with water (200 ml). Solution was dried over anhyrous magnesium sulphate and concentrated, to a yellow semi-solid. Trituration with diethyl ether (100 ml) gave the 1-(2,4-dihydroxy-phenyl)-2-(4-methoxy-phenyl)-ethanone as a pale orange solid, dried in vacuo, (2.2 g)

LC retention time 2.39 minutes [M+H]$^+$ 259.2 (Run time 3.75 mins)

δ (DMSO-d$_6$) 7.95(d J 8.9 Hz ArH) 7.2(d J 8.7 Hz 2ArH) 6.9(d J 8.7 Hz 2ArH) 6.4(d J 9.9 ArH) 6.25(s ArH) 4.2(s 2CH$_2$) 3.75(s 3OCH$_3$)

Similarly

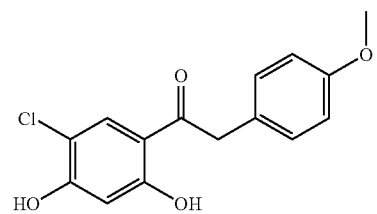

4-Chlororesorcinol gave 1-(5-Chloro-2,4-dihydroxy-phenyl)-2-(4-methoxy-phenyl)-ethanone LC retention time 2.74 minutes [M+H]$^+$ 293.2 (Run time 3.75 mins) δ (DMSO-d$_6$) 7.65(s ArH) 7.0(d J 8.7 Hz 2ArH) 6.7(d J 8.7 Hz 2ArH) 5.45(s ArH) 3.7(s 2CH$_2$) 3.5(s 3OCH$_3$)

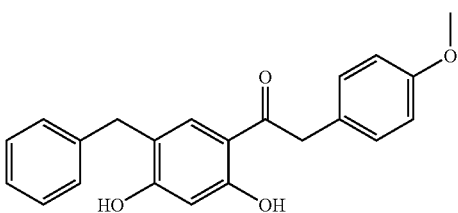

4-benzyl-benzene-1,3-diol gave 1-(5-benzyl-2,4-dihydroxy-phenyl)-2-(4-methoxy-phenyl)-ethanone LC retention time 2.78 minutes [M+H]$^+$ 349.3 (Run time 3.75 mins) δ (Chloroform-d) 7.4(s ArH) 7.3-7.0(m 5ArH) 6.95(d J 8.7 Hz 2ArH) 6.75(d J 8.7 Hz 2ArH) 6.25(s ArH) 3.95(s 2CH$_2$) 3.8(s 2CH$_2$) 3.7(s 3OCH$_3$)

The Following Reactions Refer to Scheme 11.
General Synthesis of
7-hydroxy-2-methyl-3-phenyl-chromen-4-ones for
Examples 64, 92–96, 104, 140

7-Hydroxy-3-(4-methoxy-phenyl)-2-methyl-chromen-4-one

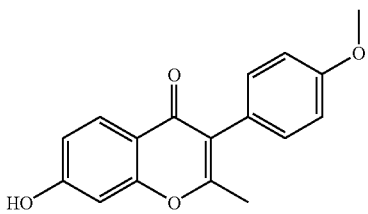

Acetic anhydride (3 ml, 30 mmol) was added to a suspension of potassium carbonate (4.0 g, 29 mmol) and 1-(2,4-dihydroxy-phenyl)-2-(4-methoxy-phenyl)-ethanone (1.95 g, 7.5 mmol) in DMF (10 ml), and the resulting suspension heated at 115° C. for ~90 mins. The mixture was allowed to cool and poured into water (200 ml), to give an off-white precipitate. The solids were removed by filtration and washed with water (100 ml) and diethyl ether (2×40 ml), to give 7-hydroxy-3-(4-methoxy-phenyl)-2-methyl-chromen-4-one as an off-white powder, dried in vacuo, (1.65 g)

LC retention time 2.26 minutes [M+H]$^+$ 283.2 (Run time 3.75 mins) δ (DMSO-d$_6$) 7.8(d J 8.7 Hz ArH) 7.2(d J 8.8 Hz 2ArH) 7.0(d J 8.8 Hz 2ArH) 6.9(d J 8.7 ArH) 6.8(s ArH) 3.8(s 3OCH$_3$) 2.2(s 3CH$_3$)

Similarly

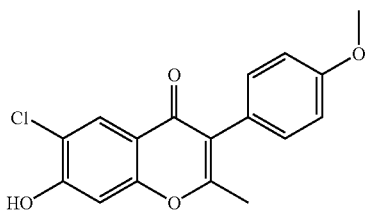

1-(5-Chloro-2,4-dihydroxy-phenyl)-2-(4-methoxy-phenyl)-ethanone gave 6-chloro-7-hydroxy-3-(4-methoxy-phenyl)-2-methyl-chromen-4-one LC retention time 2.33 minutes [M+H]$^+$ 317.2 (Run time 3.75 mins) δ (DMSO-d$_6$) 8.0(s ArH) 7.3(d J 8.7 Hz 2ArH) 7.15(s ArH) 7.1(d J 8.7 Hz 2ArH) 3.9(s 3OCH$_3$) 2.35(s 3CH$_3$)

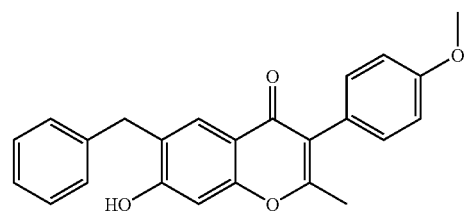

7-Hydroxy-3-(4-methoxy-phenyl)-2-methyl-chromen-4-one gave 6-benzyl-7-hydroxy-3-(4-methoxy-phenyl)-2-methyl-chromen-4-one LC retention time 2.57 minutes [M+H]$^+$ 373.3 (Run time 3.75 mins) δ (DMSO-d$_6$) 7.7(s ArH) 7.4–7.2(m 5ArH) 7.15(d J 8.8 Hz 2ArH) 6.95(d J 8.8 Hz 2ArH) 6.9(s ArH) 4.0(s 2CH$_2$) 3.8(s 3OCH$_3$) 2.25(s 3CH$_3$)

The Following Reaction Refers to Scheme 16:
Synthesis of Dichloro for Example 139

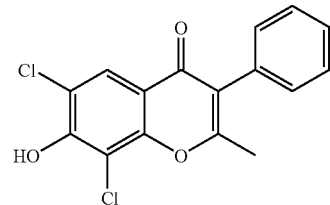

6,8-dichloro-7-hydroxy-2-methyl-3-phenyl-chromen-4-one

N-Chlorosuccinimide (0.27 g, 2 mmol) was added to a solution of 6-chloro-7-hydroxy-3-(4-methoxy-phenyl)-2-methyl-chromen-4-one (0.29 g, 1 mmol) in DMF (4 ml) and the solution stirred for 3 hrs. and at 50° C. for ~3 hrs. The resulting solution was poured into water (50 ml) and extracted with ethyl acetate (2×30 ml). The combined extracts were washed with water (5×50 ml) and saturated aqueous sodium chloride solution (30 ml). The solution was dried over anhydrous magnesium sulphate and concentrated to give a dark yellow oil. Trituration with hexane gave 6,8-dichloro-7-hydroxy-2-methyl-3-phenyl-chromen-4-one as a pale orange powder, dried in vacuo, (0.19 g)

LC retention time 2.52 minutes [M+H]$^+$ 323.1 (Run time 3.75 mins) δ (Chloroform-d) 8.1(s ArH) 7.5–7.3(m 3ArH) 7.3–7.15(m 2ArH) 2.3(s 3CH$_3$)

The Following Reaction Refers to Scheme 17:
Synthesis of Bromo Flavone for Example 135

8-bromo-7-hydroxy-2-methyl-3-phenyl-chromen-4-one

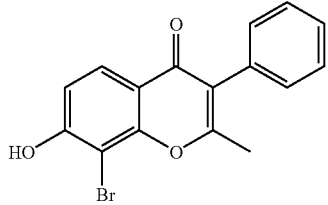

N-Bromosuccinimide (2.0 g, 11.2 mmol) was added to a solution of 7-hydroxy-2-methyl-3-phenyl-chromen-4-one (2.5 g, 10 mmol) in DMF (20 ml) and the solution stirred for ~24 hrs. to give an orange suspension. The suspension was poured into water (200 ml) to give a pale pink precipitate, solids were removed by filtation and washed with water. Solids were recrystallised from ethanol, to give the 8-bromo-7-hydroxy-2-methyl-3-phenyl-chromen-4-one as an off-white solid (1.95 g)

LC retention time 2.39 minutes [M+H]$^+$ 333.1 (Run time 3.75 mins) δ (DMSO-d$_6$) 7.75(d J 8.8 Hz ArH) 7.4–7.2(m 3ArH) 7.15(m 2ArH) 6.95(d J 8.8 Hz ArH) 2.15(s 3CH$_3$)

The Following Reactions Refer to Scheme 13.
Pyrazole synthesis for examples 64, 92–96, 104, 140

4-[4-(4-Methoxy-phenyl)-5-methyl-1H-pyrazol-3-yl]-benzene-1,3-diol

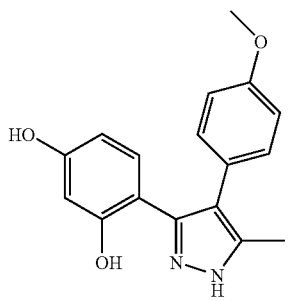

Hydrazine hydrate (2 ml, ~55%) was added to a suspension of 7-hydroxy-3-(4-methoxy-phenyl)-2-methyl-chromen-4-one (0.57 g, 2 mmol) in ethanol (15 ml) and the mixture heated under reflux for ~5 hrs., to give a pale brown solution. The solution was allowed to cool and concentrated to a pale yellow solid, the solids were washed with water, to give the pyrazole as an off-white solid, dried in vacuo, (0.45 g). Sample was recrystallised from boiling toluene, to give the 4-[4-(4-methoxy-phenyl)-5-methyl-1H-pyrazol-3-yl]-benzene-1,3-diol as a pale brown crystalline solid, washed with hexane, dried in vacuo.

LC retention time 2.16 minutes [M+H]$^+$ 297.2 (Run time 3.75 mins) δ (Acetone-d$_6$) 7.2(d J 8.8 Hz 2ArH) 7.0(d J 8.8 Hz 2ArH) 6.9(d J 8.6 Hz ArH) 6.35(s ArH) 6.1(d J 8.7 Hz ArH) 3.85(s 3OCH$_3$) 2.2(s 3CH$_3$)

Similarly

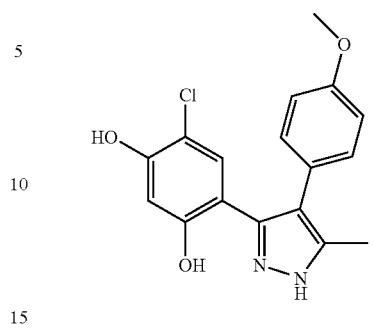

6-Chloro-7-hydroxy-3-(4-methoxy-phenyl)-2-methyl-chromen-4-one gave 4-chloro-6-[4-(4-methoxy-phenyl)-5-methyl-1H-pyrazol-3-yl]-benzene-1,3-diol LC retention time 2.34 minutes [M+H]$^+$ 331.2 (Run time 3.75 mins) δ (Acetone-d$_6$) 7.25(d J 8.8 Hz 2ArH) 7.15(d J 8.8 Hz 2ArH) 7.1(s ArH) 6.5(s ArH) 3.85(s 3OCH$_3$) 2.2(s 3CH$_3$)

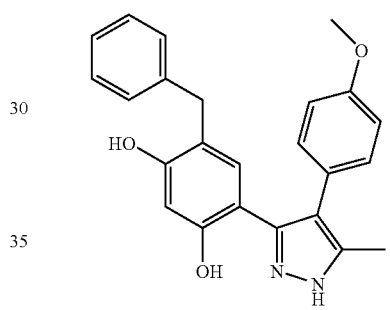

6-Benzyl-7-hydroxy-3-(4-methoxy-phenyl)-2-methyl-chromen-4-one gave 4-benzyl-6-[4-(4-methoxy-phenyl)-5-methyl-1H-pyrazol-3-yl]-benzene-1,3-diol LC retention time 2.57 minutes [M+H]+387.3 (Run time 3.75 mins) δ (Acetone-d$_6$) 7.15–6.9(m 9ArH) 6.75(s ArH) 6.3(s ArH) 3.75(s 3OCH$_3$) 2.45(br s 4CH$_2$) 2.15(s 3CH$_3$)

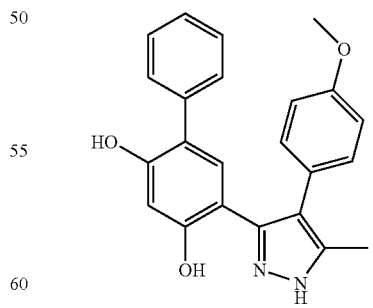

7-Hydroxy-3-(4-methoxy-phenyl)-2-methyl-6-phenyl-chromen-4-one gave 5-[4-(4-methoxy-phenyl)-5-methyl-1H-pyrazol-3-yl]-biphenyl-2,4-diol LC retention time 2.49 minutes [M+H]+ 373.3 (Run time 3.75 mins) δ (Acetone-$d_6$) 7.3–7.05(m 10ArH) 6.5(s ArH) 3.85(s 3OCH$_3$) 2.2(s 3CH$_3$)

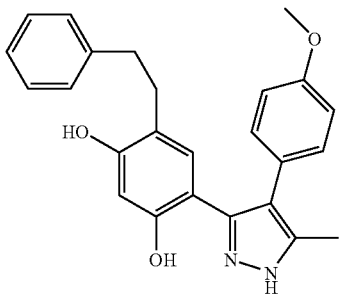

7-Hydroxy-3-(4-methoxy-phenyl)-2-methyl-6-phenethyl-chromen-4-one gave 4-[4-(4-Methoxy-phenyl)-5-methyl-1H-pyrazol-3-yl]-6-phenethyl-benzene-1,3-diol LC retention time 2.64 minutes [M+H]+ 401.3 (Run time 3.75 mins) δ (Acetone-$d_6$) 7.15–6.9(m 9ArH) 6.8(s ArH) 6.4(s ArH) 3.8(s 3OCH$_3$) 3.55(s 2CH$_2$) 2.15(s 3CH$_3$)

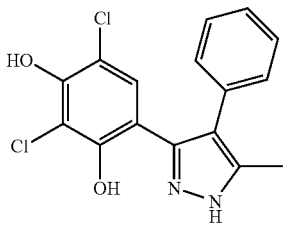

6,8-Dichloro-7-hydroxy-2-methyl-3-phenyl-chromen-4-one gave 2,4-dichloro-6-(5-methyl-4-phenyl-1H-pyrazol-3-yl)-benzene-1,3-diol LC retention time 2.56 minutes [M+H]+ 337.2 (Run time 3.75 mins) δ (Acetone-$d_6$) 7.45–7.25(m 3ArH) 7.15(m 2ArH) 6.95(s ArH) 2.25(s 3CH$_3$)

The Following Reactions Refer to Scheme 18:
Synthesis of Bromo Resorcinols for Examples 93, 135, 140

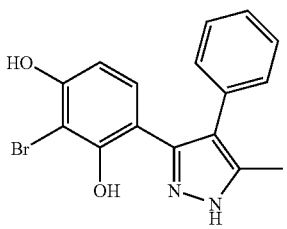

8-Bromo-7-hydroxy-2-methyl-3-phenyl-chromen-4-one gave 2-bromo-4-(5-methyl-4-phenyl-1H-pyrazol-3-yl)-benzene-1,3-diol LC retention time 2.4 minutes [M+H]+ 347.2 (Run time 3.75 mins) δ (Acetone-$d_6$) 7.5–7.35(m 3ArH) 7.3(m 2ArH) 6.85(d J 8.6 Hz ArH) 6.25(d J 8.6 Hz ArH) 2.2(s 3CH$_3$)

4-Bromo-6-[4-(4-methoxy-phenyl)-5-methyl-1H-pyrazol-3-yl]-benzene-1,3-diol

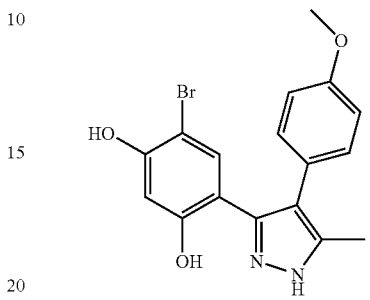

Benzyltrimethylammonium tribromide (4.0 g, 10.2 mmol) was added portion-wise to a suspension of 4-[4-(4-methoxy-phenyl)-5-methyl-1H-pyrazol-3-yl]-benzene-1,3-diol (2.95 g, 10 mmol) in dichloromethane (50 ml) and the mixture stirred for ~90 mins. The mixture washed with water (3×50 ml) and saturated aqueous sodium chloride solution (25 ml). The solution was dried over anhydrous magnesium sulphate and concentrated to give a pale yellow solid. Crude product was purified by column chromatography, on silica, eluting with ethyl acetate/hexane (1:2) to give 4-bromo-6-[4-(4-methoxy-phenyl)-5-methyl-1H-pyrazol-3-yl]-benzene-1,3-diol (1.75 g)

LC retention time 2.37 minutes [M+H]+ 375.1 (Run time 3.75 mins) δ (Acetone-$d_6$) 7.25(d J 8.8 Hz 2ArH) 7.2(s ArH) 7.1(d J 8.8 Hz 2ArH) 6.55(s ArH) 3.9(s 3OCH$_3$) 2.2(s 3CH$_3$)

Similarly:

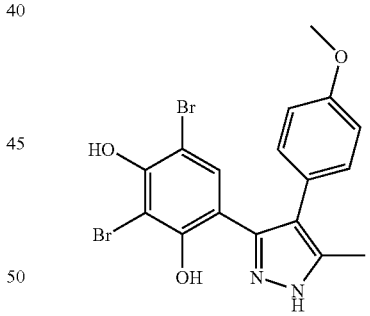

2,4-Dibromo-6-[4-(4-methoxy-phenyl)-5-methyl-1H-pyrazol-3-yl]-benzene-1,3-diol (0.14 g)

LC retention time 2.59 minutes [M+H]+ 455.1 (Run time 3.75 mins) δ (Acetone-$d_6$) 7.25(d J 8.8 Hz 2ArH) 7.2(s ArH) 7.1(d J 8.8 Hz 2ArH) 3.85(s 3OCH$_3$) 2.2(s 3CH$_3$)

The Following Reactions Refer to Scheme 21:
Synthesis of Fluorescence Probes for Examples 105, 106

3-(2,4-bis-benzyloxy-5-chloro-phenyl)-1H-pyrazole was prepared according to the procedures described above.

3-(2,4-bis-benzyloxy-5-chloro-phenyl)-4-iodo-1H-pyrazole

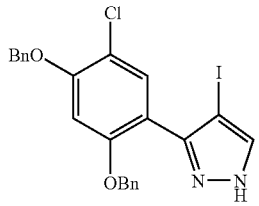

To a mixture of 3-(2,4-bis-benzyloxy-5-chloro-phenyl)-1H-pyrazole (4.06 g 10.05 mmol) in DCM (50 ml) was added N-iodosuccinimide (2.35 g, 10.45 mmol) in bulk. The mixture was stirred at room temperature for two hours and then partitioned between water and DCM. The organics were washed with saturated sodium thiosulphate solution then water and dried in vacuo to give a yellow crystalline mass, which was triturated from ethyl acetate by the gradual addition, whilst stirring, of hexanes to give 3-(2,4-bis-benzyloxy-5-chloro-phenyl)-4-iodo-1H-pyrazole (5.21 g, 97%).

LC retention time 2.93 minutes, [M+H]$^+$ 517.

3-(2,4-bis-benzyloxy-5-chloro-phenyl)-4-iodo-1-(2-trimethylsilanyl-ethoxymethyl)-1H-pyrazole

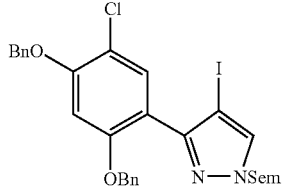

To a mixture of 3-(2,4-bis-benzyloxy-5-chloro-phenyl)-4-iodo-1H-pyrazole (4.46 g, 8.63 mmol) and caesium carbonate (8.43 g, 25.88 mmol) in DMF (50 ml) was added 2-(trimethylsilyl)ethoxymethyl chloride (2.29 ml, 12.94 mmol). The mixture was stirred at room temperature overnight before being partitioned between water and DCM. The organics were then washed with brine and water and concentrated in vacuo to give a yellow oil which was purified by column chromatography using hexanes and ethyl acetate as eluent, yielding 3-(2,4-bis-benzyloxy-5-chloro-phenyl)-4-iodo-1-(2-trimethylsilanyl-ethoxymethyl)-1H-pyrazole as a clear colourless oil (4.44 g, 80%).

LC retention time 3.24 minutes, [M+H]$^+$ 647.

4-[3-(2,4-bis-benzyloxy-5-chloro-phenyl)-1-(2-trimethylsilanyl-ethoxymethyl)-1H-pyrazol-4-yl]-benzylamine

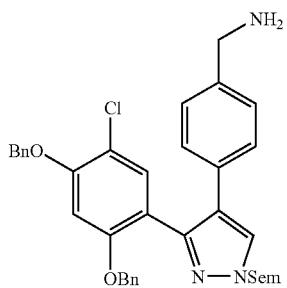

To a mixture of 3-(2,4-bis-benzyloxy-5-chloro-phenyl)-4-iodo-1-(2-trimethylsilanyl-ethoxymethyl)-1H-pyrazole (0.1 g, 0.15 mmol) in DMF (3 ml) was added 4-aminomethylboronic acid (0.028 g, 0.30 mmol). 1M sodium bicarbonate solution (0.5 ml, 0.5 mmol) was then added, followed by dichlorobis(triphenylphosphine) palladium 11 (0.011 g, 0.015 mmol). The mixture was degassed and then heated to 150° C., for 600 seconds under microwave irradiation. The mixture was then concentrated in vacuo and purified by column chromatography using dichloromethane and methanol as eluent to give 4-[3-(2,4-bis-benzyloxy-5-chloro-phenyl)-1-(2-trimethylsilanyl-ethoxymethyl)-1H-pyrazol-4-yl]-benzylamine (0.025 g, 26%).

LC retention time 2.59 minutes, [M+H]$^+$ 626.

4-[3-(2,4-bis-benzyloxy-5-chloro-phenyl)-1-(2-trimethylsilanyl-ethoxymethyl)-1H-pyrazol-4-yl]-benzylamine

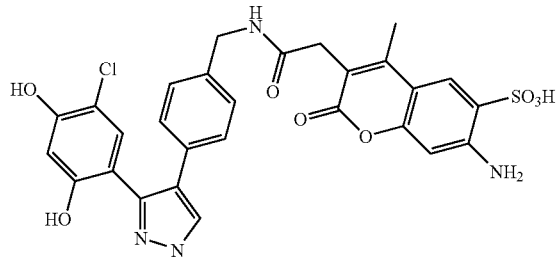

To a mixture of 4-[3-(2,4-bis-benzyloxy-5-chloro-phenyl)-1-(2-trimethylsilanyl-ethoxymethyl)-1H-pyrazol-4-yl]-benzylamine (0.0076 g, 0.012 mmol) and triethylamine (0.005 ml, 0.036 mmol) in DCM (1 ml) was added (7-amino-4,6-dimethyl-2-oxo-2H-chromen-3-yl)-acetic acid 2,5-dioxo-pyrrolidin-1-yl ester (0.005 g, 0.0121 mmol). The mixture was stirred at room temperature for 1 hour, then boron trichloride (1M in DCM, 0.06 ml, 0.06 mmol) was added dropwise. After stirring for one hour, the mixture was quenched by addition of water (0.5 ml), then concentrated in vacuo to give a white powder which was purified by prep-scale LCMS to give 4-[3-(2,4-bis-benzyloxy-5-chloro-phenyl)-1-(2-trimethylsilanyl-ethoxymethyl)-1H-pyrazol-4-yl]-benzylamine as a white powder (0.0018 g, 27%).

LC retention time 1.80 minutes, [M+H]$^+$ 611.

N-4-[3-(2,4-bis-benzyloxy-5-chloro-phenyl)-1-(2-trimethylsilanyl-ethoxymethyl)-1H-pyrazol-4-yl]-benzyl]-6-(6-hydroxy-3-oxo-3H-xanthen-9-yl)-isophthalic acid

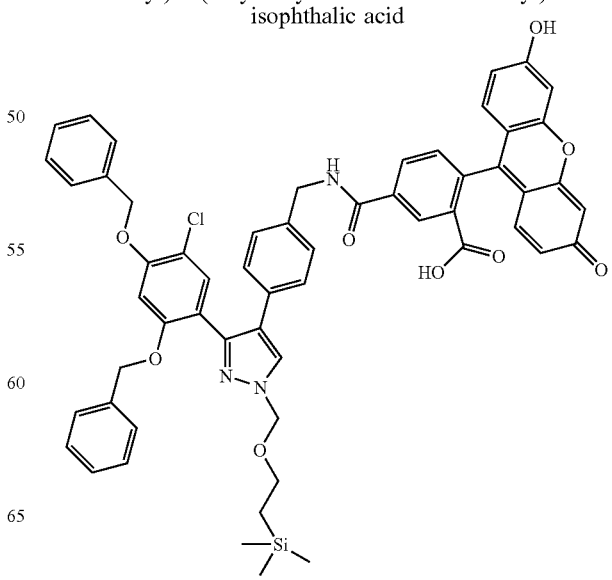

To a mixture of 4-[3-(2,4-bis-benzyloxy-5-chloro-phenyl)-1-(2-trimethylsilanyl-ethoxymethyl)-1H-pyrazol-4-yl]-benzylamine (0.02 g, 0.03 mmol) and triethylamine (0.02 ml, 0.15 mmol) in DCM (1 ml) was added 4-(6-hydroxy-3-oxo-3H-xanthen-9-yl)-isophthalic acid 2,5-dioxo-pyrrolidin-1-yl ester (0.016 g, 0.03 mmol). The mixture was stirred at room temperature for 1 hour, then concentrated in vacuo. The mixture was purified by column chromatography using ethyl acetate and hexanes as eluent to give N-4-[3-(2,4-bis-benzyloxy-5-chloro-phenyl)-1-(2-trimethylsilanyl-ethoxymethyl)-1H-pyrazol-4-yl]-benzyl)-6-(6-hydroxy-3-oxo-3H-xanthen-9-yl)-isophthalic acid as a yellow solid (0.0126 g, 40%).

LC retention time 3.16 minutes, [M+H]+ 983.

N-{4-[3-(5-Chloro-2,4-dihydroxy-phenyl)-1H-pyrazol-4-yl]-benzyl}-6-(6-hydroxy-3-oxo-3H-xanthen-9-yl)-isophthalamic acid

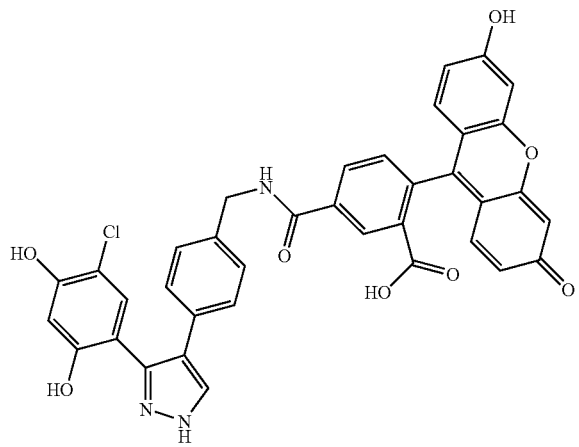

To a mixture of N-4-[3-(2,4-bis-benzyloxy-5-chloro-phenyl)-1-(2-trimethylsilanyl-ethoxymethyl)-1H-pyrazol-4-yl]-benzyl)-6-(6-hydroxy-3-oxo-3H-xanthen-9-yl)-isophthalic acid (0.0126 g, 0.013 mmol) in DCM (1 ml) was added boron trichloride (1M in DCM, 0.06 ml, 0.06 mmol) dropwise. After stirring for one hour, the mixture was quenched by addition of water (0.5 ml), then concentrated in vacuo to give a yellow powder which was purified by prep-scale LCMS to give N-{4-[3-(5-chloro-2,4-dihydroxy-phenyl)-1H-pyrazol-4-yl]-benzyl}-6-(6-hydroxy-3-oxo-3H-xanthen-9-yl)-isophthalamic acid as a yellow powder (0.00285 g, 32%).

LC retention time 2.21 minutes, [M+H]+ 675.

The Following Reactions Refer to Scheme 20:
Synthesis of 4'fluoro-2'-phenol for Examples 148, 151, 152

4-(4-Methoxy-phenyl)-5-methyl-1H-pyrazole

To p-Methoxy phenylacetone (1 eq) was added dimethylformamide dimethylacetal (1.5 eq) and the mixture was stirred at reflux overnight. The reaction was cooled to room temperature and diluted with ethanol. Hydrazine hydrate was added (3 eq) and all was heated to 85° C. over night. Once cooled the reaction mixture was concentrated in vacuo and partitioned between EtOAc and water. The organic phase was dried over MgSO4, filtered and concentrated in vacuo to give 4-(4-methoxy-phenyl)-5-methyl-1H-pyrazole as a white solid.

LC retention time 2.017 min [M+H]+ 189.2

4-(4-Methoxy-phenyl)-5-methyl-1-(2-trimethylsilanyl-ethoxymethyl)-1H-pyrazole and 4-(4-Methoxy-phenyl)-3-methyl-1-(2-trimethylsilanyl-ethoxymethyl)-1H-pyrazole

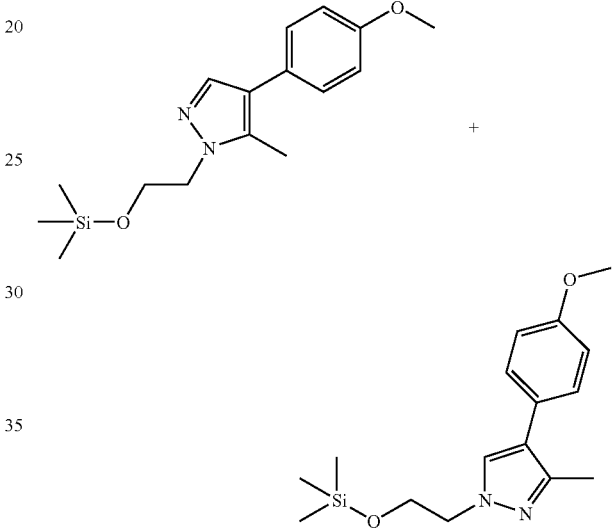

4-(4-Methoxy-phenyl)-5-methyl-1H-pyrazole (1 eq) was taken up in DMF and under N2 was cooled to 0° C. Caesium carbonate (1 eq) was added and the solution was stirred for five minutes. 2-(Trimethylsilyl)ethoxy methyl chloride (0.95 eq) was added dropwise and all was stirred for 2 hours. The reaction mixture was partitioned between water and EtOAc. The organic phase was dried over MgSO4, filtered and concentrated in vacuo to give a gum. This was purified by flash chromatography (8:1 hexane: EtOAc) to give 4-(4-methoxy-phenyl)-5-methyl-1-(2-trimethylsilanyl-ethoxymethyl)-1H-pyrazole and 4-(4-methoxy-phenyl)-3-methyl-1-(2-trimethylsilanyl-ethoxymethyl)-1H-pyrazole as a mixture of isomers.

LC retention time 2.868 min [M+H]+ 319.3

4-(4-Methoxy-phenyl)-3-methyl-1-(2-trimethylsilanyl-ethoxymethyl)-1H-pyrazole-5-boronic acid

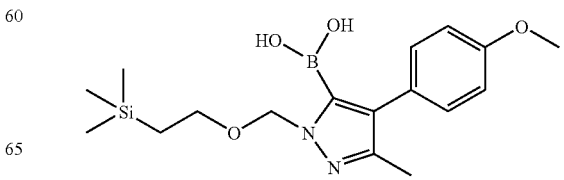

A mixture of 4-(4-methoxy-phenyl)-5-methyl-1-(2-trimethylsilanyl-ethoxymethyl)-1H-pyrazole and 4-(4-methoxyphenyl)-3-methyl-1-(2-trimethylsilanyl-ethoxymethyl)-1H-pyrazole (1 eq) was taken up in THF and cooled under nitrogen to −78° C. "BuLi (1.2 eq) was added dropwise and all was stirred for 30 minutes. Triisopropylborate (2.5 eq) was added and the reaction was stirred to room temperature. After 45 minutes, the reaction mixture was quenched with water and extracted with EtOAc. The organic phase was dried over MgSO$_4$, filtered and concentrated in vacuo to give a gum. This was purified by flash chromatography (9:1 hexane: EtOAc) to give 4-(4-methoxy-phenyl)-3-methyl-1-(2-trimethylsilanyl-ethoxymethyl)-1H-pyrazole-5-boronic acid as an oil.

LC retention time 2.538 min [M+H]$^+$ 363.3

2-Bromo-4-chloro-5-fluoro-phenol

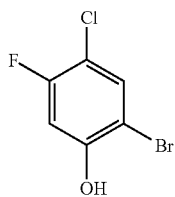

4-Chloro-3-fluorophenol was treated as described in JOC 1997 62 4504–4506, to give 2-bromo-4-chloro-5-fluorophenol as a gum.

LC retention time 2.468 min; sample doesn't ionise.

1-Benzyloxy-2-bromo-4-chloro-5-fluoro-benzene

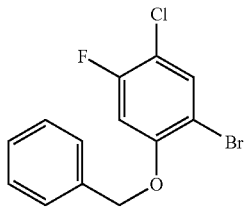

2-Bromo-4-chloro-5-fluoro-phenol (1 eq) was taken up in DMF. Caesium Carbonate (2.5 eq) was added and the solution was stirred for 5 minutes. Benzyl bromide (1.05 eq) was added and all was stirred at room temperature for 3 hours under nitrogen. The reaction mixture was diluted with brine and extracted into diethyl ether. The organic phase was washed several time with brine, dried over MgSO$_4$, filtered and concentrated in vacuo, to give 1-benzyloxy-2-bromo-4-chloro-5-fluoro-benzene as an oil, which solidified on standing.

LC retention time 2.930 min sample doesn't ionise.

5-(2-Benzyloxy-5-chloro-4-fluoro-phenyl)-4-(4-methoxy-phenyl)-3-methyl-1-(2-trimethylsilanyl-ethoxymethyl)-1H-pyrazole

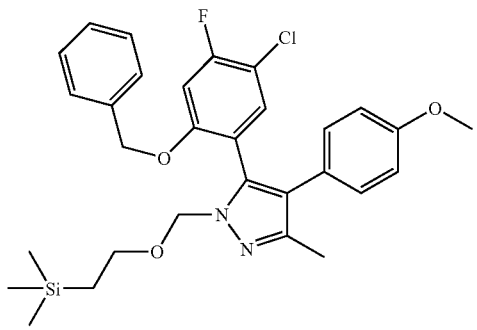

1-Benzyloxy-2-bromo-4-chloro-5-fluoro-benzene (1.5 eq) was taken up in ethyl glycol dimethylether and degassed with nitrogen. Example 3 (1 eq) was added and the solution was diluted with the same volume of 1M Na$_2$CO$_3$. A catalytic amount of Pd(PPh$_3$)$_4$ was added and the reaction mixture was heated to 150° C. for 5 minutes in the Smith Personal Synthesiser microwave. The resulting reaction mixture was diluted with water and extracted into diethyl ether. The organic phase was dried over MgSO$_4$, filtered, concentrated in vacuo and purified by preparative LC/MS, to give 5-(2-benzyloxy-5-chloro-4-fluoro-phenyl)-4-(4-methoxy-phenyl)-3-methyl-1-(2-trimethylsilanyl-ethoxymethyl)-1H-pyrazole LC retention time 3.197 min [M+H]$^+$ 553.5/555.5 (chlorine splitting pattern)

4-Chloro-5-fluoro-2-[4-(4-methoxy-phenyl)-5-methyl-2H-pyrazol-3-yl]-phenol

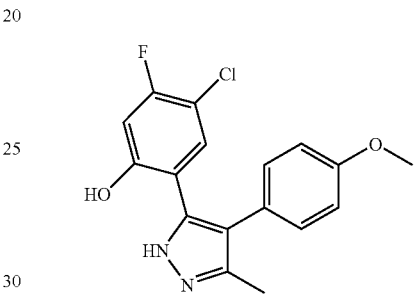

5-(2-Benzyloxy-5-chloro-4-fluoro-phenyl)-4-(4-methoxy-phenyl)-3-methyl-1-(2-trimethylsilanyl-ethoxymethyl)-1H-pyrazole (1 eq) was taken up in anhydrous dichloromethane and the solution was cooled under nitrogen to 0° C. 1M boron trichloride in dichloromethane (6 eq) was added dropwise and the solution was allowed to stir for 1 hour. The reaction mixture was added dropwise to sat. NaHCO$_3$ (aq) and the resulting solution was extracted into dichloromethane. The organic phases were washed with brine, dried over MgSO$_4$, filtered and concentrated in vacuo. The residue was purified by preparative LC/MS, to give 4-chloro-5-fluoro-2-[4-(4-methoxy-phenyl)-5-methyl-2H-pyrazol-3-yl]-phenol as a white solid.

LC/MS retention time=2.755 min [M+H]$^+$ 333.2/335.2 (chlorine splitting pattern)

The Following Reactions Refer to Scheme 23:
Synthesis of Aminopyrimidine for Example 152

4-[4-(4-Methoxy-phenyl)-5-methyl-2-(2-trimethylsilanyl-ethoxymethyl)-2H-pyrazol-3-yl]-6-methyl-pyrimidin-2-ylamine

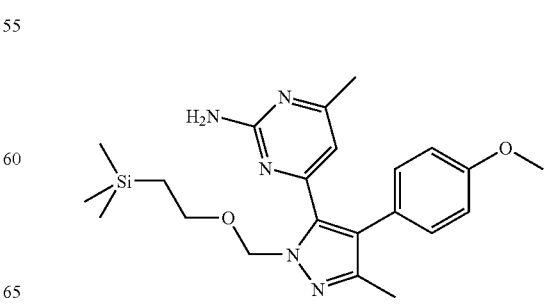

4-Chloro-6-methylpyrimidine-2-yl amine (1.5 eq) was taken up in ethyl glycol dimethylether and degassed with nitrogen. Example 3 (1 eq) was added and the solution was diluted with the same volume of 1M Na$_2$CO$_3$. A catalytic amount of Pd(PPh$_3$)$_4$ was added and the reaction mixture was heated to 150° C. for 5 minutes in the Smith Personal Synthesiser microwave. The resulting reaction mixture was diluted with water and extracted into diethyl ether. The organic phase was dried over MgSO$_4$, filtered, concentrated in vacuo and purified by preparative LC/MS, to give 4-[4-(4-methoxy-phenyl)-5-methyl-2-(2-trimethylsilanyl-ethoxymethyl)-2H-pyrazol-3-yl]-6-methyl-pyrimidin-2-ylamine.

LC retention time 2.686 min [M+H]$^+$ 426.4 d

4-[4-(4-Methoxy-phenyl)-5-methyl-2H-pyrazol-3-yl]-6-methyl-pyrimidin-2-ylamine

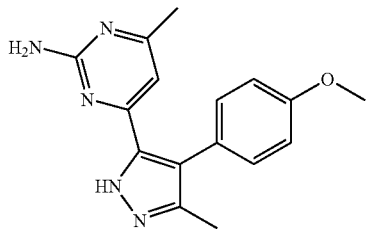

4-[4-(4-Methoxy-phenyl)-5-methyl-2-(2-trimethylsilanyl-ethoxymethyl)-2H-pyrazol-3-yl]-6-methyl-pyrimidin-2-ylamine was dissolved in anhydrous dichloromethane under nitrogen. 2M borontrichloride.dimethylether in dichloromethane (7 eq) was added dropwise, and all was stirred for 2 hours. The reaction mixture was added dropwise to sat. NaHCO$_3$(aq) and extracted into dichloromethane. The organic phase was dried over MgSO$_4$, filtered and concentrated in vacuo. The residue was purified by preparative LC/MS to give 4-[4-(4-methoxy-phenyl)-5-methyl-2H-pyrazol-3-yl]-6-methyl-pyrimidin-2-ylamine as a solid.

LC retention time 1.885 min [M+H]$^+$ 296.1

The Following Reactions Refer to Scheme 22:
Synthesis of methyl-aminopyrimidine for Examples 151

5-[4-(4-Methoxy-phenyl)-5-methyl-2-(2-trimethylsilanyl-ethoxymethyl)-2H-pyrazol-3-yl]-pyrimidin-2-ylamine

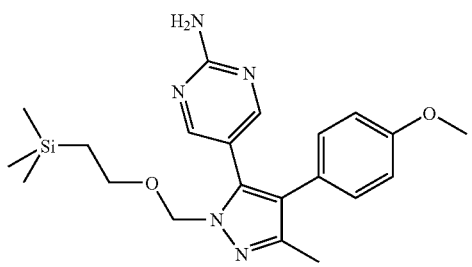

5-Bromo-pyrimidine-2-yl amine (1.5 eq) was taken up in ethyl glycol dimethylether and degassed with nitrogen. Example 3 (1 eq) was added and the solution was diluted with the same volume of 1M Na$_2$CO$_3$. A catalytic amount of Pd(PPh$_3$)$_4$ was added and the reaction mixture was heated to 150° C. for 5 minutes in the Smith Personal Synthesiser microwave. The resulting reaction mixture was diluted with water and extracted into diethyl ether. The organic phase was dried over MgSO$_4$, filtered, concentrated in vacuo and purified by preparative LC/MS, to give 5-[4-(4-methoxy-phenyl)-5-methyl-2-(2-trimethylsilanyl-ethoxymethyl)-2H-pyrazol-3-yl]-pyrimidin-2-ylamine.

LC retention time 2.631 min [M+H]$^+$ 412.4

5-[4-(4-Methoxy-phenyl)-5-methyl-2H-pyrazol-3-yl]-pyrimidin-2-ylamine

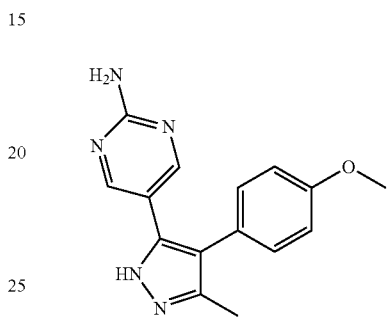

5-[4-(4-Methoxy-phenyl)-5-methyl-2-(2-trimethylsilanyl-ethoxymethyl)-2H-pyrazol-3-yl]-pyrimidin-2-ylamine was dissolved in anhydrous dichloromethane under nitrogen. 2M borontrichloride.dimethylether in dichloromethane (7 eq) was added dropwise, and all was stirred for 2 hours. The reaction mixture was added dropwise to sat. NaHCO$_3$ (aq) and extracted into dichloromethane. The organic phase was dried over MgSO$_4$, filtered and concentrated in vacuo. The residue was purified by preparative LC/MS to give 5-[4-(4-methoxy-phenyl)-5-methyl-2H-pyrazol-3-yl]-pyrimidin-2-ylamine as a solid.

LC retention time 1.894 min [M+H]$^+$ 282.2

The Following Reactions Refer to Scheme 19:
Synthesis of 2-methyl resorcinol for Example 133, 134

1-(2,4-Dihydroxy-3-methyl-phenyl)-2-(4-methoxy-phenyl)-ethanone

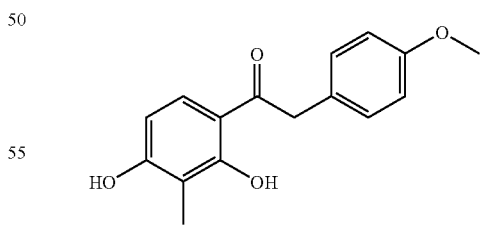

A solution of 2-methyl resorcinol (1 eq) and p-methoxy phenyl acetic acid (1 eq) in boron trifluoride diethyl etherate (8 eq) was refluxed for 3½ h, whilst stirring, under nitrogen. The brown solution was allowed to cool to room temperature, quenched with NaOAc solution (10% w/v) and left to stand overnight. The resultant precipitate was filtered, washed with water and dried to give 1-(2,4-dihydroxy-3-methyl-phenyl)-2-(4-methoxy-phenyl)-ethanone as a solid.

LC-MS retention time 2.453 min [M+H]+ 273.2 ¹HNMR δ$_H$ (400 MHz; DMSO-d$_6$): 10.76(1H, s, —OH), 8.01(1H, d, J 9 Hz, 6-H), 7.37(1H, d, J 5 Hz, Ha), 7.05(1H, d, J 5 Hz, Hb), 6.64(1H, d, J 9 Hz, 5-H) 4.37(2H, s, —CH$_2$), 3.89(3H, s, —OCH$_3$), 2.18(3H, s, —CH$_3$).

3-(4-Methoxy-phenyl)-2,8-dimethyl-4H-chromene-4,7-diol

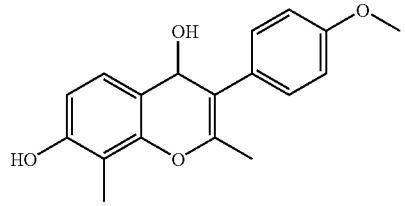

To a solution of 1-(2,4-dihydroxy-3-methyl-phenyl)-2-(4-methoxy-phenyl)-ethanone (1 eq) in anhydrous DMF was added K$_2$CO$_3$ (3 eq). Acetic anhydride (3 eq) was added dropwise to the solution, which was then refluxed, under nitrogen whilst stirring for 5 h. The solution was taken up in water and extracted using ethyl acetate, dried over MgSO$_4$ and concentrated in vacuo to give 3-(4-methoxy-phenyl)-2,8-dimethyl-4H-chromene-4,7-diol as a yellow solid.

LC-MS retention time 2.373 min [M+H]+ 297.2

4-[4-(4-Methoxy-phenyl)-5-methyl-1H-pyrazol-3-yl]-2-methyl-benzene-1,3-diol

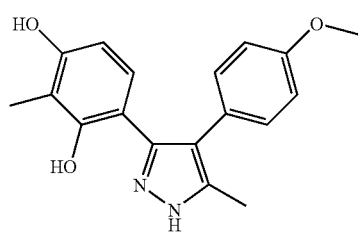

3-(4-Methoxy-phenyl)-2,8-dimethyl-4H-chromene-4,7-diol (1 eq) was taken up in a 1:1 solution of EtOH:Hydrazine hydrate and heated under microwave conditions (120° C., 300 sec). The solution was concentrated in vacuo, residue quenched with cold water, extracted with ethyl acetate and purified by flash chromatography (1% MeOH-DCM). The yellow oil was then triturated with ether:hexane to give 4-[4-(4-methoxy-phenyl)-5-methyl-1H-pyrazol-3-yl]-2-methyl-benzene-1,3-diol as a solid.

LC-MS retention time 2.328 min [M+H]+=311.2 ¹HNMR δ$_H$ (400 MHz; Acetone-d$_6$): 7.18(1H, m, Ha), 7.00(1H, m, Hb), 6.76(1H, d, J 9 Hz, 6-H), 6.08(1H, d, J 9 Hz, 5-H), 3.84(3H, s, —OCH$_3$), 2.14(3H, s, pyrazole-CH$_3$), 2.10(3H, s, —CH$_3$).

4-Chloro-2-methyl-benzene-1,3-diol

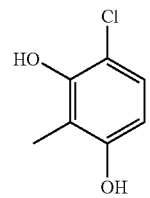

To a solution of 2-methyl resorcinol (1 eq) in MeCN (5 ml) was added N-chlorosuccinimide (1 eq) and refluxed under nitrogen overnight. The yellow solution was concentrated in vacuo and purified by flash chromatography to give 4-chloro-2-methyl-benzene-1,3-diol as a solid.

LC-MS retention time 3.27 min [M+H]+=159/157 ¹HNMR δ$_H$ (400 MHz; DMSO-d$_6$): 6.93(1H, d, J 9 Hz, 5-H), 6.34(1H, d, J 9 Hz, 6-H), 2.00(3H, s, —CH$_3$).

1-(5-Chloro-2,4-dihydroxy-3-methyl-phenyl)-2-(4-methoxy-phenyl)-ethanone

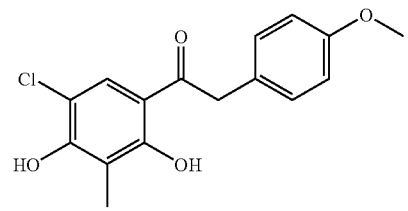

A solution of 4-chloro-2-methyl-benzene-1,3-diol (1 eq) and p-methoxy phenyl acetic acid (1 eq) in boron trifluoride diethyl etherate (8 eq) was refluxed for 5 h, whilst stirring, under nitrogen. The solution was allowed to cool to room temperature, quenched with 10% NaOAc (aq) and left to stand overnight. The resultant precipitate was filtered, washed with water and dried to give 1-(5-chloro-2,4-dihydroxy-3-methyl-phenyl)-2-(4-methoxy-phenyl)-ethanone as a solid.

LC-MS retention time 2.618 min [M+H]+=307.2
¹HNMR δ$_H$ (400 MHz; DMSO-d$_6$): 7.89(1H, s, 6-H), 7.17(2H, m, Ha), 6.75(2H, m, Hb), 4.16(2H, s, —CH$_2$), 3.60(3H, s, —OCH$_3$), 1.92(3H, s, —CH$_3$).

6-Chloro-3-(4-methoxy-phenyl)-2,8-dimethyl-4H-chromene-4,7-diol

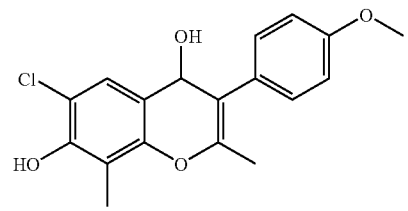

To a solution of 1-(5-chloro-2,4-dihydroxy-3-methyl-phenyl)-2-(4-methoxy-phenyl)-ethanone (1 eq) in an. DMF (7 ml) was added K$_2$CO$_3$ (3 eq). Acetic anhydride (3 eq) was added dropwise to the solution, which was then refluxed under nitrogen whilst stirring for 5 h. The solution was taken up in water and extracted using ethyl acetate, dried over MgSO$_4$ and concentrated in vacuo to give 6-chloro-3-(4-methoxy-phenyl)-2,8-dimethyl-4H-chromene-4,7-diol as a crystalline solid.

LC-MS retention time 2.528 min [M+H]$^+$=331.2

$^1$HNMR $\delta_H$ (400 MHz; DMSO-d$_6$): 7.87(1H, s, 6-H), 7.25(2H, m, Ha), 7.05(2H, m, Hb), 3.86(3H, s, —OCH$_3$), 2.39(3H, s, Ar—CH$_3$), 2.35(3H, s, —CH$_3$).

4-Chloro-6-[4-(4-methoxy-phenyl)-5-methyl-1H-pyrazol-3-yl]-2-methyl-benzene-1,3-diol

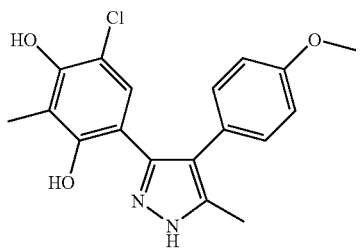

6-Chloro-3-(4-methoxy-phenyl)-2,8-dimethyl-4H-chromene-4,7-diol (1 eq) was taken up in a 1:1 solution of EtOH:Hydrazine hydrate and heated under microwave conditions (120° C., 300 sec). The solution was concentrated in vacuo, residue quenched with cold water, extracted with ethyl acetate and purified by flash chromatography (neat DCM). The yellow oil was then triturated with ether:hexane to give 4-chloro-6-[4-(4-methoxy-phenyl)-5-methyl-1H-pyrazol-3-yl]-2-methyl-benzene-1,3-diol as a solid.

LC-MS retention time 2.531 min [M+H]$^+$=345.2 $^1$H NMR $\delta_H$ (400 MHz; Acetone-d$_6$): 7.09(2H, m, Ha), 6.92 (2H, m, Hb), 6.79(1H, s, 6-H), 3.73(3H, s, —OCH$_3$), 2.10(3H, s, pyrazole-CH$_3$), 2.04(3H, s, Ar—CH$_3$).

The Following Descriptions Refer to Scheme 14:
Synthesis of Non-Resorcinols for Examples 107, 108, 111–119, 149–151

General Procedure for Benzylation of the Phenolic Compounds

To a solution of phenol (mmol) in acetone (30 ml), K$_2$CO$_3$ (mmol) and benzyl bromide (mmol) were added. The suspension was heated under reflux for 24 hours. After being cooled, it was filtered. After evaporation of the solvent, the crude products were recrystallized from EtOH unless otherwise stated.

General Procedure for the Preparation of Diketones by Using Na/EtOAc (Method A)

All diketones were synthesised by using this method unless otherwise stated. To a solution of ketone (4 mmol) in EtOAc (10 ml), sodium metal (8 mmol) in small pieces were added. The suspension was stirred at room temperature for an hour and then refluxed for 4 hours. When the solution cooled down, acetic acid (0.5 ml) was added and followed by water (15 ml). The solution was extracted with EtOAc (3×15 ml) and the combined organic layers were washed with brine (2×10 ml) and water (2×10 ml) and dried with Na$_2$SO$_4$. After filtration and evaporation of the solvent, the products were either purified by recrystallization or chromatography.

General Procedure for the Preparation of Diketones by Using BF$_3$/Acetic Anhydride (Method B)

To a solution of ketone (20 mmol) in acetic anhydride (15 ml) at 0° C. was added dropwise ethereal BF$_3$ (15 ml). The solution was stirred at this temperature for 4 h and room temperature 48 hours. Water (80 ml) was added slowly (CAUTION), the solids formed were filtered, washed with water and collected. They were dried in vacuum. If in the cases of no precipitation being formed, NaOAc solution (13%, 50 ml) was added. The suspension was refluxed for 20 minutes. When being cooled in ice, solids were formed. They were then filtered, washed with water and collected.

General Procedure for the Preparation of pyrazoles

To a refluxing solution (or suspension) of dione (1 mmol) in EtOH (10 ml), hydrazine hydrate (0.3 ml) was added. The solution was refluxed for a further 3 hours. After that the products were obtained either by extracting with EtOAc or precipitating by water.

General Procedure for the Preparation of iodo-pyrazoles

To a microwave vessel containing a mixture of water (3 ml) and THF (3 ml) and pyrazole (0.15 mmol) were added iodine (0.3 mmol), NaI (0.9 mmol) and Na$_2$CO$_3$ (0.3 mmol). A magnetic stirrer was added and the vessel sealed. The sample was irradiated for 30 min using 200 W. After cooling to room temperature, the vessel was open and brine (10 ml) was added. The solution was extracted with EtOAc (3×10 ml) and the combined organic layers were washed with sat. sodium thiosulphate solution (2×10 ml), brine (10 ml) and water (10 ml) and dried with Na$_2$SO$_4$. After filtration and evaporation of the solvent, the products were purified either by preparative TLC or recrystallization.

General Procedure for the Preparation of biaryl-pyrazoles

To a microwave vessel containing a mixture of water (3 ml) and 1-propanol (3 ml) and iodide (0.15 mmol) were added 2,3-dihydro-benzo[1,4]dioxine-6-boronic acid (0.23 mmol), Cs$_2$CO$_3$ (0.33 mmol), Pd(PPh$_3$)$_4$ (3 mol %) and LiCl (1.5 mmol). A magnetic stirrer was added and the vessel sealed. The sample was irradiated for 30 min using 200 W. After cooling to room temperature, the vessel was open and brine (10 ml) was added. The solution was extracted with EtOAc (3×10 ml) and the combined organic layers were washed with brine (10 ml) and water (10 ml) and dried with Na$_2$SO$_4$. After filtration and evaporation of the solvent, the products were purified by preparative TLC.

General Procedure for the de-benzylation

The corresponding compounds were debenzylated either by hydrogenation in EtOH with Pd/C or stirring in acetonitrile with NaI/ethereal BF$_3$ for 24 hours at room temperature.

1-(2-Benzyloxy-5-methylphenyl)-3-hydroxybut-2-en-1-one

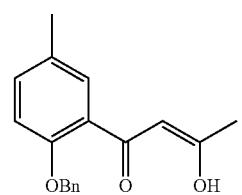

The product was obtained (40% yield) as a yellow solid, in a mixture of enol and keto-form isomers (ca. 5:1). [Enol]:

¹H NMR (CDCl₃) δ=16.18 (1H, s, broad); 7.78 (1H, d, J=2.0 Hz); 7.40 (5H, m); 7.22 (1H, dd, J=2.0 and 8.5 Hz); 6.92 (1H, d, J=8.5 Hz); 6.56 (1H, s); 5.18 (2H, s); 2.34 (3H, s) and 2.10 (3H, s). ¹³C NMR (CDCl₃) δ=192.70, 180.93, 155.52, 136.53, 133.37, 130.51, 128.82, 128.56, 128.06, 127.32, 113.22, 102.18, 70.92, 26.00 and 20.39. MS: 283.1 (M+H)⁺, 305.2 (M+Na)⁺.

1-(2-Benzyloxy-5-chlorophenyl)-3-hydroxybut-2-en-1-one

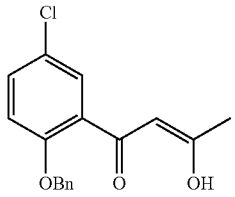

The product was obtained (90% yield) as a yellow solid, mainly in enol-form isomer. [Enol]: ¹H NMR (CDCl₃) δ=16.20 (1H, s, broad); 7.82 (1H, d, J=2.5 Hz); 7.44–7.40 (5H+1H, m); 6.90 (1H, d, J=8.8 Hz); 6.41 (1H, s); 5.08 (2H, s) and 2.00 (3H, s). ¹³C NMR (CDCl₃) δ=195.07, 179.00, 155.99, 135.86, 132.28, 129.97, 128.68, 128.33, 127.35, 126.44, 114.50, 102.27, 71.19, and 26.10. MS: 302.9 (M+H)⁺.

1-(4-Benzyloxy-3-chlorophenyl)-3-hydroxybut-2-en-1-one

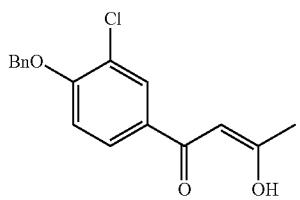

The product was obtained (40% yield) as a yellow solid, in a mixture of enol and keto-form isomers (ca. 14:1). [Enol]: ¹H NMR (CDCl₃) δ=16.00 (1H, s, broad); 8.00 (1H, d, J=2.0 Hz); 7.78 (1H, dd, J=2.0 and 8.6 Hz); 7.44 (5H, m); 7.02 (1H, d, J=8.6 Hz); 6.11 (1H, s); 5.25 (2H, s) and 2.21 (3H, s). ¹³C NMR (CDCl₃)

δ=192.43, 183.24, 157.74, 136.15, 132.28, 129.75, 129.17, 128.64, 127.44, 123.94, 113.53, 96.41, 71.24, and 25.71. MS: 302.9 (M+H)⁺.

1-(2-Benzyloxy-5-fluorophenyl)-3-hydroxybut-2-en-1-one

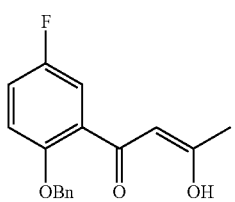

The product was obtained (40% yield) as a yellow solid, in a mixture of enol and keto-form isomers (ca. 17:1). [Enol]: ¹H NMR (CDCl₃) δ=16.00 (1H, s, broad); 7.68 (1H, dd, J=3.0 and 9.0 Hz); 7.47 (5H, m); 7.14 (1H, ddd, J=3.0, 7.5 and 9.0 Hz); 7.00 (1H, dd, J=4.2 and 9.0 Hz); 6.58 (1H, s); 5.17 (2H, s) and 2.10 (3H, s). ¹³C NMR (CDCl₃) δ=195.29, 178.78, 157.03 (d, J=240 Hz), 153.72, 136.06, 128.91, 128.63, 128.27, 127.40, 119.00 (d, J=24 Hz), 116.50 (d, J=24 Hz), 114.50 (d, J=8 Hz), 102.22, 71.56, and 26.14. MS: 287.1 (M+H)⁺.

1-(2,4-Bis-benzyloxy-5-chlorophenyl)-3-hydroxybut-2-en-1-one

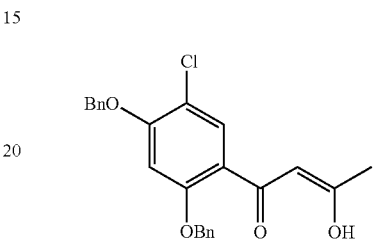

The product was obtained (76% yield) as a yellow solid, mainly in enol-form isomer. ¹H NMR (CDCl₃) δ=16.25 (1H, s, broad); 8.04 (1H, s); 7.47 (10H, m); 6.59 (1H, s); 6.51 (1H, s); 5.18 (2H, s); 5.10 (2H, s) and 2.07 (3H, s). ¹³C NMR (CDCl₃) δ=193.87, 179.47, 157.68, 157.35, 135.68, 131.49, 128.75, 128.43, 128.28, 127.40, 127.00, 101.35, 70.99, and 25.78. MS: 409.2 (M+H)⁺.

1-(2,4-Bis-benzyloxy-5-ethylphenyl)-3-hydroxybut-2-en-1-one

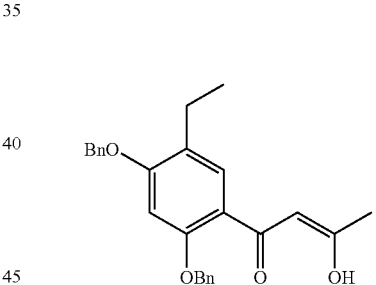

The product was obtained (36% yield) as a yellow solid, in a mixture of enol and keto-form isomers (ca. 5:1). [Enol]: ¹H NMR (CDCl₃) δ=16.20 (1H, s, broad); 7.87 (2H, d, J=9.2 Hz); 6.90 (2H, d, J=9.2 Hz); 6.12 (1H, s); 3.80 (2H, m); 3.66 (2H, m); 3.38 (4H, m); 2.18 (3H, s) and 2.17 (3H, s). ¹³C NMR (CDCl₃) δ=190.91, 184.10, 169.05, 153.32, 130.92, 128.89, 125.47, 114.22, 113.57, 95.41, 47.65, 47.42, 45.71, 40.89, 25.16 and 21.27.

3-(3-Hydroxy-but-2-enoyl)-benzonitrile

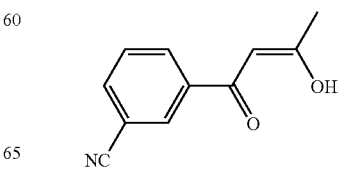

The product was obtained (45% yield) as a yellow solid, only in enol-form isomer. [Enol]: $^1$H NMR (CDCl$_3$) δ=16.10 (1H, s, broad); 8.18 (1H, ddd, J=0.6, 1.5 and 4.2 Hz); 8.11 (1H, ddd, J=1.5, 3.2 and 8.0 Hz); 7.81 (1H, ddd, J=1.5, 3.2 and 7.8 Hz); 7.61 (1H, ddd, J=0.6, 7.8 and 8.0 Hz); 6.20 (1H, s) and 2.26 (3H, s). $^{13}$C NMR (CDCl$_3$) δ=194.60, 180.53, 136.16, 135.02, 130.90, 130.58, 129.55, 117.97, 113.09, 96.97 and 25.87. MS: 186.3 (M−H)$^-$.

4-(3-Hydroxy-but-2-enoyl)-benzonitrile

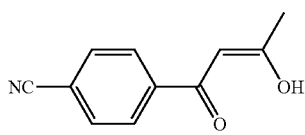

The product was obtained (30% yield) as a yellow solid, only in enol-form isomer. [Enol]: $^1$H NMR (CDCl$_3$) δ=15.90 (1H, s, broad); 8.00 (2H, d, J=8.7 Hz); 7.75 (2H, d, J=8.7 Hz); 6.22 (1H, s) and 2.28 (3H, s). $^{13}$C NMR (CDCl$_3$) δ=195.73, 179.77, 138.73, 132.38, 127.38, 118.06, 115.37, 97.64 and 26.33. MS: 186.3 (M−H)$^-$.

3-(3-Hydroxy-but-2-enoyl)-benzoic acid ethyl ester

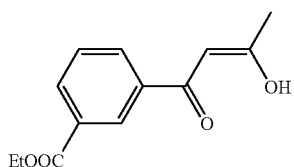

The product was obtained (65% yield) as a yellow solid, mainly in enol-form isomer. [Enol]: $^1$H NMR (CDCl$_3$) δ=16.20 (1H, s, broad); 8.53 (1H, ddd, J=0.6, 1.2 and 2.4 Hz); 8.24 (1H, ddd, J=1.2, 2.4 and 7.8 Hz); 8.09 (1H, ddd, J=1.2, 2.4 and 7.8 Hz); 7.54 (1H, ddd, J=0.6, 7.8 and 7.8 Hz); 6.27 (1H, s); 4.43 (2H, q, J=7.0 Hz); 2.26 (3H, s) and 1.45 (3H, t, J=7.0 Hz).

4-(3-Hydroxy-but-2-enoyl)-benzoic acid ethyl ester

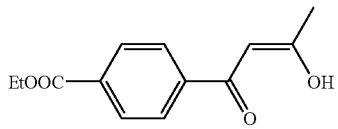

The product was obtained (60% yield) as a yellow solid, only in enol-form isomer. [Enol]: $^1$H NMR (CDCl$_3$) δ=16.10 (1H, s, broad); 8.10 (2H, d, J=8.7 Hz); 7.93 (2H, d, J=8.7 Hz); 6.23 (1H, s); 4.41 (2H, q, J=7.0 Hz); 2.24 (3H, s) and 1.43 (3H, t, J=7.0 Hz). $^{13}$C NMR (CDCl$_3$) δ=195.28, 180.99, 165.75, 138.48, 129.66, 126.76, 97.44, 61.30, 50.07, 26.19 and 14.21.

4-(3-Hydroxy-but-2-enoyl)-benzenesulfonamide

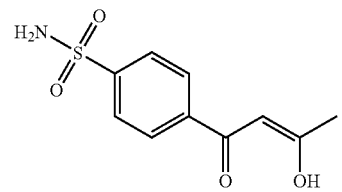

(Method B) The product was obtained (69% yield) as a yellow solid, only in enol-form isomer. [Enol]: $^1$H NMR (d$_6$-DMSO) δ=12.40 (1H, s, broad); 8.30 (2H, d, J=8.5 Hz); 8.05 (2H, d, J=8.5 Hz); 7.32 (1H, s); 2.50 (2H, s) and 1.92 (3H, s). $^{13}$C NMR (d$_6$-DMSO) δ=194.32, 169.43, 144.78, 135.43, 129.87, 128.67, 100.01 and 23.61.

3-(2-Benzyloxy-5-methyl-phenyl)-5-methyl-1H-pyrazole

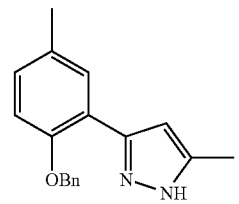

The product was obtained (90% yield) as a yellow solid. $^1$H NMR (d$_6$-DMSO) δ=12.49 (1H, s, broad); 7.61 (1H, s); 7.42 (5H, m); 7.02 (1H+1H, s, overlapped); 6.47 (1H, s); 5.19 (2H, s); 2.25 (3H, s) and 2.20 (3H, s). MS: 279.2 (M+H)$^+$.

3-(2-Benzyloxy-5-chloro-phenyl)-5-methyl-1H-pyrazole

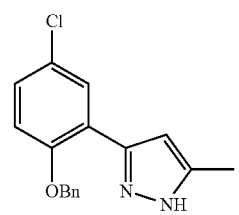

The product was obtained (78% yield) as off-white solids. $^1$H NMR (d$_6$-DMSO) δ=12.68 (1H, s, broad); 7.87 (1H, s); 7.40 (5H+1H, m); 7.16 (1H, d, J=8.4 Hz); 6.52(1H, s); 5.23(2H, s) and 2.21 (3H, s). MS: 299.2 (M+H)$^+$.

3-(4-Benzyloxy-3-chloro-phenyl)-5-methyl-1H-pyrazole

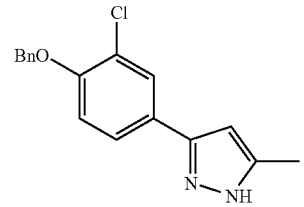

The product was obtained (96% yield) as creamy yellow solids. ¹H NMR (CDCl₃) δ=12.68 (1H, s, broad); 7.78 (1H, d, J=2.0 Hz); 7.35–7.60 (5H+1H, m); 6.97 (1H, d, J=8.5 Hz); 6.29 (1H, s); 5.20 (2H, s) and 2.35 (3H, s). ¹³C NMR (d₆-DMSO) δ=154.20, 149.73, 145.44, 136.84, 129.00, 128.40, 128.06, 127.51, 125.26, 114.55, 102.16, 71.30 and 11.90.

3-(2-Benzyloxy-5-fluoro-phenyl)-5-methyl-1H-pyrazole

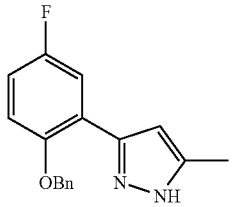

The product was obtained (80% yield) as creamy white solids. ¹H NMR (d₆-DMSO) δ=12.66 (1H, s, broad); 7.62 (1H, s); 7.40 (5H, m); 7.12 (2H, m); 6.53 (1H, s); 5.20 (2H, s) and 2.21 (3H, s). MS: 283.2 (M+H)⁺.

3-(2,4-Bis-benzyloxy-5-chloro-phenyl)-5-methyl-1H-pyrazole

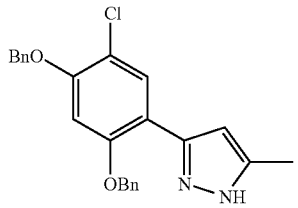

The product was obtained (65% yield) as yellow solids. ¹H NMR (d₆-DMSO) δ=12.51 (1H, s, broad); 7.83 (1H, s); 7.46 (10H, m); 7.08 (1H, s), 6.42 (1H, s); 5.26 (2H, s); 5.24 (2H, s) and 2.19 (3H, s). MS: 405.2 (M+H)⁺.

3-(2,4-Bis-benzyloxy-5-ethyl-phenyl)-5-methyl-1H-pyrazole

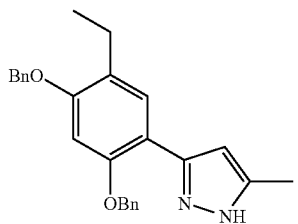

The product was obtained (84% yield) as creamy white solids. ¹H NMR (d₆-DMSO) δ=12.32 (1H, s, broad); 7.53 (1H, s); 7.38 (10H, m); 6.84 (1H, s), 6.34 (1H, s); 5.17 (2H, s); 5.10 (2H, s); 2.50 (2H, q, J=7.5 Hz); 2.14 (3H, s) and 1.09 (3H, t, J=7.5 Hz). MS: 399.3 (M+H)⁺.

3-(5-Methyl-1H-pyrazol-3-yl)-benzonitrile

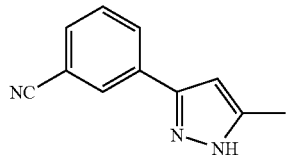

The product was obtained (74% yield) as creamy white solids. ¹H NMR (CDCl₃) δ=10.20 (1H, s, broad); 8.03 (1H, m); 7.98 (1H, ddd, J=1.5, 1.7 and 7.7 Hz); 7.57 (1H, ddd, J=1.5, 3.0 and 7.7 Hz); 7.48 (1H, ddd, J=0.6, 7.7 and 7.7 Hz); 6.39 (1H, s) and 2.35 (3H, s). ¹³C NMR (CDCl₃) δ=149.68, 142.40, 134.86, 131.40, 130.21, 129.88, 129.56, 119.18, 113.15, 102.68 and 11.61. MS: 184.3 (M+H)⁺.

4-(5-Methyl-1H-pyrazol-3-yl)-benzonitrile

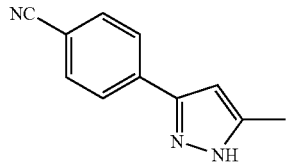

The product was obtained (88% yield) as yellow solids. ¹H NMR (CDCl₃) δ=10.30 (1H, s, broad); 7.85 (2H, d, J=8.7 Hz); 7.65 (2H, d, J=8.7 Hz); 6.42 (1H, s) and 2.31 (3H, s). ¹³C NMR (CDCl₃) δ=149.94, 142.47, 137.90, 132.93, 126.41, 119.35, 111.34, 103.15 and 11.58. MS: 184.3 (M+H)⁺.

3-(5-Methyl-1H-pyrazol-3-yl)-benzoic acid ethyl ester

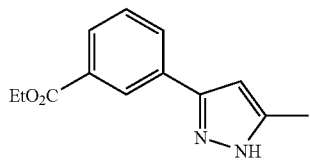

The product was obtained (45% yield) as yellow solids. ¹H NMR (CDCl₃) δ=8.39 (1H, m); 7.96 (1H+1H, m); 7.45 (1H, dd, J=7.7 and 8.3 Hz); 6.42 (1H, s); 4.40 (2H, q, J=7.0 Hz); 2.36 (3H, s) and 1.40 (3H, t, J=7.0 Hz).

4-(5-Methyl-1H-pyrazol-3-yl)-benzoic acid ethyl ester

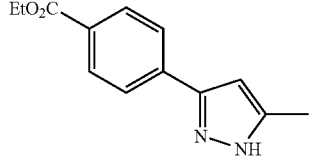

The product was obtained (50% yield) as yellow solids. ¹H NMR (CDCl₃) δ=8.05 (2H, d, J=8.7 Hz); 7.80 (2H, d, J=8.7 Hz); 6.42 (1H, s); 4.41 (2H, q, J=7.0 Hz); 2.32 (3H, s) and 1.42 (3H, t, J=7.0 Hz). $^{13}$C NMR (CDCl$_3$) δ=166.84, 149.96, 142.93, 137.35, 130.37, 129.86, 125.74, 103.02, 61.34, 14.68 and 11.78.

4-(5-Methyl-1H-pyrazol-3-yl)-benzenesulfonamide

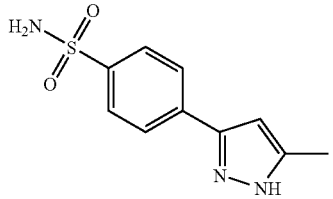

The product was obtained (73% yield) as creamy white solids. $^1$H NMR (d$_6$-DMSO) δ=12.78 (1H, s, broad); 7.92 (2H, d, J=8.7 Hz); 7.82 (2H, d, J=8.7 Hz); 7.30 (2H, s, broad); 6.55 (1H, s); and 2.27 (3H, s). $^{13}$C NMR (d$_6$-DMSO) δ=194.32, 169.43, 144.78, 135.43, 129.87, 128.67, 100.01 and 23.61. MS: 238.2 (M+H)$^+$.

3-(2-Benzyloxy-5-methyl-phenyl)-4-iodo-5-methyl-1H-pyrazole

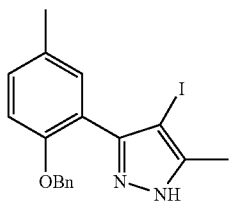

The product was obtained (60% yield) as yellow solids. $^1$H NMR (CDCl$_3$) δ=7.76 (1H, d, J=2.7 Hz); 7.34 (5H, m); 7.15 (1H, dd, J=2.7 and 8.5 Hz); 6.95 (1H, d, J=8.5 Hz); 5.01 (2H, s); 2.36 (3H, s) and 2.33 (3H, s).

3-(4-Benzyloxy-3-methyl-phenyl)-4-iodo-5-methyl-1H-pyrazole

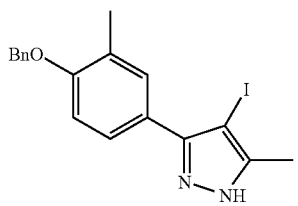

The product was obtained (60% yield) as brown semi-solids. R$_f$=0.46 (EtOAc:hexane/1:1). $^1$H NMR (CDCl$_3$) δ=7.44 (5H+2H, m); 6.93 (1H, d, J=9.0 Hz); 5.14 (2H, s); 2.38 (3H, s) and 2.27 (3H, s).

3-(2-Benzyloxy-5-chloro-phenyl)-4-iodo-5-methyl-1H-pyrazole

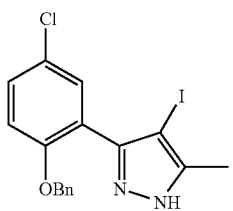

The product was obtained (75% yield) as solids. R$_f$=0.46 (EtOAc:hexane/2:1). $^1$H NMR (CDCl$_3$) δ=7.85 (1H, d, J=2.5 Hz); 7.36 (5H, m); 7.32 (1H, dd, J=2.5 and 8.8 Hz); 7.00 (1H, d, J=8.8 Hz); 5.12 (2H, s) and 2.34 (3H, s). $^{13}$C NMR (CDCl$_3$) δ=154.93, 148.22, 142.50, 136.33, 130.88, 129.07, 128.58, 127.62, 126.40, 121.75, 114.84, 71.54, 62.89 and 13.90.

3-(4-Benzyloxy-3-chloro-phenyl)-4-iodo-5-methyl-1H-pyrazole

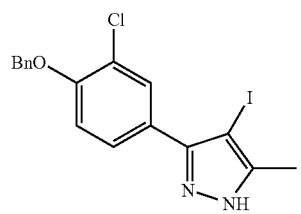

The product was obtained (80% yield) as orange semi-solids. R$_f$=0.66 (EtOAc:hexane/1:1). $^1$H NMR (CDCl$_3$) δ=7.76 (1H, d, J=2.0 Hz); 7.40 (5H+1H, m); 6.92 (1H, d, J=8.6 Hz); 5.16 (2H, s); and 2.19 (3H, s).

3-(2-Benzyloxy-5-fluoro-phenyl)-4-iodo-5-methyl-1H-pyrazole

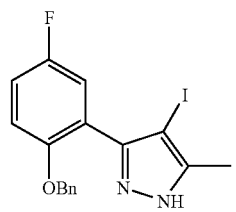

The product was obtained (75% yield) as solids. R$_f$= (EtOAc:hexane/2:1). $^1$H NMR (CDCl$_3$) δ=7.61 (1H, dd, J=3 and 9.0 Hz); 7.32 (5H, m); 6.95–7.05 (1H+1H, m); 5.05 (2H, s) and 2.28 (3H, s).

3-(2,4-Bis-benzyloxy-5-chloro-phenyl)-4-iodo-5-methyl-1H-pyrazole

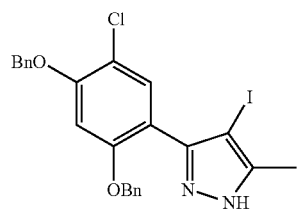

The product was obtained (85% yield) as solids. R$_f$=0.65 (EtOAc:hexane/2:1). $^1$H NMR (d$_6$-DMSO) δ=12.95 (1H, s, broad); 7.38 (10H+1H, m); 7.12 (1H, s); 5.28 (2H, s); 5.16 (2H, s) and 2.18 (3H, s).

3-(2,4-Bis-benzyloxy-5-ethyl-phenyl)-4-iodo-5-methyl-1H-pyrazole

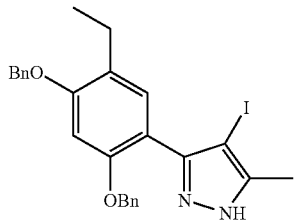

The product was obtained (85% yield) as solids. $R_f$=0.65 (EtOAc:hexane/2:1). $^1$H NMR (d$_6$-DMSO) δ=12.80 (1H, s, broad); 7.38 (10H, m); 7.10 (1H, s), 6.92 (1H, s); 5.18 (2H, s); 5.11 (2H, s); 2.56 (2H, q, J=7.5 Hz); 2.19 (3H, s) and 1.14 (3H, t, J=7.5 Hz).

3-(4-iodo-5-Methyl-1H-pyrazol-3-yl)-benzonitrile

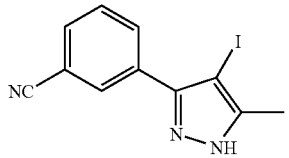

The product was obtained (80% yield) as yellow solids. $R_f$=0.49 (EtOAc:hexane/1:1). $^1$H NMR (CDCl$_3$) δ=7.95–8.05 (1H+1H, m); 7.65 (1H, ddd, J=1.3, 2.5 and 8.0 Hz); 7.57 (1H, ddd, J=0.8, 8.0 and 8.0 Hz); and 2.23 (3H, s). $^{13}$C NMR (CDCl$_3$) δ=149.20, 145.73, 133.98, 132.71, 131.86, 129.74, 118.89, 112.96, 60.81 and 12.81.

4-(4-iodo-5-Methyl-1H-pyrazol-3-yl)-benzonitrile

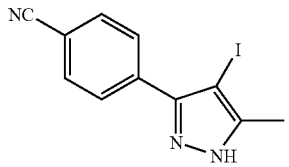

The product was obtained (50% yield) as yellow solids. $^1$H NMR (d$_6$-DMSO) δ=13.40 (1H, s, broad); 8.02 (2H, d, J=8.0 Hz); 7.92 (2H, d, J=8.0 Hz) and 2.28 (3H, s). $^{13}$C NMR (d$_6$-DMSO) δ=149.44, 142.97, 138.00, 132.74, 128.14, 119.15, 110.65, 60.00 and 12.02.

3-(4-iodo-5-Methyl-1H-pyrazol-3-yl)-benzoic acid ethyl ester

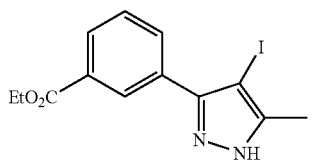

The product was obtained (18% yield) as brown oil. $R_f$=(EtOAc:hexane/3:4). $^1$H NMR (CDCl$_3$) δ=9.70 (1H, s, broad); 8.41 (1H, dd, J=1.2 and 1.8 Hz); 8.03 (1H, ddd, J=1.2, 1.8 and 7.7 Hz); 7.93 (1H, ddd, J=1.2, 2.0 and 7.7 Hz); 7.46 (1H, ddd, J=0.5, 7.7 and 8.0 Hz); 4.38 (2H, q, J=7.0 Hz); 2.22 (3H, s) and 1.37 (3H, t, J=7.0 Hz). $^{13}$C NMR (CDCl$_3$) δ=166.25, 148.77, 146.22, 132.22, 132.02, 130.56, 129.46, 129.08, 128.48, 61.14, 59.00, 14.27 and 12.71.

4-(4-iodo-5-Methyl-1H-pyrazol-3-yl)-benzoic acid ethyl ester

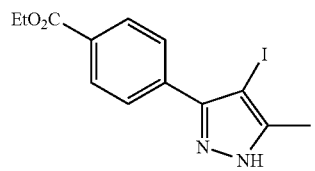

The product was obtained (80% yield) as yellow solids. $^1$H NMR (CDCl$_3$) δ=11.20 (1H, s, broad); 8.02 (2H, d, J=8.6 Hz); 7.78 (2H, d, J=8.6 Hz); 4.40 (2H, q, J=7.0 Hz); 2.14 (3H, s) and 1.40 (3H, t, J=7.0 Hz). $^{13}$C NMR (CDCl$_3$) δ=166.66, 149.38, 146.49, 136.50, 130.55, 130.04, 128.89, 128.23, 61.53, 61.01, 14.73 and 12.98.

N-[3-(4-Iodo-5-methyl-1H-pyrazol-3-yl)-phenyl]-acetamide

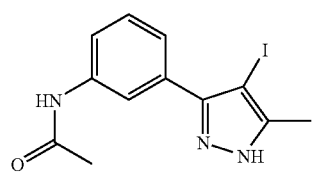

The product was obtained (55% yield) as white solids. $^1$H NMR (CDCl$_3$) δ=9.70 (1H, s, broad); 8.55 (1H, s, broad); 7.75 (1H, s, broad); 7.48 (1H, d, J=8.5 Hz); 7.40 (1H, d, J=7.7 Hz); 7.24 (1H, dd, J=7.7 and 8.5 Hz); 2.20 (3H, s) and 2.04 (3H, s). $^{13}$C NMR (CDCl$_3$) δ=169.44, 147.94, 147.22, 138.12, 131.78, 128.80, 123.85, 120.22, 119.47, 60.40, 21.02 and 13.00.

N-[4-(4-Iodo-5-methyl-1H-pyrazol-3-yl)-phenyl]-acetamide

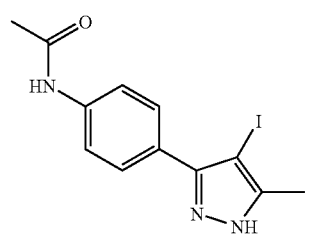

The product was obtained (35% yield) as orange oil. $^1$H NMR (d$_6$-acetone) δ=9.30 (1H, s, broad); 7.74 (4H+1H, s, broad); 2.30 (3H, s) and 2.10 (3H, s).

4-(4-iodo-5-Methyl-1H-pyrazol-3-yl)-benzenesulfonamide

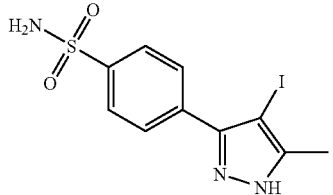

The product was obtained (55% yield) as solids. $R_f$=0.49 (EtOAc:hexane/3:1). $^1$H NMR (d$_6$-acetone) δ=12.50 (1H, s, broad); 8.03 (2H, d, J=8.7 Hz); 7.97 (2H, d, J=8.7 Hz); 6.62 (2H, s) and 2.36 (3H, s).

3-(2-Benzyloxy-5-methyl-phenyl)-4-(2,3-dihydro-benzo[1,4]dioxin-6-yl)-5-methyl-1H-pyrazole

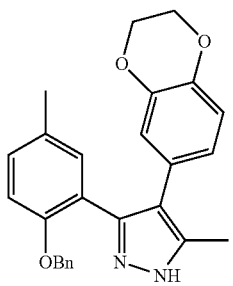

The product was obtained (35% yield) as yellow solids. $^1$H NMR (CDCl$_3$) δ=7.30 (5H, m); 6.96–7.03 (1H+1H, m); 6.86 (1H, d, J=8.3 Hz); 6.83 (1H, d, J=8.3 Hz); 6.76 (1H, d, J=2.0 Hz); 6.68 (1H, dd, J=2.0 and 8.3 Hz); 5.04 (2H, s); 4.27 (4H, s); 2.2 (3H, s) and 2.10 (3H, s). $^{13}$C NMR (CDCl$_3$) δ=154.05, 146.35, 143.78, 142.70, 136.93, 131.23, 130.72, 129.96, 129.12, 128.52, 128.12, 127.80, 123.60, 119.39, 118.93, 118.57, 117.59, 113.53, 71.43, 64.82, 20.83 and 12.64.

3-(2-Benzyloxy-5-chloro-phenyl)-4-(2,3-dihydro-benzo[1,4]dioxin-6-yl)-5-methyl-1H-pyrazole

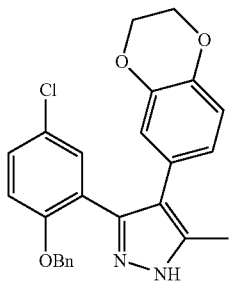

The product was obtained (30% yield) as an oil. $^1$H NMR (CDCl$_3$) δ=7.35 (5H, m); 7.24 (1H, m); 7.20 (1H, d, J=2.5 Hz); 7.14 (1H, dd, J=2.5 and 8.8 Hz); 6.86 (1H, d, J=8.8 Hz); 6.84 (1H, d, J=8.3 Hz); 6.71 (1H, d, J=2.0 Hz); 6.62 (1H, dd, J=2.0 and 8.3 Hz); 5.02 (2H, s); 4.27 (4H, s) and 2.25 (3H, s). $^{13}$C NMR (CDCl$_3$) δ=154.72, 143.92, 142.91, 136.35, 130.40, 129.17, 129.07, 128.69, 127.74, 127.47, 126.50, 123.33, 121.83, 119.13, 118.74, 117.80, 114.68, 71.59, 64.81 and 12.37.

3-(2-Benzyloxy-5-fluoro-phenyl)-4-(2,3-dihydro-benzo[1,4]dioxin-6-yl)-5-methyl-1H-pyrazole

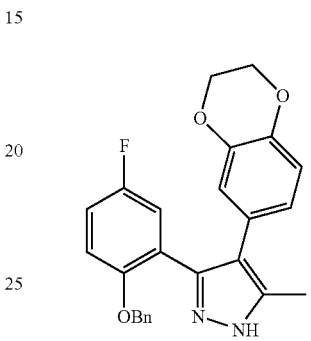

The product was obtained (50% yield) as solids. $^1$H NMR (CDCl$_3$) δ=7.25 (5H, m); 6.89 (1H, ddd, J=0.9, 2.5 and 10.5 Hz); 6.76–6.81 (1H+1H, m); 7.14 (1H, d, J=8.3 Hz); 6.63 (1H, d, J=2.0 Hz); 6.54 (1H, dd, J=2.0 and 8.3 Hz); 6.71 (1H, d, J=2.0 Hz); 6.62 (1H, dd, J=2.0 and 8.3 Hz); 4.92 (2H, s); 4.17 (4H, s) and 2.13 (3H, s). $^{13}$C NMR (CDCl$_3$) δ=157.35 (d, J=240 Hz), 152.37, 143.94, 142.93, 136.58, 129.14, 128.65, 127.81, 127.53, 123.40, 121.77, 119.04, 118.81, 117.83, 117.35, 116.33 (d, J=25 Hz), 115.10 (d, J=25 Hz), 114.73, 72.02, 64.76 and 12.31.

3-(2,4-Bis-benzyloxy-5-chloro-phenyl)-4-(2,3-dihydro-benzo[1,4]dioxin-6-yl)-5-methyl-1H-pyrazole

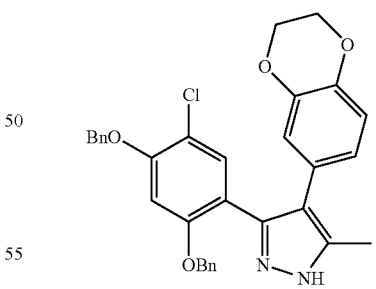

The product was obtained (32% yield) as yellow solids. $R_f$=0.48 (EtOAc:hexane/2:1). $^1$H NMR (CDCl$_3$) δ=7.40 (10H, m); 7.24 (1H, s); 6.84 (1H, d, J=8.2 Hz), 6.74 (1H, d, J=2.0 Hz); 6.63 (1H, dd, J=2.0 and 8.2 Hz); 6.55 (1H, s); 5.06 (2H, s); 4.95 (2H, s); 4.28 (4H, s) and 2.24 (3H, s). $^{13}$C NMR (CDCl$_3$) δ=155.16, 154.23, 143.46, 142.42, 136.09, 135.84, 131.01, 128.71, 128.64, 128.31, 128.10, 127.30, 127.06, 122.96, 118.38, 117.34, 115.22, 113.53, 100.81, 71.37, 71.01, 64.35 and 12.02. MS: 539.3 (M+H)$^+$.

3-(4-Benzyloxy-3-chloro-phenyl)-4-(2,3-dihydro-benzo[1,4]dioxin-6-yl)-5-methyl-1H-pyrazole

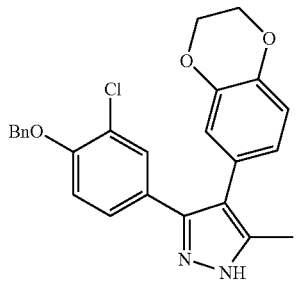

The product was obtained (65% yield) as yellow oil. $R_f$=0.65 (EtOAc:hexane/1:1). $^1$H NMR (CDCl$_3$) δ=7.50 (1H, d, J=2.0 Hz); 7.48–7.30 (5H, m); 7.19 (1H, dd, J=2.0 and 8.7 Hz); 6.85 (1H, d, J=8.7 Hz); 6.83 (1H, d, J=8.7 Hz); 6.72 (1H, d, J=2.0 Hz); 6.62 (1H, dd, J=2.0 and 8.7 Hz); 5.13 (2H, s); 4.29 (4H, s) and 2.27 (3H, s). MS: 433.3 (M+H)$^+$.

3-(2,4-Bis-benzyloxy-5-ethyl-phenyl)-4-(2,3-dihydro-benzo[1,4]dioxin-6-yl)-5-methyl-1H-pyrazole

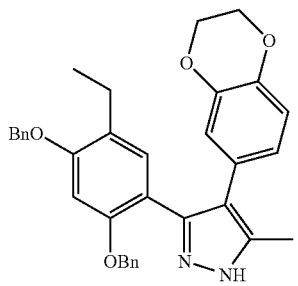

The product was obtained (30% yield) as yellow oil. $R_f$=0.4 (EtOAc:hexane/2:1). $^1$H NMR (CDCl$_3$) δ=7.41–7.32 (10H, m); 6.99 (1H, s); 6.85 (1H, d, J=8.3 Hz), 6.77 (1H, d, J=2.0 Hz); 6.70 (1H, dd, J=2.0 and 8.3 Hz); 6.57 (1H, s); 5.05 (2H, s); 5.02 (2H, s); 4.27 (4H, s); 2.41 (2H, q, J=7.0 Hz); 2.25 (3H, s) and 0.92 (3H, t, J=7.0 Hz). MS: 533.3 (M+H)$^+$.

3-[4-(2,3-Dihydro-benzo[1,4]dioxin-6-yl)-5-methyl-1H-pyrazol-3-yl]-benzonitrile

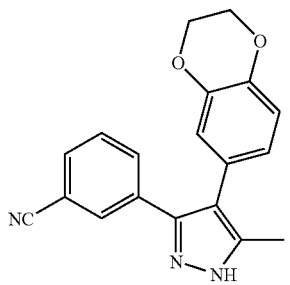

The product was obtained (25% yield) as yellow solids. $R_f$=0.54 (EtOAc:hexane:CHCl$_3$/3:1:4). $^1$H NMR (CDCl$_3$) δ=7.75 (1H, dd, J=1.2 and 1.6 Hz); 7.67 (1H, ddd, J=1.2, 1.6 and 7.9 Hz); 7.51 (1H, ddd, J=1.2, 1.6 and 7.9 Hz); 7.35 (1H, dd, J=7.9 and 7.9 Hz); 6.85 (1H, d, J=8.3 Hz); 6.68 (1H, d, J=2.0 Hz); 6.61 (1H, dd, J=2.0 and 8.3 Hz); 4.29 (4H, s) and 2.25 (3H, s). $^{13}$C NMR (CDCl$_3$) δ=143.35, 143.61, 142.83, 139.77, 134.44, 132.01, 131.19, 130.93, 129.07, 125.79, 123.15, 118.77, 118.52, 117.89, 117.58, 112.40, 64.36 and 10.35.

4-[4-(2,3-Dihydro-benzo[1,4]dioxin-6-yl)-5-methyl-1H-pyrazol-3-yl]-benzonitrile

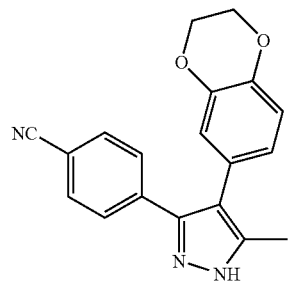

The product was obtained (20% yield) as yellow solids. $R_f$=0.2 (EtOAc:hexane/1:1). $^1$H NMR (d$_6$-acetone) δ=12.2 (1H, s, broad); 7.65 (4H, s); 6.85 (1H, d, J=8.1 Hz); 6.70 (1H, d, J=2.0 Hz); 6.65 (1H, dd, J=2.0 and 8.1 Hz) and 2.26 (3H, S). $^{13}$C NMR (d$_6$-acetone) δ=147.36, 145.72, 144.79, 141.42, 140.52, 134.27, 133.78, 129.74, 128.52, 127.58, 124.84, 120.47, 119.56, 119.22, 112.14, 103.85, 61.53 and 11.20. MS: 318.4 (M+H)$^+$.

3-[4-(2,3-Dihydro-benzo[1,4]dioxin-6-yl)-5-methyl-1H-pyrazol-3-yl]-benzoic acid ethyl ester

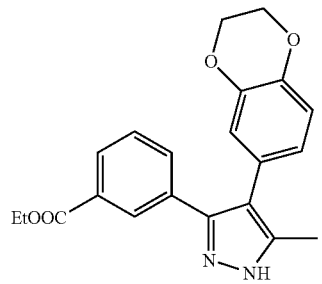

The product was obtained (32% yield) as yellow oil. $R_f$=0.36 (EtOAc:hexane/1:1). $^1$H NMR (CDCl$_3$) δ=8.70 (1H, dd, J=1.7 and 1.7 Hz); 7.92 (1H, ddd, J=1.3, 1.7 and 7.8 Hz); 7.54 (1H, ddd, J=1.3, 1.7 and 7.8 Hz); 7.30 (1H, dd, J=7.8 and 7.8 Hz); 6.83 (1H, d, J=8.2 Hz); 6.72 (1H, d, J=2.0 Hz); 6.64 (1H, dd, J=2.0 and 8.2 Hz); 4.33 (2H, q, J=7.0 Hz); 4.27 (4H, s); 2.24 (3H, s) and 1.34 (3H, t, J=7.0 Hz). $^{13}$C NMR (CDCl$_3$) δ=166.38, 145.75, 143.43, 142.51, 141.42, 132.64, 132.10, 130.64, 128.69, 128.33, 126.45, 123.32, 118.64, 117.74, 117.32, 64.33, 60.90, 14.23 and 10.80. MS: 365.3 (M+H)$^+$.

4-[4-(2,3-Dihydro-benzo[1,4]dioxin-6-yl)-5-methyl-1H-pyrazol-3-yl]-benzoic acid ethyl ester

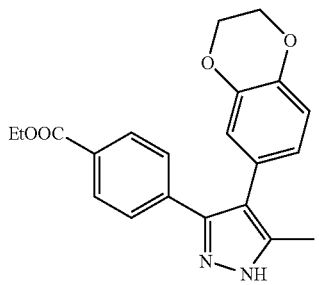

The product was obtained (48% yield) as yellow solids. $R_f$=0.28 (EtOAc:hexane/1:1). $^1$H NMR (CDCl$_3$) δ=7.92 (2H, d, J=8.7 Hz); 7.49 (2H, d, J=8.7 Hz); 6.82 (1H, d, J=8.2 Hz); 6.71 (1H, d, J=2.0 Hz); 6.61 (1H, dd, J=2.0 and 8.2 Hz); 4.36 (2H, q, J=7.0 Hz); 4.28 (4H, s); 2.22 (3H, s) and 1.26 (3H, t, J=7.0 Hz). $^{13}$C NMR (CDCl$_3$) δ=166.41, 143.46, 142.62, 140.98, 140.33, 129.59, 129.36, 127.53, 126.29, 123.28, 118.62, 118.15, 117.36, 64.35, 60.90, 14.30 and 10.68. MS: 365.3 (M+H)$^+$.

N-{3-[4-(2,3-Dihydro-benzo[1,4]dioxin-6-yl)-5-methyl-1H-pyrazol-3-yl]-phenyl}-acetamide

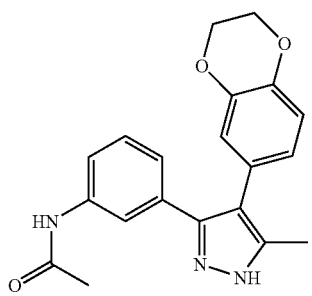

The product was obtained (30% yield) as yellow oil. $R_f$=0.23 (EtOAc:hexane/4:1). $^1$H NMR (d$_4$-MeOH) δ=7.60 (1H+1H, m, broad); 7.50 (1H, t, broad); 7.18 (1H, d, broad); 6.82 (1H, d, J=8.2 Hz); 6.69 (1H, d, J=2.0 Hz); 6.64 (1H, dd, J=2.0 and 8.2 Hz); 4.27 (4H, s); 2.28 (3H, s) and 2.13 (3H, s). $^{13}$C NMR (d$_4$-MeOH) δ=171.71, 145.00, 144.06, 140.01, 129.75, 127.90, 125.10, 124.28, 122.42, 120.72, 119.75, 118.28, 65.66, 23.82 and 11.29.

N-{4-[4-(2,3-Dihydro-benzo[1,4]dioxin-6-yl)-5-methyl-1H-pyrazol-3-yl]-phenyl}-acetamide

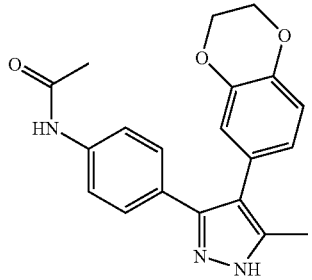

The product was obtained (50% yield) as yellow oil. $R_f$=0.15 (EtOAc). $^1$H NMR (d4-MeOH) δ=7.50 (1H, s, broad); 7.35 (2H, d, J=8.2 Hz); 7.28 (2H, d, J=8.2 Hz); 6.82 (1H, d, J=8.2 Hz); 6.71 (1H, d, J=2.0 Hz); 6.62 (1H, dd, J=2.0 and 8.2 Hz); 4.27 (4H, s); 2.27 (3H, s) and 2.16 (3H, s). $^{13}$C NMR (d$_4$-MeOH) δ=171.68, 151.69, 145.04, 144.11, 140.70, 139.74, 129.32, 128.14, 127.05, 124.33, 120.87, 119.82, 118.32, 65.68, 23.87 and 9.43. MS: 350.4 (M+H)$^+$.

4-[4-(2,3-Dihydro-benzol[1,4]dioxin-6-yl)-5-methyl-1H-pyrazol-3-yl]-benzenesulfonamide

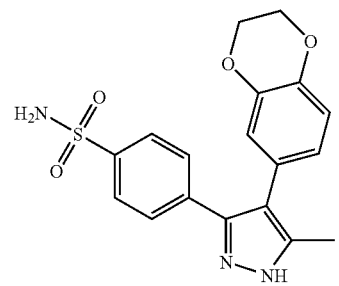

The product was obtained (73% yield) as yellow solids. $R_f$=0.15 (EtOAc:hexane/3:2). $^1$H NMR (d$_6$-acetone) δ=12.2 (1H, s, broad); 7.78 (2H, d, J=8.8 Hz); 7.62 (2H, d, J=8.8 Hz); 6.86 (1H, d, J=8.0 Hz); 6.70 (1H, d, J=2.0 Hz); 6.65 (1H, dd, J=2.0 and 8.0 Hz); 6.54 (2H, s); 4.28 (4H, s) and 2.26 (3H, s). $^{13}$C NMR (d$_6$-acetone) δ=145.66, 144.71, 144.44, 141.60, 139.92, 129.43, 128.72, 128.30, 127.80, 127.16, 124.86, 120.39, 119.16, 66.19 and 11.37. MS: 370.3 (M−H)$^-$.

2-[4-(2,3-Dihydro-benzo[1,4]dioxin-6-yl)-5-methyl-1H-pyrazol-3-yl]-4-methyl-phenol

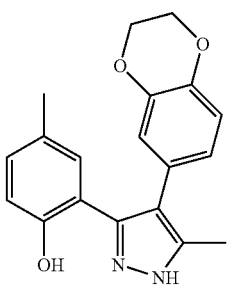

The product was obtained (64% yield) as yellow oil. $^1$H NMR (CDCl$_3$) δ=7.40 (1H+1H, s, broad); 6.85 (1H+1H+1H, m); 6.84 (1H, d, J=8.1 Hz); 6.68 (1H, d, J=2.0 Hz); 6.64 (1H, dd, J=2.0 and 8.1 Hz); 4.30 (4H, s); 2.25 (3H, s) and 2.03 (3H, s). MS: 323.4 (M+H)$^+$.

4-Chloro-2-[4-(2,3-dihydro-benzo[1,4]dioxin-6-yl)-5-methyl-1H-pyrazol-3-yl]-phenol

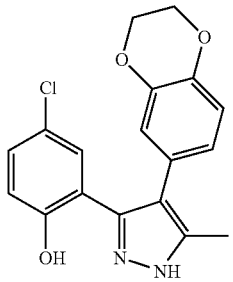

The product was obtained (36% yield) as yellow oil. $R_f$=0.47 (EtOAc:hexane/1:1). $^1$H NMR (CDCl$_3$) δ=7.26 (1H, s); 7.08 (1H, d, J=2.0 Hz); 7.04 (1H, d, J=2.0 Hz); 6.84 (1H, d, J=8.3 Hz); 6.78 (1H, d, J=2.0 Hz); 6.70 (1H, dd, J=2.0 and 8.3 Hz); 4.32 (4H, s) and 2.25 (3H, s). MS: 343.3 (M+H)$^+$.

2-Chloro-4-[4-(2,3-dihydro-benzo[1,4]dioxin-6-yl)-5-methyl-1H-pyrazol-3-yl]-phenol

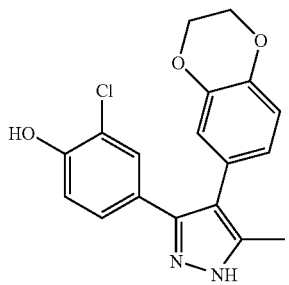

The product was obtained (40% yield) as yellow oil. $R_f$=0.2 (EtOAc:hexane/1:1). $^1$H NMR (CDCl$_3$) δ=7.85 (1H+1H, s, broad); 7.36 (1H, d, J=2.0 Hz); 7.10 (1H, dd, J=2.0 and 8.4 Hz); 6.82 (1H+1H, d, J=8.4 Hz); 6.70 (1H, d, J=2.0 Hz); 6.62 (1H, dd, J=2.0 and 8.4 Hz); 4.27 (4H, s) and 2.25 (3H, s).

2-[4-(2,3-Dihydro-benzo[1,4]dioxin-6-yl)-5-methyl-1H-pyrazol-3-yl]-4-fluoro-phenol

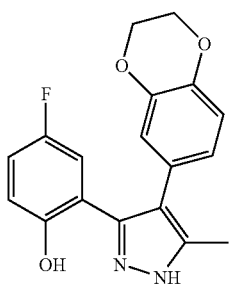

The product was obtained (75% yield) as yellow oil. $R_f$=0.55 (EtOAc:hexane/1:1). $^1$H NMR (d$_4$-MeOH) δ=7.10 (1H, m); 6.98 (1H, m); 6.94 (1H, d, J=8.3 Hz); 6.86 (1H, m); 6.80 (1H, d, J=2.0 Hz); 6.74 (1H, dd, J=2.0 and 8.3 Hz); 4.94 (4H, s) and 2.44 (3H, s). MS: 327.3 (M+H)$^+$.

1-(2,3-Dichloro-phenyl)-3-hydroxy-but-2-en-1-one

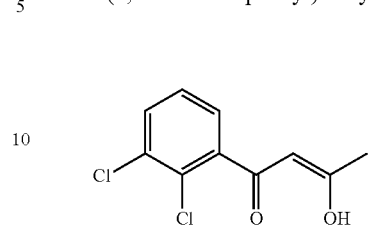

The product was obtained (40% yield) as brown oil. [Enol]: $^1$H NMR (CDCl$_3$) δ=7.55 (1H, dd, J=1.7 and 8.0 Hz); 7.49 (1H, dd, J=1.7 and 8.0 Hz); 7.25 (1H, dd, J=8.0 and 8.0 Hz); 5.59 (1H, s) and 2.20 (3H, s).

3-(2,3-Dichloro-phenyl)-5-methyl-1H-pyrazole

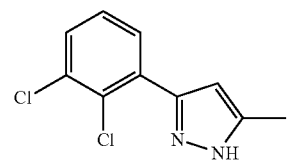

The product was obtained (58% yield) as brown oil. $^1$H NMR (CDCl$_3$) δ=11.00 (1H, s, broad); 7.50 (1H, dd, J=1.7 and 8.0); 7.40 (1H, dd, J=1.7 and 8.0 Hz); 7.10 (1H, dd, J=8.0 and 8.0 Hz); 6.46 (1H, s) and 2.10 (3H, s).

3-(2,3-Dichloro-phenyl)-4-iodo-5-methyl-1H-pyrazole

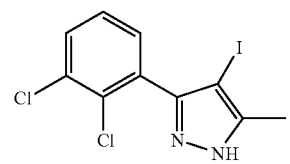

The product was obtained (70% yield) as orange oil. $R_f$=0.54 (EtOAc:hexane/1:1). $^1$H NMR (CDCl$_3$) δ=7.58 (1H, m); 7.30 (2H, m) and 2.21 (3H, s).

3-(2,3-Dichloro-phenyl)-4-(2,3-dihydro-benzo[1,4]dioxin-6-yl)-5-methyl-1H-pyrazole

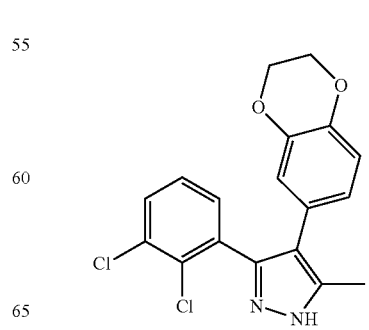

The product was obtained (30% yield) as yellow oil. $R_f$=0.36 (EtOAc:hexane/1:1). $^1$H NMR (CDCl$_3$) δ=7.44 (1H, dd, J=2.0 and 7.6 Hz); 7.18 (2H, m); 6.75 (1H, d, J=8.3 Hz), 6.62 (1H, d, J=2.0 Hz); 6.50 (1H, dd, J=2.0 and 8.3 Hz); 4.23 (4H, s) and 2.29 (3H, s).

4-[4-(2,3-Dichloro-benzo[1,4]dioxin-6-yl)-5-methyl-1H-pyrazol-3-yl]-benzoic acid

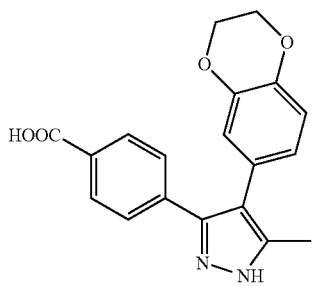

The product was obtained (70% yield) as yellow solids. $R_f$=0.43 (EtOAc). $^1$H NMR (d$_6$-acetone) δ=7.92 (2H, d, J=8.7 Hz); 7.60 (2H, d, J=8.7 Hz); 6.85 (1H, d, J=8.2 Hz); 6.70 (1H, d, J=2.0 Hz); 6.64 (1H, dd, J=2.0 and 8.2 Hz); 4.30 (4H, s) and 2.25 (3H, s). MS: 337.4 (M+H)$^+$.

Example 161

4-[4-(4-Bromo-phenyl)-1-methyl-1H-pyrazol-3-yl]-6-chloro-benzene-1,3-diol

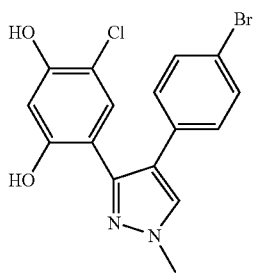

An ethanolic solution (5 ml) of 3-(4-Bromo-phenyl)-6-chloro-7-hydroxy-chromen-4-one (100 mg, 28 mmol) was heated to boiling, methyl hydrazine (0.30 ml, 20 equiv.) added in one portion, and refluxing continued for 16 hrs. After cooling, the volatiles were evaporated under reduced pressure and water added to the residue causing a precipitate to form. This was filtered off and dried under vacuum in the presence of P$_2$O$_5$ to provide 78 mg (73% yield) as a tan coloured powder. Although pure by LCMS further purification by column chromatography, eluting with first 40% EtOAc in Hexane and increasing to 60%, gave a grey-white powder (6 mg). The exact regioisomer was confirmed by NOESY $^1$H NMR.

$δ_H$ (d$_6$-Acetone) 10.29 (broad s, OH), 7.70 (1H, s, Het-H), 7.48 (2H, d, Ar—H), 7.19 (2H, d, Ar—H), 6.96 (1H, s, Ar—H), 6.46 (1H, s, Ar—H), 3.88 (3H, s, N—CH$_3$). LCMS $t_R$=7.58, MS m/z 379.4/381.4 [M+H]$^+$.

Example 162

4-[4-(3,4-Dimethoxy-phenyl)-1-methyl-1H-pyrazol-3-yl]-6-ethyl-benzene-1,3-diol

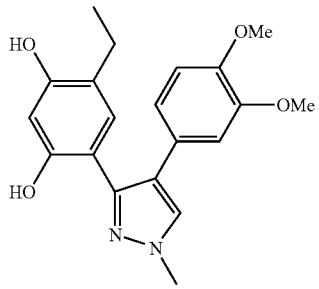

The procedure as described in the previous example using 3-(3,4-Dimethoxy-phenyl)-6-ethyl-7-hydroxy-chromen-4-one (50 mg, 0.15 mmol) was employed with refluxing continued for 24 hours. The crude recovered was purified by preparative TLC to provide 5 mg (28% yield) as white crystals. The exact regioisomer was confirmed by NOESY $^1$H NMR.

$δ_H$ (d$_6$-Acetone) 10.28 (broad s, OH), 8.07 (1H, broad s, OH), 7.54 (1H, s, Het-H), 6.77 (4H, m, Ar—H), 6.29 (1H, s, Ar—H), 3.84 (3H, s, CH$_3$), 3.70 (3H, s, OCH$_3$), 3.61 (3H, s, OCH$_3$), 2.19 (2H, q, CH$_2$CH$_3$), 0.77 (3H, t, CH$_2$CH$_3$). LCMS $t_R$=6.78, MS m/z 355.4 [M+H]$^+$.

Example 163

(4-[4-(4-Bromo-phenyl)-1,5-dimethyl-1H-pyrazol-3-yl]-6-chloro-benzene-1,3-diol

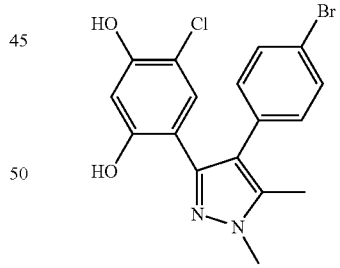

The procedure as described in the previous example using 3-(4-Bromo-phenyl)-6-chloro-7-hydroxy-2-methyl-chromen-4-one (50 mg, 0.14 mmol) was employed with refluxing continued for 60 hours. The crude recovered was purified by preparative TLC to provide 7 mg (13% yield) as white crystals. The exact regioisomer was confirmed by NOESY $^1$H NMR.

$δ_H$ (d$_6$-Acetone) 10.81 (broad s, OH), 8.60 (1H, broad s, OH), 7.55 (2H, d, Ar—H), 7.12 (2H, d, Ar—H), 6.77 (1H, s, Ar—H), 6.42 (1H, s, Ar—H), 3.79 (3H, s, CH$_3$), 2.09 (3H, s, CH$_3$). LCMS $t_R$=8.04, MS m/z 392.9/394.9 [M+H]$^+$.

Example 164

4-Chloro-6-(1,5-dimethyl-4-phenyl-1H-pyrazol-3-yl)-benzene-1,3-diol

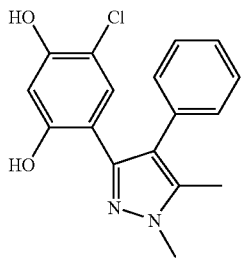

The procedure as described in the previous example using 6-Chloro-7-hydroxy-2-methyl-3-phenyl-chromen-4-one (50 mg, 0.17 mmol) was employed with refluxing continued for 60 hours. The crude recovered was purified by preparative TLC to provide 10 mg (18% yield) as white crystals. The exact regioisomer was confirmed by NOESY $^1$H NMR.

$\delta_H$ ($d_6$-Acetone) 7.38 (3H, m, Ar—H), 7.15 (2H, m, Ar—H, 6.78 (1H, s, Ar—H), 6.41 (1H, s, Ar—H), 3.79 (3H, s, CH$_3$), 2.07 (3H, s, CH$_3$). LCMS $t_R$=7.41, MS m/z 315.4 [M+H]$^+$.

Example 165

(4-Chloro-6-[4-(3,4-dimethoxy-phenyl)-1-methyl-1H-pyrazol-3-yl]-benzene-1,3-diol-

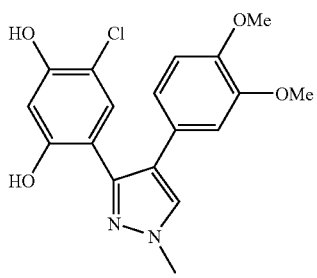

The procedure as described in the previous example using 6-Chloro-3-(3,4-dimethoxy-phenyl)-7-hydroxy-chromen-4-one (100 mg, 0.30 mmol) was employed. The crude provided 69 mg (64% yield) as a light brown powder which required no further purification. The exact regioisomer was confirmed by NOESY $^1$H NMR.

$\delta_H$ ($d_6$-DMSO) 7.91 (1H, s, Het-H), 6.85 (3H, m, Ar—H), 6.53 (1H, s, Ar—H), 5.75 (1H, s, Ar—H), 3.87 (3H, s, CH$_3$), 3.77 (3H, s, OCH$_3$), 3.61 (3H, s, OCH$_3$). LCMS $t_R$=6.53, MS m/z 361.3 [M+H]$^+$.

Example 166

Synthesis of 4-[4-(4-Bromo-phenyl)-1-(2-hydroxy-ethyl)-1H-pyrazol-3-yl]-6-chloro-benzene-1,3-diol

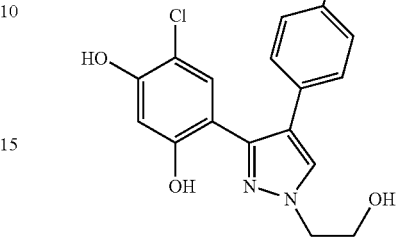

3-(4-Bromo-phenyl)-6-chloro-7-hydroxy-chromen-4-one (0.1 g, 0.28 mmol), and 2-Hydrazino-ethanol (0.04 g) were suspended in ethanol (10 ml) and refluxed for 1 hr. 4-[4-(4-Bromo-phenyl)-1-(2-hydroxy-ethyl)-1H-pyrazol-3-yl]-6-chloro-benzene-1,3-diol precipitated out on quenching as a white solid (0.09 g, 78.8%).

$\delta_H$ (DMSO): 8.01 (1H, s, =CH), 7.48 (2H, d, J=9 Hz, ArH), 7.19 (2H, d, J=9 Hz, ArH), 7.06 (1H, s, ArH), 6.51 (1H, s, ArH), 4.16 (2H, t, CH$_2$), 3.79 (2H, t, CH$_2$). LCMS Single peak $t_R$ 7.34, MS m/z 409/411 [M+H]$^+$.

6-Chloro-7-hydroxy-3-(4-methoxy-phenyl)-4-oxo-4H-chromene-2-carboxylic acid methyl ester (See Scheme 25)

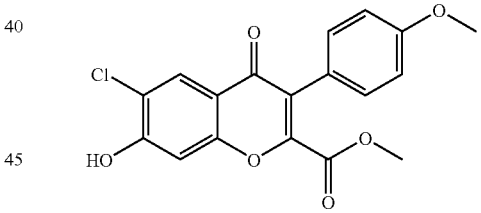

1-(5-Chloro-2,4-dihydroxy-phenyl)-2-(4-methoxy-phenyl)-ethanone (1 eq) was taken up in anhydrous pyridine and cooled on an ice bath to 0° C. Methyl chlorooxoacetate (3 eq) was added dropwise and the solution was stoppered and allowed to stand in the refrigerator over night.

The bright orange solution was added carefully to 100 ml 1M HCl (aq) and extracted into 2×70 ml DCM. The organic phases were combined and washed with 2×50 ml brine. All was concentrated in vacuo to a yellow solid. This was suspended in a 1:1 mixture of 1M HCl (aq) and methanol. All was heated at reflux for 4 hrs. Allowed to cool.

The reaction mixture was concentrated in vacuo to give 6-chloro-7-hydroxy-3-(4-methoxy-phenyl)-4-oxo-4H-chromene-2-carboxylic acid methyl ester as a pale yellow solid LC retention time 2.423 minutes [M+H]$^+$ 361.2/363.2 chlorine splitting pattern.

6-Chloro-7-hydroxy-3-(4-methoxy-phenyl)-4-oxo-4H-chromene-2-carboxylic acid

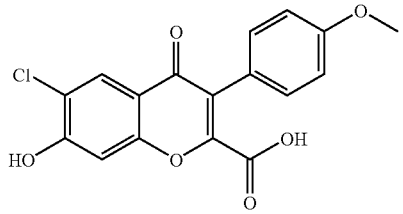

6-Chloro-7-hydroxy-3-(4-methoxy-phenyl)-4-oxo-4H-chromene-2-carboxylic acid methyl ester was taken up in a 2:1 mixture of sat. NaHCO$_3$ (aq): Methanol and all was heated at 65° C. for 5 hours. The solution was cooled to room temperature and concentrated in vacuo to remove the methanol. The residual aqueous solution was acidified with 1M HCl (aq) and a buff coloured precipitated dropped out of solution. This was collected by vacuum filtration, washed with water and with diethyl ether, to give 6-chloro-7-hydroxy-3-(4-methoxy-phenyl)-4-oxo-4H-chromene-2-carboxylic acid.

LC retention time 1.814 minutes 347.2/349.2 chlorine splitting pattern.

Example 167

5-(5-Chloro-2,4-dihydroxy-phenyl)-4-(4-methoxy-phenyl)-2H-pyrazole-3-carboxylic acid

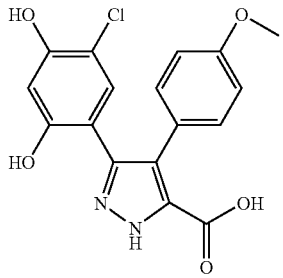

6-Chloro-7-hydroxy-3-(4-methoxy-phenyl)-4-oxo-4H-chromene-2-carboxylic acid (1 eq) was taken up in ethanol and hydrazine hydrate (3 eq) was added. To aid dissolution a few drops of NaHCO3 (aq) was added, and then all was heated at 70° C. under nitrogen for 2 hours. The solution was cooled to room temperature and concentrated in vacuo to a brown oil. This was partitioned between 1M HCl (aq) and diethyl ether. The organic phases were combined, washed with 1M HCl (aq), dried over MgSO$_4$, filtered and concentrated in vacuo to give 5-(5-chloro-2,4-dihydroxy-phenyl)-4-(4-methoxy-phenyl)-2H-pyrazole-3-carboxylic acid as a yellow foam.

LC retention time 2.020 min [M+H]$^+$ 361.2/363.2 chlorine splitting pattern.

General Synthesis of R$^5$ Amides

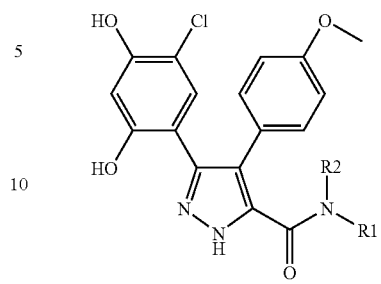

5-(5-Chloro-2,4-dihydroxy-phenyl)-4-(4-methoxy-phenyl)-2H-pyrazole-3-carboxylic acid (1 eq) was taken up as a suspension in anhydrous dichloromethane. The resulting solution was cooled to 0° C. under nitrogen. 1-hydroxybenzotriazole hydrate (3 eq) was added, followed by N-methylmorpholine (10 eq), N-Ethyl-N'-(3-dimethylaminopropyl) carbodiimide. HCl (3 eq) and amine (2 eq). All was stirred to room temperature overnight. The resulting solutions were diluted with dichloromethane and extracted with 1M HCl (aq), sat. NaHCO$_3$ (aq) and sat. NaCl (aq), then dried over MgSO$_4$, filtered and concentrated in vacuo. The residue was purified by preparative LC/MS to give the amide product.

Example 168

5-(5-Chloro-2,4-dihydroxy-phenyl)-4-(4-methoxy-phenyl)-2H-pyrazole-3-carboxylic acid methylamide

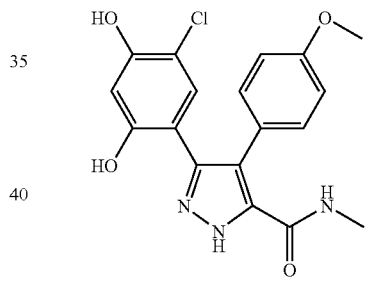

LC retention time 1.968 min [M+H]$^+$ 374.3/376.2 chlorine splitting pattern.

Example 169

5-(5-Chloro-2,4-dihydroxy-phenyl)-4-(4-methoxy-phenyl)-2H-pyrazole-3-carboxylic acid methylamide

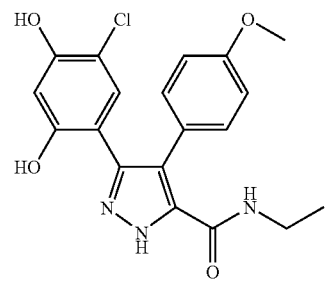

LC retention time 2.108 min [M+H]$^+$ 388.3/390.2 chlorine splitting pattern.

Example 170

5-(5-Chloro-2,4-dihydroxy-phenyl)-4-(4-methoxyphenyl)-2H-pyrazole-3-carboxylic acid isopropylamide

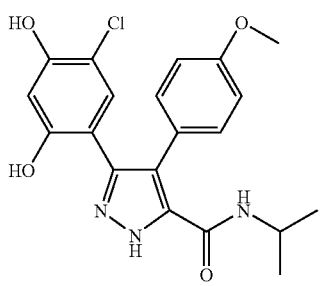

LC retention time 2.204 min [M+H]+ 402.3/404.3 chlorine splitting pattern.

Example 171

5-(5-Chloro-2,4-dihydroxy-phenyl)-4-(4-methoxyphenyl)-2H-pyrazole-3-carboxylic acid benzylamide

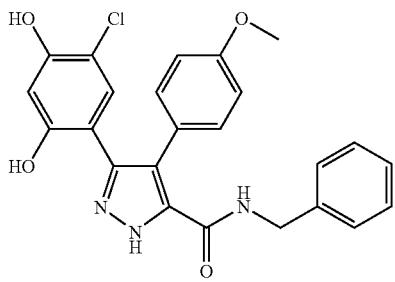

LC retention time 2.421 min [M+H]+ 450.3/452.3 chlorine splitting pattern.

Example 172

5-(5-Chloro-2,4-dihydroxy-phenyl)-4-(4-methoxyphenyl)-2H-pyrazole-3-carboxylic acid amide

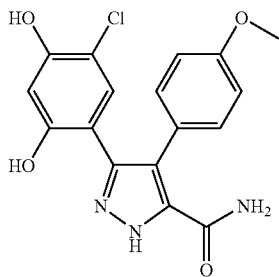

Example 4 (1 eq) was taken up in anhydrous DMF at room temperature, under a nitrogen atmosphere. 2-(1H-Benzotriazole-1-yl)-1,1,3,3-tetramethyluronium hexafluorophosphate (2 eq) was added, followed by N,N-diisopropylethylamine (3 eq). The reaction mixture was stirred for 5 minutes, after which time, 0.88 aqueous ammonia (vast excess) was added. All was allowed to stir at room temperature under nitrogen for two days.

The reaction mixture was quenched into 1M HCl (aq) and extracted with dichloromethane. The organic phases were combined, washed with sat. NaCl (aq), dried over MgSO$_4$, filtered and concentrated in vacuo. Purified by preparative LC/MS.

LC retention time 1.920 min [M+H]+ 360.2/362.2 chlorine splitting pattern.

Example 179 was Prepared According to Scheme 26

1-(2,4-Bis-benzyloxy-5-chloro-phenyl)-2-(4-methoxy-phenyl)-ethanone

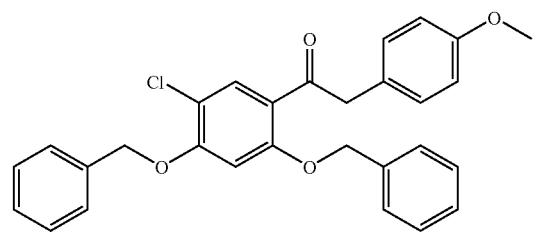

1-(5-Chloro-2,4-dihydroxy-phenyl)-2-(4-methoxy-phenyl)-ethanone (1 eq) was dissolved in acetonitrile and potassium carbonate (4 eq) was added portion wise. The suspension was stirred for five minutes, before the addition of benzyl bromide (2.4 eq), and after which, the reaction mixture was stirred under nitrogen at reflux for 3 hours. The reaction was allowed to cool to room temperature and diluted with water. This was extracted into ethyl acetate. The organic phase was dried over MgSO$_4$, filtered and concentrated in vacuo to give a syrup. This was triturated with 1:1 diethyl ether:hexane to give 1-(2,4-bis-benzyloxy-5-chloro-phenyl)-2-(4-methoxy-phenyl)-ethanone as a white solid.

LC retention time 3.019 minutes, [M+H]+ 475.3/473.3 chlorine splitting pattern.

3-(2,4-Bis-benzyloxy-5-chloro-phenyl)-4-(4-methoxy-phenyl)-1H-pyrazole

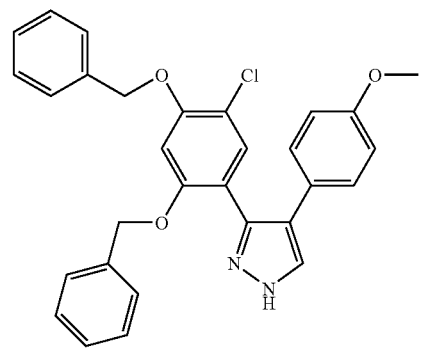

1-(2,4-Bis-benzyloxy-5-chloro-phenyl)-2-(4-methoxy-phenyl)-ethanone was suspended in dimethylformamide dimethylacetal (1.5 eq). A few drops of DMF were added to aid solubility. The resulting solution was heated to 110° C. overnight, under a nitrogen atmosphere. The solution was cooled to ambient temperature. Hydrazine hydrate (3 eq) was added and the solution was stirred at 80° C. for 2 hrs, under nitrogen.

The reaction mixture was cooled to room temperature, diluted with ethyl acetate and was washed several times with water. The organic phase was dried over MgSO$_4$, filtered and concentrated in vacuo to give a pink gum. This was triturated with 1:1 diethyl ether: hexane to give 3-(2,4-bis-benzyloxy-5-chloro-phenyl)-4-(4-methoxy-phenyl)-1H-pyrazole as a cream coloured solid.

LC retention time 2.848 minutes [M+H]$^+$ 497.3/499.3 chlorine splitting pattern.

3-(2,4-Bis-benzyloxy-5-chloro-phenyl)-5-bromo-4-(4-methoxy-phenyl)-1H-pyrazole

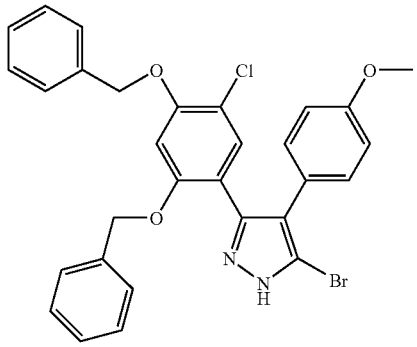

3-(2,4-bis-benzyloxy-5-chloro-phenyl)-4-(4-methoxy-phenyl)-1H-pyrazole (1 eq) was dissolved in anhydrous dichloromethane and under a nitrogen atmosphere was cooled to 0° C. N-Bromosuccinimide (1 eq) was added portion wise, and the reaction mixture was stirred to room temperature over 3 hours. A further portion of N-bromosuccinimide (1 eq) was added to complete the bromination in 45 minutes.

The reaction mixture was diluted with water and stirred for 5 minutes. After this time the mixture was extracted into dichloromethane. The organic phases were washed several times with water, dried over MgSO$_4$, filtered and concentrated in vacuo. The residue was purified by flash chromatography, eluting with 5% Ethyl acetate/Hexane, to give 3-(2,4-bis-benzyloxy-5-chloro-phenyl)-5-bromo-4-(4-methoxy-phenyl)-1H-pyrazole as a foam.

LC retention time 2.845 minutes [M+H]$^+$ 575.3/577.3 chlorine splitting pattern.

4-[5-Bromo-4-(4-methoxy-phenyl)-1H-pyrazol-3-yl]-6-chloro-benzene-1,3-diol

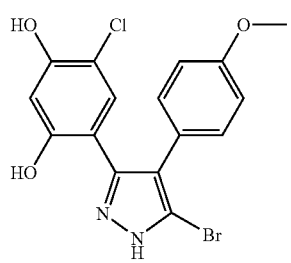

3-(2,4-Bis-benzyloxy-5-chloro-phenyl)-5-bromo-4-(4-methoxy-phenyl)-1H-pyrazole (1 eq) was dissolved in anhydrous dichloromethane, and under a nitrogen atmosphere, was cooled to 0° C. 1M boron trichloride in dichloromethane (8 eq) was added drop wise and the solution was stirred at 0° C. for 30 minutes. The solution was added drop wise to sat. NaHCO$_3$(aq), and extracted into dichloromethane. The organic phase was washed with brine, dried over MgSO$_4$, filtered and concentrated in vacuo, to give a white solid. This was purified by preparative LC/MS to give 4-[5-bromo-4-(4-methoxy-phenyl)-1H-pyrazol-3-yl]-6-chloro-benzene-1, 3-diol (Example 179) as a white solid.

LC retention time 2.355 minutes [M+H]$^+$ 395.1/397.1/399.1 mono chlorine/mono bromine splitting pattern.

Several examples of compounds of the present invention were obtained from commercial sources (e.g., ChemDiv Inc., San Diego, Calif., USA).

HSP90 activity was determined using, inter alia, the assays described below.

Assay Methods

Two methods have been developed to measure the intrinsic ATPase activity of HSP90, using yeast HSP90 as a model system. The first method utilises a regenerating coupled enzyme assay. The second assay, based on the use of malachite green for the measurement of inorganic phosphate, was designed for high throughput screening (HTS) to identify novel HSP90 inhibitor drug candidates.

Molecular markers, indicative of HSP90 inhibition, have been identified (see, e.g., Whitesell et al., 1994; Clarke et al., 2000) and these can be readily measured using Western blotting techniques.

A cell-based ELISA (enzyme-linked immunosorbent assay), similar to those described for other proteins and post-translational modifications (see, e.g., Stockwell et al., 1999; Versteeg et al., 2000), has also been developed. This technique provides an alternative higher throughput assay for determining pharmacodynamic endpoints for the evaluation of HSP90 inhibitors. The assay may also prove useful as a cell-based primary screen for the identification of compounds that inhibit HSP90 by a non-ATPase directed mechanism.

A growth inhibition assay was also employed for the evaluation of candidate HSP90 inhibitors.

Coupled Enzyme ATPase Assay

The ATPase assay is performed using the pyruvate kinase/lactate dehydrogenase linked assay described by Ali et al, 1993, the basis of which is illustrated in the following scheme:

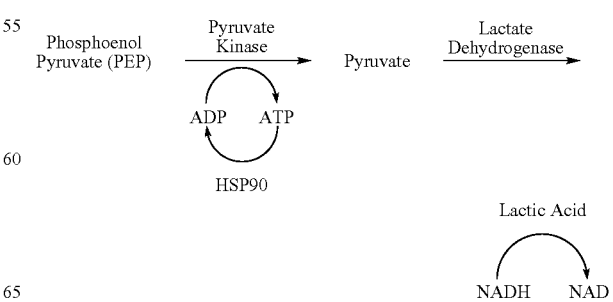

The ADP that is generated by HSP90 is phosphorylated by pyruvate kinase, utilising phosphoenol pyruvate (PEP) as substrate, to produce ATP and pyruvate as products. Pyruvate is then converted to lactic acid by lactate dehydrogenase utilising NADH, which is converted to NAD. This consumption of NADH concentration leads to a decrease in the absorbance at 340 nm that is monitored spectrophotometrically. Thus, for every mole of ADP that is generated by the ATPase activity of HSP90, one mole of NADH is utilised. It should be noted that prior to the addition of HSP90, the enzyme system converts any contaminating ADP, which is present in the ATP substrate, to ATP. This is important for enzymes such as HSP90, which show a stronger affinity for the binding of ADP than ATP.

Materials

Chemicals are of the highest purity commercially available and all aqueous solutions are made up in AR water.
(1) 1 M Tris-HCl buffer, pH 7.5.
(2) 100 mM KCl.
(3) 100 mM $MgCl_2$.
(4) 10 mg $ml^{-1}$ phosphenol pyruvate (PEP, 108 294, Roche Diagnostics Ltd., Lewes, UK) stored at 4° C.
(5) 4 mg $ml^{-1}$ ATP (A-9187, Sigma Aldrich Ltd., Poole, UK) stored at −20° C.
(6) 35.5 mg $ml^{-1}$ NADH (837 075, Roche Diagnostics Ltd.) stored at 4° C.
(7) 10 mg $ml^{-1}$ pyruvate kinase (109 045, Roche Diagnostics Ltd.) stored at 4° C.
(8) 10 mg $ml^{-1}$ lactate dehydrogenase (127 221, Roche Diagnostics Ltd.) stored at 4° C.
(9) 15 mM geldanamycin (in 100% DMSO) freshly prepared.

Method

The following protocol was used:
(1) Mix together: (a) 10 ml of 1 M Tris buffer pH 7.5, (b) 20 ml 100 mM KCl and (c) 6 ml of 100 mM $MgCl_2$. This is buffer A and is kept at 37° C. for the duration of the assay and then discarded at the end of each day.
(2) Incubate some distilled water ($dH_2O$) at 37° C.
(3) Dissolve 12.8 mg of ATP in 2 ml of buffer A and maintain on ice.
(4) Dissolve 10 mg of PEP in 1 ml of buffer A and incubate on ice.
(5) Add 0.25 ml buffer A to 8.9 mg NADH and place on ice.
(6) Place the pyruvate kinase and lactate dehydrogenase on ice.
(7) To the reference cell, add (a) 360 μl buffer A, (b) 520 μl $dH_2O$, (c) 80 μl ATP solution and (d) 40 μl PEP solution.
(8) To the test cells, add (a) 360 μl buffer A, (b) 490 μl $dH_2O$, (c) 80 μl ATP, (d) 40 μl PEP, (e) 20 μl pyruvate kinase and (f) 2 μl lactate dehydrogenase.
(9) Mix the contents of the cuvettes and zero the absorbance at 340 nm. Then add 2 μl of the NADH and the absorbance should increase. Follow the reaction at 37° C. until a stable base line is obtained.
(10) Add the HSP90 to the test cuvettes and adjust the volume of the cuvettes to 1 ml with $dH_2O$, and follow the decrease in the absorbance at 340 nm using a suitable spectrophotometer (e.g., Shimadzu UV-240).
(11) Add 2 μl of geldanamycin and follow the decrease in the absorbance at 340 nM. The HSP90 ATPase activity is given by the difference between the rates in steps 9 and 10.
(12) The rate of the reaction (moles $min^{-1}$ $ml^{-1}$) is derived from $\Delta OD/(1000 \times 6200$ $M^{-1}$ $cm^{-1})$, where the value 6200 is the extinction coefficient of NADH. This can be converted to specific activity (mole ATP $min^{-1}$ $mg^{-1}$) or turnover (moles $min^{-1}$ $mole^{-1}$) by dividing the rate by the mass (mg) or molar amount of HSP90 used in the reaction.

Comments (1) Details of the purification of the yeast HSP90 protein have previously been described (Panaretou et al., 1998). The ATPase activity of yeast HSP90 at 37° C. is ~0.7 moles ATP $min^{-1}$ mg protein. Relative to other ATPases, this activity is very low and consequently HSP90 preparations must be highly purified.
(2) To show that the measured ATPase activity is due to HSP90, rather than background contaminating ATPase activity, the activity must be shown to be geldanamycin sensitive.
(3) All assays are conducted in triplicate with a HSP90 concentration of 2 μM.
(4) This assay is relatively time consuming and throughput is consequently low. Each assay takes around 60 min to complete.

Malachite Green ATPase Assay

Colorimetric assays for the determination of phosphate, based on the formation of a phosphomolybdate complex, can be carried out in a few steps with inexpensive reagents and are well suited to the automation required for high throughput screening (see, e.g., Cogan et al., 1999). Enzymes that release inorganic phosphate are assayed using the reaction of the cationic dye, malachite green, with the a complex formed by a reaction of the inorganic phosphate with molybdate to generate a blue-green colour with an absorbance maximum at 610 nm (see, e.g., Baykov et al., 1988; Harder et al., 1994; Maehama et al., 2000). The method has been used in both high throughput (see, e.g., Rumsfeld et al., 2000) and ultra-high throughput screening formats (see, e.g., Layery et al., 2001) for a variety of non-HSP90 ATPases. However, this method is complicated by the non-enzymatic hydrolysis of ATP in the presence of acidic malachite green reagent, causing an increase in colour (see, e.g., Chan et al., 1986; Henkel et al., 1988). This process is mediated by molybdate and can be overcome by the addition of sodium citrate immediately after the reagent (see, e.g., Lanzetta et al., 1979; Schirmer et al., 1998; Baginski et al., 1975). This modification has been adapted to the 96-well microtitre plate assay previously described for other ATPases (see, e.g., Lanzetta et al., 1979) to produce the following protocol for HSP90 ATPase, which is suitable for high throughput screening.

Materials

Chemicals are of the highest purity commercially available and all aqueous solutions are made up in AR water. Because of the need to minimise contamination with inorganic phosphate, precautions should be taken with solutions and apparatus used in the assays. Glassware and pH meters are rinsed with double distilled or deionised water before use and, wherever possible, plastic ware should be used. Gloves are worn for all procedures.
(1) Immulon 96-well (Thermo Labsystems, Basingstoke, UK) or Cliniplate 384-well flat-bottomed polystyrene multiwell plates (Thermo Labsystems).
(2) Assay buffer of (a) 100 mM Tris-HCl, pH 7.4, (b) 20 mM KCl, (c) 6 mM $MgCl_2$. Stored at 4° C.
(3) 0.0812% (w/v) malachite green (M 9636, Sigma Aldrich Ltd., Poole, UK). Stored at room temperature.
(4) 2.32% (w/v) polyvinyl alcohol USP (P 1097, Sigma Aldrich Ltd, Poole, UK) in boiling water (see Comment 1), allowed to cool, and stored at room temperature.

(5) 5.72% (w/v) ammonium molybdate in 6 M hydrochloric acid. Stored at room temperature.
(6) 34% (w/v) sodium citrate. Stored at room temperature.
(7) ATP, disodium salt, special quality (519979, Boehringer Mannheim, Lewes, UK). Stored at 4° C.
(8) *E. coli* expressed yeast HSP90 protein, purified >95% (see, e.g., Panaretou et al., 1998) and stored at −80° C. as 10 μl aliquots containing 0.5 mg of protein.

Method

The following protocol was used:
(1) On the day of use, prepare the malachite green reagent from the stock solutions. Mix (a) 2 parts of malachite green, (b) 1 part of polyvinyl alcohol, (c) 1 part of ammonium molybdate, and (d) 2 parts of water. Initially, the reagent is a dark brown colour, but after standing at room temperature for about 2 h, this becomes a golden yellow colour and is ready for use.
(2) For the high throughput screening assays, the test compounds are dissolved at 200 μM in 2.0% DMSO and contained in daughter plates derived from the chemical libraries. Transfer 5 μl of each sample from the daughter plate to each well of the assay plate using automated equipment (see Comment 3). This represents a final concentration in the well of 40 μM. The first and last rows of the 96-well plate contain solvent only and represent the control and background values, respectively.
(3) In order to determine an IC50 value, prepare a range of stock concentrations of the compound in DMSO. Five appropriate concentrations are used depending on the relative potency of each compound. Transfer a 1 μl aliquot of each concentration to the wells of the assay plate and add 4 μL of the assay buffer.
(4) Dissolve the ATP in the assay buffer to give a stock concentration of 2.5 mM and store at room temperature.
(5) Add a 10 μl aliquot of the ATP solution to each well to give a final assay concentration of 1 mM.
(6) Just before use, thaw the HSP90 protein on ice and suspend in chilled assay buffer to a stock concentration of 0.25 mg/ml and keep on ice. Start the incubation by adding 10 μl of stock HSP90 to each well, except for the background wells which receive 10 μl of assay buffer, giving a final assay volume of 25 μl.
(7) Shake the plates (approximately 2 min) using a plate shaker (e.g., Wellmixx (Thermo Labsystems) or MTS4 (IKA-Schuttler)), seal with plastic film and incubate for 3 h at 37° C.
(8) To stop the incubation, add 80 μl of the malachite green reagent to each well and shake the plate again.
(9) Add 10 μl of 34% sodium citrate (see Comment 2) to each well and shake again. This leads to the development of the blue-green colour in the controls, while the backgrounds are yellowish.
(10) Measure the absorbance at 620 nm using a suitable plate reader (e.g., Victor 2, Perkin Elmer Life Sciences, Milton Keynes, UK). Under the above conditions, the control absorbance value is 0.7 to 1.0, while the background is 0.15 to 0.20; the signal to noise ratio is ~30. The Z' factor (see, e.g., Zhang et al., 1999) calculated from data obtained using these conditions was 0.8 indicating an assay highly suitable for screening purposes.

Comments (1) The polyvinyl alcohol dissolves in boiling water with difficulty and stirring for 2–3 h is required.
(2) The time interval between addition of the malachite green reagent and the sodium citrate should be kept as short as possible in order to reduce the non-enzymatic hydrolysis of ATP. Once the sodium citrate is added, the colour is stable for up to 4 h at room temperature.
(3) Compounds can be added to the assay plates using a Rapidplate 96/384 (Zymark, Runcorn, UK). A Multidrop 384 dispenser (Thermo Labsystems, Basingstoke, UK) can be conveniently used to add reagents to the plate.
(4) The assay conditions were optimised with respect to time, protein and substrate concentration in order to achieve linearity of enzyme activity under the described protocol.
(5) The above assay protocol is used with 96-well plates, but a reduction in volumes readily allows the use of 384-well plates.
(6) Signal to noise (S/N) is calculated using the following equation:

$$(S-B)/\sqrt{(SD \text{ of } S)^2 + (SD \text{ of } B)^2}$$

(7) To determine specific activity of HSP90, a range of inorganic phosphate concentrations (0–10 μM) are prepared and the absorbance at 620 nm measured as described. Specific activity is calculated from the resulting calibration curve.

Western Blotting Assay

The cellular effects of HSP90 inhibitors can be measured using a number of molecular markers. As already mentioned, HSP90 inhibition leads to the depletion of several important cellular signalling proteins. RAF-1 is readily detectable by Western blotting and has been shown to be depleted in a number of human tumour cell lines following exposure to HSP90 inhibitors (see, e.g., Kelland et al., 1999; Hostein et al., 2001; Schulte et al., 1998; Clarke et al., 2000). Depletion is normally observed by 6 h, with maximum depletion occurring at 24 h. As well as RAF-1, depletion of several other HSP90 client proteins can be measured by immunoblotting e.g., CDK4, ERBB2. However, it is important to note that some of these proteins are cell line specific e.g., ERBB2 is expressed mainly in breast, thyroid, kidney and some ovarian tumour cell lines. Another very important marker of HSP90 inhibition is heat shock protein 70 (HSP70). A HSF-1 (heatshock factor 1) dependent increase in HSP70 levels has been reported by us and other groups (see, e.g., Whitesell et al., 1994; Clarke et al., 2000) and this effect can serve as a positive indicator of HSP90 inhibitor action. The immunoblotting method described is based on standard techniques but is described in detail for ease of reference.

Materials

Chemicals are of the highest purity commercially available.
(1) 17AAG, geldanamycin, and radicicol are stored as 2 mM stocks in DMSO at −20° C.
(2) Human tumour cell lines (e.g., from ATCC) are grown in Dulbecco's modified Eagle's medium (DMEM) supplemented with 4500 mg/ml glucose, 10% foetal bovine serum (FBS), 200 mM L-glutamine and 5 ml non-essential amino acids in a humidified atmosphere of 5% $CO_2$ at 37° C.
(3) Lysis buffer: (a) 150 mM NaCl, (b) 50 mM Tris-HCl, (c) 1% NP40, (d) 0.2% sodium dodecyl sulphate (SDS), (e) 2 mM phenylmethylsulfonylfluoride (PMSF), (f) 10 μg/l aprotinin, (g) 10 μg/l leupeptin, (h) 1 mM sodium orthovanadate, (i) 0.5 mM dithiothreitol (DTT), (j) 0.5 mM NaF, (k) 0.5 mM β-glycerophosphate. Prepare as required and store at −20° C.
(4) Bicinchoninic acid (BCA) protein assay reagents (PerBio Science UK, Ltd., Chester, UK).

(5) Casein blocking buffer (0.5% casein, 0.02% thimerosal, in PBS). Store at 4° C. for up to 2 weeks.
(6) Wash buffer (phosphate buffered saline, PBS) containing 0.05% Tween 20).
(7) Tris-glycine gradient polyacrylamide precast gels (4–20%) (1 mm thick) (Novex, InVitrogen, Groningen, NL).
(8) Nitro-cellulose membrane (0.2 µm pore size) (InVitrogen, Groningen, NL).
(9) Ponceau Red stain (2% w/v in 30% TCA/30% BSA, Sigma Aldrich Ltd., Pool, UK).
(10) Enhanced chemiluminescence (SuperSignal) reagents (PerBio Science UK, Ltd., Chester, UK).
(11) Photographic film (Hyperfilm ECL, Amersham Pharmacia Biotech, Little Chalfont, Bucks, UK).

Method

The following protocol was used:
(1) Lyse cells (approx $4 \times 10^6$) in 100 µl lysis buffer for 30 minutes on ice. When adding the lysis buffer, shear cells by pipetting up and down using a Gilson P200 pipette.
(2) Spin lysates for 10 min at 13,000 rpm at 4° C., retrieve supernatant and store at −70° C.
(3) Determine protein concentration using BCA protein assay reagents.
(4) Load samples of cell lysates (50 µg protein/lane) onto gel and separate proteins by SDS-polyacrylamide gel electrophoresis (SDS-PAGE) using a 4–20% Tris-glycine gel.
(5) Transfer proteins to nitrocellulose membrane using optimum conditions for the equipment available. For example, 150 mA for 2 h using the Mighty Small transfer system (Hoeffer TE22 Mini Tank Transphor Unit, Amersham Pharmacia Biotech, Little Chalfont, Bucks, UK). At this stage, the membrane is usually stained with Ponceau Red solution for 5 minutes to visualise protein bands and to check for equal loading.
(6) Block the blotted nitrocellulose membrane in casein blocking buffer for at least 1 h at room temperature with constant agitation (e.g., using a Gyro-Rocker STR9 (Stuart)).
(7) Dilute all primary antibodies to the recommended dilution (see table below) in the casein blocking buffer and incubate with the nitrocellulose membrane overnight at room temperature with agitation.
(8) Wash the nitrocellulose membrane twice for 10 minutes each with wash solution and incubate in the appropriate enzyme-labelled secondary antibody (see table below) for 1 h at room temperature with agitation. Both anti-mouse and anti-rabbit secondary antibodies were diluted 1:1000 in casein blocking buffer.
(9) Wash the nitrocellulose membrane 4 times for 10 min each with wash solution.
(10) Visualise the protein bands using enhanced chemiluminescence reagents as described by the manufacturer and expose to photographic film (usually requires between 1 and 5 min exposure).

TABLE 3

Sources and dilutions of antibodies used for Western blotting

| Marker protein | Source | Primary antibody dilution | Secondary Antibody (a) |
| --- | --- | --- | --- |
| Polyclonal rabbit RAF-1 (C-19) | (b) | 1:500 | Anti-rabbit-IgG-HRP |
| Monoclonal mouse HSP70 SPA-810 | (c) | 1:1000 | Anti-mouse-IgG-HRP |
| Polyclonal rabbit CDK4 (C-22) | (b) | 1:1000 | Anti-rabbit-IgG-HRP |

(a) All from: Amersham Pharmacia Biotech., Little Chalfont, Bucks, UK.
(b) Santa Cruz Biotechnology, Inc., Autogen Bioclear UK, Ltd., Calne, UK.
(c) Bioquote, York, UK.

Comments (1) The protein bands are normally evaluated visually. Densitometry has proved to be an unreliable method for the evaluation of HSP70 expression as the intensity of the band can exceed the linear range of the photographic film.
(2) It is important to note when choosing the time points for the experiment that in some cell lines RAF-1 protein levels recover after 24 h.
(3) Western blotting is currently being utilised in a 17AAG Phase I clinical trial to analyse these pharmacodynamic markers in peripheral blood lymphocytes and tumour tissue to determine whether the compound is acting via its proposed mechanism of action.
(4) RAF-1 is not expressed in all peripheral blood lymphocytes and shows inter-patient variation (unpublished observations). It has been determined that another marker for examining client protein depletion in peripheral blood lymphocytes is the tyrosine kinase, LCK.
(5) Increased expression of HSP70 following HSP90 inhibition can also be measured at the messenger RNA level. Such a methodology for determining the affects of HSP90 inhibitors on the expression of HSP70 and other genes using microarray analysis has been published (see, e.g., Clarke et al., 2000).

ELISA

Although Western blotting has become a universally used technique for evaluating the level of protein expression in cell lines and tissue lysates, the number of samples that can be included on each gel is limited. In addition, relatively large numbers of cells are required to detect proteins that are expressed at a low level and precise quantitation is difficult.

Cell-based ELISA methods (see, e.g., Stockwell et al., 1999; Versteeg et al., 2000) offer several advantages for evaluating the pharmacodynamic effects of novel mechanism-based inhibitors and may be the method of choice for comparing inhibitors that are identified during the iterative process of lead identification and optimisation. The technique can be used to rapidly rank the effectiveness of compounds as well as to investigate the molecular mechanisms of their action. The increased sample throughput possible with ELISA means that compounds can be simultaneously studied in multiple replicates at different doses and exposure times. Also, the number of cells required per observation can be greatly reduced compared to those required for immunoblotting. The assays are carried out directly on cells grown and treated in microtitre plates, thereby removing the necessity for preparing cell lysates. ELISA techniques can in theory be applied to any cellular protein or post-translational modification for which an antibody is available and results are at least semi-quantitative.

Materials

Chemicals are of the highest purity commercially available.

(1) Human colon tumour cell lines (e.g., HCT116 and HT29 from American Tissue Culture Collection, ATCC) grown in Dulbecco's modified Eagle's medium (DMEM) (CSSD, Institute of Cancer Research, London, UK) supplemented with 4500 mg/ml glucose, 10% foetal bovine serum (FBS), 200 mM L-glutamine, and 5 ml non-essential amino acids in a humidified atmosphere of 5% $CO_2$ at 37° C.

(2) 96 well Falcon clear microtitre tissue culture plates (BD Labware, Hospital Management and Supplies, Ltd., Northampton, UK).

(3) DMSO diluted in $dH_2O$ (8%).

(4) HSP90 inhibitors at required concentration dissolved in DMSO.

(5) Fixing solution (0.25% glutaraldehyde, 3% paraformaldehyde and 0.25% Triton-X 100) (all from Sigma Aldrich Ltd, Poole, UK).

(6) Blocking solution (5% dried milk (Marvel) in PBS) prepared daily.

(7) Anti HSP70 monoclonal antibody (SPA 810, Bioquote, York, UK).

(8) DELFIA® wash buffer, enhancement solution, assay buffer and Europium labelled anti-mouse IgG (1244–1330) (PerkinElmer Life Sciences, Milton Keynes, UK).

(9) BCA protein assay reagents (Perbio Science UK Ltd., Chester, UK).

Method

The following protocol was used:

(1) Plate cells (42,000 cells/ml; 8000 cells/190 µl/well) manually or using a Multidrop dispenser (Thermo Labsystems, Basingstoke, UK).

(2) Incubate cells for 36 hours at 37° C. in a 5% $CO_2$ atmosphere.

(3) Add 10 µl 8% DMSO (control) or compound dissolved in 8% DMSO to each well (this results in a final concentration of 0.4% DMSO in each well).

(4) Incubate cells in the presence of DMSO or compound for up to 48 h.

(5) "Flick out" medium by hand and fix and permeabilise the cells by the addition of 100 µl fixing solution. Incubate at 37° for 30 min.

(6) Wash plates twice in PBS using an automated washer (Wellwash 5000 ten plate stacker-washer or Wellwash Ascent single plate washer, Thermo Labsystems, Basingstoke, UK).

(7) Block the plates by addition of blocking solution (100 µl) and incubate for 30 min.

(8) Add 100 µl primary antibody diluted to 0.95 µg/ml in PBS to each well and incubate plate for 1.5 h. Wash plates once with DELFIA® wash solution.

(9) Add 100 µl Europium labelled anti-mouse IgG diluted in DELFIA® assay buffer to 75 ng/ml and incubate for 1 hour. Wash plates once with DELFIA® wash solution as before.

(10) Add 100 µl DELFIA® enhancement solution to each well.

(11) Measure the fluorescence (615 nm) in Victor 2 1420 multilabel counter (Perkin Elmer Life Sciences, Milton Keynes, UK) using time-resolved measurement mode.

(12) Wash plates once with PBS and measure protein concentration by the addition of 200 µl BCA reagent to each well, shake for 1–2 min and incubate for 30 mins at 37° C. Read absorption at 570 nm.

(13) Express ELISA results by normalising to protein in the well (Eu counts (cpm) divided by OD@ 570 nm). Compare the effect of HSP90 inhibitors on HSP70 expression with DMSO treated controls.

Comments (1) Cells plated into 96 well plates are incubated in a plastic box to reduce evaporation from the outside wells. In addition, ELISA incubation steps are carried out in a 37° C. laboratory incubator and in a moist environment e.g., plastic box lined with damp tissue paper.

(2) All additions to the microtitre plate can be achieved using a multichannel pipette or for larger numbers of plates an automated dispenser such as a Multidrop (Thermo Labsytems, Basingstoke, UK).

(3) For convenience, if the effects of compounds are being studied at several time points the ELISA can be carried out in batches, plates being stored (in a container) at 4° C. following the fixation step. In this case the plates are washed only once following fixation and again immediately before the first ELISA step (step 6 above). In addition all the plates can be stored for subsequent protein estimation.

(4) Reproducibility of both the measured Europium counts and the protein measurements was between 10–15% (CV).

(5) DELFIA® reagents (see, e.g., Hemmila and Webb, 1997) have been routinely used in cell-based ELISAs. This endpoint provides high sensitivity and the time-resolved measurements reduce interference from non-specific fluorescence. However, it is also possible to use a horse radish peroxidase second antibody conjugate and either a calorimetric (e.g., tetramethylbenzidine) or chemiluminescent reagent (e.g., ECL reagent (Amersham Pharmacia Biotech, Little Chalfont, Bucks, UK) for endpoint measurement.

(6) It is recommended that a blank consisting of second-antibody only (i.e., no first antibody) together with an appropriate first antibody control (e.g., isotype matched IgG) are included in assays during the process of optimising reagent concentrations.

Growth Inhibition Assay

The growth inhibition assay employed was based on that described previously (Kelland et al., 1993). HCT116 and HT29 human colon tumour cells (American Tissue Culture Collection) were seeded into 96-well tissue culture plates (approximately 1600–2000 cells per well) and allowed to attach for 36 hours. Eight wells were treated with a single concentration from a range of compound concentrations and incubated for 96 hours. Cells were fixed using ice cold 10% trichloroacetic acid (TCA). Plates were then washed five times with water, air dried, and stained with 0.4% sulphorhodamine B (SRB) in 1% acetic acid for 10 minutes. The SRB stain was solubilised in 10 mM Tris-HCl and the absorbance measured at 540 nm using a Titertek Multiscan MCC/340 MKII plate reader (Flow Laboratories, IEC, Basingstoke, N.H.). The absorbance values correspond to total protein content and are used as a measure of cell growth. These values were plotted on log/linear graph paper and the $IC_{50}$ was calculated as the drug concentration that inhibits cell growth by 50% compared with control cell growth.

Biological Data

Malachite Green ATPase Assay

The inhibition of HSP90 ATPase activities (IC50, ±SD, if n=3–5) for several compounds of the present invention, assessed using the malachite green assay described above, are summarised in the following table. A substrate concentration of 1 mM ATP ($K_m$=0.44 mM) was used. Values for geldanamycin and 17AAG are included for comparison. In the coupled enzyme assay, geldanamycin has an IC50 of 5 µM.

TABLE 4

HSP90 ATPase inhibition

| Compound | IC50 (µM) |
| --- | --- |
| CCT018159 | 9.2 ± 0.65 |
| CCT018158 | 19.0 |
| CCT018157 | 60.5 ± 8.0 |
| CCT018156 | 52.8 ± 12 |
| CCT016391 | >100 |
| Geldanamycin | 4.8 ± 0.8 |
| 17AAG | 8.7 ± 2.3 |

Western Blotting Assay

The effect of CCT018159 on HSP70 and client protein (CDK4) expression was assessed using the Western blotting assay, as described above. The elevation of HSP70 following exposure to the compound (also observed using the cell-based ELISA) was confirmed.

FIG. 1 is an immunoblot showing expression of HSP70 (induced) and RAF-1 (depleted) at various times following exposure of A2780 human ovarian cancer cells to 17AAG (60 nM equivalent to 5×IC50).

Figure 2:
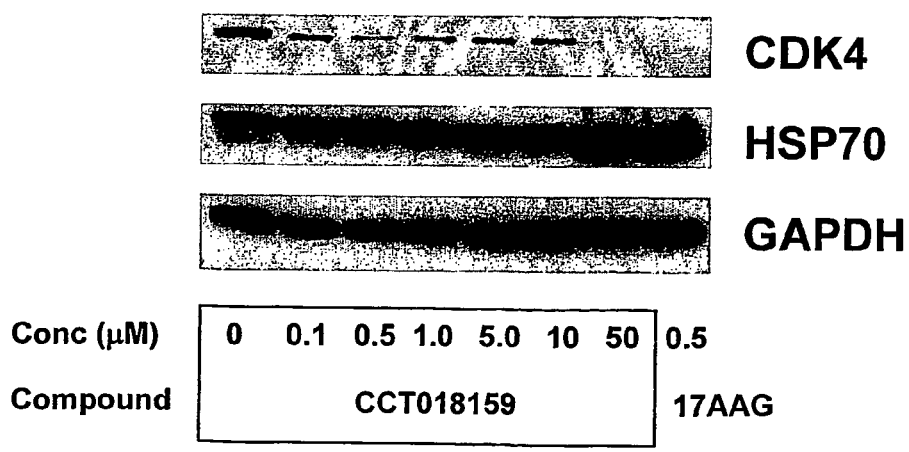
FIG. 2 is an immunoblot showing expression of CDK4 (depleted), HSP70 (induced), and GAPDH at 24 hours following exposure of HT29 cells to various concentrations of CCT018159 and 17AAG.

FIG. 2 is an immunoblot showing expression of CDK4 (depleted), HSP70 (induced), and GAPDH at 24 hours following exposure of HT29 cells to various concentrations of CCT018159 and 17AAG.

In HT29 cells, CCT018159 elevated HSP70 expression. The extent to which this protein was elevated following exposure to compound was similar to that observed for 17AAG. Glyceraldehyde phosphate dehydrogenase (GAPDH) was used to compare protein loading in each lane.

At the same time points and using the same concentration of compound, the client protein CDK4 was depleted. These results are similar to those observed with 17AAG and other HSP90 inhibitors (Kelland et al., 1999; Hostein et al., 2001; Schulte et al., 1998).

ELISA

The effect of various compounds of the present invention on the expression of the molecular marker HSP70 was determined using the cell-based ELISA and a specific monoclonal antibody to HSP70 in HCT116 cells, as described above. The results are summarised in the following table. Cellular protein following compound exposure was determined using BCA assay as described in the method.

TABLE 5

Effects on Molecular Markers

| Compound | % increase in HSP70 (Normalised Europium Counts compared to DMSO controls) | | Cellular Protein (% DMSO controls) | |
| --- | --- | --- | --- | --- |
| DMSO | 100 | 100 | 100 | 100 |
| 1 µM Geldanamycin | 169 | 270 | 75.3 | 46.3 |
| 10 µM CCT018159 | 158 | 278 | 20.8 | 50.0 |
| 10 µM CCT018157 | 105 | 103 | 21.2 | 91.3 |
| 10 µM CCT016391 | — | 95.0 | — | 96.8 |

The results show that, in HCT116 cells, HSP70 was induced up to 2.8-fold, following exposure to CCT018159 (10 µM) for 48 h. At the same time, cellular protein measured by BCA was reduced by 50–80% of DMSO controls. These results were similar to those obtained with geldanamycin (1 µM). This is indicative of cell growth inhibition at a compound concentration that also results in depletion of client proteins and elevation of HSP90.

Growth Inhibition Assay

The effects of various compounds of the present invention on the growth of HCT116 and HT29 human colon tumour cell lines, assessed using the growth inhibition assay described above, are summarised in the following table.

TABLE 6

96 h Growth Inhibition

| | IC50 (µM) | |
| --- | --- | --- |
| Compound | HCT116 | HT29 |
| CCT018159 | 4.5 | 13.5 |
| CCT018157 | 26.0 | 14.0 |
| Geldanamycin | 0.07 | 0.05 |
| 17AAG | 0.1 | 0.01 |

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the appended claims.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Ali J A, Jackson A P, Howells A J and Maxwell A. 1993 "The 43-kilodalton N-terminal fragment of the DNA gyrase β protein hydrolyses ATP and binds coumarin drugs", *Biochemistry*, Vol. 32, pp. 2717–2724.

Anderson C, Freeman J, Lucus L H, Farley M, Dalhoumi H and Widlanski T S. 1997 "Estrone sulfatase: probing structural requirements for substrate and inhibitor recognition, *Biochemistry*, Vol. 36, pp. 2586–2594.

Argon Y and Simen B B. 1999 "Grp94, an ER chaperone with protein and peptide binding properties", *Semin. Cell Dev. Biol.*, Vol. 10, pp. 495–505.

Baginski E S, Epstein E and Zak B. 1975 "Review of phosphate methodologies", *Ann. Clin. Lab. Sci.*, Vol. 5, pp. 399–416.

Baker W, Chadderton J, Harbome J B and Ollis W D. 1953 "Pt 1. A new synthesis of isoflavones", *J. Chem Soc*, p. 1852.

Baker W, Harbome J B and Ollis W D. 1953 "Pt II. A new synthesis of isoflavones, 5:7:2'-trihydroxyisoflavones", *J. Chem. Soc.*, p. 1860.

Bass R J. 1976 "Synthesis of chromones by cyclization of 2-hydroxyphenyl ketones with boron trifluoride—diethyl ether and methanesulphonyl chloride", *J. Chem. Soc., Chem. Commun.*, p. 78.

Baykov A A, Evtushenko O A and Avaeva S M. 1988 "A malachite green procedure for orthophosphate determination and its use in alkaline phosphatase-based enzyme immunoassay", *Anal. Biochem.*, Vol. 171, pp. 266–270.

Berk S C, Knochel P and Yeh M C P. 1988 "General approach to highly functionalized benzylic organometallics of zinc and copper", *J. Org. Chem.*, Vol. 53, pp. 5789–5791.

Chan K M, Delfert D and Junger K D. 1986 "A direct colorimetric assay for $Ca^{2+}$ stimulated ATPase activity", *Anal. Biochem.*, Vol. 157, pp. 375–380.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", *Mol. Cell. Biol.*, Vol. 16, pp. 4691–4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", *Chem. Biol.*, Vol. 8, pp. 289–299.

Clarke P A, Hostein I, Banerji U, Stefano F D, Maloney A, Walton M, Judson I and Workman P. 2000 "Gene expression profiling of human colon cancer cells following inhibition of signal transduction by 17-allylamino-17-demethoxygeldanamycin, an inhibitor of the HSP90 molecular chaperone", *Oncogene*, Vol. 19, pp. 4125–33.

Cogan E B, Birrell G B and Griffith O H. 1999 "A robotics-based automated assay for inorganic and organic phosphates", *Anal. Biochem.*, Vol. 271, pp. 29–35.

Connell P, Ballinger C A, Jiang J, Wu Y, Thompson L J, Hohfeld J and Patterson C. 2001 "The co-chaperone CHIP regulates protein triage decisions mediated by heat shock proteins", *Nature Cell Biol.*, Vol. 3, pp. 93–96.

Conroy S E and Latchman D S. 1996 "Do heat shock proteins have a role in breast cancer?", *Brit. J. Cancer*, Vol. 74, pp. 717–721.

Deboer C, Meulman P A, Wnuk R J and Peterson D H. 1970 "Geldanamycin, a new antibiotic", *J. Antibiot.* (Tokyo), Vol. 23, pp. 442.

Farkas J, Bekassy S, Agai B, Hegedus M and Figueras F. 2000 "Acylation of resorcinol on clay catalysts", *Syn. Commun.*, Vol. 30, pp. 2479.

Felts S J, Owen B A L, Nguyen P, Trepel J, Donner D B and Toft D O. 2000 "The HSP90-related protein TRAP1 is a mitochondrial protein with distinct functional properties", *J. Biol. Chem.*, Vol. 5, pp. 3305–3312.

Hajipour AR, Baltork I M and Kianfar G. 1998 "Bis (1-benzyl-4-aza-1-azoniabicyclo[2.2.2]octane) peroxodisulphate: a mild and efficient oxidant for cleavage of nitrogen double bonds and oxidation of alcohols under anhydrous conditions", *Bull. Chem. Soc. Japan*, Vol. 71, pp. 2655.

Harder K W, Owen P, Wong L K H, Aebersold R, Clark-Lewis I and Jirik F R. 1994 "Characterization and kinetic analysis of the intracellular domain of human protein tyrosine phosphatase β (HPTPβ) using synthetic phosphopeptides", *Biochem. J.*, Vol. 298, pp. 395–401.

Hemmila I and Webb S. 1997 "Time-resolved fluorometry: an overview of the labels and core technologies for drug screening applications", *Drug Discovery Today*, Vol. 2, pp. 373–381.

Henkel R D, Vandeberg J L and Walsh R A. 1988 "A microassay for ATPase", *Anal. Biochem.*, Vol. 169, pp. 312–318.

Hickey E, Brandon S E, Smale G, Lloyd D and Weber L A. 1999 "Sequence and regulation of a gene encoding a human 89-kilodalton heat shock protein", *Mol. Cell. Biol.*, Vol. 9, pp. 2615–2626.

Hoang A T, Huang J, Rudra-Gonguly N, Zheng J, Powell W C, Rabindron S K, Wu C and Roy-Burman P. 2000 "A novel association between the human heat shock transcription factor I (HSF1) and prostate adenocarcinoma, *Am. J. Pathol.*, Vol. 156, pp. 857–864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", *Cancer Res.*, Vol. 61, pp. 4003–4009.

Jameel A, Skilton R A, Campbell T A, Chander S K, Coombes R C and Luqmani Y A. 1992 "Clinical and biological significance of HSP89a in human breast cancer", *Int. J. Cancer*, Vol. 50, pp. 409–415.

Jolly C and Morimoto R I. 2000 "Role of the heat shock response and molecular chaperones in oncogenesis and cell death", *J. Natl. Cancer Inst.*, Vol. 92, pp. 1564–1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", *Cancer*, Vol. 85, pp. 1649–1657.

Kelland L R, Abel G, McKeage M J, Jones M, Goddard P M, Valenti M, Murrer B A and Harrap K R. 1993 "Preclinical antitumour evaluation of bis-acetalo-amino-dichloro-cyclohexylamine platinum (IV): an orally active platinum drug", *Cancer Research*, Vol. 53, pp. 2581–2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", *J. Natl. Cancer Inst.*, Vol. 91, pp. 1940–1949.

Khilya V P, Aitmambetov A, Ismailov M and Grishko L G. 1994 "Synthetic and modified isoflavanoids XV. Interaction of synthetic analogs of isoflavones with hydrazine hydrate and its derivatives", *Chem. Natural Compounds*, Vol. 30, pp. 580–583.

Knochel P, Yeh M C P, Berk S and Talbert J. 1988 "Synthesis and reactivity towards acyl chlorides and enones of the new highly functionalized copper reagents RCu (CN) ZnI", *J. Org. Chem.*, Vol. 53, pp. 2390.

Kwon H J, Yoshida M, Abe K, Horinouchi S and Bepple T. 1992 "Radicicol, an agent inducing the reversal of transformed phentoype of src-transformed fibroblasts, *Biosci., Biotechnol., Biochem.*, Vol. 56, pp. 538–539.

Lanzefta P H, Alvarez L J, Reinach P S and Candia O A. 1979 "An improved assay for nanomole amounts of inorganic phosphate", *Anal. Biochem.*, Vol. 100, pp. 95–97.

Layery P, Brown M J B and Pope A J. 2001 "Simple absorbance-based assays for ultra-high throughput screening", *J. Biomol. Screen.*, Vol. 6, pp. 3–9.

Le Q T H, Umetani S and Matsui M. 1997 "Ion-size recognition of group 13 metals ($Al^{3+}$, $In^{3+}$) with modified β-diketones", *J. Chem. Soc. Dalton Trans.*, Vol. 20, pp. 3835–3840.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJ/T24 Harvey-ras oncogene", *Oncogene*, Vol. 6, pp. 1125–1132.

Leigh W J and Arnold D R. 1979 "Photochemical and thermal rearrangements of some 3H-pyrazoles", *Can. J. Chem.*, Vol. 57, pp. 1186–1200.

Maehama T, Taylor G S, Slama J T and Dixon J E. 2000 "A sensitive assay for phosphoinositide phosphatases", *Anal. Biochem.*, Vol. 279, pp. 248–250.

Maloney A, Walton M I, Sharp S Y, Kelland L R, Jarman M, Prodromou C, Pearl L and Workman P. 1999 "Structure-activity relationships of the HSP90 inhibitor 17-allylamino 17-demethoxy geldanamycin analogues (17AAG)", *Clin. Cancer Res.*, Vol. 5, pp. 3781.

Marcu M G, Chadli A, Bouhouche I, Catelli M and Neckers L. 2000a "The heat shock protein 90 antagonist novobiocin interacts with a previously unrecognized ATP-binding domain in the carboxyl terminus of the chaperone", *J. Biol. Chem.*, Vol. 275, pp. 37181–37186.

Marcu M G, Schulte T W and Neckers L. 2000b "Novobiocin and related coumarins and depletion of heat shock protein 90-dependent signaling proteins", *J. Natl. Cancer Inst.*, Vol. 92, pp. 242–248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", *Cancer Res.*, Vol. 60, pp. 2232–2238.

Morimoto R I. 1998 "Regulation of the heat shock transcriptional response: cross talk between a family of heat shock factors, molecular chaperones, and negative regulators", *Genes and Dev.*, Vol. 12, pp. 3788–3796.

Nakano T, Alonso J, Grillet R and Martin A. 1979 "Pt1, Isoflavonoids of the bark of dipteryx odorata willd (Aubl)", *J. Chem. Soc.* pp. 2107.

Neckers L, Schulte T W and Momnaaugh E. 1999 "Geldanamycin as a potential anti-cancer agent: its molecular target and biochemical activity", *Invest. New Drugs*, Vol. 17, pp. 361–373.

Ochel H-J, Eichhorn K and Gademann G. 2001 "Geldanamycin: the prototype of a class of antitumor drugs targeting the heat shock protein 90 family of molecular chaperones", *Cell Stress and Chaperones*, Vol. 6, pp. 105–112.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", *Proc. Am. Assoc. Cancer Res.*, Vol. 38, pp. 308.

Panaretou B, Prodromou C, Roe S M, O'Brien R, Ladbury J E, Piper P W and Pearl L H. 1998 "ATP binding and hydrolysis are essential to the function of the HSP90 molecular chaperone in vivo", *EMBO J.*, Vol. 17, pp. 4829–4836.

Penning T D, Kramer S W, Lee L F, Collins P W, Koboldt C M, Seibert K, Veenhuizen A W, Zhang Y Y and Isakson P C. 1997 "3,4-diarylpyrazoles: Potent and Selective Inhibitors of Cyclooxygenase-2", *Bioorg. & Med. Chem. Lett.*, Vol. 7, pp. 2121–2124.

Pratt W B. 1997 "The role of the HSP90-based chaperone system in signal transduction by nuclear receptors and receptors signalling via MAP kinase", *Annu. Rev. Pharmacol. Toxicol.*, Vol. 37, pp. 297–326.

Prodromou C and Pearl L H. 2000a "Structure and in vivo function of HSP90", *Curr. Opin. Struct. Biol.*, Vol. 10, pp. 46–51.

Prodromou C, Roe S M, O'Brien R, Ladbury J E, Piper P W and Pearl L H. 1997 "Identification and structural characterization of the ATP/ADP-binding site in the HSP90 molecular chaperone", *Cell*, Vol. 90, pp. 65–75.

Prodromou C, Panaretou B, Chohan S, Siligardi G, O'Brien R, Ladbury J E, Roe S M, Piper P W and Pearl L H. 2000b "The ATPase cycle of HSP90 drives a molecular 'clamp' via transient dimerization of the N-terminal domains", *EMBO J.*, Vol. 19, pp. 4383–4392.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", *J. Med. Chem.*, Vol. 42, pp. 260–266.

Rumsfeld J, Ziegelbauer K and Spaltmann F. 2000 "High-throughput assay for inorganic pyrophosphatases using the cytosolic enzymes of *Saccharomyces cerevisiae* and human as an example", *Protein Expr. Purif.*, Vol. 18, pp. 303–309.

Rutherford S L and Lindquist S. 1998 "HSP90 as a capacitor for morphological evolution. *Nature*, Vol. 396, pp. 336–342.

Scheibel T and Buchner J. 1998 "The HSP90 complex-A super-chaperone machine as a novel drug target", *Biochem. Pharmacol.*, Vol. 56, pp. 675–682.

Schirmer E C, Queitsch C, Kowal A S, Parsell D A and Lindquist S. 1998 "The ATPase activity of hsp104, effects of environmental conditions and mutations", *J. Biol. Chem.*, Vol. 273, pp. 15546–15552.

Schnur R C, Corman M L, Gallascun R J, Cooper B A, Dee M F, Doty J L, Muzzi M L, Diorio C I, Barbacci E G and Miller P E. 1995a "erbB2 oncogene inhibition by geldanamycin derivatives: synthesis, mechanism of action, and structure-activity relationships", *J. Med. Chem.*, Vol. 38, pp. 3813–3820.

Schnur R C, Corman M L, Gallascun R J, Cooper B A, Dee M F, Doty J L, Muzzi M L, Moyer J D, Diorio C I and Barbacci E G. 1995b "Inhibition of the oncogene product p185erbB2 in vitro and in vivo by geldanamycin and dihydrogeldanamycin derivatives", *J. Med. Chem.*, Vol. 38, pp. 3806–3812.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", *Mol. Endocrinology*, Vol. 13, pp. 1435–1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", *Cell Stress and Chaperones*, Vol. 3, pp. 100–108.

Schulte T W and Neckers L M. 1998 "The benzoquinone ansamycin 17-allylamino-17-deemthoxygeldanamcyin binds to HSP90 and shares important biologic activities with geldanamycin", *Cancer Chemother. Pharmacol.*, Vol. 42, pp. 273–279.

Smith D F. 2001 "Chaperones in signal transduction", in: *Molecular chaperones in the cell* (P Lund, ed.; Oxford University Press, Oxford and NY), pp. 165–178.

Smith D F, Whitesell L and Katsanis E. 1998 "Molecular chaperones: Biology and prospects for pharmacological intervention", *Pharmacological Reviews*, Vol. 50, pp. 493–513.

Soga S, Neckers L M, Schulte T W, Shiotsu Y, Akasaka K, Narumi H, Agatsuma T, Ikuima Y, Murakata C, Tornaoki T and Akinaga S. 1999 "KF25706, a novel oxime derivative of radicicol, exhibits in vivo antitumor activity via selective depletion of HSP90 binding signaling molecules", *Cancer Res.*, Vol. 59, pp. 2931–2938.

Song H Y, Dunbar J D, Zhang Y X, Guo D and Donner D B. 1995 "Identification of a protein with homology to hsp90 that binds the type 1 tumour necrosis factor receptor", *J. Biol. Chem.*, Vol. 270, pp. 3574–3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", *Cell*, Vol. 89, pp. 239–250.

Stockwell B R, Haggarty S J and Schreiber S L. 1999 "High-throughput screening of small molecules in miniaturised mammalian cell-based assays involving post-translational modifications", *Chem. Biol.*, Vol. 6, pp. 71–83.

Supko J G, Hickman R L, Grever M R and Malspeis L. 1995 "Preclinical pharmacologic evaluation of geldanamycin as an antitumour agent", *Cancer Chemother. Pharmacol.*, Vol. 36, pp. 305–315.

Sybert K and Spiegel J. 2001 *Federal Register*, Vol. 66, pp. 35443–35444.

Terrett N K, Bell A S, Brown D and Ellis P. 1996 "Sildenafil (viagra™): a potent and selective inhibitor of type 5 CGMP phosphodiesterase with utility for the treatment of male erectile dysfunction", *Bioorg. Med. Chem. Lett.*, Vol. 6, pp. 1819–1824.

Tytell M and Hooper P L. 2001 "Heat shock proteins: new keys to the development of cytoprotective therapies", *Emerging Therapeutic Targets*, Vol. 5, pp. 267–287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", *Mol. Cell. Biol.*, Vol. 6, pp. 2198–2206.

Versteeg H H, Nijhuis E, Van Den Brink G R, Evertzen M, Pynaert G N, Van deventer J H, Coffer P J and Peppelenbosch M P. 2000 "A new phosphospecific cell-based ELISA for p42/p44 mitogen-activated protein kinase (MAPK), p38 MAPK, protein kinase B and cAMP-response-element-binding protein", *Biochem. J.*, Vol. 350, pp. 717–722.

Wahala K and Hase T A. 1991 "Expedient synthesis of polyhydroxyisoflavones", *J. Chem. Soc, PT1*, pp. 3005.

Whitesell L, Mimnaugh E G, De Costa B, Myers C E and Neckers L M. 1994 "Inhibition of heat shock protein HSP90-pp60v-src heteroprotein complex formation by benzoquinone ansamycins: essential role for stress proteins in oncogenic transformation", *Proc. Natl. Acad. Sci. USA.*, Vol. 91, pp. 8324–8328.

Young J C, Moarefi I and Hartl F U. 2001 "HSP90: a specialized but essential protein-folding tool", *J. Cell. Biol.*, Vol. 154, pp. 267–273.

Zhang J H, Chung T D and Oldenburg K R. 1999 "A simple statistical parameter for use in evaluation and validation of high throughput screening assays", *J. Biomol. Screen.*, Vol. 4, pp. 67–73.

Zhao J F, Nakano H and Sharma S. 1995 "Suppression of RAS and MOS transformation by radicicol", *Oncogene*, Vol. 11, pp. 161–173.

Zhu L, Wehmeyer R M and Rieke, R D. 1991 "The direct formation of functionalized alky(aryl)zinc halides by oxidation addition of highly reactive zinc with organic halides and their reactions with acid chlorides, α,β-unsaturated ketones, and allylic, aryl and vinyl halides", *J. Org. Chem.*, Vol. 56, pp. 1445, 1991.

The invention claimed is:

1. A compound of formula:

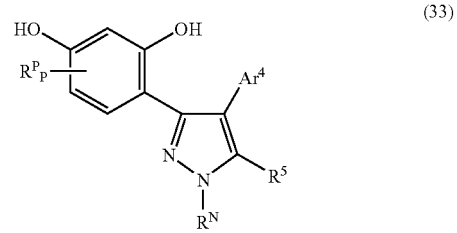

(33)

wherein:

Ar$^4$ is a C$_{5-10}$ aryl group and is optionally substituted, wherein when Ar$^4$ is phenyl Ar$^4$ is not substituted so as to form a polycyclic group;

R$^5$ is selected from the group consisting of hydrogen; halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; and C$_{1-7}$alkyl;

R$^N$ is —H or C$_{1-7}$alkyl;

each R$^P$ is independently selected from the group consisting of hydrogen; halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; and C$_{1-7}$alkyl; and p is an integer from 0 to 3;

or a pharmaceutically acceptable salt, solvate, or prodrug thereof.

2. A compound according to claim 1 having the formula:

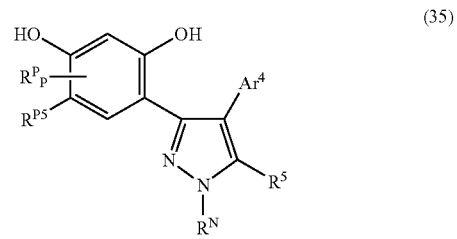

(35)

wherein:

p is an integer from 0 to 2; and, $R^{P5}$ and each $R^P$ are each independently selected from the group consisting of hydrogen; halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; and $C_{1-7}$alky.

3. A compound according to claim 2 having the formula:

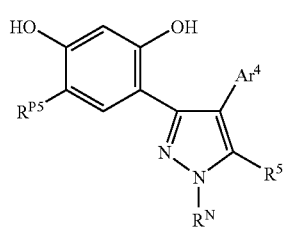

(36)

4. A compound according to claim 3 wherein $R^{P5}$ is halo; or $C_{1-4}$alkyl.

5. A compound according to claim 3 wherein $R^{P5}$ is selected from the group consisting of -F, -Cl, -Br, -I, -Me, -Et, -nPr, -iPr, -nBu, -iBu, -sBu, -tBu, and —CF$_3$.

6. A compound according to claim 3 wherein: $R^{P5}$ is -Me or -iPr.

7. A compound according to claim 2 having the formula:

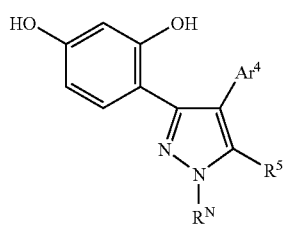

(34)

8. A compound according to claim 7 wherein $Ar^4$ is a monocyclic $C_{5-6}$ heteroaryl group and is optionally substituted.

9. A compound according to claim 7 wherein $Ar^4$ is a monocyclic $C_{5-6}$ carboaryl group and is optionally substituted.

10. A compound according to claim 7 wherein $Ar_4$ is a $C_{5-10}$ aryl group derived from one of the following and is optionally substituted: benzene, pyridine, furan, indole, pyrrole, imidazole, thiazole, isothiazole, naphthalene, quinoline, benzimidazole, benzothiofuran, benzothiazole, benzodioxolane, and benzodioxetane.

11. A compound according to claim 7 wherein $Ar^4$ is phenyl, thiazol-5-yl, or benzothiazol-2-yl; and is optionally substituted.

12. A compound according claim 7 wherein $Ar^4$ is phenyl.

13. A compound according to claim 3 wherein $R^5$ is amido.

14. A compound according to claim 3 wherein $R^N$ is —H or $C^{1-4}$alkyl.

15. A compound according to claim 3 wherein $R^N$ is —H, -Me, or -Et.

16. A compound of formula:

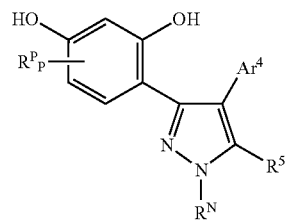

(33)

wherein:

$Ar^4$ is a $C_{5-16}$aryl group and is optionally substituted;

$R^5$ is selected from the group consisting of halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; and sulfonamido;

$R^N$ is —H or $C_{1-7}$alkyl;

each $R^P$ is independently selected from the group consisting of halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; and sulfonamido; and p is an integer from 1 to 3;

or a pharmaceutically acceptable salt, solvate, or prodrug thereof.

17. A compound of formula:

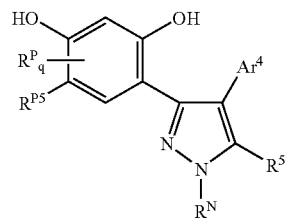

(35)

wherein:

$Ar^4$ is a $C_{5-10}$aryl group and is optionally substituted;

$R_5$ is selected from the group consisting of halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; and sulfonamido;

$R^N$ is —H or $C_{1-7}$alkyl;

each $R^P$ is independently selected from the group consisting of hydrogen, halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; sulfonamido; and $C_{1-7}$alkyl; and wherein:

q is an integer from 0 to 2; and $R^{P5}$ is selected from the group consisting of halo; hydroxy; ether; formyl; acyl; carboxy; ester; acyloxy; oxycarbonyloxy; amido; acylamido; aminocarbonyloxy; tetrazolyl; amino; nitro; cyano; azido; sulfhydryl; thioether; and sulfonamido; or a pharmaceutically acceptable salt, solvate, amide, ester, ether, chemically protected form, or prodrug thereof.

18. A compound according to claim 17 having the formula:
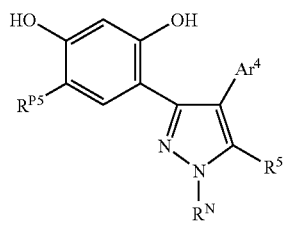
(36)
19. A compound according to claim 18 wherein $R^{P5}$ is halo.
20. A compound according to claim 18 wherein $R^{P5}$ is selected from the group consisting of —F, —Cl, —Br, —I, and —CF$_3$.
* * * * *

UNITED STATES PATENT AND TRADEMARK OFFICE
CERTIFICATE OF CORRECTION

PATENT NO. : 7,247,734 B2
APPLICATION NO. : 10/499030
DATED : July 24, 2007
INVENTOR(S) : Martin James Drysdale et al.

It is certified that error appears in the above-identified patent and that said Letters Patent is hereby corrected as shown below:

Column 223, Line 51:
　　Please delete "$Ar_4$" and insert --$Ar^4$--

Column 223, Line 65:
　　Please delete "$C^{1-4}$" and insert --$C_{1-4}$--

Column 224, Line 15:
　　Please delete "$C_{5-16}$" and insert --$C_{5-10}$--

Signed and Sealed this

Eighth Day of April, 2008

JON W. DUDAS
*Director of the United States Patent and Trademark Office*